United States Patent
Osaka et al.

(10) Patent No.: US 8,421,346 B2
(45) Date of Patent: Apr. 16, 2013

(54) COMPOSITE MATERIAL, LIGHT-EMITTING ELEMENT, LIGHT-EMITTING DEVICE, LIGHTING DEVICE, ELECTRONIC DEVICE, AND FLUORENE DERIVATIVE

(75) Inventors: Harue Osaka, Kanagawa (JP); Hiroki Suzuki, Kanagawa (JP); Hiromi Nowatari, Kanagawa (JP); Satoshi Seo, Kanagawa (JP); Nobuharu Ohsawa, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 13/358,975

(22) Filed: Jan. 26, 2012

(65) Prior Publication Data

US 2012/0194062 A1 Aug. 2, 2012

(30) Foreign Application Priority Data

Jan. 28, 2011 (JP) ................. 2011-017164

(51) Int. Cl.
*H05B 33/00* (2006.01)
(52) U.S. Cl.
USPC ............................. 313/504; 428/690; 313/506
(58) Field of Classification Search .......... 313/504–506; 428/690, 917
See application file for complete search history.

(56) References Cited

U.S. PATENT DOCUMENTS

| | | |
|---|---|---|
| 7,732,808 B2 | 6/2010 | Ikeda et al. |
| 2009/0026922 A1 | 1/2009 | Iwaki et al. |
| 2010/0301744 A1 | 12/2010 | Osaka et al. |
| 2011/0095678 A1 | 4/2011 | Ogita et al. |

FOREIGN PATENT DOCUMENTS

JP 2006-324650 11/2006

OTHER PUBLICATIONS

Yang, Y. et al, "Polyaniline as a Transparent Electrode for Polymer Light-Emitting Diodes: Lower Operating Voltage and Higher Efficiency," Applied Physics Letters, vol. 64, No. 10, Mar. 7, 1994, pp. 1245-1247.

*Primary Examiner* — Joseph L Williams
(74) *Attorney, Agent, or Firm* — Husch Blackwell LLP

(57) ABSTRACT

Provided is a composite material which makes it possible to provide a light-emitting element having at least one of the following characteristics by applying the composite material to the light-emitting element: low voltage driving, high emission efficiency, and a long life (high reliability). The composite material includes a hydrocarbon compound and an inorganic compound which exhibits an electron-accepting property with respect to the hydrocarbon compound. The hydrocarbon compound has a molecular weight of greater than or equal to 400 and less than or equal to 2000, where one or more aryl groups are bonded to a fluorene unit.

33 Claims, 36 Drawing Sheets

US 8,421,346 B2

COMPOSITE MATERIAL, LIGHT-EMITTING ELEMENT, LIGHT-EMITTING DEVICE, LIGHTING DEVICE, ELECTRONIC DEVICE, AND FLUORENE DERIVATIVE

BACKGROUND OF THE INVENTION

1. Field of the Invention

The present invention relates to composite materials which can be suitably used as materials included in light-emitting elements. The present invention further relates to light-emitting elements, light-emitting devices, lighting devices, and electronic devices including the composite materials. Furthermore, the present invention relates to fluorene derivatives which can be suitably used for the composite materials.

2. Description of the Related Art

As next generation lighting devices or display devices, light-emitting devices including organic EL elements (light-emitting elements in which organic compounds are used as light-emitting substances) have been developed at an accelerated pace owing to their advantages of thinness, light-weightness, high speed response, low power consumption, and the like.

In an organic EL element, a light-emitting layer including a light-emitting substance is interposed between a pair of electrodes. Application of voltage between the electrodes causes electrons and holes to be injected from the electrodes to recombine and form an excited state. When the excited state relaxes to a ground state, light is emitted. The wave length of light emitted from a light-emitting substance is peculiar to the light-emitting substance; thus, by using different types of organic compounds as light-emitting substances, light-emitting elements which exhibit various wave lengths, i.e., various colors can be obtained.

In a case of a display device which is expected to display images, such as a display, at least three colors of light, i.e., red, green, and blue are required to be obtained in order to reproduce full-color images. In a case of a lighting device, in order to obtain a high color rendering property, it is ideal to obtain light having wave length components thoroughly in the visible light region. Actually, two or more kinds of light having different wave lengths are mixed to be used for lighting application in many cases. Note that it is known that by mixing light of three colors, red, green, and blue, white light emission having a high color rendering property can be obtained.

Important characteristics of a light-emitting element include emission efficiency in addition to the color of the light-emitting element. Compared with other light-emitting elements, a light-emitting element with high emission efficiency needs lower energy to obtain the same luminance. Therefore, it is possible to provide a light-emitting device having a high energy-saving property. Now that much attention has been paid on the energy issue, increase in emission efficiency is a significant object.

One of useful methods for increasing emission efficiency, particularly power efficiency, is reduction in driving voltage. When the driving voltage becomes lower, a larger current can flow at a low voltage, which results in lower power consumption and higher power efficiency. Thus, many researches have been made aiming at reducing a driving voltage (e.g., see Non-Patent Document 1).

In addition to emission efficiency, important characteristics of a light-emitting element also include a life (reliability) which relates to the credibility as a product. As a matter of course, the life (reliability) is one of characteristics required in commercialization, so that a life (reliability) at a certain level or higher can be a big selling point. That is, the longer the life is (the higher the reliability is), the more preferable. Thus, researches have been made on prolonging the life (increasing the reliability) of a light-emitting element by a variety of methods (e.g., see Patent Document 1).

[Reference]
[Patent Document]
[Patent Document 1] Japanese Published Patent Application No. 2006-324650
[Non-Patent Document]
[Non-Patent Document 1] Y. Yang and A. Heeger, "Polyaniline as a transparent electrode for polymer light-emitting diodes: Lower operating voltage and higher efficiency", Applied Physics Letters, Vol. 64, No. 10; pp. 1245-1247 (1994).

SUMMARY OF THE INVENTION

Another approach to increasing emission efficiency is to increase luminance per unit current density (current efficiency). As described above, the higher the emission efficiency is, the more preferable. Since the luminance of an organic EL element is in proportion to current, in a light-emitting element where a larger current can flow at a low voltage (light-emitting element which can be driven at a low driving voltage), increase in luminance per unit current density (current efficiency) can provide a light-emitting element with very high current efficiency.

In view of the above, an object of one embodiment of the present invention is to provide a composite material which makes it possible to provide a light-emitting element with high emission efficiency by applying the composite material to the light-emitting element.

Another object of one embodiment of the present invention is to provide a composite material which makes it possible to provide a light-emitting element which is driven at a low driving voltage and has high emission efficiency by applying the composite material to the light-emitting element.

A characteristic such as a life (reliability) is significantly important for any light-emitting element.

In view of the above, another object of one embodiment of the present invention is to provide a composite material which makes it possible to provide a light-emitting element with a long life (high reliability).

Another object of one embodiment of the present invention is to provide a composite material which makes it possible to provide a light-emitting element with high emission efficiency and a long life (high reliability).

Another object of one embodiment of the present invention is to provide a composite material which makes it possible to provide a light-emitting element which is driven at a low voltage and has high emission efficiency and a long life (high reliability).

Another object of one embodiment of the present invention is to provide a light-emitting element with high emission efficiency.

Another object of one embodiment of the present invention is to provide a light-emitting element which is driven at a low driving voltage and has high emission efficiency.

Another object of one embodiment of the present invention is to provide a light-emitting element with a long life (high reliability).

Another object of one embodiment of the present invention is to provide a light-emitting element with high emission efficiency and a long life (high reliability).

Another object of one embodiment of the present invention is to provide a light-emitting element which is driven at a low driving voltage and has high emission efficiency and a long life (high reliability).

Another object of one embodiment of the present invention is to provide a light-emitting device with low power consumption.

Another object of one embodiment of the present invention is to provide a light-emitting device with high reliability.

Another object of one embodiment of the present invention is to provide a light-emitting device with low power consumption and high reliability.

Another object of one embodiment of the present invention is to provide an electronic device with low power consumption.

Another object of one embodiment of the present invention is to provide an electronic device with high reliability.

Another object of one embodiment of the present invention is to provide an electronic device with low power consumption and high reliability.

Another object of one embodiment of the present invention is to provide a lighting device with low power consumption.

Another object of one embodiment of the present invention is to provide a lighting device with high reliability.

Another object of one embodiment of the present invention is to provide a lighting device with low power consumption and high reliability.

Another object of one embodiment of the present invention is to provide a novel compound suitable for forming the above-described composite material.

Note that in one embodiment of the present invention, it is only necessary that at least one of the above objects is achieved.

The present inventors have found out that at least one of the above objects can be achieved by using a composite material including the following: a hydrocarbon compound which has a molecular weight of greater than or equal to 400 and less than or equal to 2000 and in which one or more aryl groups are bonded to a fluorene unit (hereinafter, fluorene); and an inorganic compound which exhibits an electron-accepting property with respect to the hydrocarbon compound. Further, by using the composite material, it has become possible to provide a light-emitting element with high emission efficiency. It has also become possible to fabricate a light-emitting element with a long life and a small reduction in emission efficiency relative to the driving time.

That is, one embodiment of the present invention is a composite material including a hydrocarbon compound which has a molecular weight of greater than or equal to 400 and less than or equal to 2000 and in which one or more aryl groups are bonded to a fluorene, and an inorganic compound which exhibits an electron-accepting property with respect to the hydrocarbon compound.

Owing to a bulky structure of the fluorene skeleton included in the hydrocarbon compound in the composite material according to one embodiment of the present invention, a film formed using the composite material has a good quality, and a light-emitting element with a long life can be fabricated.

Since a fluorene itself has a wide energy gap between the HOMO level and the LUMO level, appropriate selection of an aryl group(s) bonded thereto can provide a composite material having a high light-transmitting property with little absorption of light in the visible light region. Specifically, an aryl group with little absorption of light for itself is selected. Accordingly, by using the composite material, a light-emitting element with high emission efficiency can be fabricated. Since the hydrocarbon compound is formed of only hydrocarbon, conjugation is barely likely to extend between the fluorene and a substituent thereof (as compared to a hydrocarbon compound where aryls are bonded to each other via an electron-donating group such as an amine); thus, it is possible to obtain a hydrocarbon compound having a moderately great molecular weight while the wide energy gap is kept. Accordingly, a thermally stable hydrogen compound can be obtained. Further, when the hydrocarbon compound is evaporated, the evaporation rate can be easily controlled; accordingly, a light-emitting element with a stable quality can be provided. The composite material according to one embodiment of the present invention is formed by co-evaporation of the hydrocarbon compound and an inorganic compound having higher evaporation temperature than the hydrocarbon compound. The composite material according to one embodiment of the present invention includes the hydrocarbon compound having the fluorene, skeleton; therefore, the energy gap is prevented from narrowing and the molecular weight can be moderately great, and co-evaporation can be performed at a temperature closer to the evaporation temperature of the inorganic compound. Since the hydrocarbon compound is formed of only hydrocarbon, the polarity is barely likely to be large. Even when the hydrocarbon compound is included in a composite material, additional absorption is barely likely to occur. Accordingly, a composite material having a higher light-transmitting property can be obtained.

By using the composite material including the hydrocarbon compound having the fluorene skeleton, a light-emitting element with a good carrier balance and high emission efficiency can be fabricated.

When the composite material is formed by vacuum evaporation, the molecular weight is more preferably 1200 or less, considering the evaporation temperature.

Another embodiment of the present invention is a composite material including a hydrocarbon compound which has a molecular weight of greater than or equal to 400 and less than or equal to 2000 and in which an aryl group is bonded to a 9-position of a fluorene via one phenylene group or two phenylene groups, and an inorganic compound which exhibits an electron-accepting property with respect to the hydrocarbon compound.

The composite material according to one embodiment of the present invention having the above structure includes the hydrocarbon compound in which the aryl group is bonded via a carbon atom at the 9-position of the fluorene. Accordingly, conjugation can be prevented from extending from the aryl group to the fluorene skeleton, and the energy gap can be more effectively prevented from narrowing, and a hydrocarbon compound having a wide energy gap can be obtained. Therefore, a composite material including the hydrocarbon compound can be a composite material having a high light-transmitting property with little absorption of light in the visible light region.

More specifically, another embodiment of the present invention is a composite material including a hydrocarbon compound which has a molecular weight of greater than or equal to 400 and less than or equal to 2000 and is represented by the following general formula (G1), and an inorganic compound which exhibits an electron-accepting property with respect to the hydrocarbon compound.

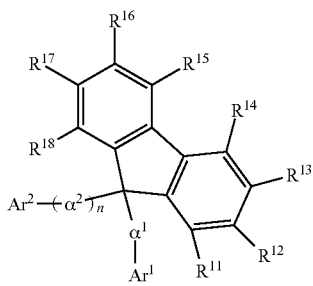

(G1)

Note that in the formula, $\alpha^1$ and $\alpha^2$ separately represent a substituted or unsubstituted phenylene group or a substituted or unsubstituted biphenyldiyl group, and n is 0 or 1. $Ar^1$ represents a substituted or unsubstituted aryl group, and $Ar^2$ represents a substituted or unsubstituted aryl group. $R^{11}$ to $R^{18}$ separately represent any of hydrogen, an alkyl group having 1 to 6 carbon atoms, a substituted or unsubstituted phenyl group, a substituted or unsubstituted biphenyl group, a substituted or unsubstituted naphthyl group, and a substituted or unsubstituted phenanthryl group.

Another embodiment of the present invention is a composite material including a hydrocarbon compound which has a molecular weight of greater than or equal to 400 and less than or equal to 2000 and in which a bicyclic condensed ring, a tricyclic condensed ring, or a tetracyclic condensed ring is bonded to a 9-position of the fluorene via one phenylene group or two phenylene groups, and an inorganic compound which exhibits an electron-accepting property with respect to the hydrocarbon compound.

When two aryl groups are bonded to the 9-positions of the fluorene, these aryl groups are bonded to each other via a sigma bonding at the 9-positions of the fluorene. Accordingly, conjugation is barely likely to extend between the aryl groups, so that a bulky structure can be achieved while the band gap is kept wide. Therefore, it is possible to provide a material that is hardly crystallized despite having a high light-transmitting property.

The composite material according to one embodiment of the present invention having the above structure can be, by including any of a bicyclic condensed ring, a tricyclic condensed ring, and a tetracyclic condensed ring, a suitable material as a light-emitting element material with a good balance between an electron- or hole-transport property and a light-transmitting property when being formed as a film.

Another embodiment of the present invention is a composite material including a hydrocarbon compound which has a molecular weight of greater than or equal to 400 and less than or equal to 2000 and is represented by the following general formula (G1), and an inorganic compound which exhibits an electron-accepting property with respect to the hydrocarbon compound.

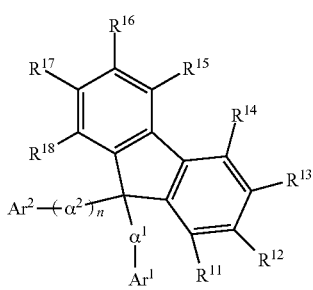

(G1)

Note that in the formula, $\alpha^1$ and $\alpha^2$ separately represent a substituted or unsubstituted phenylene group or a substituted or unsubstituted biphenyldiyl group, and n is 0 or 1. $Ar^1$ represents any of a substituted or unsubstituted bicyclic condensed aryl group, a substituted or unsubstituted tricyclic condensed aryl group, and a substituted or unsubstituted tetracyclic condensed aryl group, and $Ar^2$ represents a substituted or unsubstituted aryl group having 6 to 18 carbon atoms. $R^{11}$ to $R^{18}$ separately represent any of hydrogen, an alkyl group having 1 to 6 carbon atoms, a substituted or unsubstituted phenyl group, a substituted or unsubstituted biphenyl group, a substituted or unsubstituted naphthyl group, and substituted or unsubstituted phenanthryl group.

The composite material according to one embodiment of the present invention having the above structure can be, by including any of a bicyclic condensed ring, a tricyclic condensed ring, and a tetracyclic condensed ring, a suitable material as a light-emitting element material with a good balance between an electron- or hole-transport property and a light-transmitting property when being formed as a film.

Another embodiment of the present invention is a composite material including a hydrocarbon compound which has a molecular weight of greater than or equal to 400 and less than or equal to 2000 and is represented by the following general formula (G2), and an inorganic compound which exhibits an electron-accepting property with respect to the hydrocarbon compound.

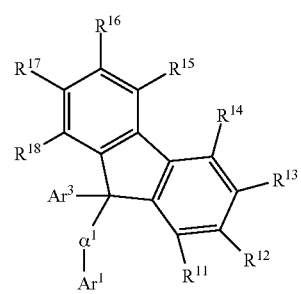

(G2)

Note that in the formula, $\alpha^1$ represents a substituted or unsubstituted phenylene group or a substituted or unsubstituted biphenyldiyl group. $Ar^1$ represents any of a substituted or unsubstituted bicyclic condensed aryl group, a substituted or unsubstituted tricyclic condensed aryl group, and a substituted or unsubstituted tetracyclic condensed aryl group, and $Ar^3$ represents a substituted or unsubstituted phenyl group or a substituted or unsubstituted biphenyl group. $R^{11}$ to $R^{18}$ separately represent any of hydrogen, an alkyl group having 1 to 6 carbon atoms, a substituted or unsubstituted phenyl group, a substituted or unsubstituted biphenyl group, a substituted or unsubstituted naphthyl group, and substituted or unsubstituted phenanthryl group.

The composite material according to one embodiment of the present invention having the above structure can have a high light-transmitting property owing to the wide energy gap of the hydrocarbon compound represented by the above general formula.

Another embodiment of the present invention is a composite material having the above structure in which $R^{11}$ to $R^{18}$ separately represent any of hydrogen, an alkyl group having 1 to 6 carbon atoms, and a group represented by any of the following structural formulas (R-1) to (R-6).

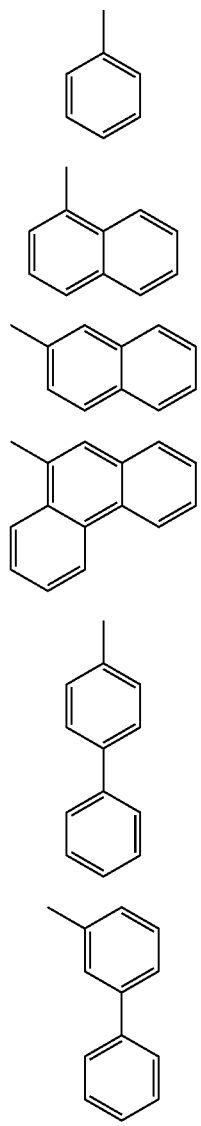

(R-1)

(R-2)

(R-3)

(R-4)

(R-5)

(R-6)

It is preferable to have any of these substituents because a more bulky material can be obtained. However, in terms of synthesis, it is preferable to have no substituents because the synthesis becomes easier.

Another embodiment of the present invention is a composite material including a hydrocarbon compound which has a molecular weight of greater than or equal to 400 and less than or equal to 2000 and is represented by the following general formula (G3), and an inorganic compound which exhibits an electron-accepting property with respect to the hydrocarbon compound.

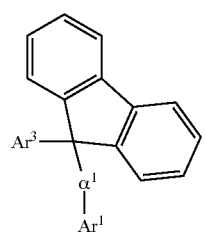

(G3)

Note that in the formula, $\alpha^1$ represents a substituted or unsubstituted phenylene group or a substituted or unsubstituted biphenyldiyl group. $Ar^1$ represents any of a substituted or unsubstituted bicyclic condensed aryl group, a substituted or unsubstituted tricyclic condensed aryl group, and a substituted or unsubstituted tetracyclic condensed aryl group, and $Ar^3$ represents a substituted or unsubstituted phenyl group or a substituted or unsubstituted biphenyl group.

The composite material according to one embodiment of the present invention having the above structure has a simple structure; therefore, the composite material can be obtained at a low cost.

Another embodiment of the present invention is a composite material having the above structure in which $Ar^1$ is one selected from a substituted or unsubstituted naphthyl group, a substituted or unsubstituted anthryl group, a substituted or unsubstituted phenanthryl group, a substituted or unsubstituted triphenylenyl group, a substituted or unsubstituted pyrenyl group, a substituted or unsubstituted chrysenyl group, and a substituted or unsubstituted tetracenyl group.

Another embodiment of the present invention is a composite material having the above structure, where the aryl group represented by $Ar^1$ is selected so that a substance where the bond of the aryl group is bonded to hydrogen ($Ar^1$—H) does not have a peak in a range of greater than or equal to 450 nm and less than or equal to 800 nm in an absorption spectrum thereof.

A composite material having such a structure can have a high light-transmitting property owing to little absorption in the visible light region, which originates from a skeleton included therein.

Another embodiment of the present invention is a composite material having the above structure in which $Ar^1$ is one selected from a substituted or unsubstituted naphthyl group, a substituted or unsubstituted anthryl group, a substituted or unsubstituted phenanthryl group, and a substituted or unsubstituted triphenylenyl group.

A composite material having the above structure can have a high visible light transmittance because additional absorption in the visible light region is barely likely to occur owing to formation of a charge-transfer complex by the hydrocarbon compound and the inorganic compound.

Another embodiment of the present invention is a composite material having the above structure in which $Ar^1$ is one selected from a substituted or unsubstituted pyrenyl group, a substituted or unsubstituted chrysenyl group, a substituted or unsubstituted tetracenyl group, and a substituted or unsubstituted triphenylenyl group.

A composite material having the above structure can have high carrier mobility.

Another embodiment of the present invention is a composite material in which, when $Ar^1$ has a substituent, the substituent is any of a phenyl group, a naphthyl group, a phenanthryl group, and a group represented by the following general formula ($Ar^1$-1).

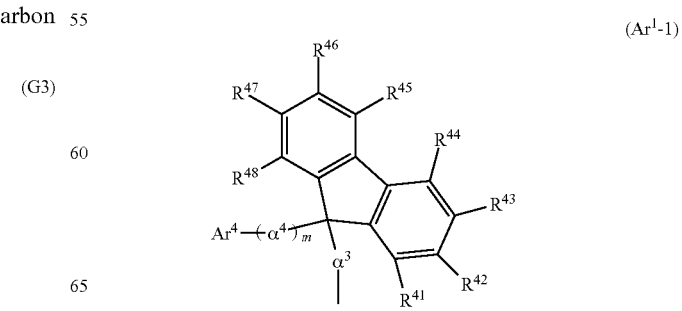

($Ar^1$-1)

Note that in the formula, $\alpha^3$ and $\alpha^4$ separately represent a substituted or unsubstituted phenylene group or a substituted or unsubstituted biphenyldiyl group, and m is 0 or 1. Ar$^4$ represents any of a substituted or unsubstituted aryl group having 6 to 18 carbon atoms, and R$^{41}$ to R$^{48}$ separately represent any of hydrogen, an alkyl group having 1 to 6 carbon atoms, a phenyl group, a biphenyl group, a naphthyl group, and a phenanthryl group.

Another embodiment of the present invention is a composite material including a hydrocarbon compound which has a molecular weight of greater than or equal to 400 and less than or equal to 2000 and is represented by the following general formula (G4), and an inorganic compound which exhibits an electron-accepting property with respect to the hydrocarbon compound.

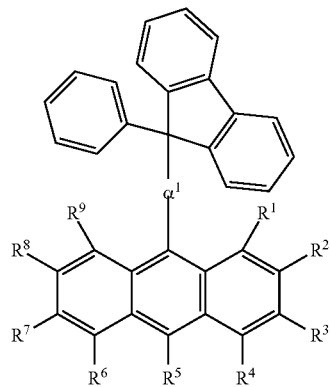
(G4)

Note that in the formula, $\alpha^1$ represents a substituted or unsubstituted phenylene group or a substituted or unsubstituted biphenyldiyl group. R$^1$ to R$^9$ separately represent any of hydrogen, an alkyl group having 1 to 6 carbon atoms, a phenyl group, a biphenyl group, a naphthyl group, a phenanthryl group, and a group represented by the following general formula (Ar$^1$-2).

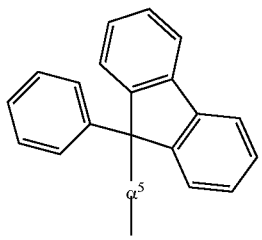
(Ar$^1$-2)

Note that in the formula, $\alpha^5$ represents a substituted or unsubstituted phenylene group or a substituted or unsubstituted biphenyldiyl group.

Another embodiment of the present invention is a composite material including a hydrocarbon compound which has a molecular weight of greater than or equal to 400 and less than or equal to 2000 and is represented by the following general formula (G5), and an inorganic compound which exhibits an electron-accepting property with respect to the hydrocarbon compound.

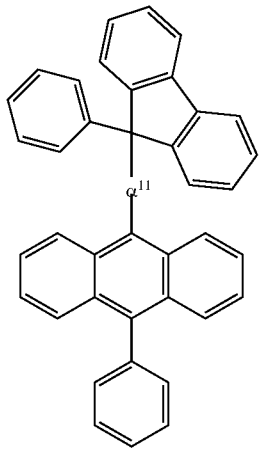
(G5)

Note that in the formula, $\alpha^{11}$ represents a phenylene group or a biphenyldiyl group.

Another embodiment of the present invention is a composite material having the above structure in which $\alpha^1$ to $\alpha^5$ and $\alpha^{11}$ separately represent any of the following structural formulas ($\alpha$-1) to ($\alpha$-6).

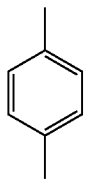
($\alpha$-1)

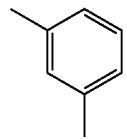
($\alpha$-2)

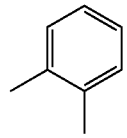
($\alpha$-3)

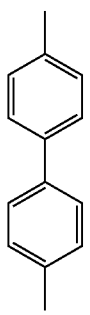
($\alpha$-4)

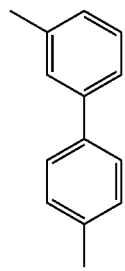
(α-5)

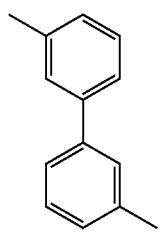
(α-6)

Another embodiment of the present invention is a composite material including a hydrocarbon compound which has a molecular weight of greater than or equal to 400 and less than or equal to 2000 and in which one or more aryl groups are bonded to a fluorene, and an inorganic compound which exhibits an electron-accepting property with respect to the hydrocarbon compound, in which the aryl group is bonded to the 2-position of the fluorene, or the aryl groups are bonded to the 2-position and the 7-position of the fluorene.

Another embodiment of the present invention is a composite material having the above structure in which the aryl group is one selected from a substituted or unsubstituted phenyl group, a substituted or unsubstituted naphthyl group, a substituted or unsubstituted anthryl group, a substituted or unsubstituted phenanthryl group, a substituted or unsubstituted triphenylenyl group, a substituted or unsubstituted pyrenyl group, a substituted or unsubstituted chrysenyl group, and a substituted or unsubstituted tetracenyl group.

Another embodiment of the present invention is a composite material having the above structure in which the aryl group is bonded to the fluorene via one phenylene group or two phenylene groups.

Another embodiment of the present invention is a composite material including a hydrocarbon compound which has a molecular weight of greater than or equal to 400 and less than or equal to 2000 and is represented by the following general formula (G6), and an inorganic compound which exhibits an electron-accepting property with respect to the hydrocarbon compound.

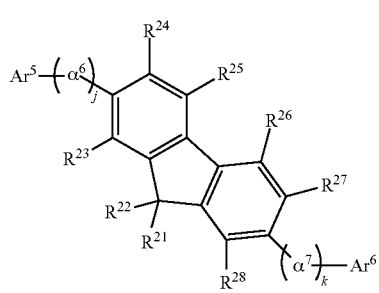
(G6)

Note that in the formula, $Ar^5$ represents a substituted or unsubstituted aryl group having 6 to 18 carbon atoms, $Ar^6$ represents hydrogen or a substituted or unsubstituted aryl group having 6 to 18 carbon atoms, and $\alpha^6$ and $\alpha^7$ separately represent a substituted or unsubstituted phenylene group or a substituted or unsubstituted biphenyldiyl group. In addition, j and k are separately 0 or 1. $R^{21}$ to $R^{28}$ separately represent any of hydrogen, an alkyl group having 1 to 6 carbon atoms, a substituted or unsubstituted phenyl group, a substituted or unsubstituted biphenyl group, a substituted or unsubstituted naphthyl group, and substituted or unsubstituted phenanthryl group.

Another embodiment of the present invention is a composite material including a hydrocarbon compound which has a molecular weight of greater than or equal to 400 and less than or equal to 2000 and is represented by the following general formula (G6'), and an inorganic compound which exhibits an electron-accepting property with respect to the hydrocarbon compound.

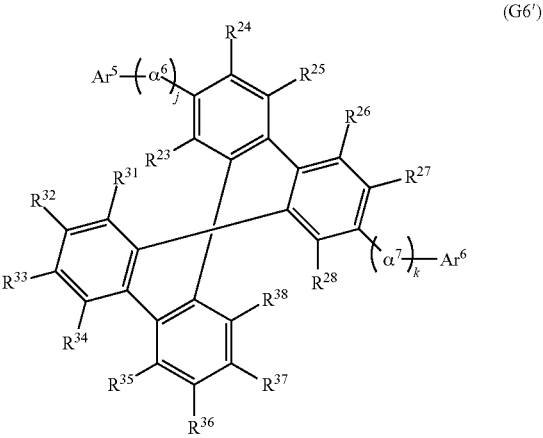
(G6')

Note that in the formula, $Ar^5$ represents a substituted or unsubstituted aryl group having 6 to 18 carbon atoms, $Ar^6$ represents hydrogen or a substituted or unsubstituted aryl group having 6 to 18 carbon atoms, and $\alpha^6$ and $\alpha^7$ separately represent a substituted or unsubstituted phenylene group or a substituted or unsubstituted biphenyldiyl group. In addition, j and k are separately 0 or 1. $R^{23}$ to $R^{28}$ and $R^{31}$ to $R^{38}$ separately represent any of hydrogen, an alkyl group having 1 to 6 carbon atoms, a substituted or unsubstituted phenyl group, a substituted or unsubstituted biphenyl group, a substituted or unsubstituted naphthyl group, and substituted or unsubstituted phenanthryl group.

A spirofluorene skeleton is preferably used because fluorenes in molecules can have a bulky structure, the molecular weight is great, and the thermophysical property is excellent.

Another embodiment of the present invention is a composite material including a hydrocarbon compound which has a molecular weight of greater than or equal to 400 and less than or equal to 2000 and is represented by the following general formula (G7), and an inorganic compound which exhibits an electron-accepting property with respect to the hydrocarbon compound.

(G7)

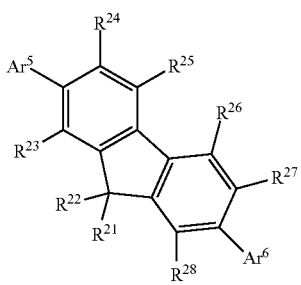

Note that in the formula, Ar⁵ represents a substituted or unsubstituted aryl group having 6 to 18 carbon atoms, Ar⁶ represents hydrogen or a substituted or unsubstituted aryl group having 6 to 18 carbon atoms, $R^{21}$ to $R^{28}$ separately represent any of hydrogen, an alkyl group having 1 to 6 carbon atoms, a substituted or unsubstituted phenyl group, a substituted or unsubstituted biphenyl group, a substituted or unsubstituted naphthyl group, and substituted or unsubstituted phenanthryl group.

Another embodiment of the present invention is a composite material including a hydrocarbon compound which has a molecular weight of greater than or equal to 400 and less than or equal to 2000 and is represented by the following general formula (G7'), and an inorganic compound which exhibits an electron-accepting property with respect to the hydrocarbon compound.

(G7')

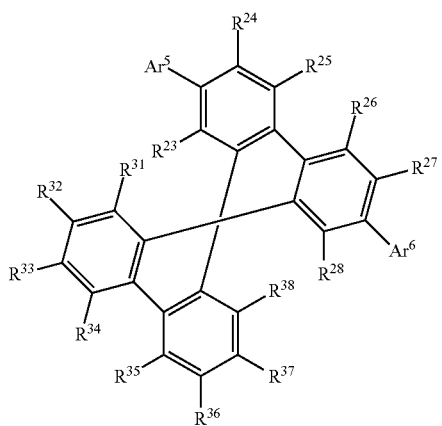

Note that in the formula, Ar⁵ represents a substituted or unsubstituted aryl group having 6 to 18 carbon atoms, and Ar⁶ represents hydrogen or a substituted or unsubstituted aryl group having 6 to 18 carbon atoms. $R^{23}$ to $R^{28}$ and $R^{31}$ to $R^{38}$ separately represent any of hydrogen, an alkyl group having 1 to 6 carbon atoms, a substituted or unsubstituted phenyl group, a substituted or unsubstituted biphenyl group, a substituted or unsubstituted naphthyl group, and substituted or unsubstituted phenanthryl group.

Note that in any of the above hydrocarbon compounds in which an aryl group is bonded to each of the 2- and 7-positions of the fluorene skeleton, conjugation of the aryl groups is barely likely to extend via the fluorene skeleton, so that the energy gap can be kept wide (an absorption spectrum is barely likely to greatly shift to a long wave length side as compared to the case of a hydrocarbon compound having an aryl group only at the 2-position). Two or more aryl groups can achieve a more bulky structure; accordingly, it is possible to obtain a material which has a wide energy gap and a high light-transmitting property but is hardly crystallized.

Another embodiment of the present invention is a composite material having the above structure in which Ar⁵ is one selected from a substituted or unsubstituted phenyl group, a substituted or unsubstituted naphthyl group, a substituted or unsubstituted anthryl group, a substituted or unsubstituted phenanthryl group, a substituted or unsubstituted triphenylenyl group, a substituted or unsubstituted pyrenyl group, a substituted or unsubstituted chrysenyl group, and a substituted or unsubstituted tetracenyl group, and Ar⁶ is one selected from hydrogen, a substituted or unsubstituted phenyl group, a substituted or unsubstituted naphthyl group, a substituted or unsubstituted anthryl group, a substituted or unsubstituted phenanthryl group, a substituted or unsubstituted triphenylenyl group, a substituted or unsubstituted pyrenyl group, a substituted or unsubstituted chrysenyl group, and a substituted or unsubstituted tetracenyl group.

Another embodiment of the present invention is a composite material having one of the above structures in which the inorganic compound which exhibits an electron-accepting property with respect to the hydrocarbon compound is a transition metal oxide.

Another embodiment of the present invention is a composite material having one of the above structures in which the inorganic compound which exhibits an electron-accepting property with respect to the hydrocarbon compound is one or more selected from titanium oxide, vanadium oxide, tantalum oxide, molybdenum oxide, tungsten oxide, rhenium oxide, ruthenium oxide, chromium oxide, zirconium oxide, hafnium oxide, and silver oxide.

Another embodiment of the present invention is a composite material having one of the above structures in which the inorganic compound which exhibits an electron-accepting property with respect to the hydrocarbon compound is molybdenum oxide.

Another embodiment of the present invention is a light-emitting element including a layer including an organic compound between a pair of electrodes. The layer including the organic compound includes a layer including at least an emission center substance and a layer including one or more of the composite materials having the above structures.

A light-emitting element according to one embodiment of the present invention having the above structure can be driven at a low driving voltage because the composite material has high carrier-transport and carrier-injection properties. In addition, a film including the composite material has a good quality, so that a light-emitting element with high reliability can be provided. Further, a light-emitting element formed using the composite material has a good carrier balance, so that a light-emitting element with high emission efficiency can be provided. Furthermore, since the composite material has a high light-transmitting property, reduction in emission efficiency due to the use of the composite material is small and a light-emitting element with high emission efficiency can be provided.

Another embodiment of the present invention is a light-emitting element having one or more of the above structures in which the layer including the composite material is in contact with one of the pair of electrodes, which functions as an anode.

A light-emitting element according to one embodiment of the present invention having the above structure can be driven at a low driving voltage because the composite material has a high carrier-injection property. In addition, a film including the composite material has a good quality, so that a light-emitting element with high reliability can be provided. Further, a light-emitting element formed using the composite material has a good carrier balance, so that a light-emitting element with high emission efficiency can be provided. Furthermore, since the composite material has a high light-transmitting property, reduction in emission efficiency due to the use of the composite material is small and a light-emitting element with high emission efficiency can be provided. Moreover, even when a thick film of the composite material is used, the driving voltage is barely likely to increase; accordingly, it is possible to suppress a defect such as a short circuit due to unevenness of the anode by formation of the thick film over the anode, so that a light-emitting element with high reliability can be provided.

Another embodiment of the present invention is a light-emitting element including a layer including an organic compound between a pair of electrodes. The layer including the organic compound includes a plurality of light-emitting units and a layer including one or more of the composite materials having the above structures. The plurality of light-emitting units each including a layer including an emission center substance. The layer including the composite material is interposed between one of the light-emitting units and another light-emitting unit.

A light-emitting element according to one embodiment of the present invention having the above structure can be driven at a low driving voltage because a film including the composite material functions as a charge-generation layer. In addition, a film including the composite material has a good quality, so that a light-emitting element with high reliability can be provided. Further, a light-emitting element formed using the composite material has a good carrier balance, so that a light-emitting element with high emission efficiency can be provided. Furthermore, since the composite material has a high light-transmitting property, reduction in emission efficiency due to the use of the composite material is small and a light-emitting element with high emission efficiency can be provided.

Another embodiment of the present invention is a light-emitting device including a light-emitting element having one of the above structures.

A light-emitting device having such a structure is a light-emitting device with low power consumption. Further, a light-emitting device with high reliability can be provided.

Another embodiment of the present invention is an electronic device including a light-emitting device having one of the above structures in a display portion.

An electronic device having such a structure is an electronic device with low power consumption. Further, an electronic device with high reliability can be provided.

Another embodiment of the present invention is a lighting device including a light-emitting device having one of the above structures in a light-emitting portion.

A lighting device having such a structure is a lighting device with low power consumption. Further, a lighting device with high reliability can be provided.

Another embodiment of the present invention is a fluorene derivative represented by the following structural formula (F-1).

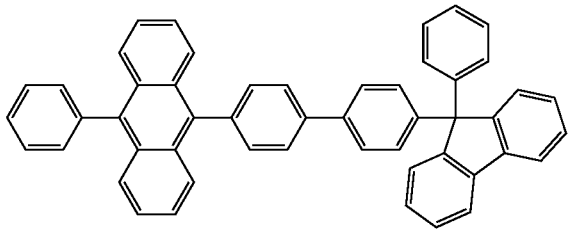

(F-1)

A fluorene derivative having the above structure can be suitably used as a hydrocarbon compound included in a composite material. In addition, the fluorene derivative is suitable for a carrier-transport layer or a light-emitting layer (host material and emission center material) of a light-emitting element. In particular, when the fluorene derivative is used as a host material for dispersing an emission center material having a spectrum in a short wave length region in the visible light region, such as an emission center material that emits blue fluorescence, light with high color purity can be emitted.

By using a composite material having one of the above structures, a light-emitting element with high emission efficiency can be fabricated. Alternatively, by using the composite material, a light-emitting element with high reliability can be provided. Further alternatively, by using the composite material, a light-emitting element with both high emission efficiency and high reliability can be provided. A light-emitting element having one of the above structures has high emission efficiency. Alternatively, the light-emitting element has high reliability. Further alternatively, the light-emitting element has both high emission efficiency and high reliability.

A light-emitting device having the above structure is a light-emitting device with low power consumption. Alternatively, the light-emitting device has high reliability. Further alternatively, the light-emitting device has both high emission efficiency and high reliability.

An electronic device having the above structure is an electronic device with low power consumption. Alternatively, the electronic device has high reliability. Further alternatively, the electronic device has both high emission efficiency and high reliability.

A lighting device having the above structure is a lighting device with low power consumption. Alternatively, the lighting device has high reliability. Further alternatively, the lighting device has both high emission efficiency and high reliability.

BRIEF DESCRIPTION OF THE DRAWINGS

In the accompanying drawings.

DETAILED DESCRIPTION OF THE INVENTION

Figure 1A:
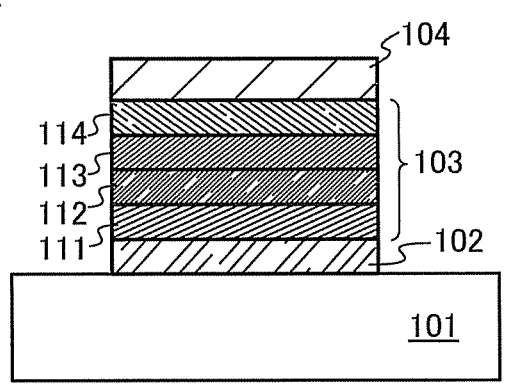
FIGS. 1A and 1B are conceptual diagrams of light-emitting elements.

Hereinafter, embodiments of the present invention are described. The present invention can be implemented in various modes, and it is easily understood by those skilled in the art that modes and details disclosed herein can be modified in various ways without departing from the spirit and the scope of the present invention. Therefore, the present invention is not construed as being limited to description of the embodiments.

(Embodiment 1)

It is known that a light-emitting element in which a composite material including a type of organic compound and an inorganic compound which exhibits an electron-accepting property with respect to the organic compound is provided in contact with an anode is driven at a much lower voltage than a light-emitting element in which only the organic compound is provided at the same position (see Patent Document 1). This results from high carrier-injection and carrier-transport properties of the composite material as compared to the single substance of the organic compound. It is also reported that crystallization of the composite material is suppressed by including the inorganic compound, so that the reliability is higher than in the case of using the single substance of the organic compound. Moreover, even when a thick film of the composite material is used, the driving voltage is barely likely to increase; accordingly, it is possible to suppress a defect such as a short circuit due to unevenness of the anode by formation of the thick film over the anode.

The inventors have fabricated a light-emitting element with higher emission efficiency than a light-emitting element formed using a conventional composite material, by using, as the organic compound included in the composite material, a hydrocarbon compound in which one or more aryl groups are bonded to a fluorene. In addition, the inventors have also fabricated a light-emitting element with a long life. For easy evaporation, a hydrocarbon compound having a molecular weight of greater than or equal to 400 and less than or equal to 2000 is suitably used, in which one or more aryl groups are bonded to a fluorene. The aryl group may be bonded to the fluorene via an arylene group.

Owing to a bulky structure of the fluorene skeleton included in the hydrocarbon compound, which is used as the organic compound in the composite material in this embodiment, a film formed using the composite material has a good quality, and a light-emitting element fabricated using the hydrocarbon compound can have a long life.

Since the fluorene itself has a wide energy gap, it is possible to provide a composite material having a high light-transmitting property with little absorption of light in the visible light region. Accordingly, by using the composite material, a light-emitting element with high emission efficiency can be fabricated. Since the fluorene has a wide energy gap despite having a certain amount of molecular weight, a hydrocarbon compound including the fluorene skeleton can be a hydrocarbon compound having a moderately great molecular weight while the energy gap between the HOMO level and the LUMO level is kept wide. Further, when the hydrocarbon compound having a moderately great molecular weight is evaporated, the evaporation rate can be easily controlled; accordingly, a light-emitting element with a stable quality can be provided. The composite material according to one embodiment of the present invention is formed by co-evaporation of the hydrocarbon compound and an inorganic compound having higher evaporation temperature than the hydrocarbon compound. The composite material according to one embodiment of the present invention includes the hydrocarbon compound having the fluorene skeleton; therefore, the energy gap is prevented from narrowing and the molecular weight can be moderately great, and co-evaporation can be perforated at a temperature closer to the evaporation temperature of the inorganic compound. Thus, the light-emitting element fabricated using the composite material in this embodiment can be a light-emitting element with high reliability.

By using the composite material including the hydrocarbon compound having the fluorene skeleton, a light-emitting element with a good carrier balance and high emission efficiency can be fabricated.

A detailed description is given of the hydrocarbon compound which has the fluorene skeleton and is included in the composite material.

One or more aryl groups included in the fluorene skeleton are preferably bonded to at least any of the 9-positions, the 2-position, and the 2- and 7-positions of the fluorene skeleton. The fluorene skeleton may have a substituent other than the aryl group(s), and examples of the substituent include an alkyl group having 1 to 6 carbon atoms, a substituted or unsubstituted phenyl group, a substituted or unsubstituted biphenyl group, a substituted or unsubstituted naphthyl group, and a substituted or unsubstituted phenanthryl group. When any of these substituents further has a substituent, the substituent can be an alkyl group, a phenyl group, a biphenyl group, a naphthyl group, a phenanthryl group, or the like.

There is no particular limitation on the aryl group, and the aryl group may or may not have a substituent; however, an aryl group having 6 to 18 carbon atoms fowling a ring is suitable. Note that an aryl group having a large number of condensed rings has a high carrier-transport property, whereas an aryl group having a small number of condensed rings has a high light-transmitting property when being included in a composite material. Therefore, it is preferable that the aryl group be a bicyclic condensed aryl group, a tricyclic condensed aryl group, or a tetracyclic condensed aryl group, considering the balance between the carrier-transport property and the light-transmitting property of a film of the composite material. Among aryl groups having the same number of condensed rings, a helicene structure or a structure comprising a part of a helicene structure (condensed rings are bended) is preferable to a polyacene structure (condensed rings are linear) for a wider band gap and a higher light-transmitting property. Note that the condensed rings may or may not have a substituent. Specific examples of such an aryl group include a substituted or unsubstituted phenyl group, a substituted or unsubstituted naphthyl group, a substituted or unsubstituted anthryl group, a substituted or unsubstituted phenanthryl group, a substituted or unsubstituted triphenylenyl group, a substituted or unsubstituted pyrenyl group, a substituted or unsubstituted chrysenyl group, and a substituted or unsubstituted tetracenyl group. A composite material including, as the aryl group, a group selected from a substituted or unsubstituted naphthyl group, a substituted or unsubstituted anthryl group, a substituted or unsubstituted phenanthryl group, and a substituted or unsubstituted triphenylenyl group has a high carrier-transport property despite having a high light-transmitting property because additional absorption due to formation of a charge-transfer complex hardly occurs and the hydrocarbon compound itself hardly absorbs light in the visible light region. A composite material including, as the aryl group, a substituted or unsubstituted anthryl group, a substituted or unsubstituted pyrenyl group, a substituted or unsubstituted chrysenyl group, a substituted or unsubstituted triphenylenyl group, or a substituted or unsubstituted tetracenyl group can have a particularly high carrier-transport property. Among aryl groups having the same number of condensed rings, a helicene structure or a structure comprising a part of a helicene structure (condensed rings are bended) is preferable to a polyacene structure (condensed rings are linear) for a wider band gap and a higher light-transmitting property. When any of these substituents further has a substituent, the substituent can be an alkyl group, a phenyl group, a biphenyl group, a naphthyl group, a phenanthryl group, or the like.

When an aryl group is bonded to the fluorene via an arylene group, the arylene group can be a substituted or unsubstituted phenylene group or a substituted or unsubstituted biphenyldiyl group. When any of the above has a substituent, the substituent can be an alkyl group, a phenyl group, a biphenyl group, a naphthyl group, a phenanthryl group, or the like.

It is more preferable that the aryl group be bonded to a 9-position of the fluorene. Since the carbon at the 9-position of the fluorene has an $sp^3$ hybridized orbital, conjugation can be prevented from extending from the aryl group to the fluorene skeleton. Therefore, the energy gap can be more effectively prevented from narrowing, and a composite material including a hydrocarbon compound having a wide energy gap can be obtained. Accordingly, the composite material can have a higher light-transmitting property with little absorption of light in the visible light region.

Next, a more detailed description is given of the hydrocarbon compound including the fluorene skeleton, which is included in the composite material in this embodiment, showing general formulas.

The hydrocarbon compound can be represented by the following general formula (G1) and has a molecular weight of greater than or equal to 400 and less than or equal to 2000.

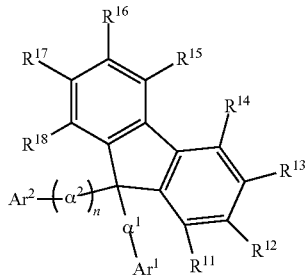

(G1)

In the formula, $\alpha^1$ and $\alpha^2$ separately represent a substituted or unsubstituted phenylene group or a substituted or unsubstituted biphenyldiyl group. When any of the above has a substituent, the substituent can be an alkyl group, a phenyl group, a biphenyl group, a naphthyl group, a phenanthryl group, or the like. When an alkyl group is used, the alkyl group preferably has 6 or less carbon atoms, considering evaporativity. When $\alpha^1$ is a phenylene group, the energy gap is slightly wider than that when $\alpha^1$ is a biphenyldiyl group. On the other hand, when $\alpha^1$ is a biphenyldiyl group, the glass transition temperature (Tg) is higher than that when $\alpha^1$ is a phenylene group. Although the evaporation temperature becomes higher as the molecular weight becomes greater, it is preferable that the evaporation temperatures of the hydrocarbon compound and an inorganic compound be close to each other in forming the composite material by co-evaporation with the inorganic compound having a high evaporation temperature; therefore, a structure having a biphenyldiyl group as $\alpha^1$ is advantageous in this respect.

More specifically, the hydrocarbon compound can be represented by the following general formula (G2) and has a molecular weight of greater than or equal to 400 and less than or equal to 2000.

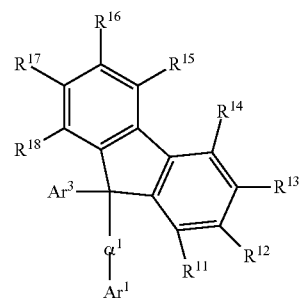

(G2)

In general formulas (G1) and (G2), $Ar^1$ represents a substituted or unsubstituted aryl group, and the aryl group is preferably a bicyclic condensed aryl group, a tricyclic condensed aryl group, or a tetracyclic condensed aryl group, considering the balance between a carrier-transport property and a light-transmitting property of the composite material. Specific examples of such an aryl group include a substituted or unsubstituted phenyl group, a substituted or unsubstituted naphthyl group, a substituted or unsubstituted anthryl group, a substituted or unsubstituted phenanthryl group, a substituted or unsubstituted triphenylenyl group, a substituted or unsubstituted pyrenyl group, a substituted or unsubstituted chrysenyl group, and a substituted or unsubstituted tetracenyl group. A composite material including, as the aryl group, a group selected from a substituted or unsubstituted naphthyl group, a substituted or unsubstituted anthryl group, a substituted or unsubstituted phenanthryl group, and a substituted or unsubstituted triphenylenyl group has a high carrier-transport property despite having a high light-transmitting property because additional absorption due to formation of a charge-transfer complex hardly occurs and the hydrocarbon compound itself hardly absorbs light in the visible light region. A composite material including, as the aryl group, a substituted or unsubstituted anthryl group, a substituted or unsubstituted pyrenyl group, a substituted or unsubstituted chrysenyl group, a substituted or unsubstituted tetracenyl group, or a substituted or unsubstituted triphenylenyl group can have a particularly high carrier-transport property. When any of the above has a substituent, the substituent can be any of a phenyl group, a naphthyl group, a phenanthryl group, and a group represented by the following general formula ($Ar^1$-1).

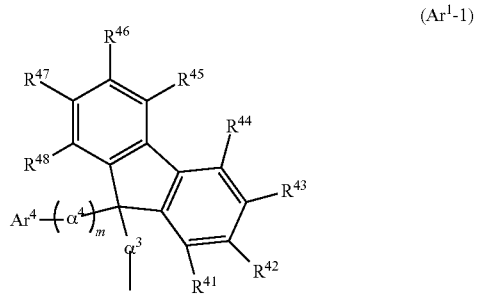

($Ar^1$-1)

Note that in the formula, $\alpha^3$ and $\alpha^4$ separately represent a substituted or unsubstituted phenylene group or a substituted or unsubstituted biphenyldiyl group. When any of the above has a substituent, the substituent can be an alkyl group, a phenyl group, a biphenyl group, a naphthyl group, a phenanthryl group, or the like. $Ar^4$ represents a substituted or unsubstituted aryl group having 6 to 18 carbon atoms, and is particularly preferably a substituted or unsubstituted phenyl group or a substituted or unsubstituted biphenyl group. In addition, m is 0 or 1. When m is 0, $Ar^4$ is preferably an unsubstituted phenyl group or a substituted or unsubstituted biphenyl group. When the group represented by $Ar^4$ has a substituent, the substituent can be an alkyl group, a phenyl group, a biphenyl group, a naphthyl group, a phenanthryl group, or the like. $R^{41}$ to $R^{48}$ separately represent any of hydrogen, an alkyl group having 1 to 6 carbon atoms, a phenyl group, a biphenyl group, a naphthyl group, and a phenanthryl group.

From another point of view, the aryl group represented by $Ar^1$ in the above general formula is preferably selected so that a substance where the bond of the aryl group is bonded to hydrogen ($Ar^1$—H) does not have a peak in a range of greater than or equal to 450 nm and less than or equal to 800 nm in an absorption spectrum thereof. A composite material in this embodiment, which includes a hydrocarbon compound having such a structure, can be a composite material having a high light-transmitting property owing to little absorption in the visible light region, which originates from the skeleton of the hydrocarbon compound.

$Ar^2$ represents a substituted or unsubstituted aryl group, and the aryl group preferably has 6 to 18 carbon atoms. When the aryl group has a substituent, the substituent can be an alkyl group, a phenyl group, a biphenyl group, a naphthyl group, a phenanthryl group, or the like.

In the general formula (G1), n is 0 or 1. When n is 0, $Ar^2$ is preferably a substituted or unsubstituted phenyl group or a substituted or unsubstituted biphenyl group, because in which case the synthesis is easy and the material can have a wide energy gap. The above structure is represented by the general formula (G2), where $Ar^3$ represents a substituted or unsubstituted phenyl group or a substituted or unsubstituted biphenyl group.

$R^{11}$ to $R^{18}$ separately represent any of hydrogen, an alkyl group having 1 to 6 carbon atoms, a substituted or unsubstituted phenyl group, a substituted or unsubstituted biphenyl group, a substituted or unsubstituted naphthyl group, and substituted or unsubstituted phenanthryl group. When any of the above has a substituent, the substituent can be an alkyl group, a phenyl group, a biphenyl group, a naphthyl group, a phenanthryl group, or the like. Note that it is more preferable that $R^{11}$ to $R^{18}$ be separately any of hydrogen, an alkyl group having 1 to 6 carbon atoms, and a group represented by any of the following structural formulas (R-1) to (R-6) in terms of cost of materials, and it is much more preferable that $R^{11}$ to $R^{18}$ be all hydrogen.

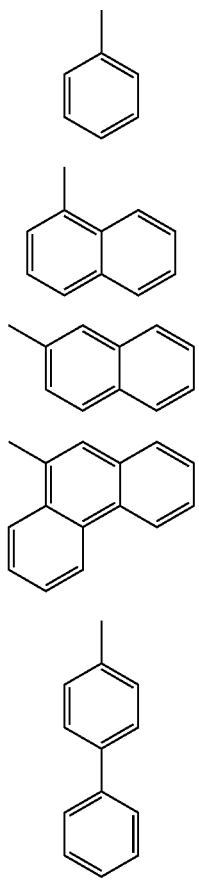

(R-1)

(R-2)

(R-3)

(R-4)

(R-5)

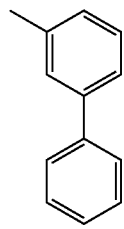

(R-6)

A general formula of the hydrocarbon compound included in the composite material in this embodiment where $R^{11}$ to $R^{18}$ are all hydrogen is represented by the following general formula (G3).

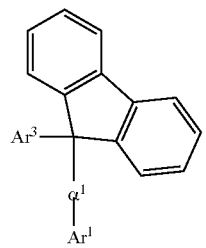

(G3)

Note that the molecular weight of the hydrocarbon compound represented by the general formula (G3) is greater than or equal to 400 and less than or equal to 2000. In the formula, $\alpha^1$, $Ar^1$, and $Ar^3$ are the same as those in the general formulas (G1) and (G2), and thus a repeated description thereof is omitted and the above corresponding description is to be referred to.

A particularly preferable structure of the hydrocarbon compound included in the composite material in this embodiment is represented by the following general formula (G4).

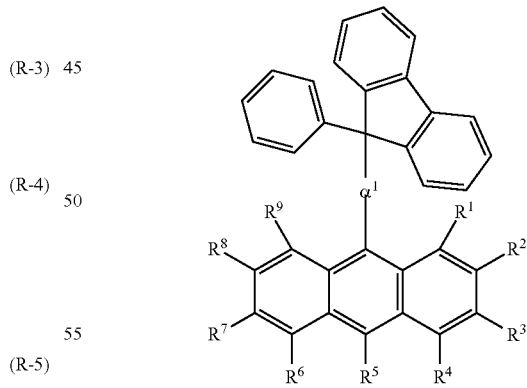

(G4)

Note that the molecular weight of the hydrocarbon compound represented by the general formula (G4) is greater than or equal to 400 and less than or equal to 2000. In the formula, $\alpha^1$ is the same as that in the general formulas (G1) to (G3), and thus the above corresponding description is to be referred to. $R^1$ to $R^9$ separately represent any of hydrogen, an alkyl group having 1 to 6 carbon atoms, a phenyl group, a biphenyl group, a naphthyl group, a phenanthryl group, and a group represented by the following general formula ($Ar^1$-2).

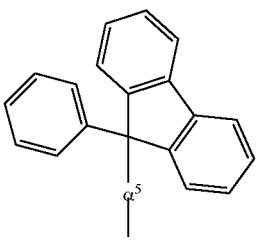
(Ar¹-2)

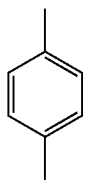
(α-1)

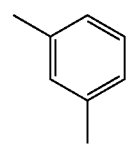
(α-2)

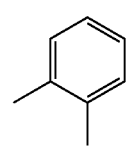
(α-3)

Note that in the formula, $\alpha^5$ represents a substituted or unsubstituted phenylene group or a substituted or unsubstituted biphenyldiyl group. When $\alpha^5$ has a substituent, the substituent can be an alkyl group, a phenyl group, a biphenyl group, a naphthyl group, a phenanthryl group, or the like.

In the general formula (G4), it is preferable that $R^1$ to $R^9$ be all hydrogen and that $\alpha^5$ do not have a substituent in terms of cost of materials and easy synthesis. A hydrocarbon compound having this structure is represented by the following general formula (G5).

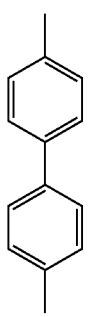
(α-4)

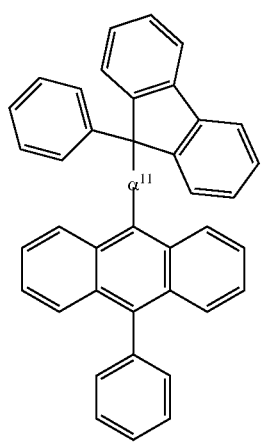
(G5)

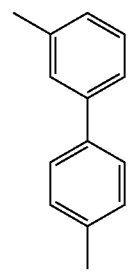
(α-5)

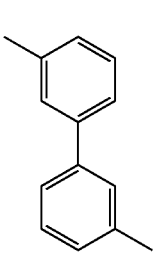
(α-6)

Note that the molecular weight of the hydrocarbon compound represented by the general formula (G5) is greater than or equal to 400 and less than or equal to 2000. In the formula, $\alpha^{11}$ represents a phenylene group or a biphenyldiyl group.

The composite material in this embodiment, which includes the hydrocarbon compound represented by the general formula (G4) or (G5) has an excellent balance between a light-transmitting property of a film and a carrier-transport property, and can be used very suitably as a material included in a light-emitting element. Further, its excellent carrier balance contributes to improvement in emission efficiency of the light-emitting element.

Note that in the general formulas (G1) to (G5), it is preferable that $\alpha^1$ to $\alpha^5$ and $\alpha^{11}$ separately represent any of the following structural formulas (α-1) to (α-6).

Next, description is given of a hydrocarbon compound where an aryl group is bonded to the 2-position of a fluorene or where aryl groups are bonded to the 2- and 7-positions of a fluorene. The hydrocarbon compound has a molecular weight of greater than or equal to 400 and less than or equal to 2000, where one or more aryl groups are bonded to the fluorene. Specifically, the aryl group(s) is/are bonded to the 2-position or the 2- and 7-positions of the fluorene. Note that when one aryl group is bonded, the aryl group is preferably bonded to the 2-position of the fluorene, and when a plurality of aryl groups are bonded, the aryl groups are preferably bonded to at least the 2-position or the 7-position thereof. Note also that the aryl group may be bonded to the fluorene via one phenylene group or two phenylene groups. In other words, the aryl group may be bonded to the fluorene via a phenylene group or a biphenyldiyl group. Note that the hydrocarbon compound may be a silicon compound. The silicon compound in this embodiment refers to a compound where one or more carbon atoms are replaced by one or more silicon atoms in any of the above-described hydrocarbon compounds.

There is no particular limitation on the aryl group, and the aryl group may or may not have a substituent; however, an aryl group having 6 to 18 carbon atoms forming a ring is suitable. Note that an aryl group having a large number of condensed rings has a high carrier-transport property, whereas an aryl group having a small number of condensed rings has a high light-transmitting property when being included in a composite material. Therefore, it is preferable that the aryl group be a bicyclic condensed aryl group, a tricyclic condensed aryl group, or a tetracyclic condensed aryl group, considering the balance between the carrier-transport property and the light-transmitting property of a film of the composite material. Among aryl groups having the same number of condensed rings, a helicene structure or a structure comprising a part of a helicene structure (condensed rings are bended) is preferable to a polyacene structure (condensed rings are linear) for a wider band gap and a higher light-transmitting property. Note that the condensed rings may or may not have a substituent. Specific examples of such an aryl group include a substituted or unsubstituted phenyl group, a substituted or unsubstituted naphthyl group, a substituted or unsubstituted anthryl group, a substituted or unsubstituted phenanthryl group, a substituted or unsubstituted triphenylenyl group, a substituted or unsubstituted pyrenyl group, a substituted or unsubstituted chrysenyl group, and a substituted or unsubstituted tetracenyl group. A composite material including, as the aryl group, a group selected from a substituted or unsubstituted naphthyl group, a substituted or unsubstituted anthryl group, a substituted or unsubstituted phenanthryl group, and a substituted or unsubstituted triphenylenyl group has a high carrier-transport property despite having a high light-transmitting property because additional absorption due to formation of a charge-transfer complex hardly occurs and the hydrocarbon compound itself hardly absorbs light in the visible light region. A composite material including, as the aryl group, a substituted or unsubstituted anthryl group, a substituted or unsubstituted pyrenyl group, a substituted or unsubstituted chrysenyl group, a substituted or unsubstituted triphenylenyl group, or a substituted or unsubstituted tetracenyl group can have a particularly high carrier-transport property. Among aryl groups having the same number of condensed rings, a structure having a long polyacene structure (condensed rings are linear) is preferable for high mobility. When any of these substituents further has a substituent, the substituent can be an alkyl group, a phenyl group, a biphenyl group, a naphthyl group, a phenanthryl group, or the like.

Next, a further description is given showing specific general formulas. The hydrocarbon compound is represented by the following general formula (G6) and has a molecular weight of greater than or equal to 400 and less than or equal to 2000.

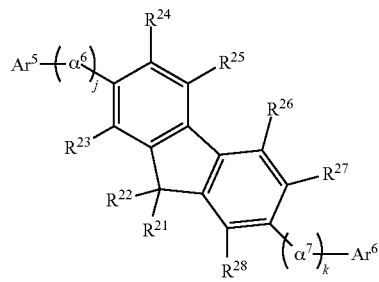

(G6)

In the formula, $\alpha^6$ and $\alpha^7$ separately represent a substituted or unsubstituted phenylene group or a substituted or unsubstituted biphenyldiyl group. When any of the above has a substituent, the substituent can be an alkyl group, a phenyl group, a biphenyl group, a naphthyl group, a phenanthryl group, or the like. When either $\alpha^6$ or $\alpha^7$ is a phenylene group or both $\alpha^6$ and $\alpha^7$ are phenylene groups, the energy gap is slightly wider than that when either $\alpha^6$ or $\alpha^7$ is a biphenyldiyl group or both $\alpha^6$ and $\alpha^7$ are biphenyldiyl groups. On the other hand, when either $\alpha^6$ or $\alpha^7$ is a biphenyldiyl group or both $\alpha^6$ and $\alpha^7$ are biphenyldiyl groups, the glass transition temperature (Tg) is higher than that when either $\alpha^6$ or $\alpha^7$ is a phenylene group or both $\alpha^6$ and $\alpha^7$ are phenylene groups. Although the evaporation temperature becomes higher as the molecular weight becomes greater, it is preferable that the evaporation temperatures of the hydrocarbon compound and an inorganic compound be close to each other in forming the composite material by co-evaporation with the inorganic compound having a high evaporation temperature; therefore, a structure having a biphenyldiyl group as either $\alpha^6$ or $\alpha^7$ or having biphenyldiyl groups as both $\alpha^6$ and $\alpha^7$ is advantageous in this respect. In addition, j and k are separately 0 or 1. In a structure where an aryl group is bonded to the 2-position of the fluorene or where aryl groups are bonded to the 2- and 7-positions thereof, it is not necessary to include arylene groups represented by $\alpha^6$ and $\alpha^7$.

In the general formula (G6), $Ar^5$ and $Ar^6$ separately represent a substituted or unsubstituted aryl group, and the aryl group preferably has 6 to 18 carbon atoms. The aryl group is particularly preferably a bicyclic condensed aryl group, a tricyclic condensed aryl group, or a tetracyclic condensed aryl group, in terms of the balance between a carrier-transport property and a light-transmitting property of the composite material. Specific examples of such an aryl group include a substituted or unsubstituted naphthyl group, a substituted or unsubstituted anthryl group, a substituted or unsubstituted phenanthryl group, a substituted or unsubstituted triphenylenyl group, a substituted or unsubstituted pyrenyl group, a substituted or unsubstituted chrysenyl group, and a substituted or unsubstituted tetracenyl group. A composite material including, as the aryl group, a group selected from a substituted or unsubstituted naphthyl group, a substituted or unsubstituted anthryl group, a substituted or unsubstituted phenanthryl group, and a substituted or unsubstituted triphenylenyl group has a high carrier-transport property despite having a high light-transmitting property because additional absorption due to formation of a charge-transfer complex hardly occurs and the hydrocarbon compound itself hardly absorbs light in the visible light region. A composite material including, as the aryl group, a substituted or unsubstituted anthryl group, a substituted or unsubstituted pyrenyl group, a substituted or unsubstituted chrysenyl group, a substituted or unsubstituted triphenylenyl group, or a substituted or unsubstituted tetracenyl group can have a particularly high carrier-transport property. When any of the above has a substituent, the substituent can be a phenyl group, a naphthyl group, a phenanthryl group, or the like.

$R^{21}$ to $R^{28}$ separately represent any of hydrogen, an alkyl group having 1 to 6 carbon atoms, a substituted or unsubstituted phenyl group, a substituted or unsubstituted biphenyl group, a substituted or unsubstituted naphthyl group, and substituted or unsubstituted phenanthryl group. When any of the above has a substituent, the substituent can be an alkyl group, a phenyl group, a biphenyl group, a naphthyl group, a phenanthryl group, or the like. Further, adjacent groups may be bonded to each other to form a ring. The following general formula (G6') represents a structure where $R^{21}$ and $R^{22}$ are phenyl groups and bonded to each other to form a ring.

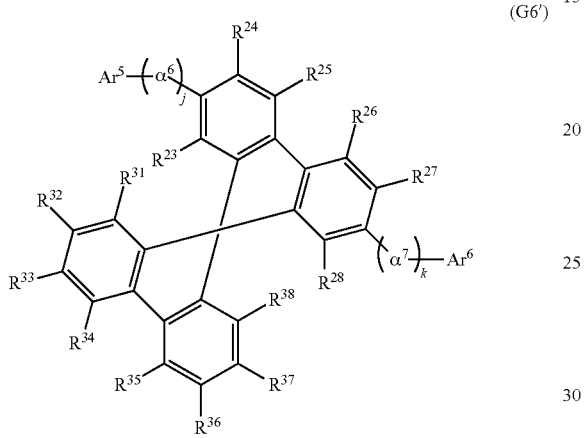

(G6')

Note that the molecular weight of the hydrocarbon compound represented by the general formula (G6') is greater than or equal to 400 and less than or equal to 2000. In addition, $R^{23}$ to $R^{28}$, $\alpha^6$, $\alpha^7$, $Ar^5$, and $Ar^6$ are the same as those in the general formula (G6), and thus a repeated description thereof is omitted and the above corresponding description of the general formula (G6) is to be referred to. $R^{31}$ to $R^{38}$ separately represent any of hydrogen, an alkyl group having 1 to 6 carbon atoms, a substituted or unsubstituted phenyl group, a substituted or unsubstituted biphenyl group, a substituted or unsubstituted naphthyl group, and substituted or unsubstituted phenanthryl group. When any of the above has a substituent, the substituent can be an alkyl group, a phenyl group, a biphenyl group, a naphthyl group, a phenanthryl group, or the like.

Specific structures of the above hydrocarbon compounds are exemplified by the following structural formulas (100) to (138), (200) to (234), (300) to (329), (400) to (415), (500) to (518), and (601) to (614). The hydrocarbon compounds that can be included in the composite material in this embodiment are not limited to the following structural formulas, and a hydrocarbon compound that can be represented by any of the above general formulas can be used.

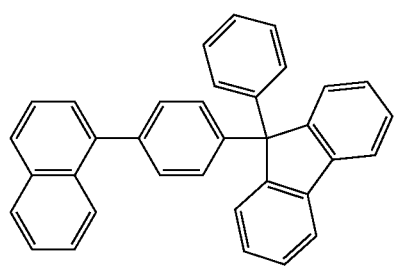

(100)

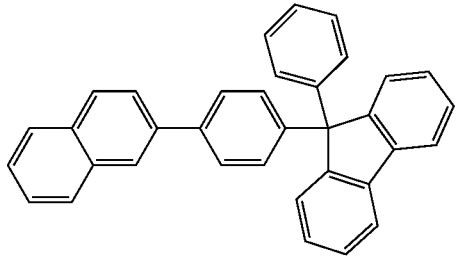

(101)

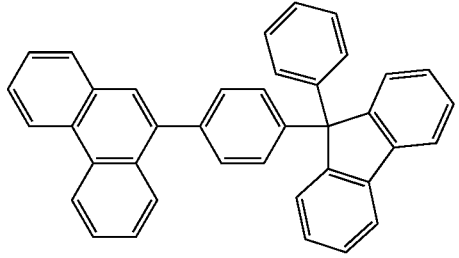

(102)

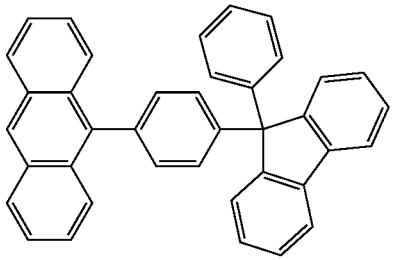

(103)

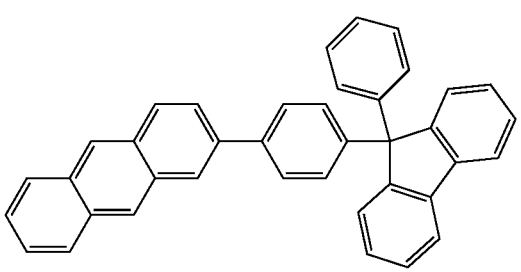

(104)

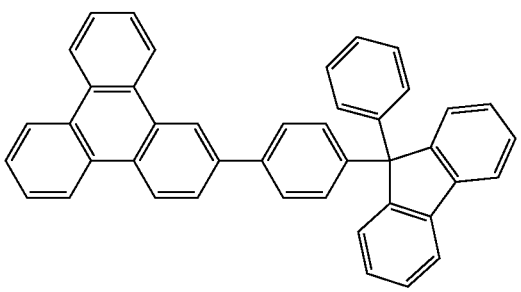

(105)

-continued
(106)
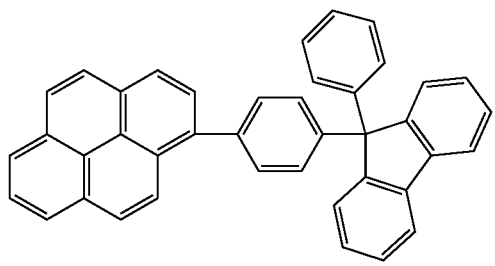
(107)
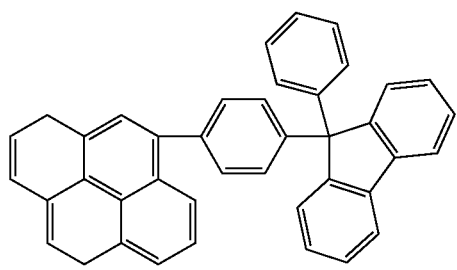
(108)
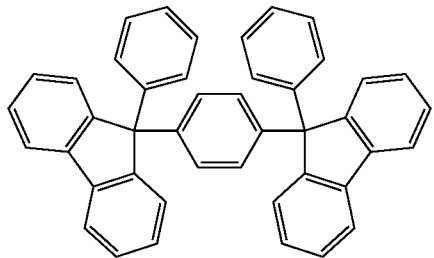
(109)
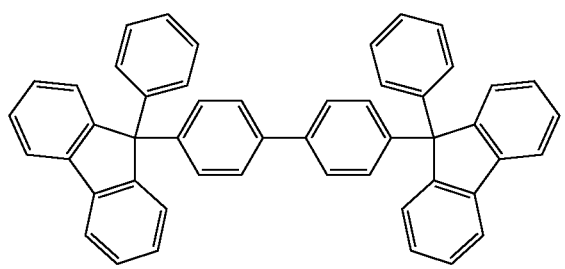
(110)
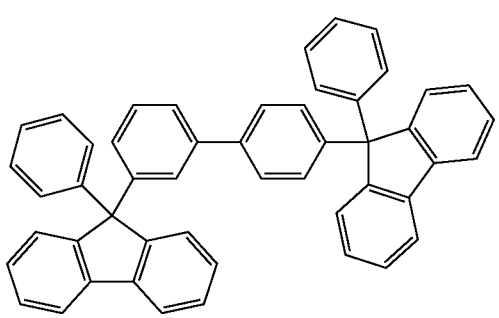
-continued
(111)
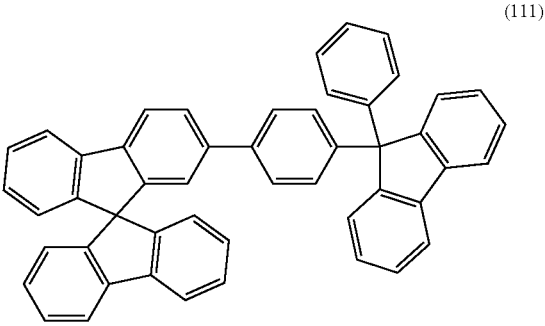
(112)
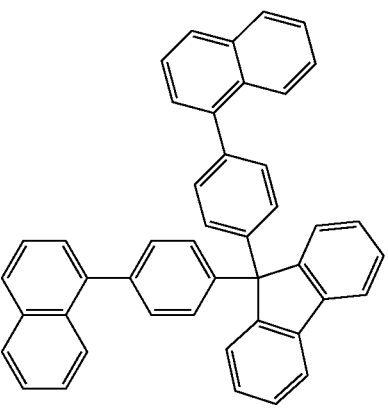
(113)
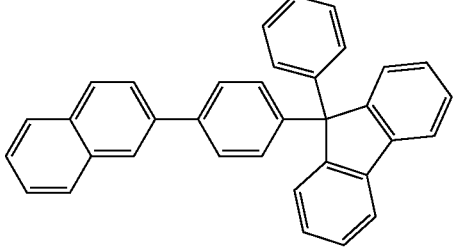
(114)
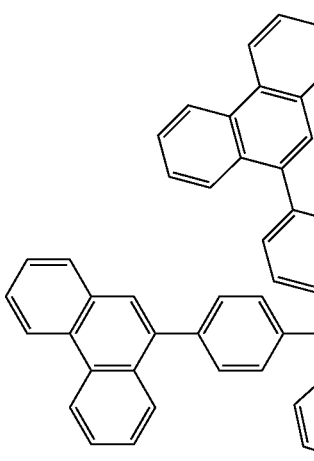

(115)
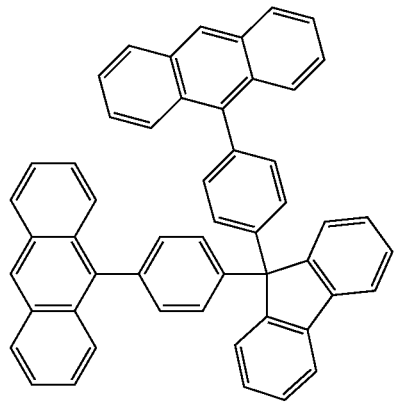
(116)
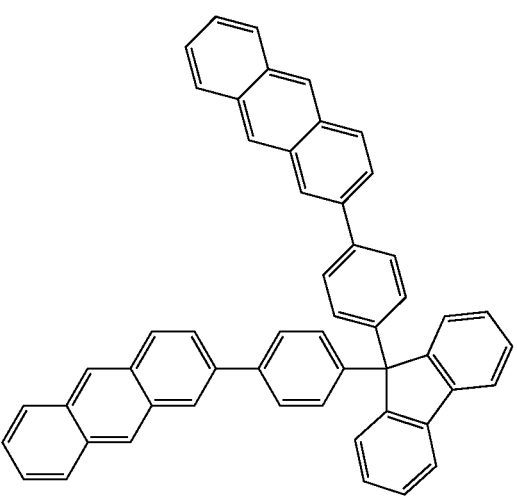
(117)
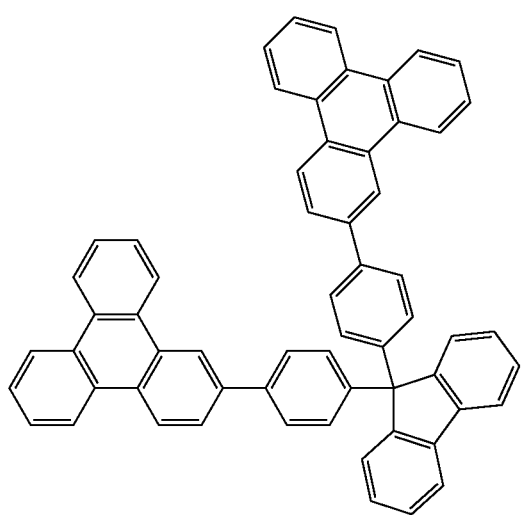
(118)
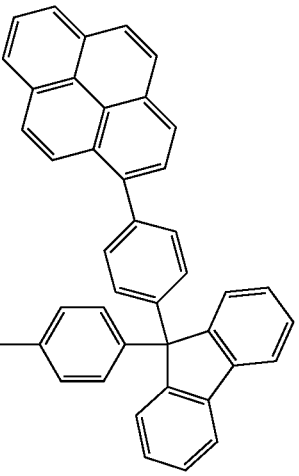
(119)
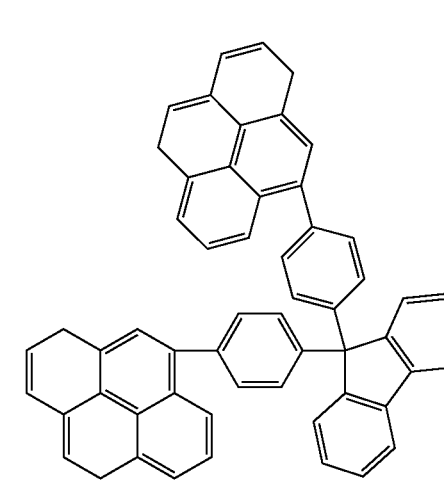
(120)
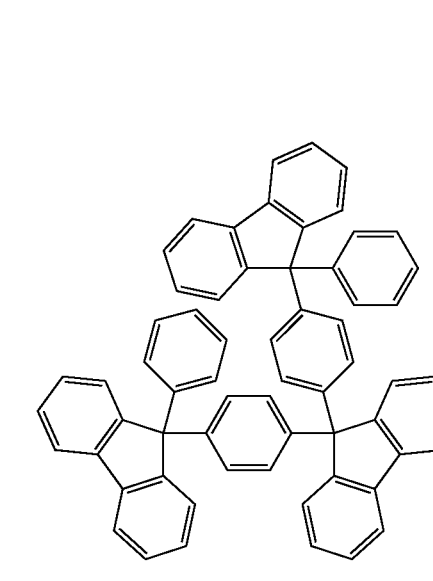

(121)
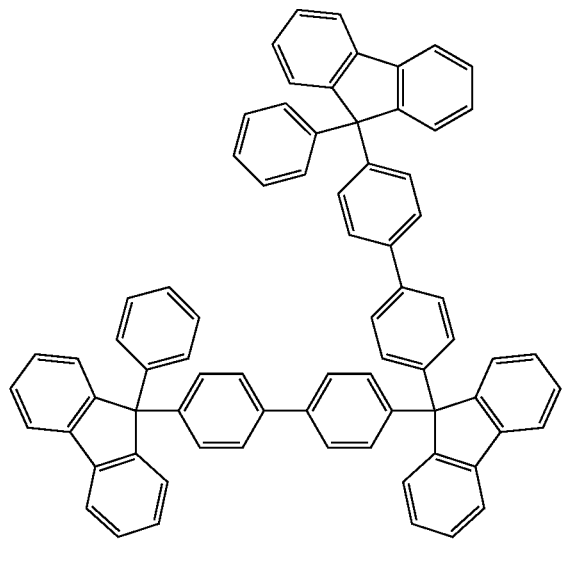
(122)
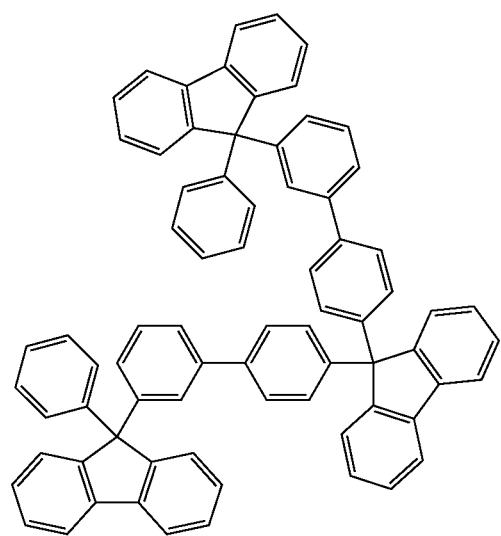
(123)
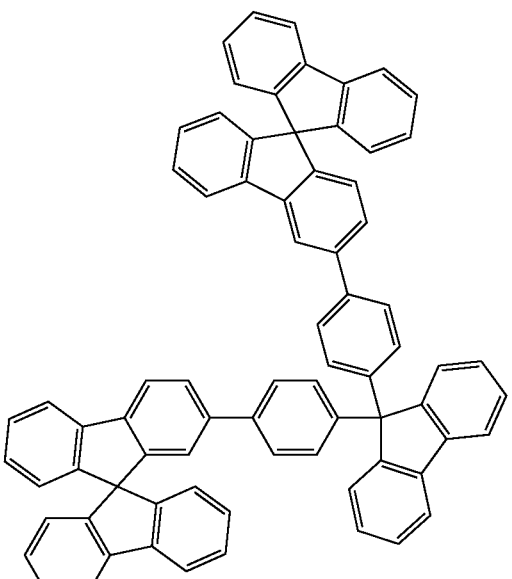
(124)
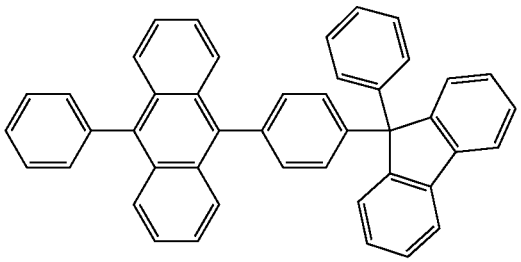
(125)
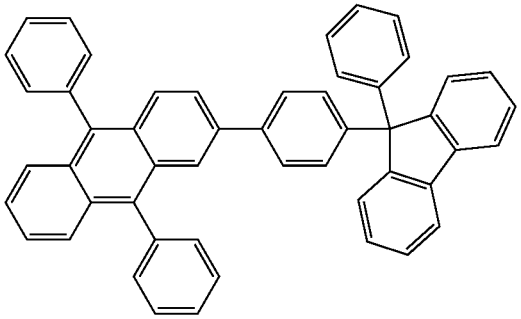

(126)
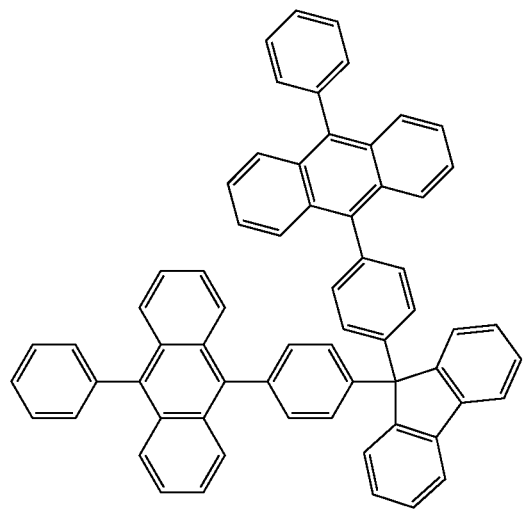
(127)
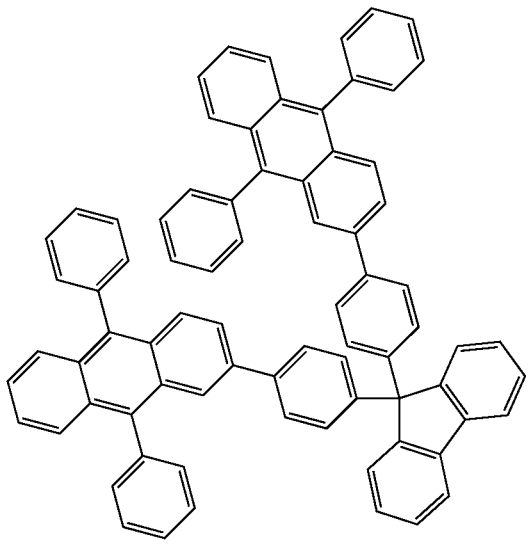
(128)
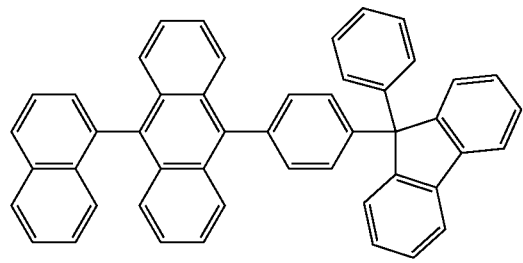
(129)
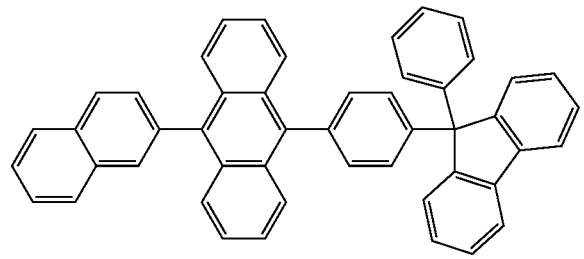
(130)
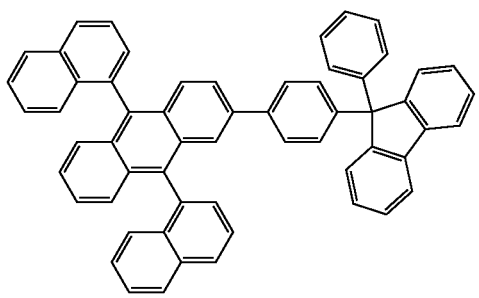
(131)
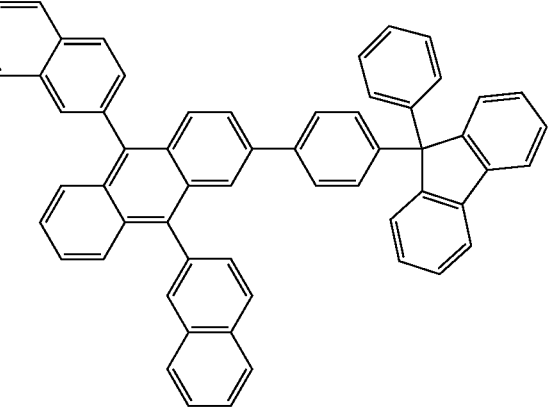
(132)
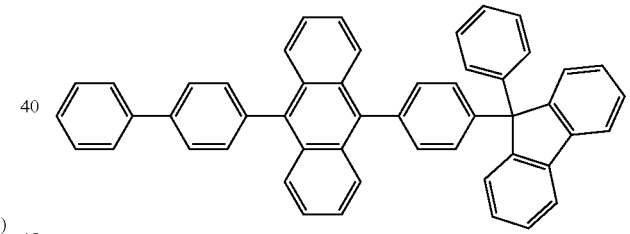
(133)
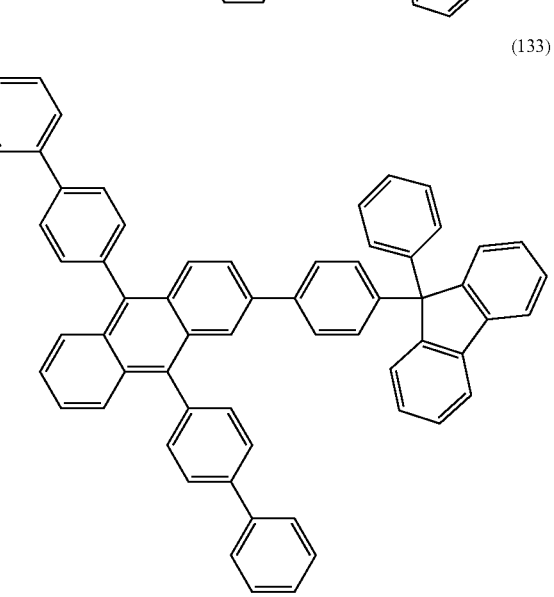

(134)
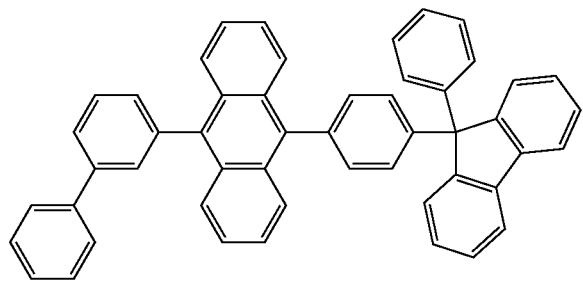
(135)
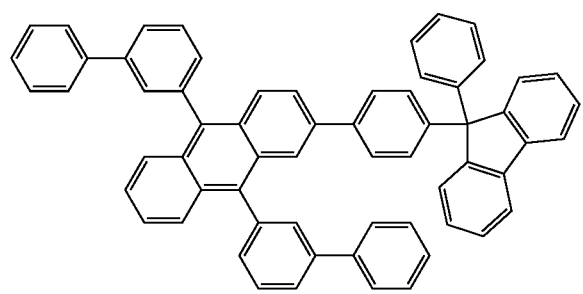
(136)
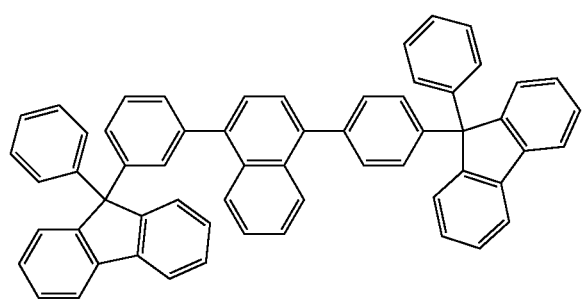
(137)
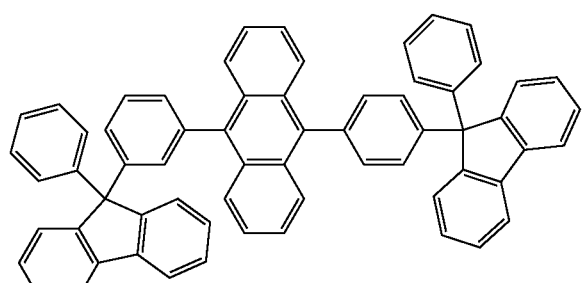
(138)
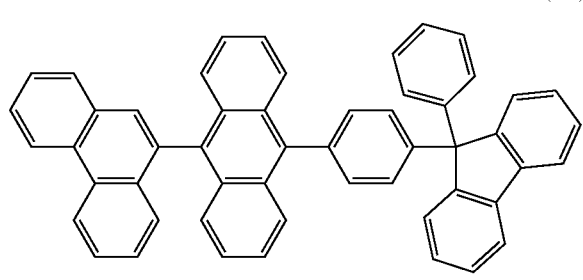
(200)
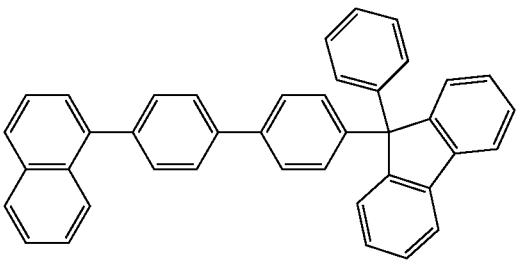
(201)
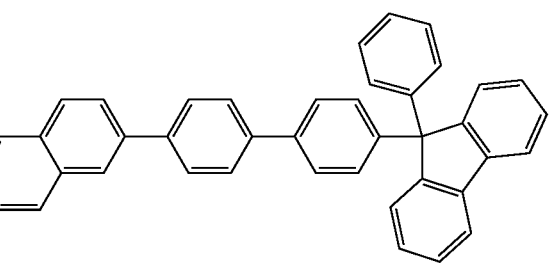
(202)
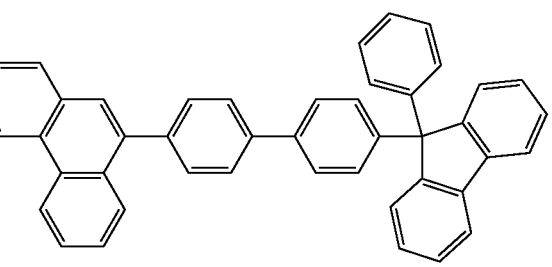
(203)
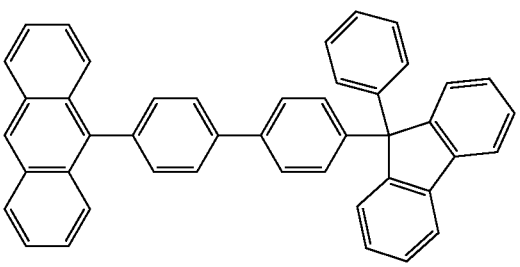
(204)
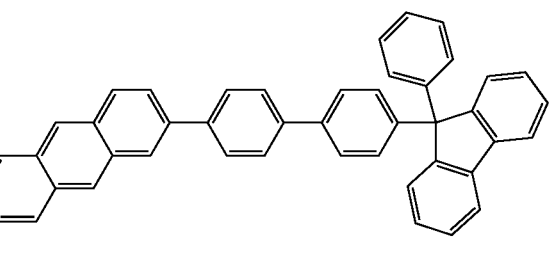

(205)
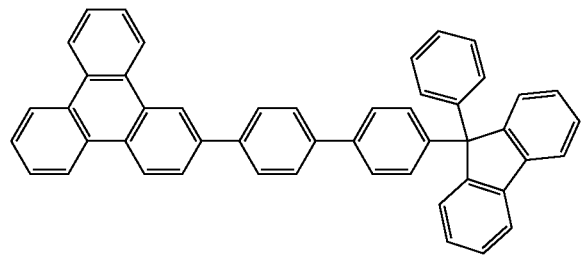
(206)
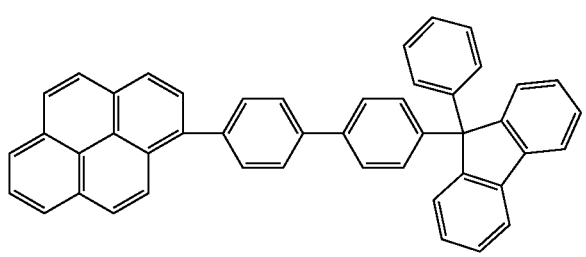
(207)
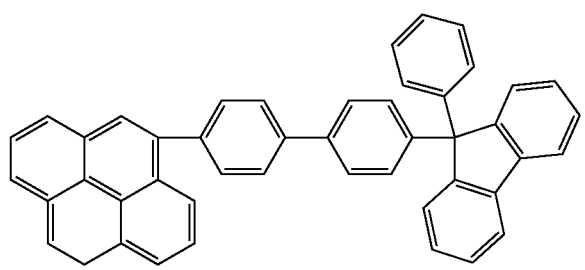
(208)
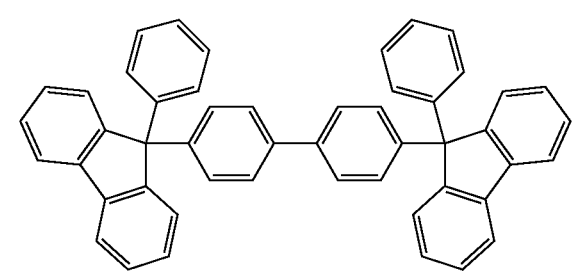
(209)
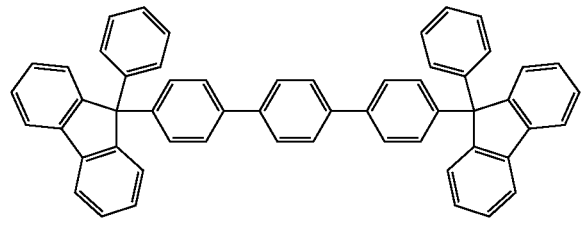
(210)
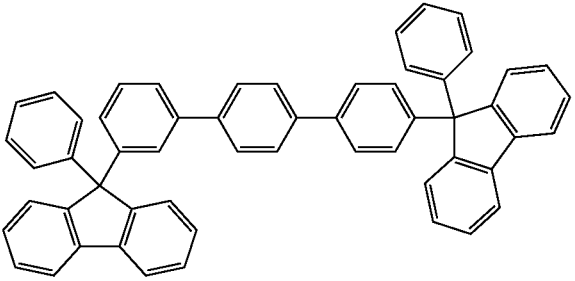
(211)
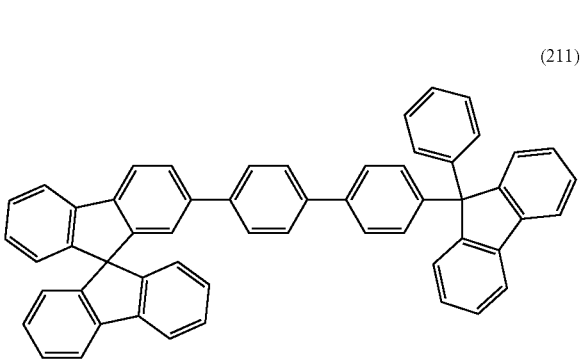
(212)
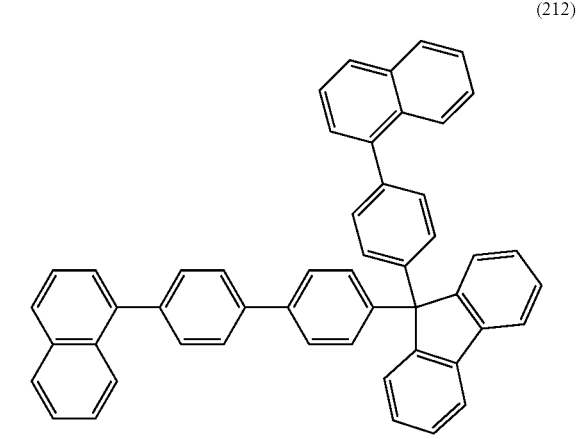
(213)
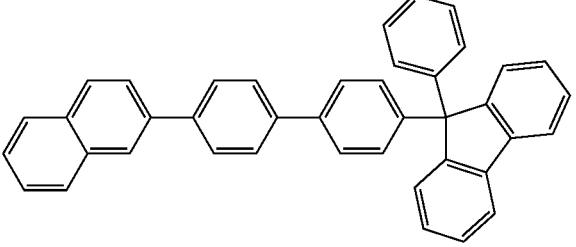

(214)
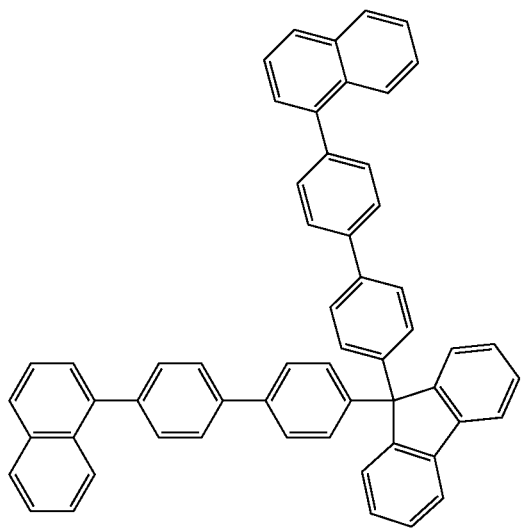
(215)
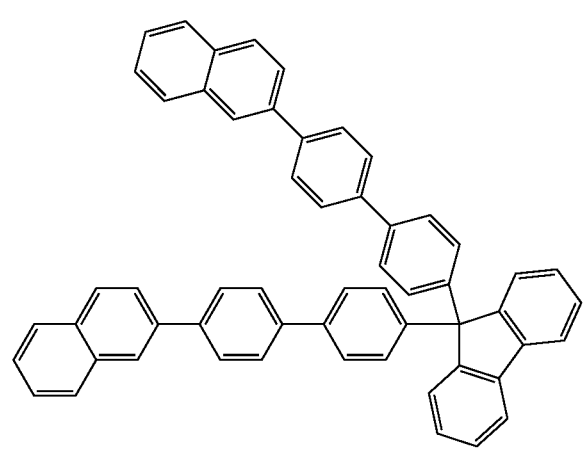
(216)
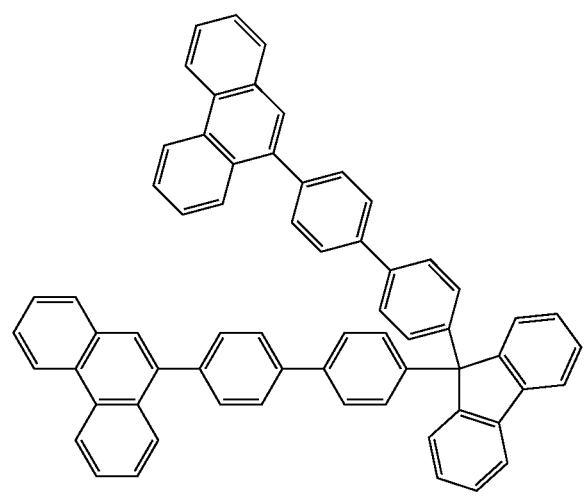
(217)
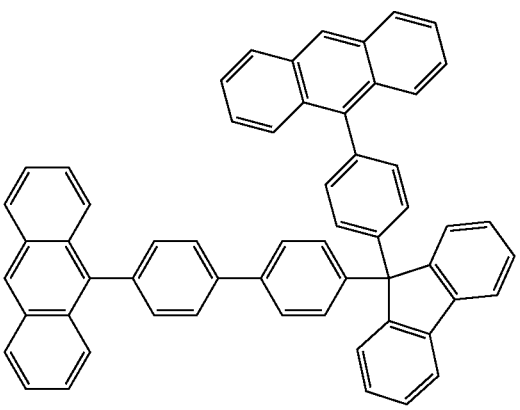
(218)
(219)
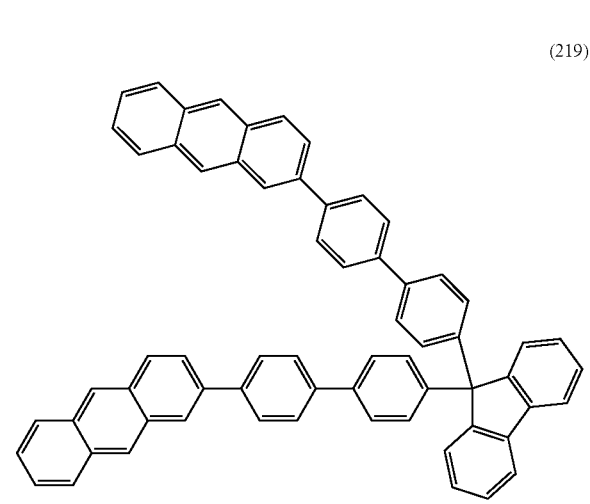

(220)
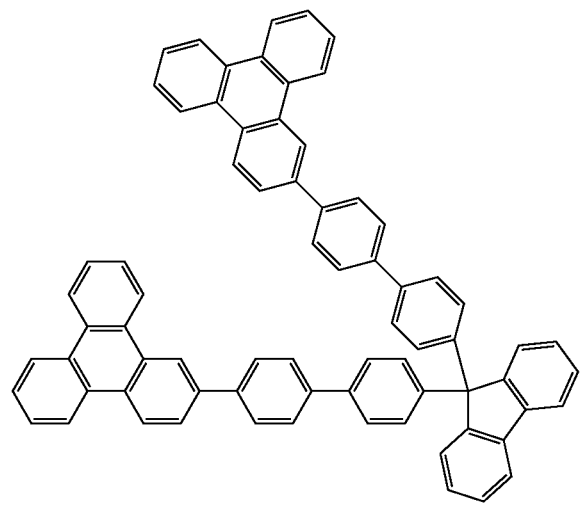
(221)
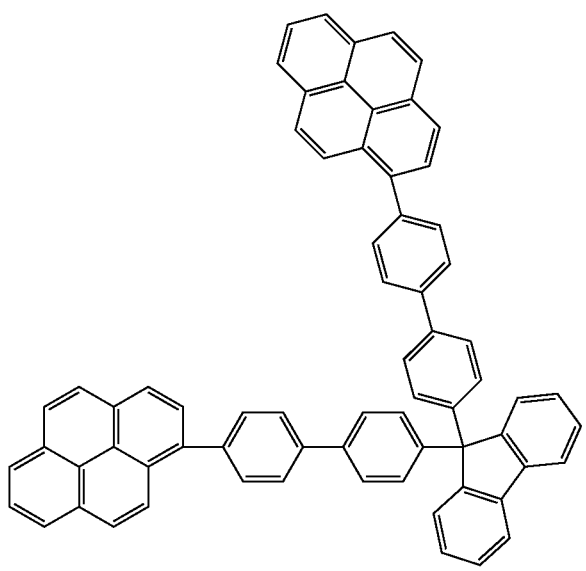
(222)
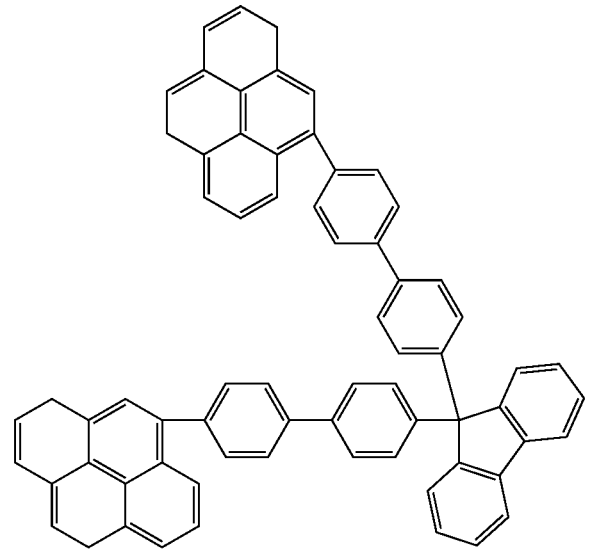
(223)
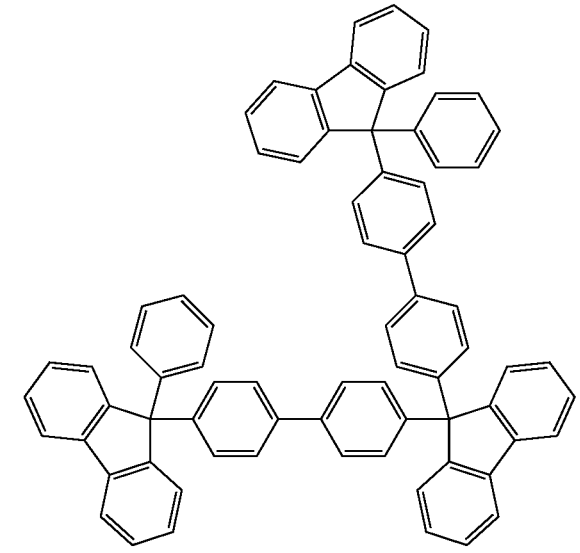

(224)
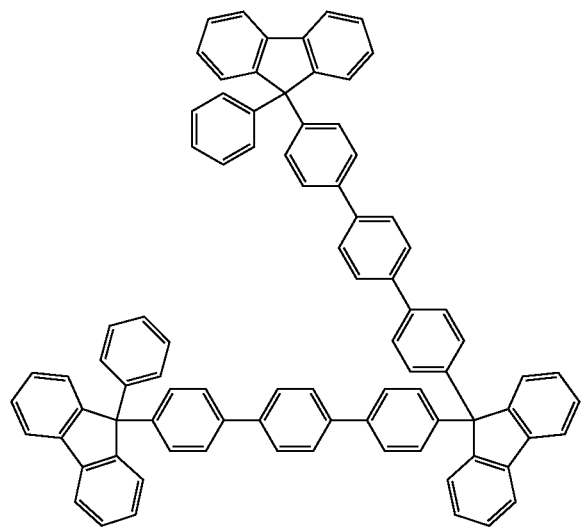
(225)
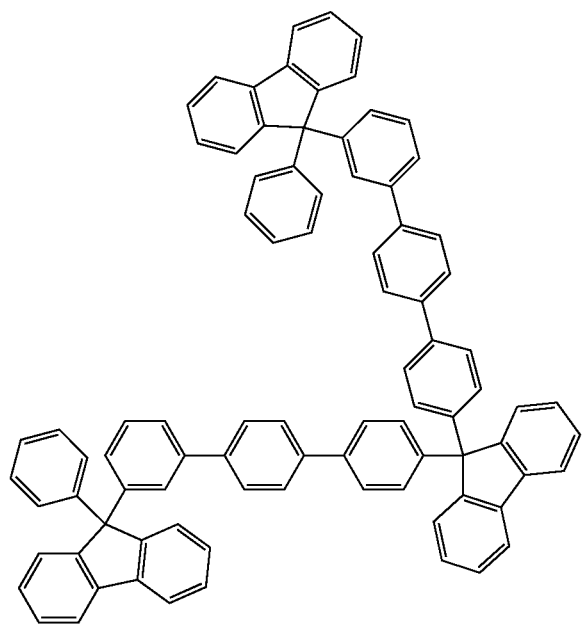
(226)
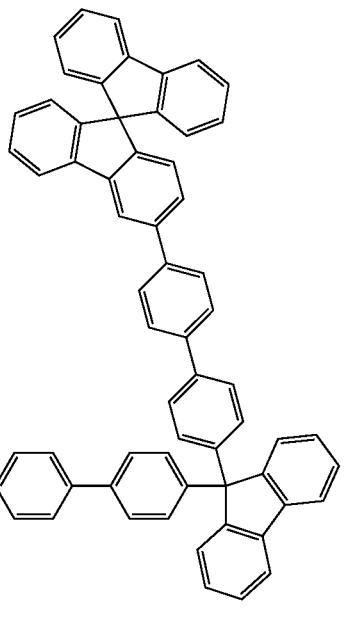
(227)
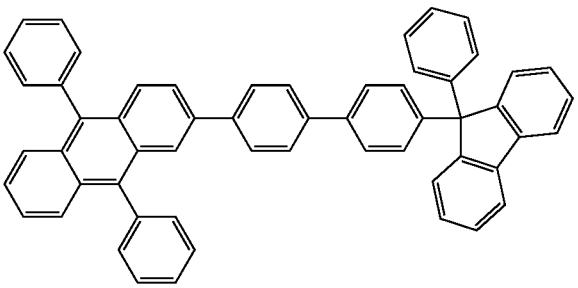
(228)

(229)
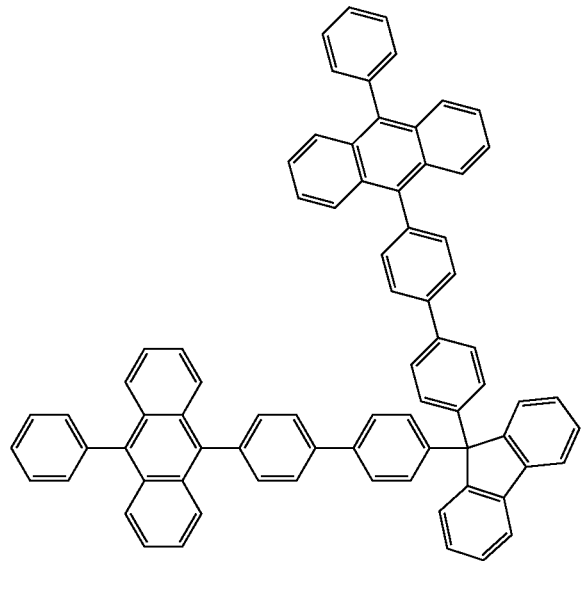
(230)
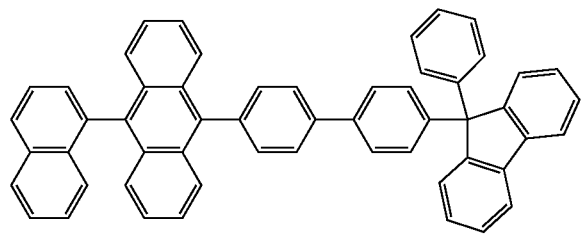
(231)
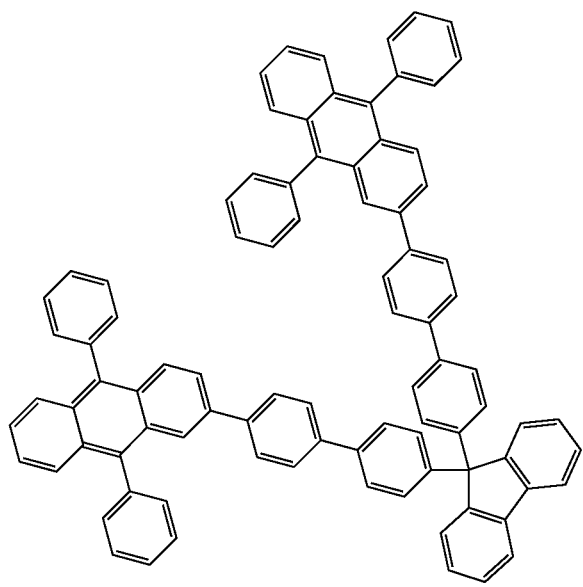
(232)
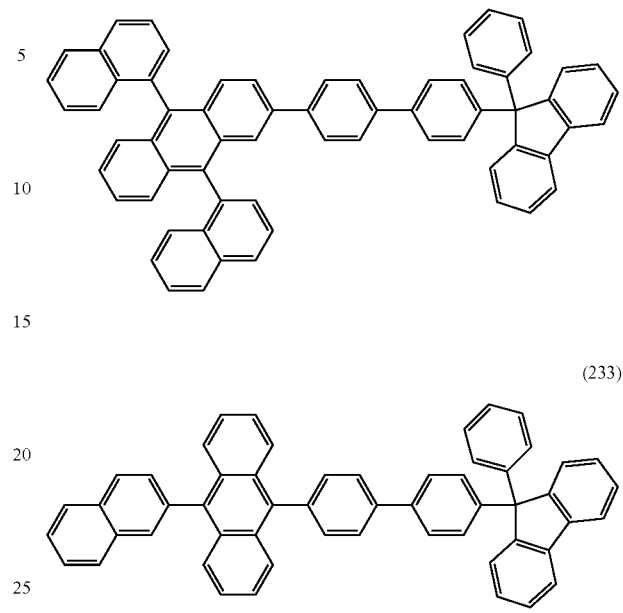
(233)
(234)
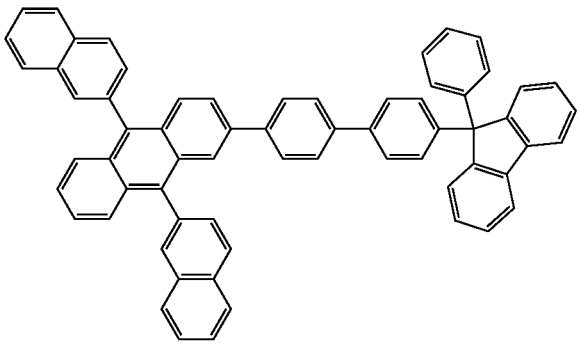
(300)
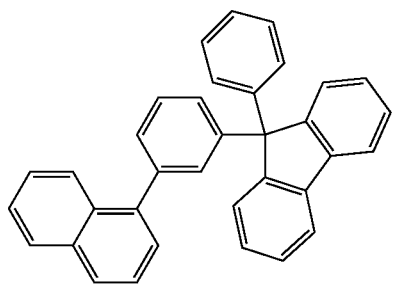
(301)
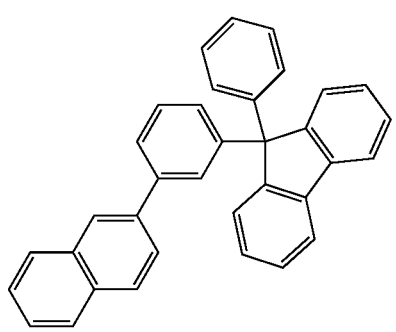

(302) 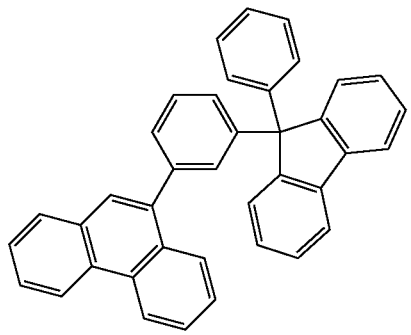
(303) 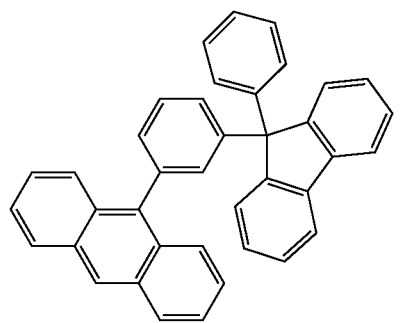
(304) 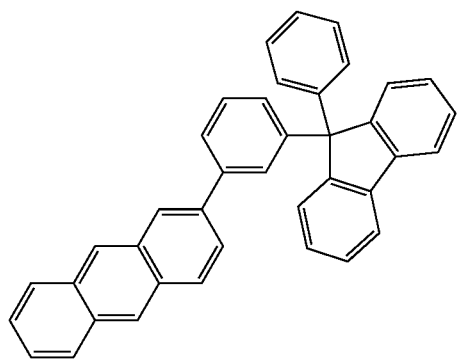
(305) 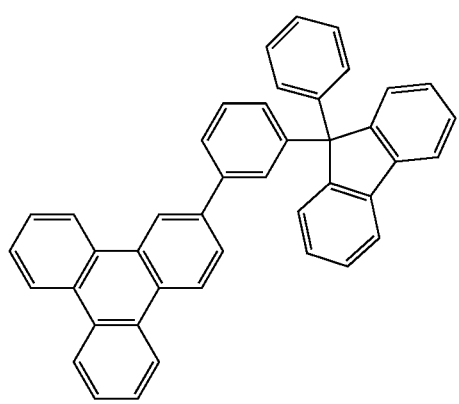
(306) 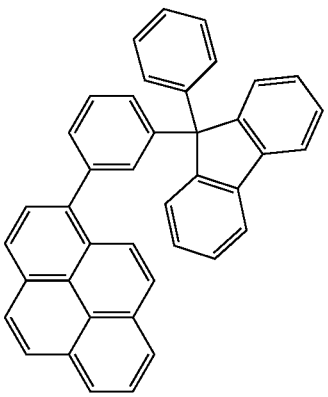
(307) 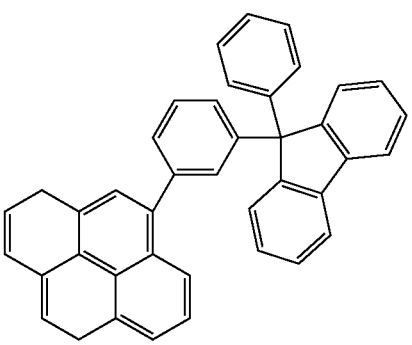
(308) 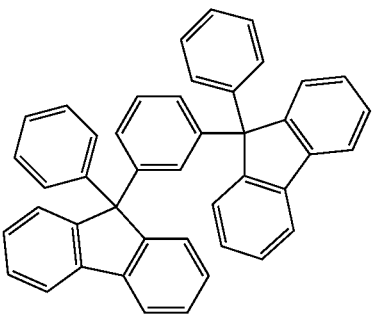
(309) 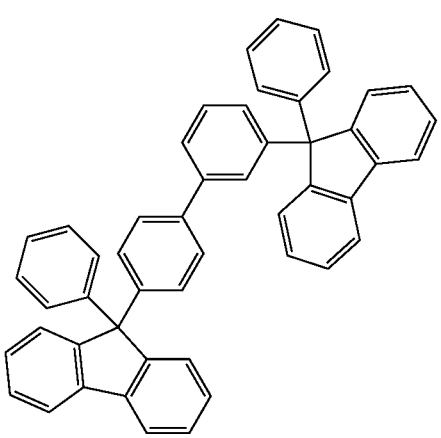

-continued
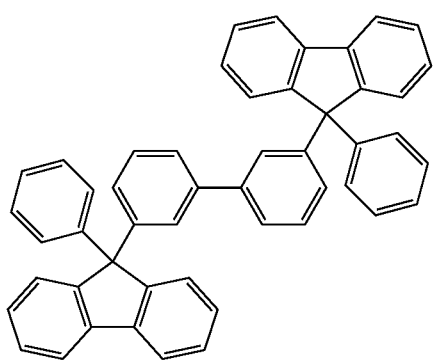
(310)
(311)
(312)
(313)
-continued
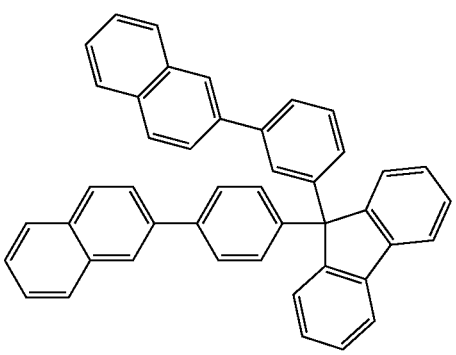
(314)
(315)
(316)
(317)

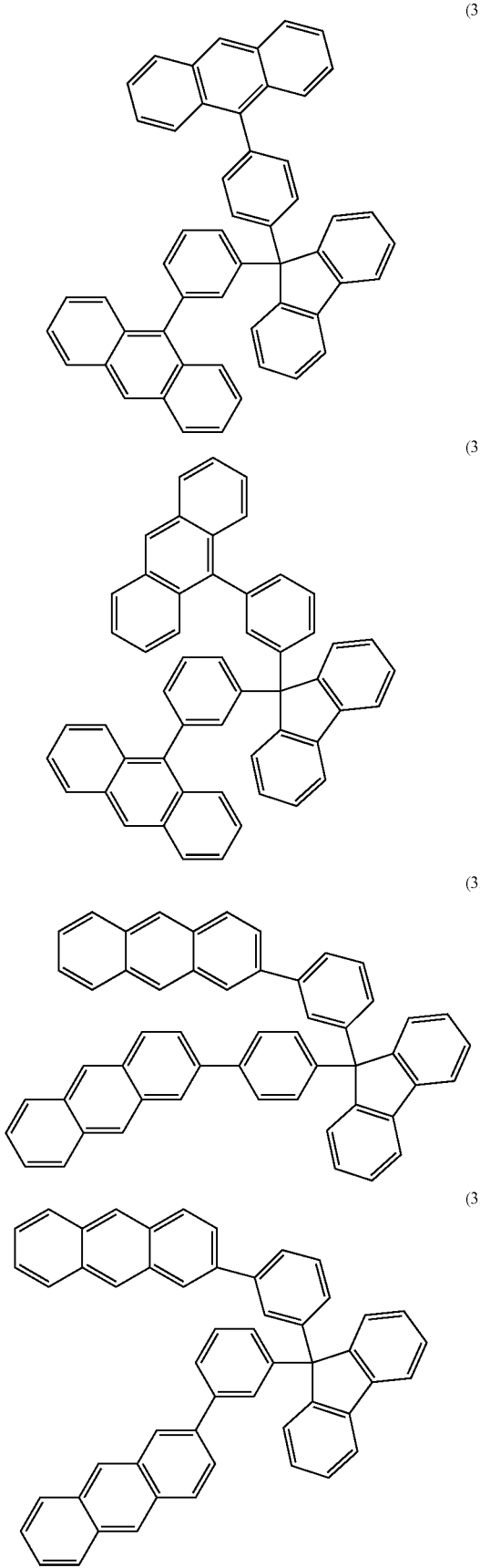
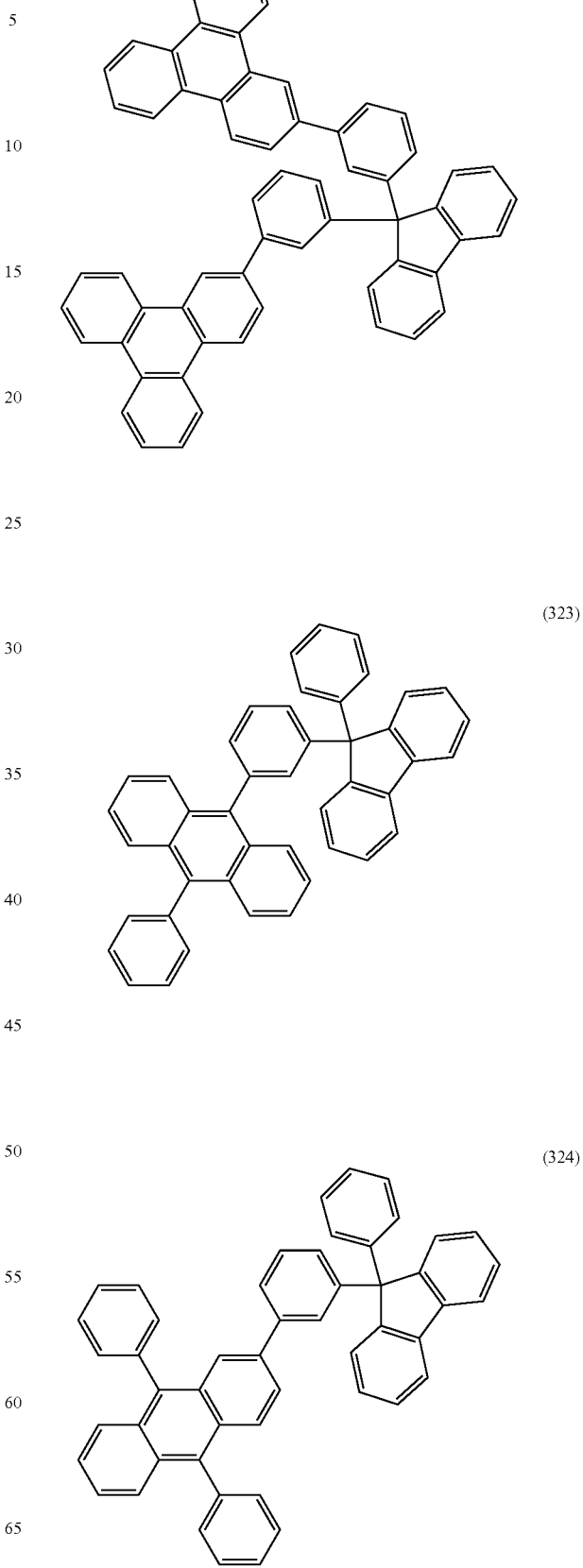

(325)
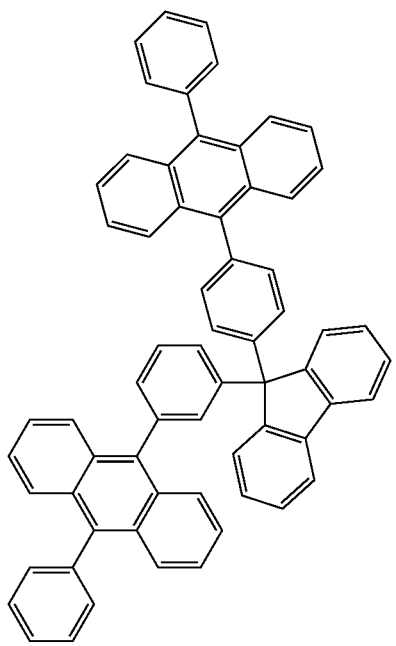
(326)
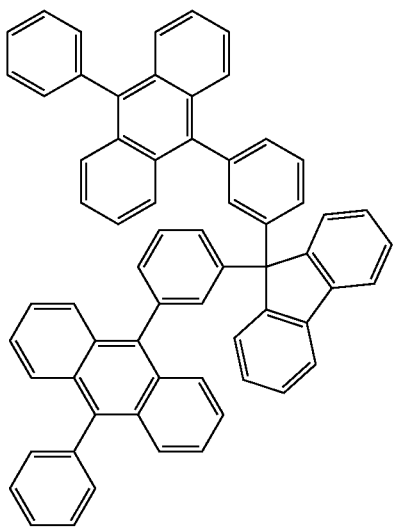
(327)
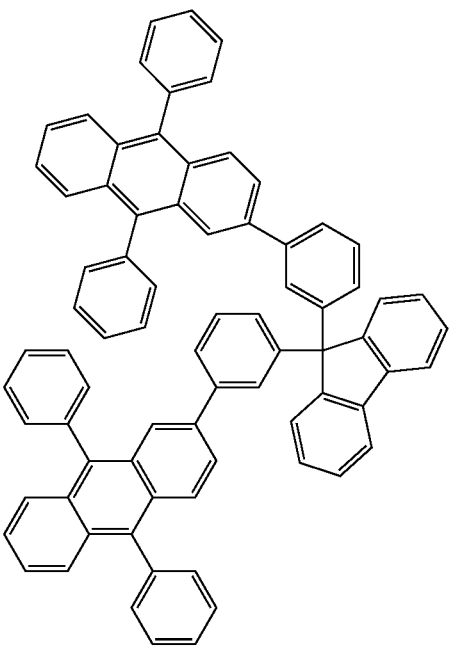
(328)
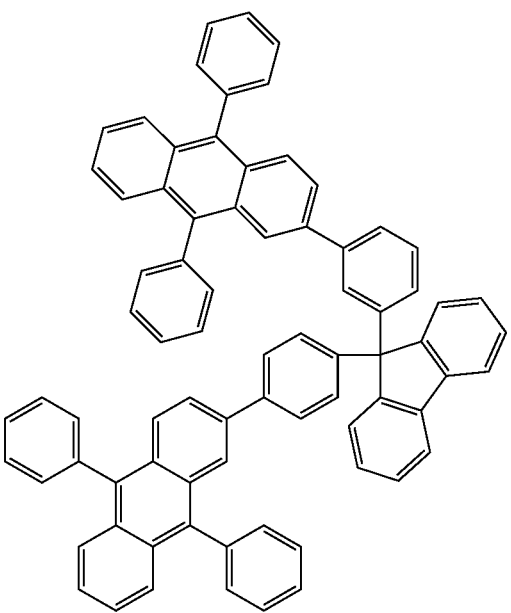

(329)
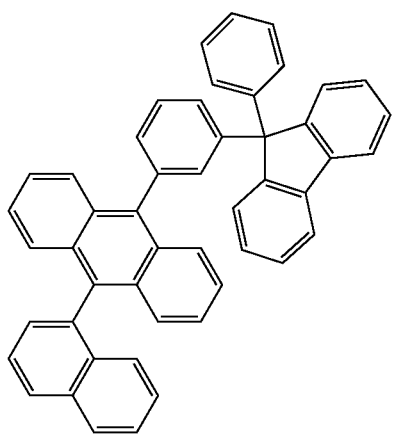
(400)
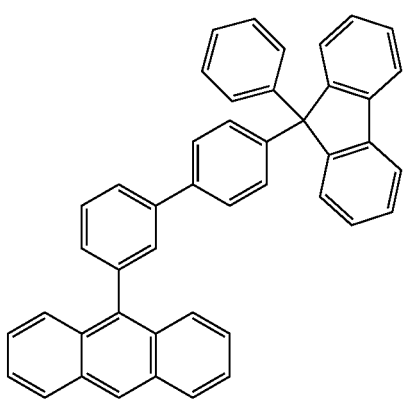
(401)
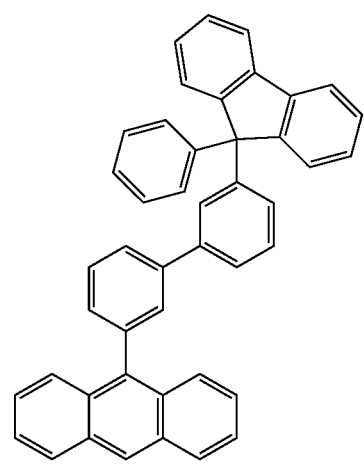
(402)
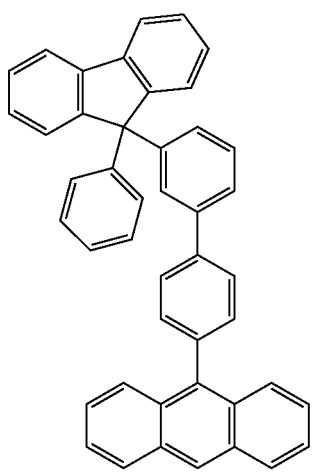
(403)
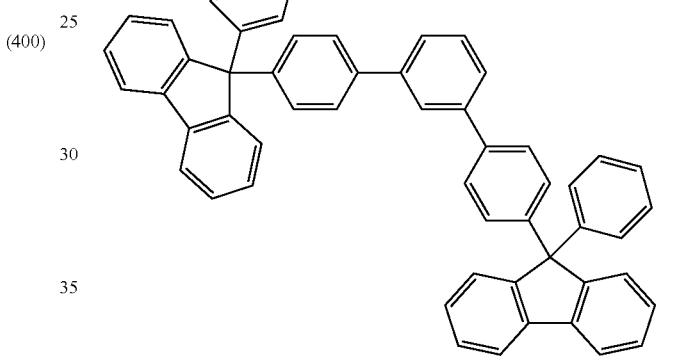
(404)
(405)

(406)
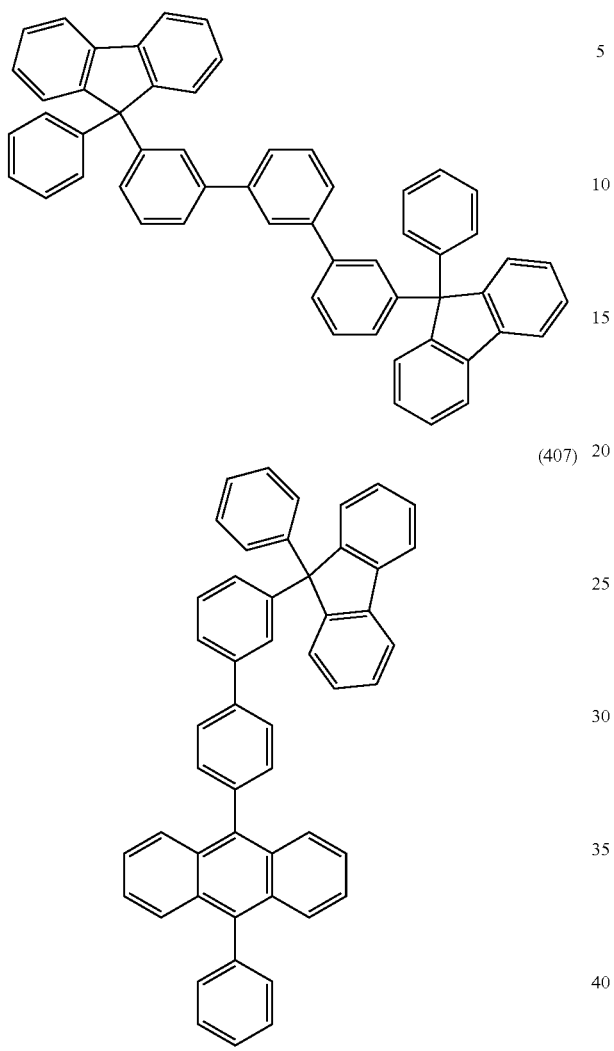
(407)
(409)
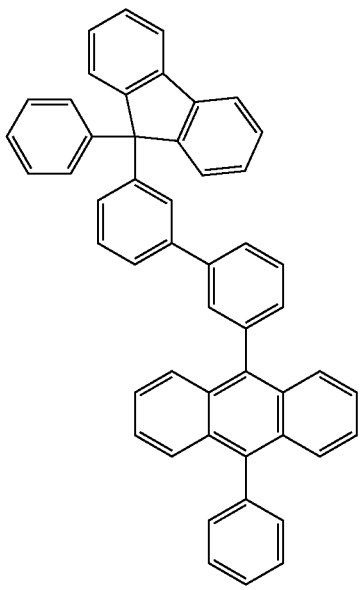
(408)
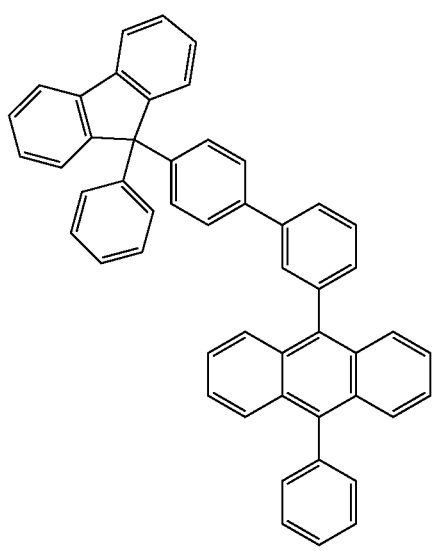
(410)
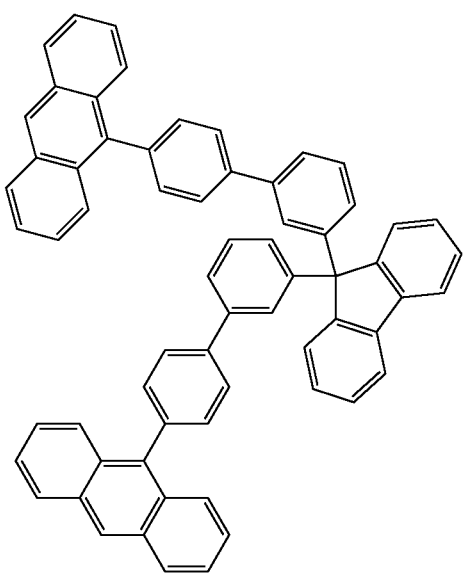

(411)
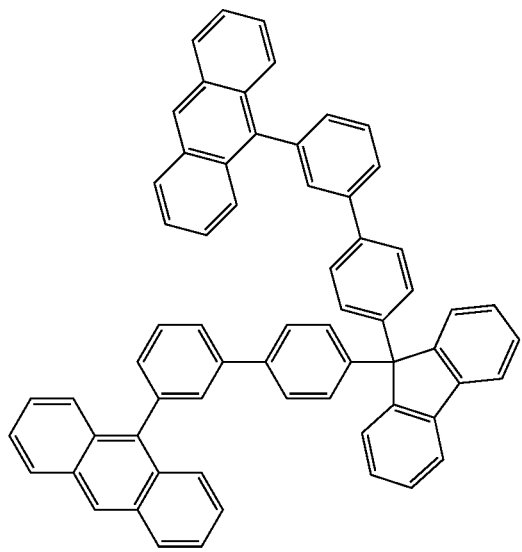
(412)
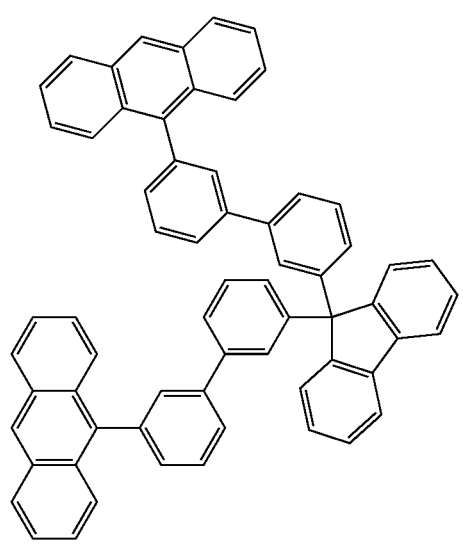
(413)
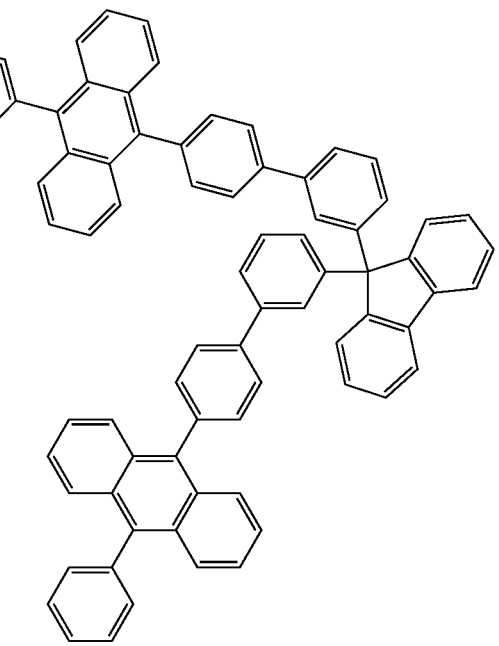
(414)
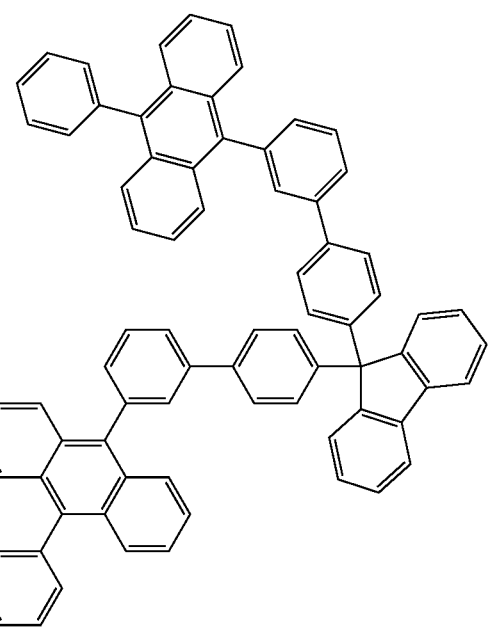

-continued
(415)
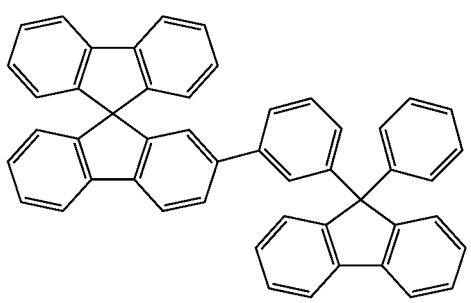
(500)
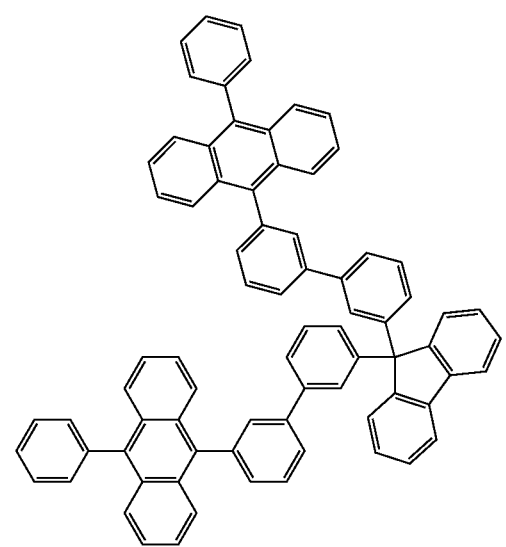
(501)
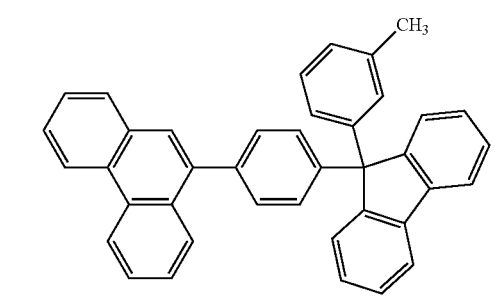
(502)
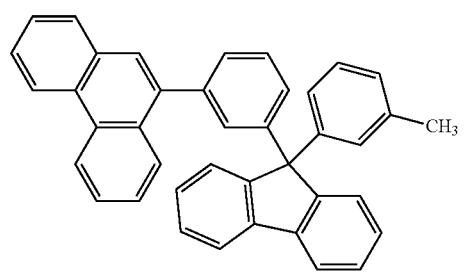
-continued
(503)
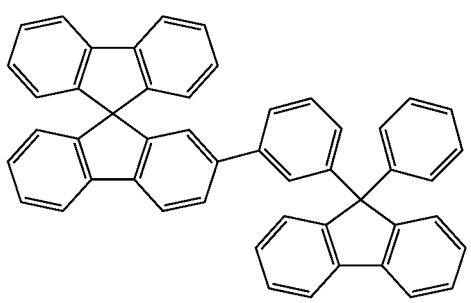
(504)
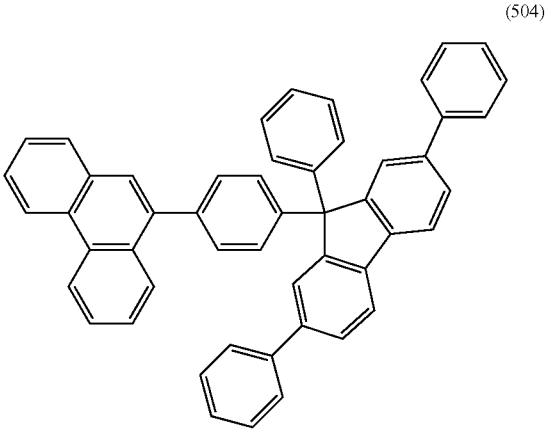
(505)
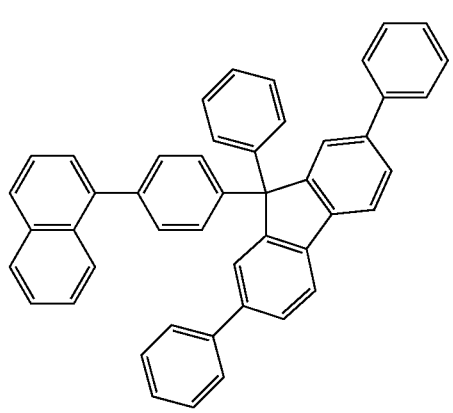
(506)
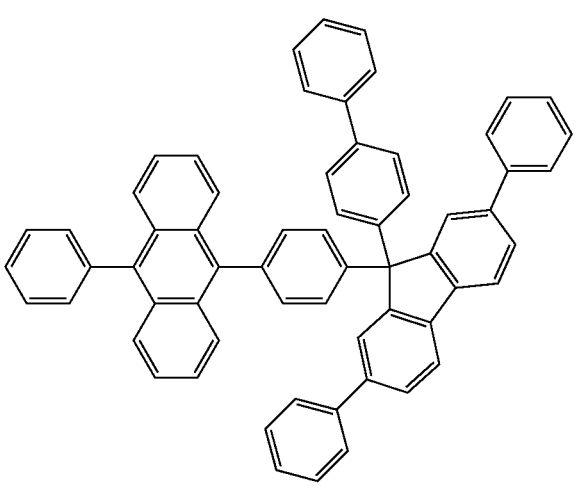

(507)
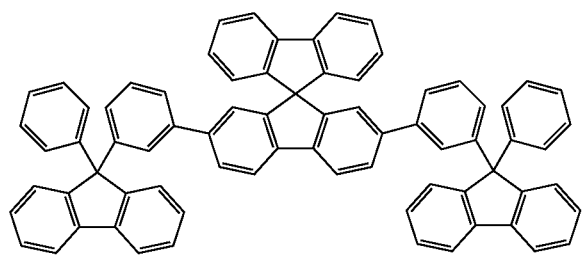
(508)
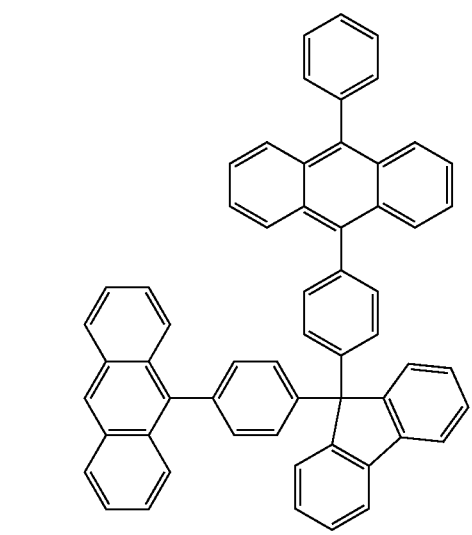
(509)
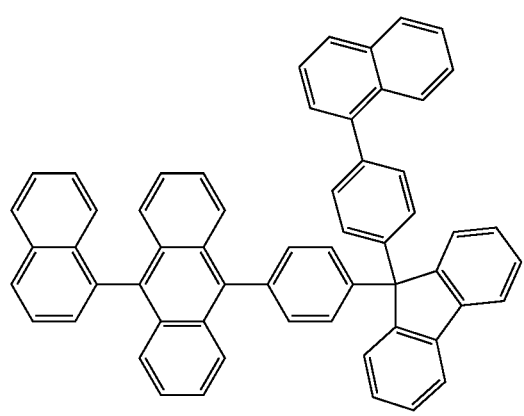
(510)
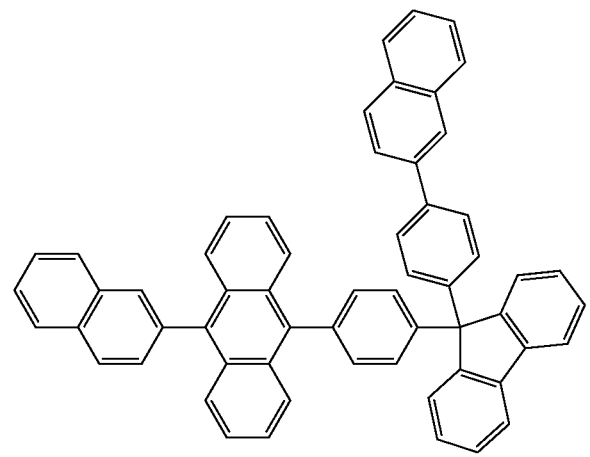
(511)
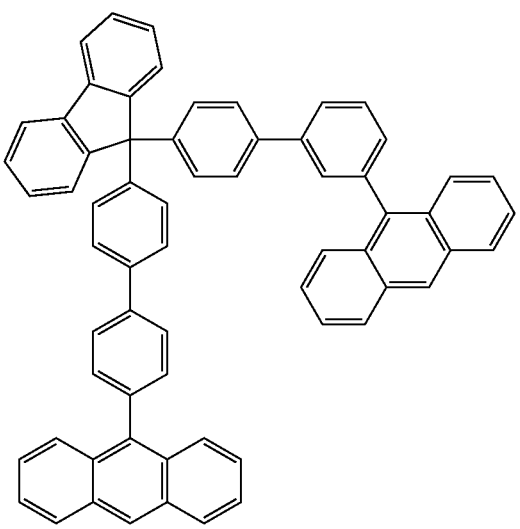
(512)
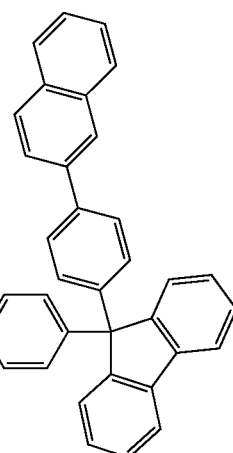

(513)
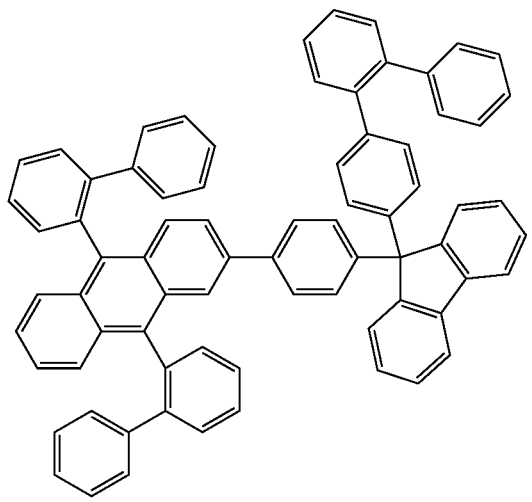
(514)
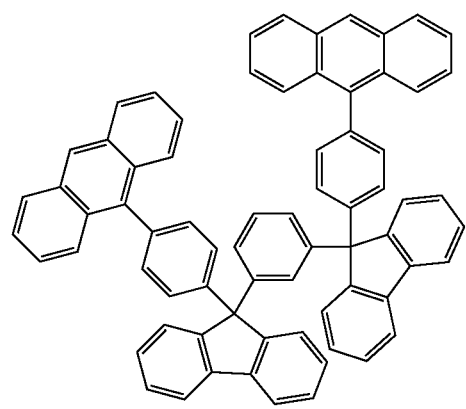
(515)
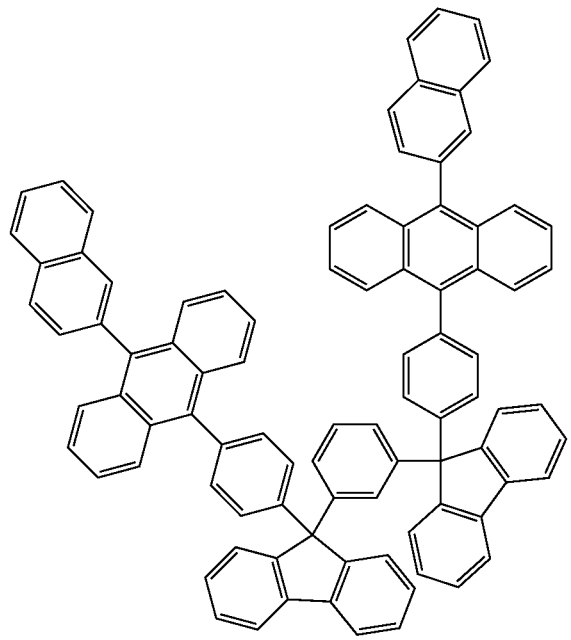
(516)
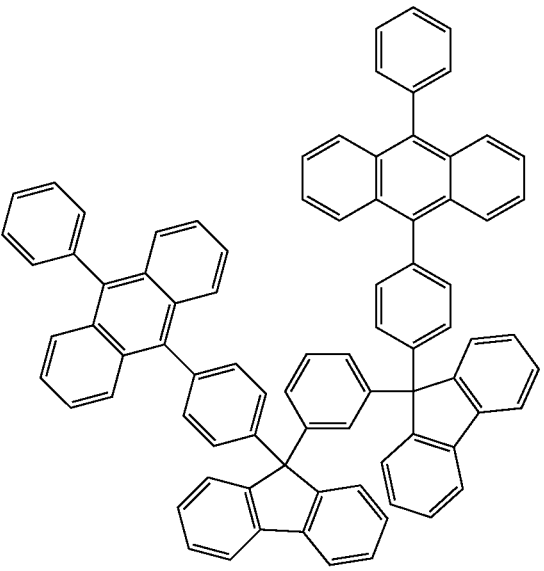
(517)
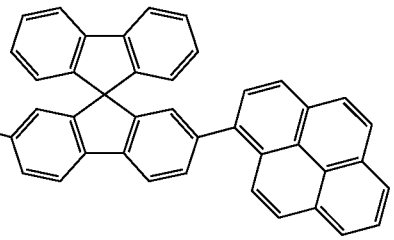
(518)
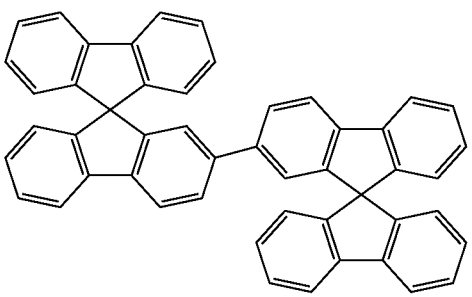
(601)
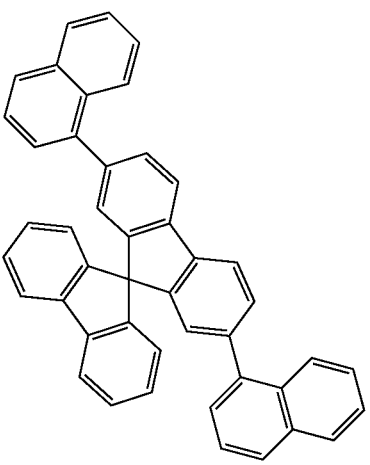

-continued
(602)
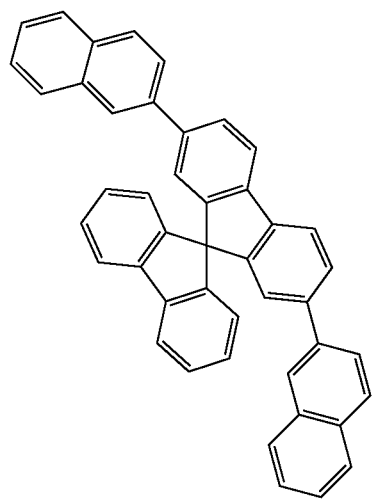
(603)
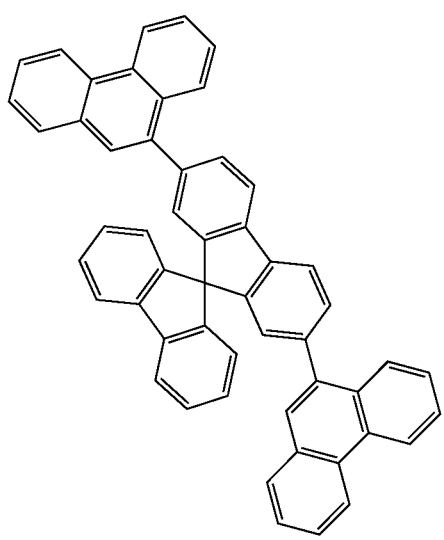
(604)
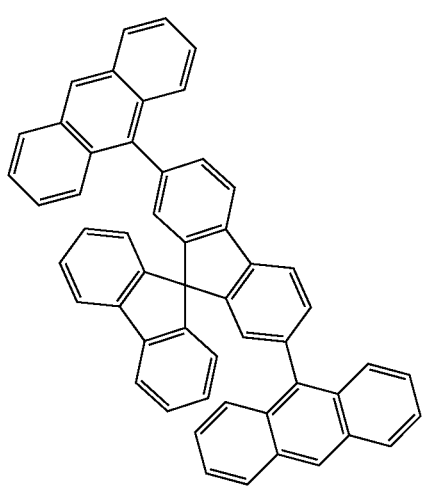
-continued
(605)
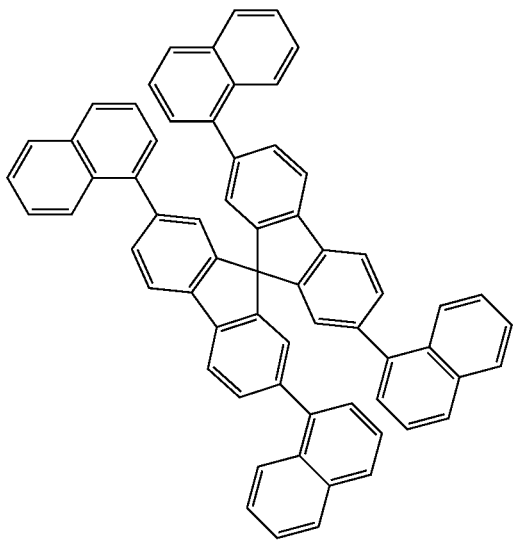
(606)
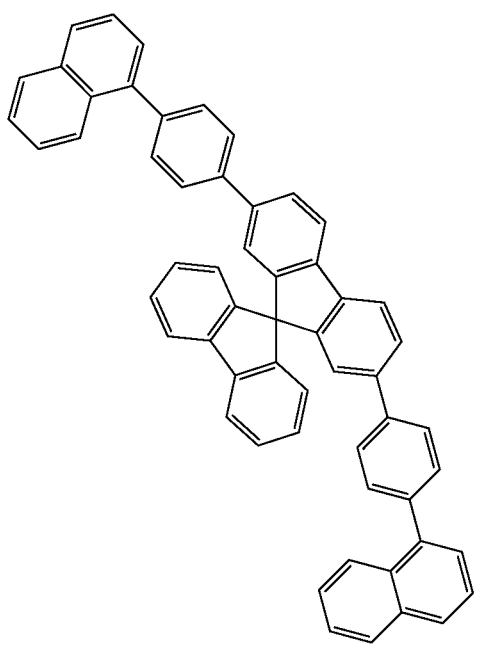
(607)
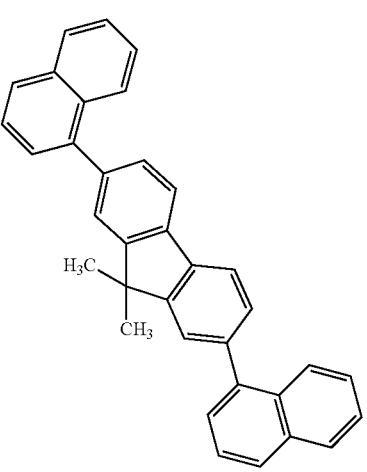

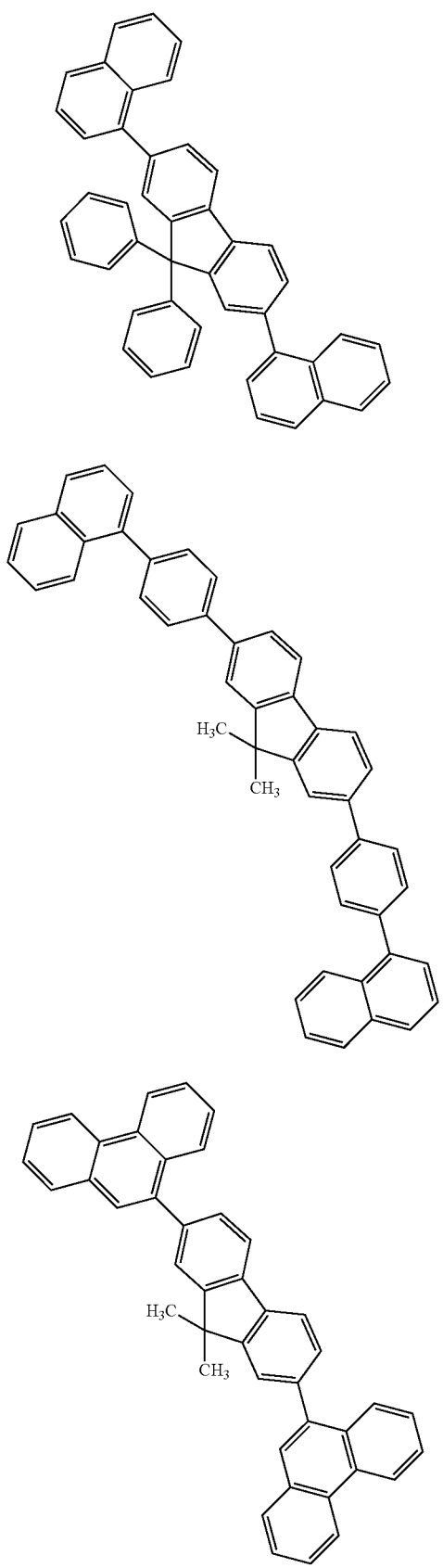
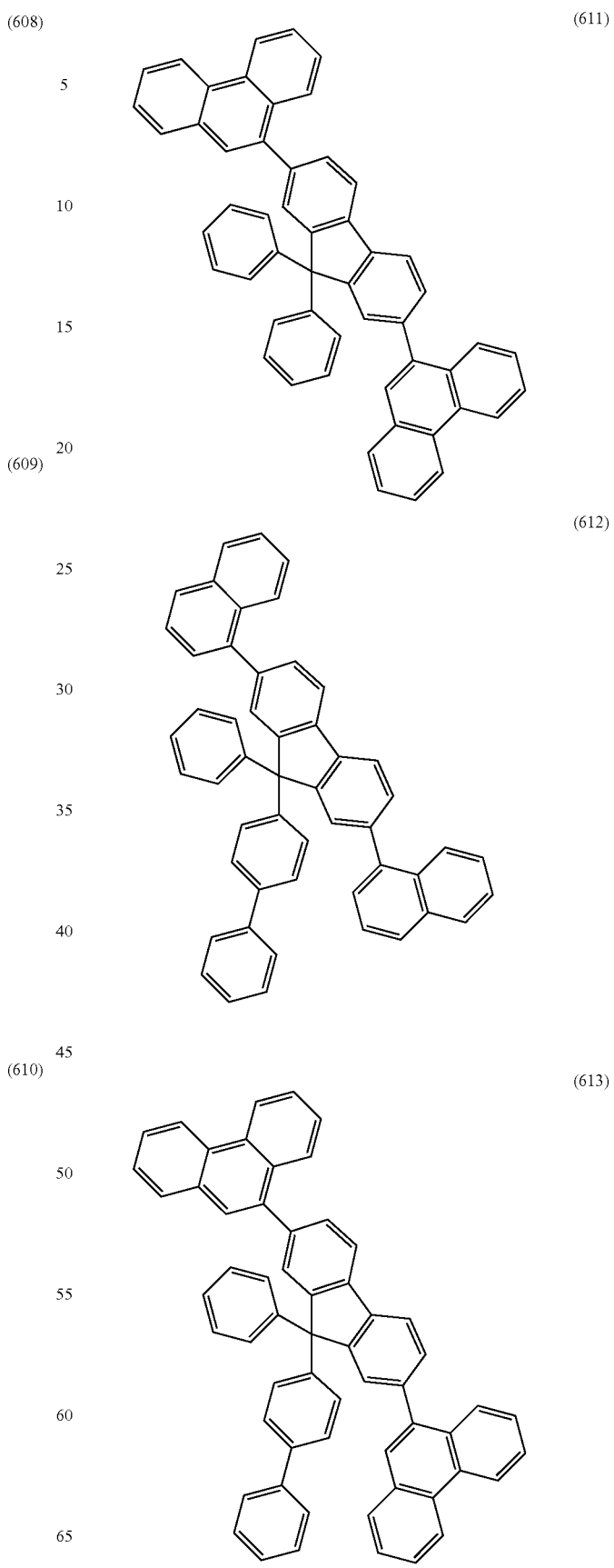

(614)

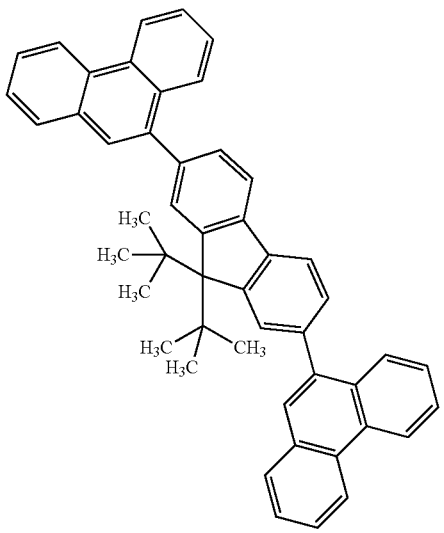

The above are structures of the hydrocarbon compound that has a fluorene skeleton and can be included in the composite material in this embodiment.

Next, a description is given of an inorganic compound that can be included in the composite material in this embodiment.

As the inorganic compound included in the composite material in this embodiment, it is possible to use an inorganic compound which exhibits an electron-accepting property with respect to the above-described hydrocarbon compound. For example, any of the following inorganic compounds having a high electron-accepting property can be suitably used: iron (III) chloride, aluminum chloride, and the like.

Alternatively, a transition metal oxide can be used as an inorganic compound for the composite material in this embodiment. Preferably, it is desirable to use an oxide of a metal belonging to Group 4 to Group 8 of the periodic table. It is particularly preferable to use titanium oxide, vanadium oxide, tantalum oxide, molybdenum oxide, tungsten oxide, rhenium oxide, ruthenium oxide, chromium oxide, zirconium oxide, hafnium oxide, or silver oxide. Molybdenum oxide is particularly easy to handle among the above oxides, because it is easily evaporated, has a low hygroscopic property, and is stable.

A transition metal oxide is considered not to have a very high electron-accepting property (considered to have low reactivity), as compared to a strong Lewis acid such as iron (III) chloride mentioned above. In the composite material in this embodiment, as described above, the occurrence of absorption based on charge transfer interaction is suppressed (or light absorption hardly occurs) in some cases. Therefore, it is difficult to prove that a transition metal oxide acts as an electron acceptor in a general sense in the composite material in this embodiment. On the other hand, as described in the following Examples, there is an experimental fact that the composite material in this embodiment conducts a larger amount of current than a simple substance of the hydrocarbon compound can do, when an electric field is applied. Thus, when a transition metal oxide is included in the composite material in this embodiment, it can be considered that carriers are easily generated at least with an assistance of application of an electric field. Therefore, in this specification, an inorganic compound (such as a transition metal oxide mentioned above) in the composite material is regarded as having an electron-accepting property as long as carriers are generated at least with an assistance of application of an electric field.

There is no limitation on methods of synthesizing the composite material in this embodiment; for example, the composite material can be formed by a co-evaporation method where the hydrocarbon compound and the inorganic compound are evaporated at the same time. The mixing ratio, in mass ratio, of the organic compound to the inorganic compound in the composite material in this embodiment is preferably approximately 8:1 to 1:2 (=Organic compound:inorganic compound), and more desirably, 4:1 to 1:1 (=Organic compound: inorganic compound). When the composite material is formed by a co-evaporation method, the mixing ratio can be controlled by separately adjusting the evaporation rates for the organic, compound and the inorganic compound.

The above-described composite material in this embodiment includes an organic compound and an inorganic compound which exhibits an electron-accepting property with respect to the organic compound, and thus has excellent carrier-injection and carrier-transport properties. Accordingly, a light-emitting element fabricated using the composite material can be driven at a low driving voltage. In addition, a light-emitting element with high reliability can be provided because a film of the composite material is barely likely to be crystallized. Moreover, even when a thick film of the composite material is used, the driving voltage is barely likely to increase; accordingly, it is possible to suppress a defect such as a short circuit due to unevenness of the anode by formation of the thick film over the anode.

Further, the composite material in this embodiment includes, as the organic compound, the above-described hydrocarbon compound having the fluorene skeleton, and thus can be a composite material with little absorption of the visible light. The composite material also has an excellent carrier balance. Accordingly, the use of the composite material can provide a light-emitting element with high current efficiency. That is, it is possible to provide a light-emitting element which is driven at a low driving voltage and has high current efficiency and thus has high power efficiency.

Furthermore, by using the hydrocarbon compound having the fluorene skeleton which has a bulky structure, a film of the composite material has a good quality, and a light-emitting element with a long life can be provided. Since the fluorene has a wide energy gap despite having a certain amount of molecular weight, a hydrocarbon compound including the fluorene skeleton can be a hydrocarbon compound having a moderately great molecular weight while the energy gap is kept wide. Further, when the hydrocarbon compound having a moderately great molecular weight is evaporated, the evaporation rate can be easily controlled; accordingly, a light-emitting element with a stable quality can be provided. The composite material according to one embodiment of the present invention is formed by co-evaporation of a hydrocarbon compound and an inorganic compound having higher evaporation temperature than the hydrocarbon compound. The composite material according to one embodiment of the present invention includes the hydrocarbon compound having the fluorene skeleton; therefore, the energy gap is prevented from narrowing and the molecular weight can be moderately great, and co-evaporation can be performed at a temperature closer to the evaporation temperature of the inorganic compound. Thus, the light-emitting element fabricated using the composite material in this embodiment can be a light-emitting element with high reliability.

(Embodiment 2)

This embodiment shows one embodiment of a light-emitting element using the composite material described in Embodiment 1, with reference to FIG. 1A.

A light-emitting element of this embodiment has a plurality of layers between a pair of electrodes. In this embodiment, the light-emitting element includes a first electrode 102, a second electrode 104 and an EL layer 103 formed between the first electrode 102 and the second electrode 104. In addition, in this embodiment, the first electrode 102 serves as an anode and the second electrode 104 serves as a cathode. In other words, when voltage is applied between the first electrode 102 and the second electrode 104 such that the potential of the first electrode 102 is higher than that of the second electrode 104, light emission can be obtained.

The substrate 101 is used as a support of the light-emitting element. As the substrate 101, glass, plastic or the like can be used, for example. Note that materials other than glass or plastic may be used as long as they can function as a support of a light-emitting element.

The first electrode 102 is preferably formed of a metal, an alloy, a conductive compound, a mixture thereof, or the like each having a high work function (specifically, a work function of 4.0 eV or higher). Specific examples include indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide (IWZO), and the like. Films of these conductive metal oxides are usually formed by sputtering; however, a sol-gel method or the like may also be used. For example, indium oxide-zinc oxide (IZO) can be formed by a sputtering method using indium oxide into which zinc oxide of 1 to 20 wt % is added, as a target. In addition, indium oxide containing tungsten oxide and zinc oxide (IWZO) can be fainted by a sputtering method using a target containing 0.5 to 5 wt % of tungsten oxide and 0.1 to 1 wt % of zinc oxide with respect to indium oxide. Besides, gold (Au), platinum (Pt), nickel (Ni), tungsten (W), chromium (Cr), molybdenum (Mo), iron (Fe), cobalt (Co), copper (Cu), palladium (Pd), graphene, nitride of a metal material (e.g., titanium nitride), and the like can be given.

There is no particular limitation on a stacked structure of the EL layer 103. The EL layer 103 may be formed as appropriate by combining a layer including a substance having a high electron-transport property, a layer including a substance having a high hole-transport property, a layer including a substance having a high electron-injection property, a layer including a substance having a high hole-injection property, a layer including a bipolar substance (a substance having a high electron- and hole-transport property), and the like. For example, the EL layer 103 can be formed in an appropriate combination of a hole-injection layer, a hole-transport layer, a light-emitting layer, an electron-transport layer, an electron-injection layer, and the like. Needless to say, it is possible to include a layer having another function or a layer having a plurality of functions. This embodiment shows is a structure in which the EL layer 103 includes a hole-injection layer 111, a hole-transport layer 112, a light-emitting layer 113, and an electron-transport layer 114 stacked in that order over the first electrode 102. Note that in this embodiment, the hole-injection layer 111 includes the composite material described in Embodiment 1. Specific materials to form each layer are given below.

It is preferable that a layer including the composite material described in Embodiment 1 be not close to a light-emitting region. This is for preventing the excitation energy that should contribute to light emission from being deactivated by an inorganic compound (in particular, an inorganic compound containing a metal). Accordingly, any of the following specific measures may be taken: to interpose a layer foamed using a different material between the layer including the composite material and a light-emitting region (to provide a hole-transport layer), to form the light-emitting region in a light-emitting layer closely to the cathode side, and the like.

The hole-injection layer 111 includes the composite material described in Embodiment 1. The composite material described in Embodiment 1 has a high carrier-injection property; accordingly, a light-emitting element driven at a low driving voltage can be fabricated. In addition, a film formed using the composite material has a good quality and crystallization is barely likely to occur; accordingly, a light-emitting element with high reliability can be fabricated. Moreover, even when a thick film of the composite material is used, the driving voltage is barely likely to increase; accordingly, even when the first electrode 102 has an uneven surface, formation of the hole-injection layer 111 having an appropriate thickness over the first electrode 102 can suppress a defect due to the unevenness, so that a light-emitting element with high reliability can be provided.

Since the composite material described in Embodiment 1 has a high light-transmitting property, a light-emitting element with high current efficiency can be provided. Further, since the composite material described in Embodiment 1 has an excellent carrier balance, a light-emitting element with high current efficiency can be provided.

Note that since the hole-injection layer 111 includes the composite material described in Embodiment 1, a material for the first electrode 102 can be selected regardless of the work function.

The hole-transport layer 112 includes a substance having a high hole-transport property. Examples of the substance having a high hole-transport property include aromatic amine compounds such as 4,4'-bis[N-(1-naphthyl)-N-phenylamino]biphenyl (abbreviation: NPB or α-NPB), N,N'-bis(3-methylphenyl)-N,N'-diphenyl[1,1'-biphenyl]-4,4'-diamine (abbreviation: TPD), 4-phenyl-4'-(9-phenylfluoren-9-yl)triphenylamine (abbreviation: BPAFLP), 4,4'-bis[N-(9,9-dimethylfluoren-2-yl)-N-phenylamino]biphenyl (abbreviation: DFLDPBi), and 4,4'-bis[N-(spiro-9,9'-bifluoren-2-yl)-N-phenylamino]biphenyl (abbreviation: BSPB). The substances mentioned here are mainly ones that have a hole mobility of $10^{-6}$ cm$^2$/V·s or higher. However, any other substance may also be used as long as the substance has a higher hole-transport property than an electron-transport property. Note that the layer including a substance having a high hole-transport property is not limited to a single layer but may have a stacked structure of two or more layers formed using any of the above-described compounds.

Alternatively, it is possible to use a carbazole derivative such as 4,4'-di(N-carbazolyl)biphenyl (abbreviation: CBP), 9-[4-(10-phenyl-9-anthryl)phenyl]-9H-carbazole (abbreviation: CzPA), or 9-phenyl-3-[4-(10-phenyl-9-anthryl)phenyl]-9H-carbazole (abbreviation: PCzPA); or an anthracene derivative such as 2-tert-butyl-9,10-di(2-naphthyl)anthracene (abbreviation: t-BuDNA), 9,10-di(2-naphthyl)anthracene (abbreviation: DNA), or 9,10-diphenylanthracene (abbreviation: DPAnth).

Further alternatively, it is possible to use a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD).

The hydrocarbon compound that can be included in the composite material described in Embodiment 1 can also be used as a material included in the hole-transport layer.

The light-emitting layer 113 includes a light-emitting substance. The light-emitting layer 113 may be formed using a film including only a light-emitting substance or a film in which an emission center substance is dispersed in a host material.

There is no particular limitation on a material that can be used as the light-emitting substance or the emission center substance in the light-emitting layer 113, and light emitted from the material may be either fluorescence or phosphorescence. The following can be given as examples of the light-emitting substance or the emission center substance. Examples of a fluorescent substance include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N'''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM). Examples of a phosphorescent substance include bis[2-(3',5'-bistrifluoromethylphenyl)pyridinato-N,$C^{2'}$]iridium(III)picolinate (abbreviation: Ir(CF$_3$ppy)$_2$(pic)), bis[2-(4',6'-difluorophenyl)pyridinato-N,$C^{2'}$]iridium(III) acetylacetonate (abbreviation: FIracac), tris(2-phenylpyridinato)iridium(III) (abbreviation: Ir(ppy)$_3$), bis(2-phenylpyridinato)iridium(III) acetylacetonate (abbreviation: Ir(ppy)$_2$(acac)), tris(acetylacetonato)(monophenanthroline)terbium(III) (abbreviation: Tb(acac)$_3$(Phen)) bis(benzo[h]quinolinato)iridium(III) acetylacetonate (abbreviation: Ir(bzq)$_2$(acac)), bis(2,4-diphenyl-1,3-oxazolato-N,$C^{2'}$)iridium(III) acetylacetonate (abbreviation: Ir(dpo)$_2$(acac)), bis[2-(4'-perfluorophenylphenyl)pyridinato]iridium(III) acetylacetonate (abbreviation: Ir(p-PF-ph)$_2$(acac)), bis(2-phenylbenzothiazolato-N,$C^{2'}$)iridium(III)acetylacetonate (abbreviation: Ir(bt)$_2$(acac)), bis[2-(2'-benzo[4,5-α]thienyl)pyridinato-N,$C^{3'}$]iridium (acetylacetonate) (abbreviation: Ir(btp)$_2$(acac)), bis(1-phenylisoquinolinato-N,$C^{2'}$)iridium(III)acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(2,3,5-triphenylpyrazinato)iridium(III) (abbreviation: Ir(tppr)$_2$(acac)), 2,3,7,8,12,13,17,18-octaethyl-21H,23H-porphine platinum (II) (abbreviation: PtOEP), tris(1,3-diphenyl-1,3-propanedionato)(monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TTA)$_3$(Phen)). The hydrocarbon compound that can be included in the composite material described in Embodiment 1 can also be used as the emission center material in some cases.

There is no particular limitation on a material that can be used as the above host material, and for example, a metal complex, a heterocyclic compound, or an aromatic amine compound can be used. Examples of the metal complex include tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), bis[2-(2-benzothiazolyl)phenolato]zinc(II) (abbreviation: ZnBTZ), and the like. Examples of the heterocyclic compound include 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), bathophenanthroline (abbreviation: BPhen), bathocuproine (abbreviation: BCP), 9-[4-(5-phenyl-1,3,4-oxadiazol-2-yl)phenyl]-9H-carbazole (abbreviation: CO11), and the like. Examples of the aromatic amine compound include 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), and the like. In addition, condensed polycyclic aromatic compounds such as anthracene derivatives, phenanthrene derivatives, pyrene derivatives, chrysene derivatives, and dibenzo[g,p]chrysene derivatives are given. Specific examples include 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9- anthryl)phenyl]phenyl}-9H-carbazol-3-amine (abbreviation: PCAPBA), N,9-diphenyl-N-(9,10-diphenyl-2-anthryl)-9H-carbazol-3-amine (abbreviation: 2PCAPA), 6,12-dimethoxy-5,11-diphenylchrysene, N,N,N',N',N''',N''',N'''-octaphenyldibenzo[g,p]chrysene-2,7,10,15-tetraamine (abbreviation: DBC1), 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3'''-(benzene-1,3,5-triyl)tripyrene (abbreviation: TPB3), and the like. The hydrocarbon compound that can be included in the composite material described in Embodiment 1 can also be used as the hose material in some cases.

One or more substances having a wider energy gap than the above-described emission center substance may be selected from these substances and known substances. Moreover, in the case where the emission center substance emits phosphorescence, a substance having higher triplet excitation energy (energy difference between a ground state and a triplet excited state) than the emission center substance may be selected as the host material.

The light-emitting layer 113 may be a stack of two or more layers. For example, in the case where the light-emitting layer 113 is formed by stacking a first light-emitting layer and a second light-emitting layer in that order from the hole-transport layer side, for example, the first light-emitting layer is formed using a substance having a hole-transport property as the host material and the second light-emitting layer is formed using a substance having an electron-transport property as the host material.

In the case where the light-emitting layer having the above-described structure is formed using a plurality of materials, the light-emitting layer can be formed using co-evaporation by a vacuum evaporation method; or an inkjet method, a spin coating method, a dip coating method, or the like using a solution of the materials.

The electron-transport layer 114 includes a substance having a high electron-transport property. For example, the electron-transport layer 114 includes a metal complex having a quinoline skeleton or a benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq), or the like. Alternatively, it is possible to use a metal complex having an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$), or the like. Besides the metal complexes, it is possible to use 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like. The substances mentioned here are mainly ones that have an electron mobility of $10^{-6}$ cm$^2$V·s or higher. The electron-transport layer may be formed using any other substance as long as the substance has a higher electron-transport property than a hole-transport property.

Furthermore, the electron-transport layer is not limited to a single layer, and two or more layers formed using the aforementioned substances may be stacked.

Further, a layer that controls transport of electron carriers may be provided between the electron-transport layer and the light-emitting layer. Specifically, the layer that controls transport of electron carriers is a layer formed by adding a small amount of substance having a high electron-trapping property to the above-described material having a high electron-transport property, so that carrier balance can be adjusted. Such a structure is very effective in suppressing a problem (such as shortening of the element life) caused when electrons pass through the light-emitting layer.

In addition, an electron-injection layer may be provided between the electron-transport layer and the second electrode 104, in contact with the second electrode 104. For the electron-injection layer, an alkali metal, an alkaline earth metal, or a compound thereof may be used, such as lithium fluoride (LiF), cesium fluoride (CsF), or calcium fluoride (CaF$_2$). For example, a layer which is formed using a material having an electron-transport property and includes an alkali metal, an alkaline earth metal, or a compound thereof may be used, such as an Alq layer which includes magnesium (Mg). By using a layer which is formed using a substance having an electron-transport property and includes an alkali metal or an alkaline earth metal as the electron-injection layer, electron injection from the second electrode 104 is performed efficiently, which is preferable.

The second electrode 104 can be formed using a metal, an alloy, an electrically conductive compound, or a mixture thereof, having a low work function (specifically, a work function of 3.8 eV or lower). Specific examples of such a cathode material include an element belonging to Group 1 or 2 in the periodic table, i.e., an alkali metal such as lithium (Li) or cesium (Cs), or an alkaline earth metal such as magnesium (Mg), calcium (Ca), or strontium (Sr); an alloy containing any of these (such as MgAg or AlLi); a rare earth metal such as europium (Eu) or ytterbium (Yb); an alloy containing such a rare earth metal; or the like. However, when the electron-injection layer is provided between the second electrode 104 and the electron-transport layer, the second electrode 104 can be formed using any of a variety of conductive materials such as Al, Ag, ITO, or indium oxide-tin oxide containing silicon or silicon oxide regardless of its work function. A film of such an electrically conductive material can be formed by a sputtering method, an inkjet method, a spin coating method, or the like.

Any of various methods can be employed for forming the EL layer 103 regardless of whether it is a dry process or a wet process. For example, a vacuum evaporation method, an inkjet method, a spin coating method or the like may be used. A different formation method may be used for each electrode or each layer.

Similarly, the electrodes may be formed by a wet process such as a sol-gel process or by a wet process using a metal paste. Alternatively, the electrodes may be formed by a dry method such as a sputtering method or a vacuum evaporation method.

In the light-emitting element having the above-described structure, current flows due to a potential difference made between the first electrode 102 and the second electrode 104, a hole and an electron recombines in the light-emitting layer 113 which includes a substance having a high light-emitting property, and light is emitted. That is, a light-emitting region is formed in the light-emitting layer 113.

The emitted light is extracted out through one or both of the first electrode 102 and the second electrode 104. Therefore, one or both of the first electrode 102 and the second electrode 104 are light-transmitting electrodes. In the case where only the first electrode 102 is a light-transmitting electrode, light is extracted from the substrate side through the first electrode 102. Meanwhile, when only the second electrode 104 is a light-transmitting electrode, light is extracted from the side opposite to the substrate side through the second electrode 104. In a case where each of the first electrode 102 and the second electrode 104 is a light-transmitting electrode, light is extracted from both of the substrate side and the side opposite to the substrate through the first electrode 102 and the second electrode 104.

The structure of the layers provided between the first electrode 102 and the second electrode 104 is not limited to the aforementioned one. However, it is preferable that a light-emitting region where holes and electrons recombine be positioned away from the first electrode 102 and the second electrode 104 so as to prevent quenching due to the proximity of the light-emitting region and a metal used for electrodes and carrier-injection layers. The order of stacking the layers is not limited to the above, and the following order, which is opposite to that in FIG. 1A, may be employed: the second electrode, the electron-injection layer, the electron-transport layer, the light-emitting layer, the hole-transport layer, the hole-injection layer, and the first electrode from the substrate side.

In addition, as for the hole-transport layer or the electron-transport layer in direct contact with the light-emitting layer, particularly a carrier-transport layer in contact with a side closer to a light-emitting region in the light-emitting layer 113, in order to suppress energy transfer from an exciton which is generated in the light-emitting layer, it is preferable that the energy gap thereof be wider than the energy gap of the light-emitting substance included in the light-emitting layer or the energy gap of the emission center substance included in the light-emitting layer.

The light-emitting element in this embodiment includes the hole-injection layer 111 including the composite material described in Embodiment 1. The composite material described in Embodiment 1 has a high carrier-injection property; accordingly, a light-emitting element driven at a low driving voltage can be fabricated. In addition, a film formed using the composite material has a good quality and crystallization is barely likely to occur; accordingly, a light-emitting element with high reliability can be fabricated. Moreover, even when a thick film of the composite material is used, the driving voltage is barely likely to increase; accordingly, even when the first electrode 102 has an uneven surface, formation of the hole-injection layer 111 having an appropriate thickness over the first electrode 102 can suppress a defect due to the unevenness, so that a light-emitting element with high reliability can be provided.

Since the composite material described in Embodiment 1 has a high light-transmitting property, a light-emitting element with high current efficiency can be provided. Further, since the composite material described in Embodiment 1 has an excellent carrier balance, a light-emitting element with high current efficiency can be provided.

(Embodiment 3)

This embodiment shows an embodiment of a light-emitting element having a structure in which a plurality of light-emitting units are stacked (hereinafter this type of light-emitting element is also referred to as a stacked element) with reference to FIG. 1B. This light-emitting element is a light-emitting element including a plurality of light-emitting units between a first electrode and a second electrode. For the light-emitting units, a structure similar to that of the EL layer 103 described in Embodiment 2 can be used. That is, the light-emitting element described in Embodiment 2 is a light-emitting element having one light-emitting unit, whereas a light-emitting element described in this embodiment has a plurality of light-emitting units. Note that the hole-injection layer in this embodiment is not necessarily formed using the composite material described in Embodiment 1.

In the case where the hole-injection layer is not formed using the composite material, the hole-injection layer includes a substance having a high hole-injection property. For example, molybdenum oxide, vanadium oxide, ruthenium oxide, tungsten oxide, manganese oxide, or the like can be used. In addition, the hole-injection layer can also be formed using a phthalocyanine-based compound such as phthalocyanine (abbreviation: $H_2Pc$) or copper phthalocyanine (abbreviation: CuPc), an aromatic amine compound such as 4,4'-bis[N-(4-diphenylaminophenyl)-N-phenylamino]biphenyl (abbreviation: DPAB) or N,N'-bis[4-[bis(3-methylphenyl)amino]phenyl]-N,N'-diphenyl-[1,1'-biphenyl]-4,4'-diamine (abbreviation: DNTPD), a high molecular compound such as poly(ethylenedioxythiophene)/poly(styrenesulfonic acid) (PEDOT/PSS), or the like.

Alternatively, the hole-injection layer can be formed using a composite material including a substance having a high hole-transport property and an electron-accepting substance. Examples of the electron-accepting substance include 7,7,8,8-tetracyano-2,3,5,6-tetrafluoroquinodimethane (abbreviation: $F_4$-TCNQ), chloranil, and transition metal oxides. In addition, an oxide of a metal belonging to Group 4 to Group 8 of the periodic table can be used. Specifically, vanadium oxide, niobium oxide, tantalum oxide, chromium oxide, molybdenum oxide, tungsten oxide, manganese oxide, and rhenium oxide are preferable since their electron-accepting property is high. Molybdenum oxide is particularly preferable among the above oxides, because it is stable in the air, has a low hygroscopic property, and is easy to handle.

As the substance having a high hole-transport property included in the composite material, any of various organic compounds can be used, such as an aromatic amine compound, a carbazole compound, aromatic hydrocarbon, and a high molecular compound (such as an oligomer, a dendrimer, or a polymer). The organic compound included in the composite material is preferably an organic compound having a high hole-transport property. Specifically, a substance having a hole mobility of $10^{-6}$ $cm^2V \cdot s$ or higher is preferably used. However, any other substance may be used as long as the substance has a high hole-transport property than an electron-transport property.

Figure 1B:
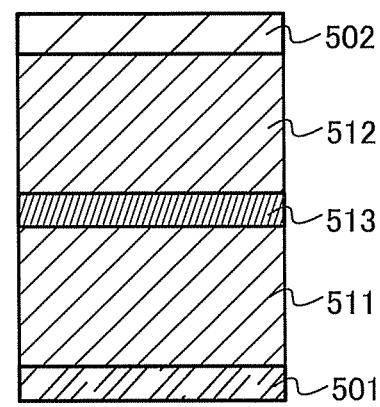

In FIG. 1B, a first light-emitting unit 511 and a second light-emitting unit 512 are stacked between a first electrode 501 and a second electrode 502, and a charge generation layer 513 is provided between the first light-emitting unit 511 and the second light-emitting unit 512. The first electrode 501 and the second electrode 502 correspond to the first electrode 102 and the second electrode 104 in Embodiment 2, respectively, and electrodes similar to those described in Embodiment 2 can be used as the first electrode 501 and the second electrode 502. Further, the first light-emitting unit 511 and the second light-emitting unit 512 may have the same structure or different structures. In addition, the charge generation layer 513 also serves as the hole-injection layer of the light-emitting unit 512 in some cases.

The charge generation layer 513 includes a composite material of an organic compound and a metal oxide. As the composite material of an organic compound and a metal oxide, it is possible to use the composite material described in Embodiment 1, i.e., the composite material of the hydrocarbon compound having the fluorene skeleton and the substance exhibiting an electron-accepting property with respect to the hydrocarbon compound.

The charge generation layer 513 may be formed by a combination of a layer including the composite material described in Embodiment 1 with a layer including another material. For example, the charge generation layer 513 may be formed by stacking the layer including the composite material described in Embodiment 1 and a layer including an electron-accepting substance and a compound having a high electron-transport property. Moreover, a layer including a composite material of an organic compound and a metal oxide may be combined with a transparent conductive film.

The charge generation layer 513 interposed between the first light-emitting unit 511 and the second light-emitting unit 512 may have any structure as long as electrons can be injected to a light-emitting unit on one side and holes can be injected to a light-emitting unit on the other side when voltage is applied between the first electrode 501 and the second electrode 502. For example, in FIG. 1B, any layer can be employed as the charge generation layer 513 as long as the layer injects electrons into the first light-emitting unit 511 and holes into the second light-emitting unit 512 when voltage is applied so that the potential of the first electrode is higher than that of the second electrode.

Although the light-emitting element having two light-emitting units is described in this embodiment, the present invention can be similarly applied to a light-emitting element in which three or more light-emitting units are stacked. As in the light-emitting element in this embodiment, a plurality of light-emitting units which are partitioned by the charge generation layer are arranged between a pair of electrodes, whereby the element can emit light in a high luminance region while current density is kept low. Since current density can be kept low, the element can have a long life. When the light-emitting element is applied for illumination, voltage drop due to resistance of an electrode material can be reduced, thereby achieving homogeneous light emission in a large area. Moreover, a light-emitting device with low power consumption, which can be driven at a low driving voltage, can be achieved.

The light-emitting units emit light having different colors from each other, thereby obtaining light emission of a desired color from the whole light-emitting element. For example, when an emission color of the first light-emitting unit and an emission color of the second light-emitting unit are made to be complementary colors (for example, blue and orange), it is possible to obtain a light-emitting element that emits white light from the whole light-emitting element. Note that the word "complementary" means color relationship in which an achromatic color is obtained when colors are mixed. That is, white light emission can be obtained by mixture of light from substances whose emission colors are complementary colors. Similarly in a light-emitting element having three light-emitting units, for example, white light emission can be obtained from the whole light-emitting element when emission colors of the first, second, and third light-emitting units are red, green, and blue, respectively.

In the light-emitting element in this embodiment, the composite material described in Embodiment 1 is used at least in the charge generation layer. The composite material described in Embodiment 1 has a high carrier-injection property; accordingly, a light-emitting element driven at a low driving voltage can be fabricated. In addition, a film formed using the composite material has a good quality and crystallization is barely likely to occur; accordingly, a light-emitting element with high reliability can be fabricated.

Since the composite material described in Embodiment 1 has a high light-transmitting property, a light-emitting element with high current efficiency can be provided. Further, since the composite material described in Embodiment 1 has an excellent carrier balance, a light-emitting element with high current efficiency can be provided.

Note that this embodiment can be combined with any of the other embodiments as appropriate.

(Embodiment 4)

This embodiment shows a light-emitting device including a light-emitting element which includes the composite material described in Embodiment 1.

Figure 2A:
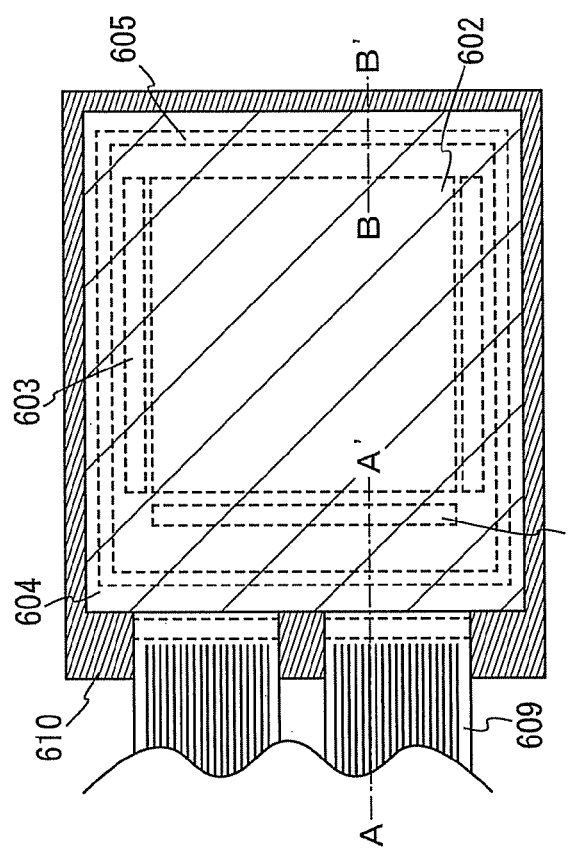
FIGS. 2A and 2B are conceptual diagrams of an active matrix light-emitting device.
Figure 2B:
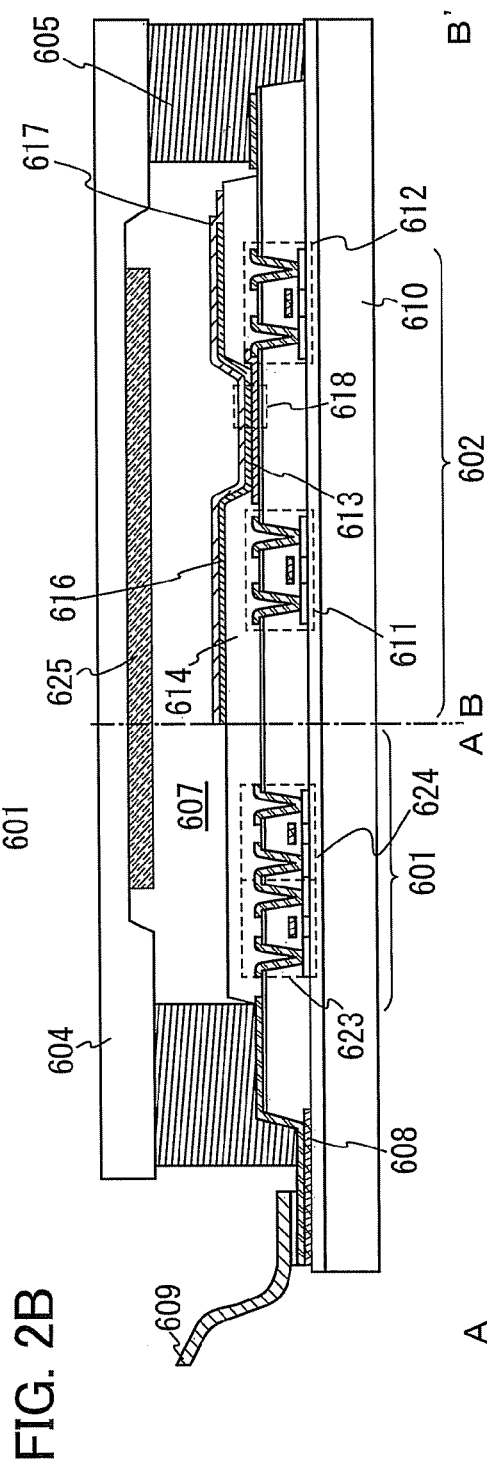

This embodiment shows an example of the light-emitting device fabricated using a light-emitting element including the composite material described in Embodiment 1 with reference to FIGS. 2A and 2B. Note that FIG. 2A is a top view illustrating the light-emitting device and FIG. 2B is a cross-sectional view taken along line A-A' and B-B' of FIG. 2A. The light-emitting device includes a driver circuit portion (source-side driver circuit) 601, a pixel portion 602, and a driver circuit portion (gate-side driver circuit) 603 which are illustrated with dotted lines. These portions control light emission of the light-emitting element. Moreover, a reference numeral 604 denotes a sealing substrate; 605, a sealing material; and 607, a space surrounded by the sealing material 605.

Reference numeral 608 denotes a wiring for transmitting signals to be inputted into the source-side driver circuit portion 601 and the gate-side driver circuit portion 603 and receiving signals such as a video signal, a clock signal, a start signal, and a reset signal from an FPC (flexible printed circuit) 609 serving as an external input terminal. Although the FPC is illustrated alone here, a printed wiring board (PWB) may be attached to the FPC. The light-emitting device in this specification includes, in its category, not only the light-emitting device itself but also the light-emitting device provided with the FPC or the PWB attached to the FPC.

Next, a cross-sectional structure is described with reference to FIG. 2B. The driver circuit portion and the pixel portion are formed over an element substrate 610. In this embodiment, the source-side driver circuit portion 601, which is the driver circuit portion, and one pixel of the pixel portion 602 are shown.

In the source-side driver circuit portion 601, a CMOS circuit is formed in which an n-channel TFT 623 and a p-channel TFT 624 are combined. Such a driver circuit may be formed by using various circuits such as a CMOS circuit, a PMOS circuit, or an NMOS circuit. Although this embodiment illustrates a driver-integrated type where the driver circuit is formed over the substrate, the present invention is not limited to this, and the driver circuit may be formed outside the substrate, not over the substrate.

The pixel portion 602 is formed with a plurality of pixels including a switching TFT 611, a current controlling TFT 612, and a first electrode 613 electrically connected with a drain of the current controlling TFT 612. An insulator 614 is formed to cover the end portions of the first electrode 613. Here, the insulator 614 is formed using a positive photosensitive acrylic resin film.

In order to improve the coverage, the insulator 614 is formed to have a curved surface with curvature at its upper or lower end portion. For example, in the case of using positive photosensitive acrylic for the insulator 614, only the upper end portion of the insulator 614 preferably has a curved surface with a radius of curvature of 0.2 μm to 3 μm. As the insulator 614, it is possible to use either a negative type which becomes insoluble in etchant by irradiation with light or a positive type which becomes soluble in etchant by irradiation with light.

A layer 616 including an organic compound and a second electrode 617 are formed over the first electrode 613. As a material used for the first electrode 613 which functions as an anode, a material having a high work function is preferably used. For example, it is possible to use a single-layer film of an ITO film, an indium tin oxide film including silicon, an indium oxide film including zinc oxide at 2 wt % to 20 wt %, a titanium nitride film, a chromium film, a tungsten film, a Zn film, a Pt film, or the like. Alternatively, it is possible to use a stack of a titanium nitride film and a film including aluminum as its main component, a stack of three layers of a titanium nitride film, a film including aluminum as its main component, and a titanium nitride film, or the like. The stacked-layer structure achieves low wiring resistance, favorable ohmic contact, and a function as an anode.

In addition, the layer 616 including an organic compound is formed by any of a variety of methods such as an evaporation method using an evaporation mask, an inkjet method, and a spin coating method. The layer 616 including an organic compound includes the composite material described in Embodiment 1. Further, the layer 616 including an organic compound may further include another material such as a low molecular compound or a high molecular compound (e.g., an oligomer or a dendrimer).

As a material used for the second electrode 617, which is formed over the layer 616 including an organic compound and serves as a cathode, a material having a low work function (such as Al, Mg, Li, Ca, or an alloy or compound thereof, such as MgAg, MgIn, or AlLi) is preferably used. In the case where light generated in the layer 616 including an organic compound passes through the second electrode 617, the second electrode 617 is preferably formed using a stack of a thin metal film and a transparent conductive film (ITO, indium oxide containing zinc oxide at 2 wt % to 20 wt %, indium tin oxide containing silicon, zinc oxide (ZnO), or the like).

Note that the light-emitting element is formed by the first electrode 613, the layer 616 including an organic compound, and the second electrode 617. The light-emitting element has any of the structures described in Embodiment 2 or 3. The pixel portion, which includes a plurality of light-emitting elements, in the light-emitting device of this embodiment may include both the light-emitting element having any of the structures described in Embodiment 2 or 3 and the light-emitting element having a structure other than those.

Further, a light-emitting element 618 is provided in the space 607 surrounded by the element substrate 610, the sealing substrate 604, and the sealing material 605 by pasting the sealing substrate 604 and the element substrate 610 using the sealing material 605. The space 607 may be filled with filler, and may be filled with an inert gas (such as nitrogen or argon), the sealing material 605, or the like.

An epoxy-based resin is preferably used for the sealing material 605. A material used for these is desirably a material which does not transmit moisture or oxygen as much as possible. As a material for the sealing substrate 604, a plastic substrate made of FRP (fiberglass-reinforced plastics), PVF (polyvinyl fluoride), polyester, acrylic, or the like can be used besides a glass substrate or a quartz substrate.

In this manner, it is possible to obtain the light-emitting device fabricated using the light-emitting element including the composite material described in Embodiment 1.

Since the light-emitting device in this embodiment is formed using the light-emitting element including the composite material described in Embodiment 1, a light-emitting device having favorable characteristics can be provided. Specifically, since the light-emitting element including the composite material described in Embodiment 1 has high emission efficiency, a light-emitting device with low power consumption can be provided. In addition, since a light-emitting element driven at a low driving voltage can be obtained, a light-emitting device driven at a low driving voltage can be provided. Further, since a light-emitting element with high reliability can be obtained, a light-emitting device with high reliability can be provided.

Figure 3A:
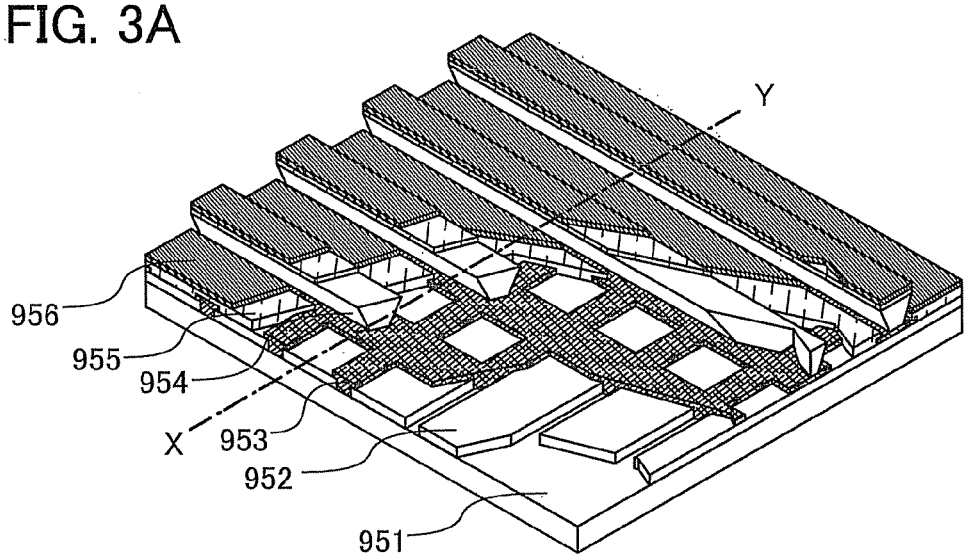
FIGS. 3A and 3B are conceptual diagrams of a passive matrix light-emitting device.
Figure 3B:
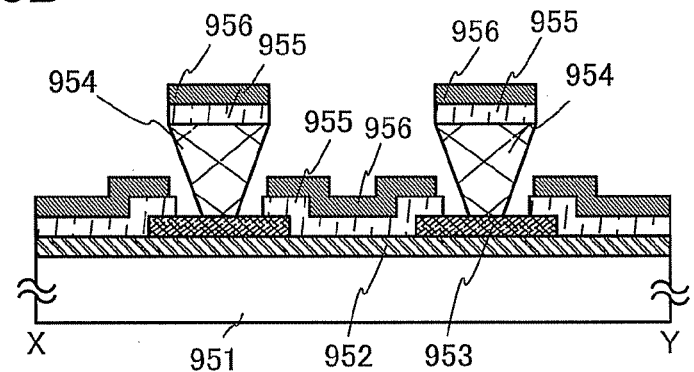

An active matrix light-emitting device is described above, whereas a passive matrix light-emitting device is described below. FIGS. 3A and 3B show views of a passive matrix light-emitting device fabricated using one embodiment of the present invention. FIG. 3A is a perspective view of the light-emitting device, and FIG. 3B is a cross-sectional view taken along line X-Y in FIG. 3A. In FIGS. 3A and 3B, an electrode 952 and an electrode 956 are provided over a substrate 951, and a layer 955 including an organic compound is provided between the electrodes 952 and 956. An end portion of the electrode 952 is covered with an insulating layer 953. A partition layer 954 is provided over the insulating layer 953. The side surfaces of the partition layer 954 are aslope such that the distance between both side surfaces is gradually narrowed toward the surface of the substrate. That is, a cross section in a short side of the partition layer 954 is a trapezoidal shape, and a lower side (the side is in contact with the insulating layer 953) is shorter than an upper side (the side is not in contact with the insulating layer 953). By providing the partition layer 954 in this manner, defects of the light-emitting element due to static charge and the like can be prevented. The passive matrix light-emitting device can also be operated with low power consumption by including the light-emitting element described in Embodiment 2 or 3, which includes the composite material described in Embodiment 1 and accordingly is driven at a low driving voltage. In addition, the light-emitting device can be driven with low power consumption by including the light-emitting element described in Embodiment 2 or 3, which includes the composite material described in Embodiment 1 and accordingly has high emission efficiency.

Since many minute light-emitting elements arranged in matrix in the light-emitting device described above can each be controlled, the light-emitting device can be suitably used as a display device for displaying images.

(Embodiment 5)

This embodiment shows electronic devices each including, as a part thereof, the light-emitting element described in Embodiment 2 or 3. The light-emitting element described in Embodiment 2 or 3 is a light-emitting element with high emission efficiency by including the composite material described in Embodiment 1, and accordingly is a light-emitting element with reduced power consumption; therefore, the electronic devices described in this embodiment can be electronic devices each including a light-emitting portion with reduced power consumption. In addition, the electronic devices can be electronic devices driven at a low driving voltage since the light-emitting element described in Embodiment 2 or 3 is a light-emitting element driven at a low driving voltage.

Examples of the electronic devices to which the above light-emitting element is applied include television devices (also referred to as TV or television receivers), monitors for computers and the like, cameras such as digital cameras and digital video cameras, digital photo frames, cellular phones (also referred to as mobile phones or mobile phone devices), portable game machines, portable information terminals, audio playback devices, large game machines such as pin-ball machines, and the like. Specific examples of these electronic devices are described below.

Figure 4A:
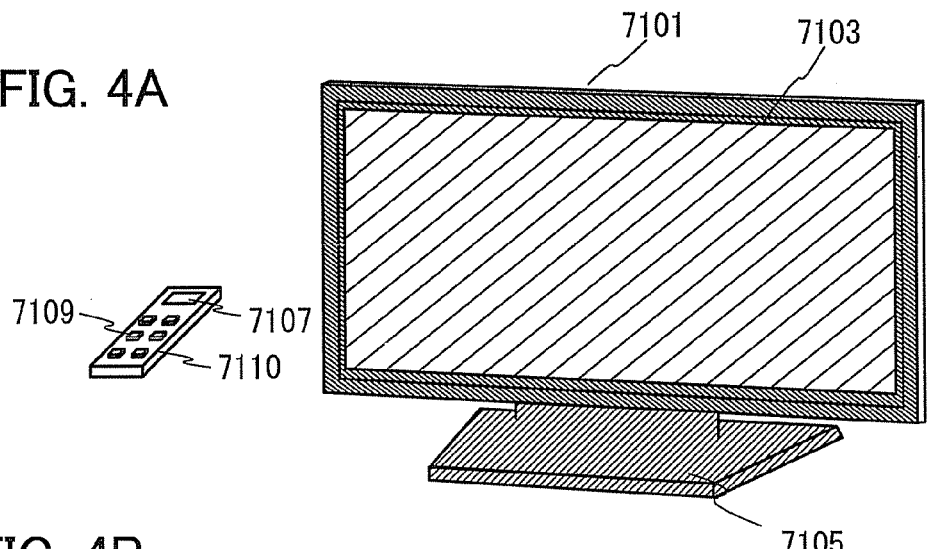
FIGS. 4A to 4D each illustrate an electronic device.

FIG. 4A illustrates an example of a television device. In the television device, a display portion 7103 is incorporated in a housing 7101. In addition, here, the housing 7101 is supported by a stand 7105. Images can be displayed on the display portion 7103, and in the display portion 7103, light-emitting elements similar to those described in Embodiment 2 or 3 are arranged in matrix. The light-emitting elements can have high emission efficiency because the light-emitting elements include the composite material described in Embodiment 1. In addition, a light-emitting element driven at a low driving voltage can be provided. Therefore, the television device having the display portion 7103 which includes the light-emitting elements consumes less power. In addition, a television device driven at a low driving voltage can be provided.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, general television broadcasting can be received. Moreover, when the display device is connected to a communication network with or without wires via the modem, one-way (from a sender to a receiver) or two-way (between a sender and a receiver or between receivers) information communication can be performed.

Figure 4B:
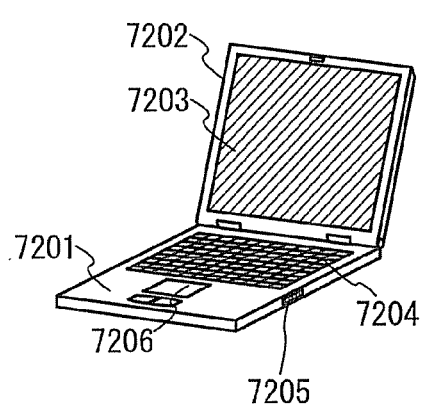

FIG. 4B illustrates a computer, which includes a main body 7201, a housing 7202, a display portion 7203, a keyboard 7204, an external connection port 7205, a pointing device 7206, and the like. Note that this computer is formed using light-emitting elements similar to those described in Embodiment 2 or 3 arranged in matrix, for the display portion 7203. The light-emitting elements can have high emission efficiency because each light-emitting element includes the composite material described in Embodiment 1. In addition, a light-emitting element driven at a low driving voltage can be provided. Therefore, this computer having the display portion 7203 which includes the light-emitting elements consumes less power. In addition, a computer driven at a low driving voltage can be provided.

Figure 4C:
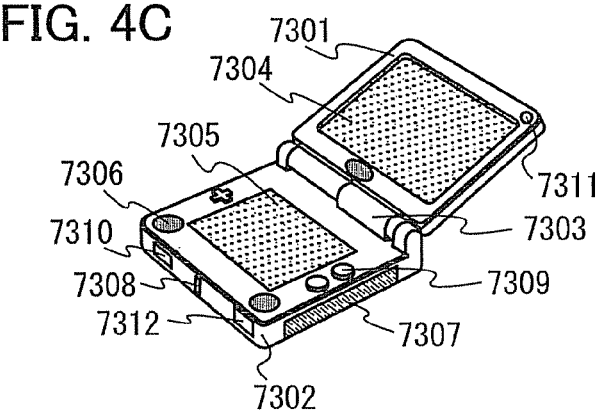

FIG. 4C illustrates a portable game machine, which includes two housings, a housing 7301 and a housing 7302, connected to each other via a joint portion 7303 so that the portable game machine can be opened or closed. The housing 7301 incorporates a display portion 7304 which includes light-emitting elements similar to those described in Embodiment 2 or 3 arranged in matrix, and the housing 7302 incorporates a display portion 7305. In addition, the portable game machine illustrated in FIG. 4C includes a speaker portion 7306, a recording medium insertion portion 7307, an LED lamp 7308, input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, electric current, voltage, electric power, radiation, flow rate, humidity, gradient, oscillation, odor, or infrared rays), and a microphone 7312), and the like. Needless to say, the structure of the portable games machine is not limited to the above as far as the display portion including light-emitting elements similar to those described in Embodiment 2 or 3 arranged in a matrix is used as at least either the display portion 7304 or the display portion 7305, or both, and the structure can include other accessories as appropriate. The portable game machine illustrated in FIG. 4C has a function of reading out a program or data stored in a storage medium to display it on the display portion, and a function of sharing information with another portable game machine by wireless communication. Note that the portable game machine illustrated in FIG. 4C can have a variety of functions without limitation to those above. The portable game machine having the display portion 7304 can consume less power, since the light-emitting elements used in the display portion 7304 include the composite material described in Embodiment 1 and have high emission efficiency. In addition, since the light-emitting elements used in the display portion 7304 include the composite material described in Embodiment 1 and thus can be driven at a low driving voltage, the portable game machine can also be driven at a low driving voltage.

Figure 4D:
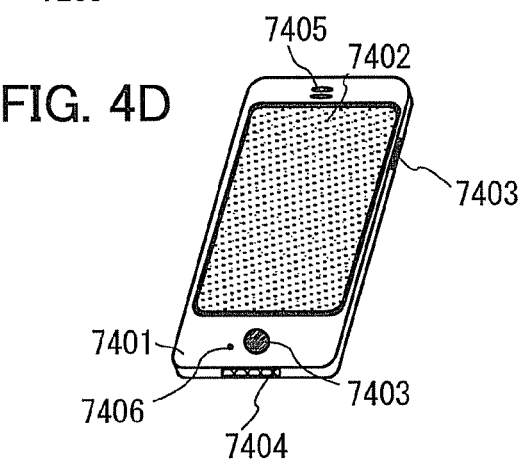

FIG. 4D illustrates an example of a cellular phone. The cellular phone is provided with a display portion 7402 incorporated in a housing 7401, operation buttons 7403, an external connection port 7404, a speaker 7405, a microphone 7406, and the like. Note that the cellular phone 7400 has the display portion 7402 including light-emitting elements similar to those described in Embodiment 2 or 3 arranged in matrix. The light-emitting elements include the composite material described in Embodiment 1 and thus can have high emission efficiency. In addition, a light-emitting element driven at a low driving voltage can be provided. Therefore, the cellular phone having the display portion 7402 which includes the light-emitting elements consumes less power. In addition, a cellular phone driven at a low driving voltage can be provided.

When the display portion 7402 of the cellular phone illustrated in FIG. 4D is touched with a finger or the like, data can be input into the cellular phone. In this case, operations such as making a call and creating e-mail can be performed by touch on the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or creating e-mail, a text input mode mainly for inputting text is selected for the display portion 7402 so that text displayed on a screen can be inputted. In that case, it is preferable to display a keyboard or number buttons on almost all the area of the screen of the display portion 7402.

When a detection device which includes a sensor for detecting inclination, such as a gyroscope or an acceleration sensor, is provided inside the cellular phone, the direction of the cellular phone (whether the cellular phone is placed horizontally or vertically for a landscape mode or a portrait mode) is determined so that display on the screen of the display portion 7402 can be automatically switched.

The screen modes are switched by touching the display portion 7402 or operating the operation buttons 7403 of the housing 7401. Alternatively, the screen modes can be switched depending on kinds of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed within a specified period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal authentication can be performed. Further, by providing a backlight or a sensing light source which emits a near-infrared light in the display portion, an image of a finger vein, a palm vein, or the like can be taken.

Note that the structure described in this embodiment can be combined with any of the structures described in Embodiments 1 to 4 as appropriate.

As described above, the application range of the light-emitting device including the light-emitting elements, such as the light-emitting element described in Embodiment 2 or 3, which includes the composite material described in Embodiment 1, is extremely wide; therefore, the light-emitting device can be applied to electronic devices of a variety of fields. By using the light-emitting element including the composite material described in Embodiment 1, an electronic device with reduced power consumption can be provided. Further, an electronic device driven at a low driving voltage can be provided.

The light-emitting element described in Embodiment 2 or 3 can also be used for a lighting device. One mode of application of the light-emitting element described in Embodiment 2 or 3 to a lighting device is described with reference to FIG. 5. Note that the lighting device includes the light-emitting element described in Embodiment 2 or 3 as a light irradiation unit and at least includes an input-output terminal portion that supplies current to the light-emitting element. Further, the light-emitting element is preferably shielded from the outside atmosphere (especially water) by sealing.

Figure 5:
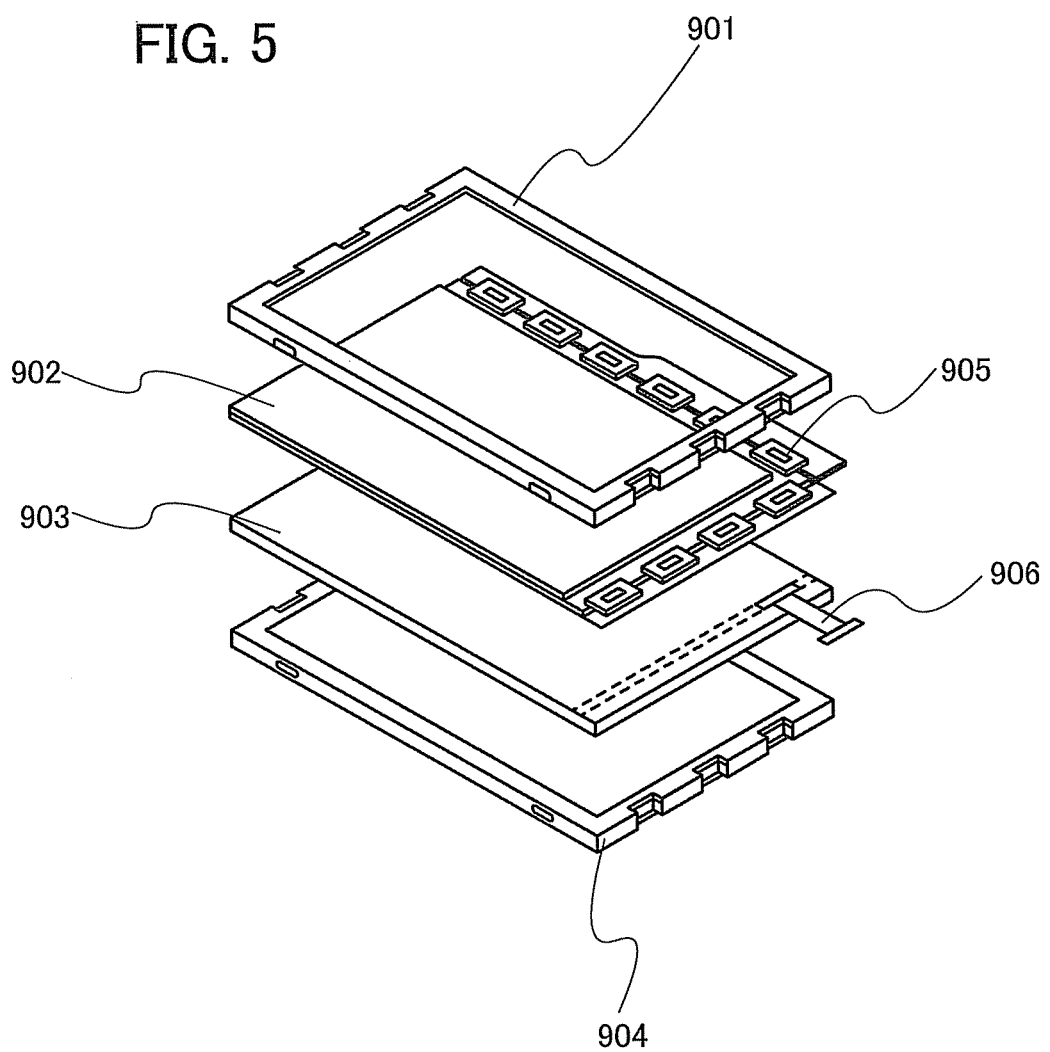
FIG. 5 illustrates an electronic device.

FIG. 5 illustrates an example of a liquid crystal display device using the light-emitting element described in Embodiment 2 or 3 for a backlight. The liquid crystal display device illustrated in FIG. 5 includes a housing 901, a liquid crystal layer 902, a backlight 903, and a housing 904. The liquid crystal layer 902 is connected to a driver IC 905. The light-emitting element described in Embodiment 2 or 3 is used in the backlight 903, to which current is supplied through a terminal 906.

The light-emitting element described in Embodiment 2 or 3 is used for the backlight of the liquid crystal display device, and thus a backlight with reduced power consumption can be obtained. By using the light-emitting element described in Embodiment 2 or 3, a planar lighting device can be fabricated, and the area can be increased. Thus, the area of the backlight can be increased, and the area of the liquid crystal display device can also be increased. Furthermore, the backlight formed using the light-emitting element described in Embodiment 2 or 3 can be thinner than a conventional one; accordingly, the display device can also be thinner.

Figure 6:
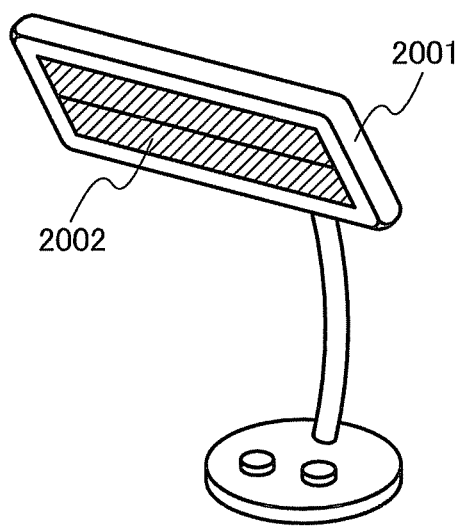
FIG. 6 illustrates a lighting device.

FIG. 6 illustrates an example in which the light-emitting element described in Embodiment 2 or 3 is used for a table lamp which is a lighting device. The table lamp illustrated in FIG. 6 includes a housing 2001 and a light source 2002, and the light-emitting element described in Embodiment 2 or 3 is used for the light source 2002.

Figure 7:
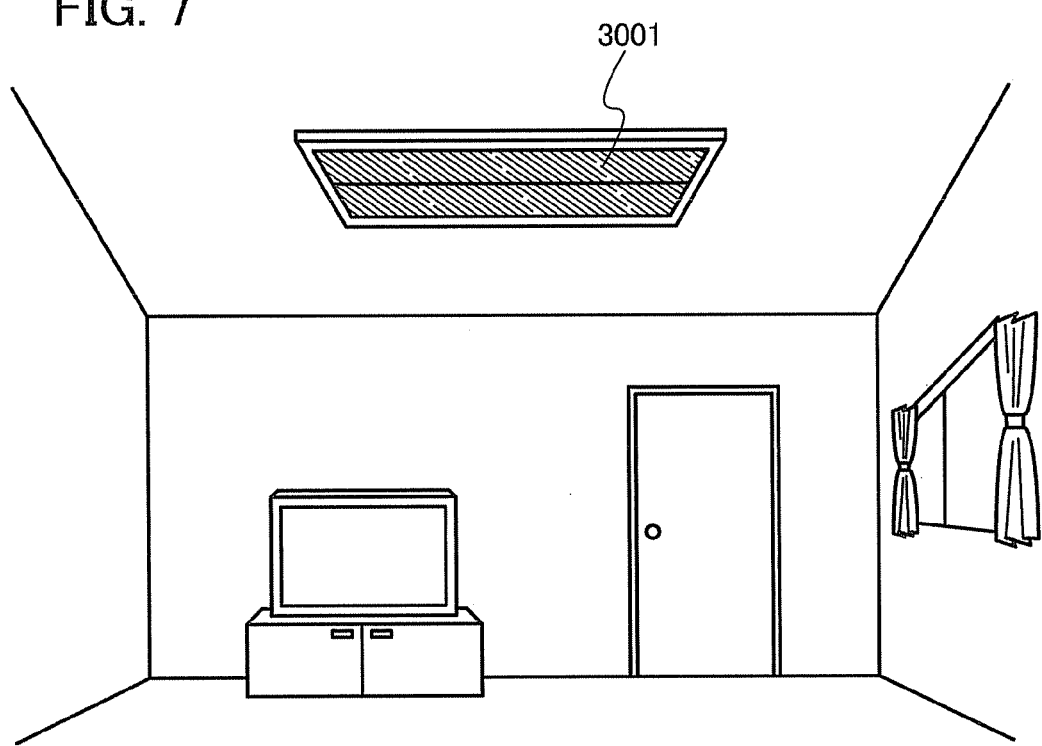
FIG. 7 illustrates a lighting device.

FIG. 7 illustrates an example in which the light-emitting element described in Embodiment 2 or 3 is used for an indoor lighting device 3001. Since the light-emitting element described in Embodiment 2 or 3 has reduced power consumption, a lighting device with reduced power consumption can be provided. Further, since the light-emitting element described in Embodiment 2 or 3 can have a large area, the light-emitting element can be used for a large-area lighting device. Furthermore, since the light-emitting element described in Embodiment 2 or 3 is thin, a lighting device having a reduced thickness can be fabricated.

Figure 8:
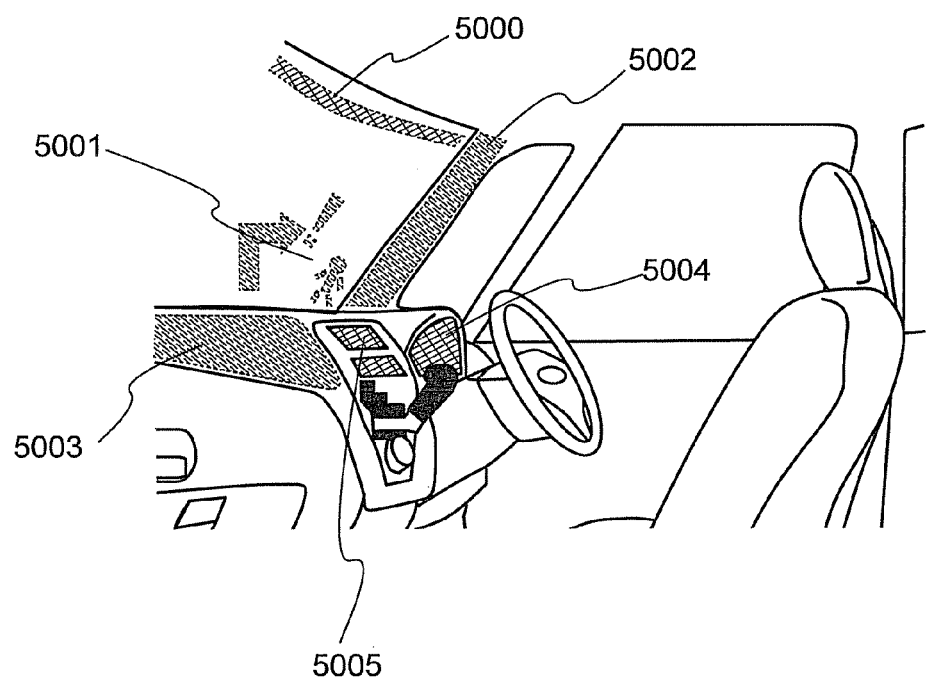
FIG. 8 illustrates car-mounted display devices and lighting devices.

The light-emitting element described in Embodiment 2 or 3 can also be used for an automobile windshield or an automobile dashboard. FIG. 8 illustrates one mode in which the light-emitting elements described in Embodiment 2 or 3 are used for an automobile windshield and an automobile dashboard. Displays 5000 to 5005 each include the light-emitting element described in Embodiment 2 or 3.

The display 5000 and the display 5001 are display devices provided in the automobile windshield and incorporate the light-emitting elements described in Embodiment 2 or 3. The light-emitting elements described in Embodiment 2 or 3 can be formed into so-called see-through display devices, through which the opposite side can be seen, by including a first electrode and a second electrode formed with electrodes having a light-transmitting property. Such see-through display devices can be provided even in the automobile windshield without hindering the vision. In addition, for example, when a transistor for driving the light-emitting element is provided, it is preferable to use a transistor having a light-transmitting property, such as an organic transistor using an organic semiconductor material or a transistor using an oxide semiconductor.

The display 5002 is a display device provided in a pillar portion and incorporates light-emitting element described in Embodiment 2 or 3. The display 5002 can compensate for the view hindered by the pillar portion by showing an image taken by an imaging unit provided in the car body. Similarly, the display 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see, makes it possible for the driver to confirm safety easily and comfortably.

The display 5004 and the display 5005 can provide a variety of kinds of information such as information of navigation, speedometer, tachometer, mileage, fuel meter, gearshift indicator, and air condition. The contents or layout of the display can be changed by a user as appropriate. Further, such information can be shown in the displays 5000 to 5003. Note that the displays 5000 to 5005 can also be used as lighting devices.

By including the composite material described in Embodiment 1, the light-emitting element described in Embodiment 2 or 3 can be driven at a low driving voltage and consume low power. Therefore, even when a large number of large screens are provided, such as the displays 5000 to 5005, load on a battery can be reduced, which provides comfortable use. Thus, the light-emitting device or the lighting device using the light-emitting element described in Embodiment 2 or 3 can be suitably used as an in-vehicle light-emitting device or lighting device.

(Embodiment 6)

Figure 29A:
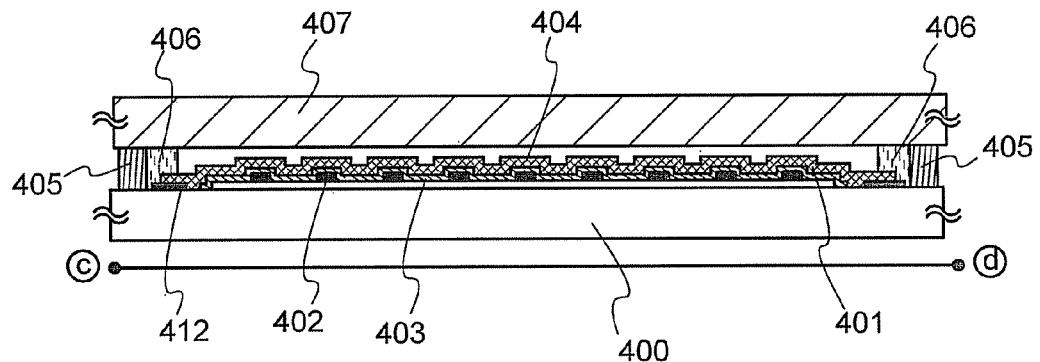
FIGS. 29A and 29B illustrate a lighting device.
Figure 29B:
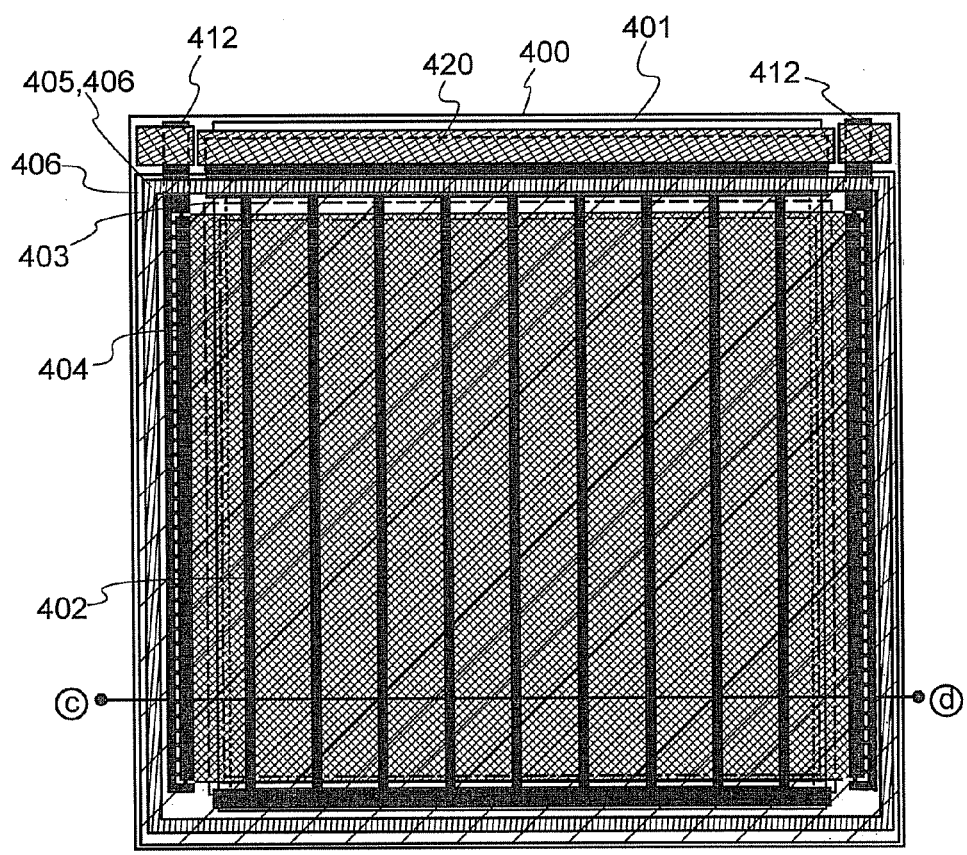

This embodiment shows an example in which a light-emitting element fabricated using the composite material described in Embodiment 1 is used for a lighting device with reference to FIGS. 29A and 29B. FIG. 29B is a top view of the lighting device, and FIG. 29A is a cross-sectional view taken along line c-d in FIG. 29B.

In the lighting device in this embodiment, a first electrode 401 is formed over a substrate 400 which is a support and has a light-transmitting property. The substrate 400 and the first electrode 401 correspond to the substrate 101 and the first electrode 102 in Embodiment 2, respectively.

An auxiliary wiring 402 is provided over the first electrode 401. Since this embodiment shows an example in which light emission is extracted through the first electrode 401 side, the first electrode 401 is formed using a material having a light-transmitting property. The auxiliary wiring 402 is provided in order to compensate for low conductivity of the material having a light-transmitting property, and has a function of suppressing luminance unevenness in a light emission surface due to voltage drop caused by high resistance of the first electrode. 401. The auxiliary wiring 402 is formed using a material having at least higher conductivity than the material of the first electrode 401, and is preferably formed using a material having high conductivity such as aluminum. Note that surfaces of the auxiliary wiring 402 other than a portion thereof in contact with the first electrode 401 are preferably covered with an insulating layer. This is for suppressing light emission over the upper portion of the auxiliary wiring 402, which cannot be extracted, for reducing a reactive current, and for suppressing reduction in power efficiency.

Note that a pad 412 for applying voltage to a second electrode 404 may be formed concurrently with the formation of the auxiliary wiring 402.

An EL layer 403 is formed over the first electrode 401 and the auxiliary wiring 402. The EL layer 403 includes the composite material described in Embodiment 1. The EL layer 403 corresponds to the structure of the EL layer 103 in Embodiment 2, or the structure in which the light-emitting units 511 and 512 and the charge generation layer 513 in Embodiment 3 are combined, so that the corresponding description is to be referred to. Note that the EL layer 403 is preferably formed to be slightly larger than the first electrode 401 when seen from above so as to also serve as an insulating layer that suppresses a short circuit between the first electrode 401 and the second electrode 404.

The second electrode 404 is formed to cover the EL layer 403. The second electrode 404 corresponds to the second electrode 104 in Embodiment 2 and has a similar structure. In this embodiment, it is preferable that the second electrode 404 be formed using a material having high reflectance because light emission is extracted through the first electrode 401 side. In this embodiment, the second electrode 404 is connected to the pad 412, whereby voltage is applied.

As described above, the lighting device described in this embodiment includes a light-emitting element including the first electrode 401, the EL layer 403, and the second electrode 404 (and the auxiliary electrode 402). Since the light-emitting element has high emission efficiency, the lighting device in this embodiment can be a lighting device with low power consumption. In addition, since the light-emitting element has high reliability, the lighting device in this embodiment can be a lighting device with high reliability.

The light-emitting element having the above structure is fixed to a sealing substrate 407 with sealing materials 405 and 406 and sealing is performed, whereby the lighting device is completed. It is possible to use only either the sealing material 405 or the sealing material 406. In addition, the inner sealing material 406 can be mixed with a desiccant, whereby moisture is adsorbed and the reliability is increased.

When parts of the pad 412, the first electrode 401, and the auxiliary wiring 402 are extended to the outside of the sealing materials 405 and 406, the extended parts can serve as external input terminals. An IC chip 420 mounted with a converter or the like may be provided over the external input terminals.

In the above manner, the lighting device described in this embodiment includes a light-emitting element including the composite material described in Embodiment 1, and thus can be a lighting device with low power consumption. Alternatively, a lighting device with high reliability can be provided. Further alternatively, a lighting device with a long life can be provided.

Example 1

Example 1 exemplifies a composite material described in Embodiment 1, i.e., a composite material in which 9-[4-(9-phenylfluoren-9-yl)phenyl]-10-phenylanthracene (abbreviation: FLPAnth) represented by the following structural formula (124) is used as a fluorene derivative and molybdenum oxide is used as an inorganic compound that can accept electrons from FLPAnth.

First, a glass substrate was fixed to a substrate holder in a vacuum evaporation apparatus. Then, FLPAnth and molybdenum(VI) oxide were separately put in different resistance-heating evaporation sources and co-evaporated in a vacuum state (this method is referred to as a co-evaporation method), so that a film formed using a composite material containing FLPAnth and molybdenum oxide was formed. At this time, three kinds of films were formed by adjusting evaporation rates such that the weight ratios of FLPAnth to molybdenum oxide were 4:2 (=FLPAnth:molybdenum oxide), 4:1, and 4:0.5. Note that the thickness of each film was 50 nm.

Figure 9:
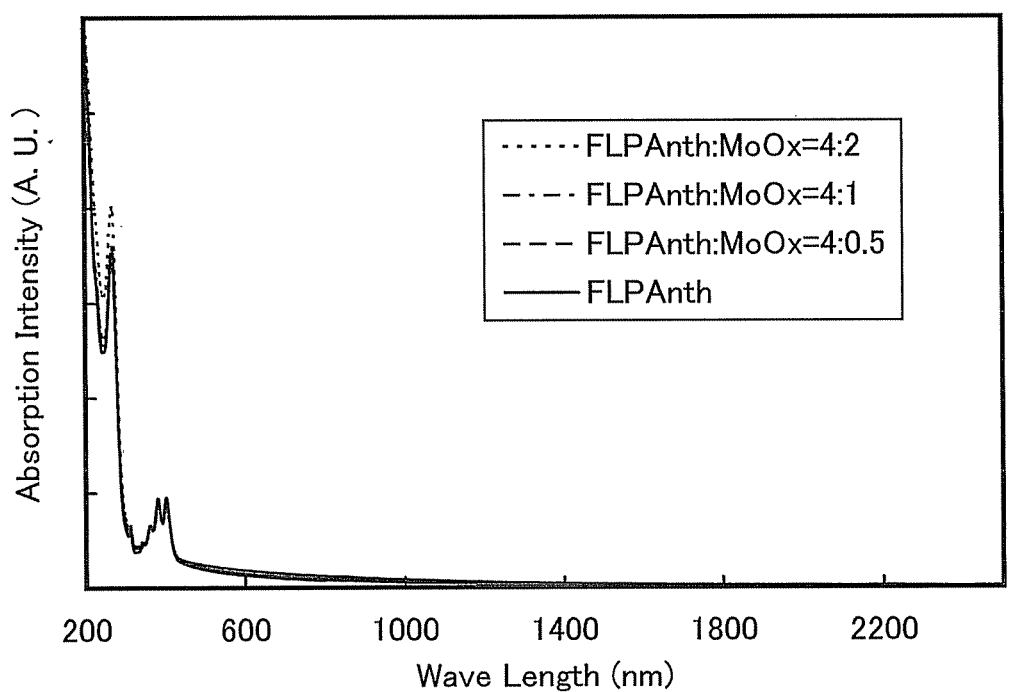
FIG. 9 shows absorption spectra of a thin film of FLPAnth and of thin films of composite materials including FLPAnth.

Absorption spectra of the three kinds of films formed using the composite materials were measured by using Spectrophotometer, manufactured by Hitachi High-Technologies Corporation (U-4000) and are shown in FIG. 9. FIG. 9 also shows an absorption spectrum that was similarly measured using a film (50 nm thick) formed by evaporating only FLPAnth, and molybdenum oxide was not evaporated simultaneously. In FIG. 9, the horizontal axis indicates wave length (nm) and the vertical axis indicates absorption intensity (arbitrary unit).

FIG. 9 indicates that the film formed by evaporating only FLPAnth has a high light-transmitting property with a little absorption of light in most of the visible light region. In addition, it is found that the films formed using the composite materials of FLPAnth and molybdenum oxide also have a high light-transmitting property with a little absorption of light in most of the visible light region. The absorption spectrum of the film formed by evaporating only FLPAnth and the other absorption spectra do not differ largely, and the absorption spectra do not differ even when the proportion of molybdenum oxide is high; therefore, it is also found that absorption based on charge transfer does not occur in films formed using the composite materials of FLPAnth and molybdenum oxide. It is known that the absorption based on charge transfer occurs in the visible light region and the infrared region, and the occurrence of the absorption means light absorption, i.e., reduction in emission efficiency of a light-emitting element fabricated using any of the films. However, the film formed using the composite materials of FLPAnth and molybdenum oxide described in this example do not cause such absorption; therefore, reduction in emission efficiency caused by the composite materials absorbing light inside the element is barely likely to occur. Further, a light-emitting element with high emission efficiency can be easily fabricated using the film as a material:

Example 2

Example 2 shows a light-emitting element (light-emitting element 1) in which a hole-injection layer is formed with a co-evaporation film of the composite material described in Embodiment 1, which contains 9-[4-(9-phenyl-fluoren-9-yl) phenyl]-10-phenylanthracene (abbreviation: FLPAnth) and molybdenum oxide. As a comparative example, a light-emitting element (comparative light-emitting element 1) in which a hole-injection layer is formed with a co-evaporation film of 9-[4-(9-phenylcarbazol-3-yl)]phenyl-10-phenylanthracene (abbreviation: PCzPA) and molybdenum oxide was also fabricated, and Example 2 also shows the comparative light-emitting element 1.

The molecular structures of organic compounds used in this example are represented by the following structural formulas. In the element structure used, an electron-injection layer was provided between an electron-transport layer 114 and a second electrode 104 in the structure in FIG. 1A.

(124)

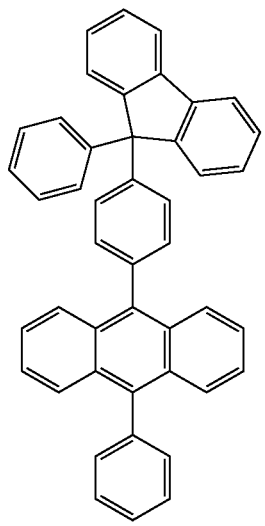

FLPAnth (i)

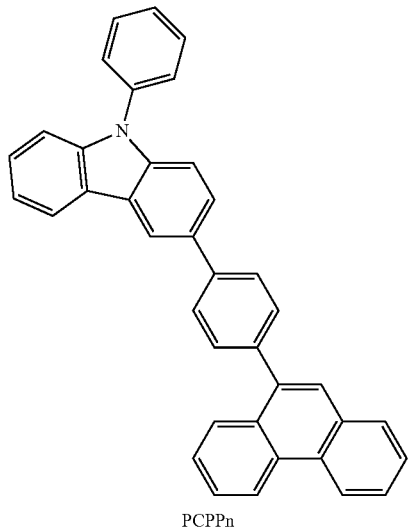

PCPPn

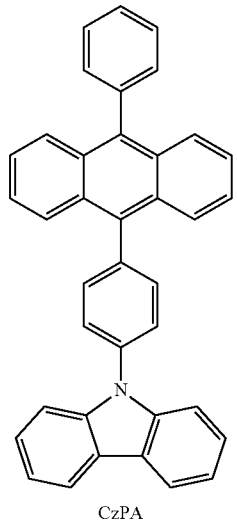

CzPA (ii)

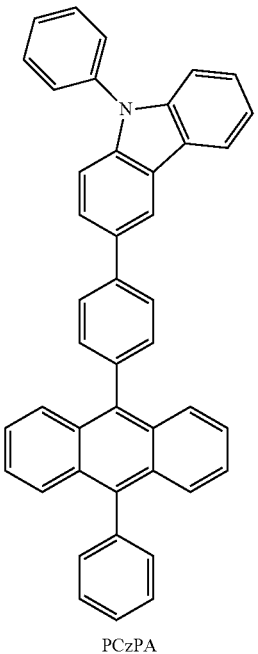

PCzPA (v)

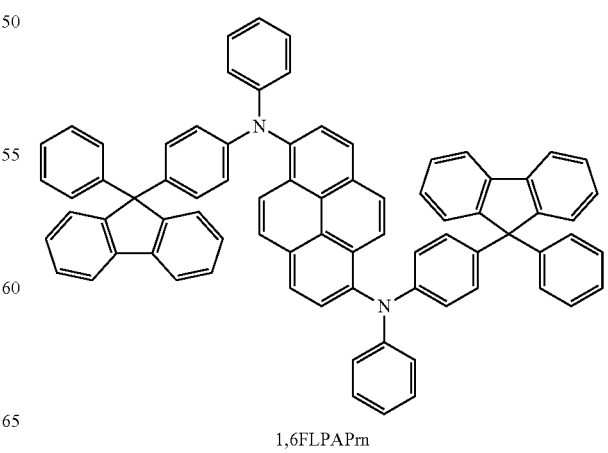

1,6FLPAPrn (iii)

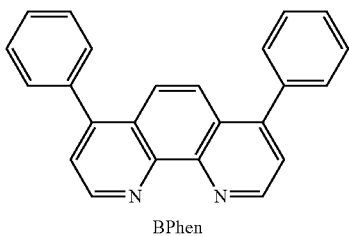

BPhen (iv)

[Fabrication of Light-Emitting Element 1 and Comparative Light-Emitting Element 1]

First, a glass substrate 101 was prepared, over which indium tin oxide containing silicon (ITSO) with a thickness of 110 nm was formed as a first electrode 102. A surface of the ITSO film was covered with a polyimide film such that an area of 2 mm×2 mm of the surface was exposed, which corresponded to the electrode area. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus in which the pressure was reduced to approximately $10^{-4}$ Pa, vacuum baking at 170° C. for 30 minutes was performed in a heating chamber of the vacuum evaporation apparatus, and then the substrate was cooled down for approximately 30 minutes.

Then, the substrate 101 was fixed on a holder provided in the vacuum evaporation apparatus such that the surface of the substrate 101 provided with ITSO faced downward.

The pressure in the vacuum evaporation apparatus was reduced to $10^{-4}$ Pa, and then FLPAnth represented by above the structural formula (124) and molybdenum(VI) oxide were co-evaporated by adjusting evaporation rates such that the weight ratios of FLPAnth to molybdenum oxide were 2:1, so that the hole-injection layer 111 was formed. The thickness was 50 nm. Note that a co-evaporation method is an evaporation method in which a plurality of different substances are concurrently vaporized from respective different evaporation sources.

Next, 9-{4-(9-H-9-phenylcarbazol-3-yl)-phenylyl}-phenanthrene (abbreviation: PCPPn) represented by the above structural formula (i) was deposited to a thickness of 10 nm, so that the hole-transport layer 112 was formed.

Further, over the hole-transport layer 112, 9-[4-(10-phenyl-9-anthryl)phenyl]-9H-carbazole (abbreviation: CzPA) represented by the above structural formula (ii) and N,N'-bis[4-(9-phenyl-9H-fluoren-9-yl)phenyl]-N,N'-diphenylpyrene-1,6-diamine (abbreviation: 1,6FLPAPrn) represented by the above structural formula (iii) were evaporated to a thickness of 30 nm by adjusting evaporation rates such that the weight ratios of CzPA to 1,6FLPAPrn were 1:0.05, so that the light-emitting layer 113 was formed.

Next, CzPA was evaporated to a thickness of 10 nm, and then bathophenanthroline (abbreviation: BPhen) represented by the above structural formula (iv) was evaporated to a thickness of 15 nm, so that the electron-transport layer 114 was formed. Further, lithium fluoride was evaporated to a thickness of 1 nm over the electron-transport layer 114, so that the electron-injection layer was formed. Finally, aluminum was deposited to a thickness of 200 nm as the second electrode 104 serving as a cathode, whereby the light-emitting element 1 was completed. Note that in the above evaporation process, evaporation was all performed by a resistance heating method.

The comparative light-emitting element 1 was fabricated in the same manner and to have the same structure as the light-emitting element 1 except that FLPAnth, which is one of materials included in the hole-injection layer 111 in the light-emitting element 1, was replaced by 9-[4-(9-phenylcarbazol-3-yl)]phenyl-10-phenylanthracene (abbreviation: PCzPA) represented by the above structural formula (v).

[Operation Characteristics of Light-Emitting Element 1 and Comparative Light-Emitting Element 1]

The thus obtained light-emitting element 1 and comparative light-emitting element 1 were put into a glove box under a nitrogen atmosphere, and the light-emitting elements were sealed so as not to be exposed to the air. Then, the operation characteristics of the light-emitting elements were measured. Note that the measurements were carried out at room temperature (in an atmosphere kept at 25° C.).

Figure 10:
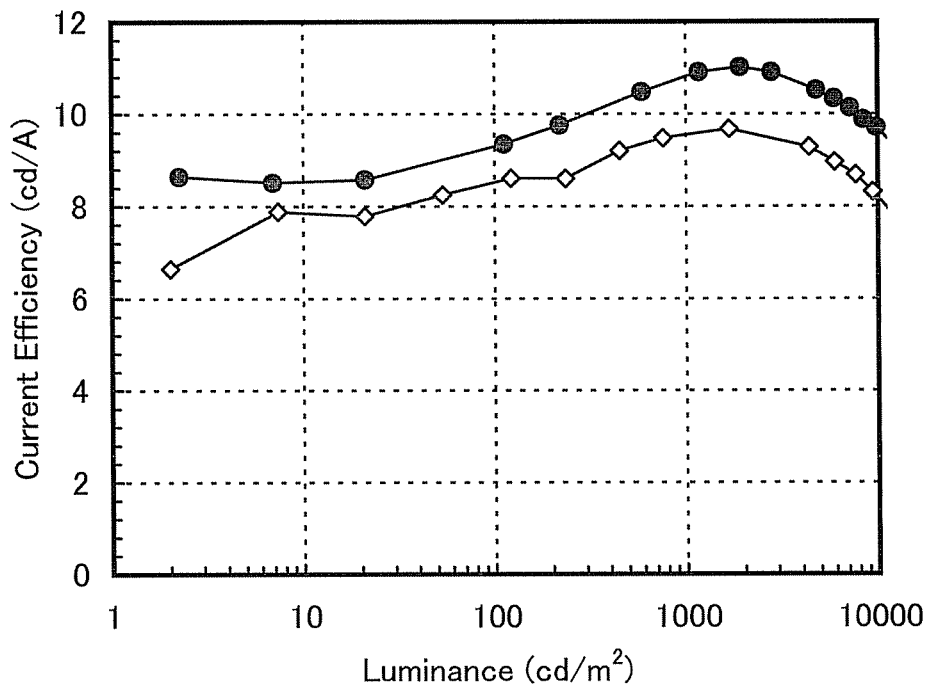
FIG. 10 shows luminance versus current efficiency characteristics of a light-emitting element 1 and a comparative light-emitting element 1.
Figure 11:
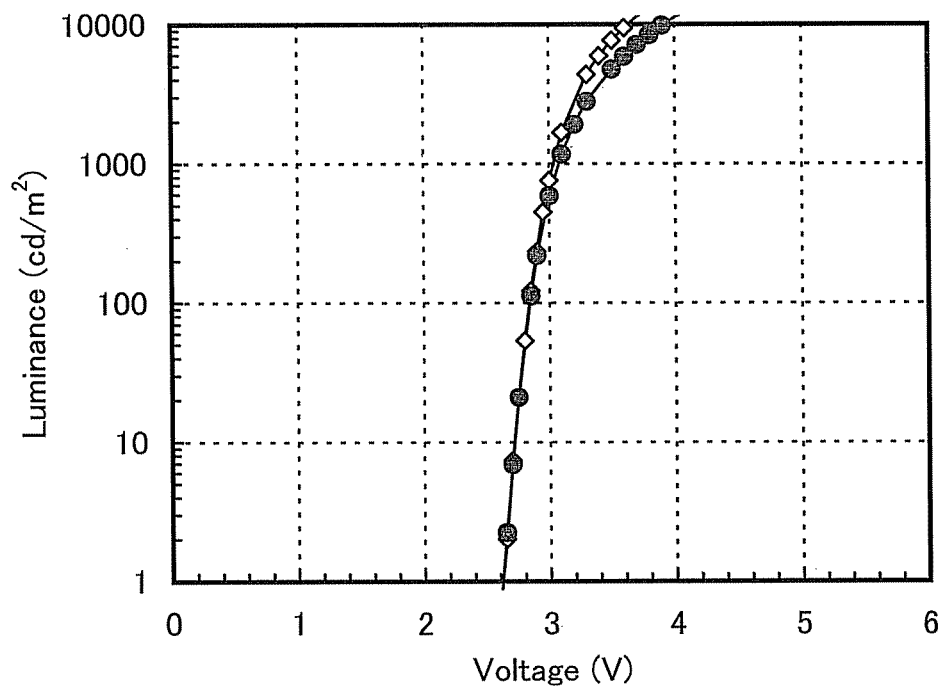
FIG. 11 shows voltage versus luminance characteristics of the light-emitting element 1 and the comparative light-emitting element 1.
Figure 12:
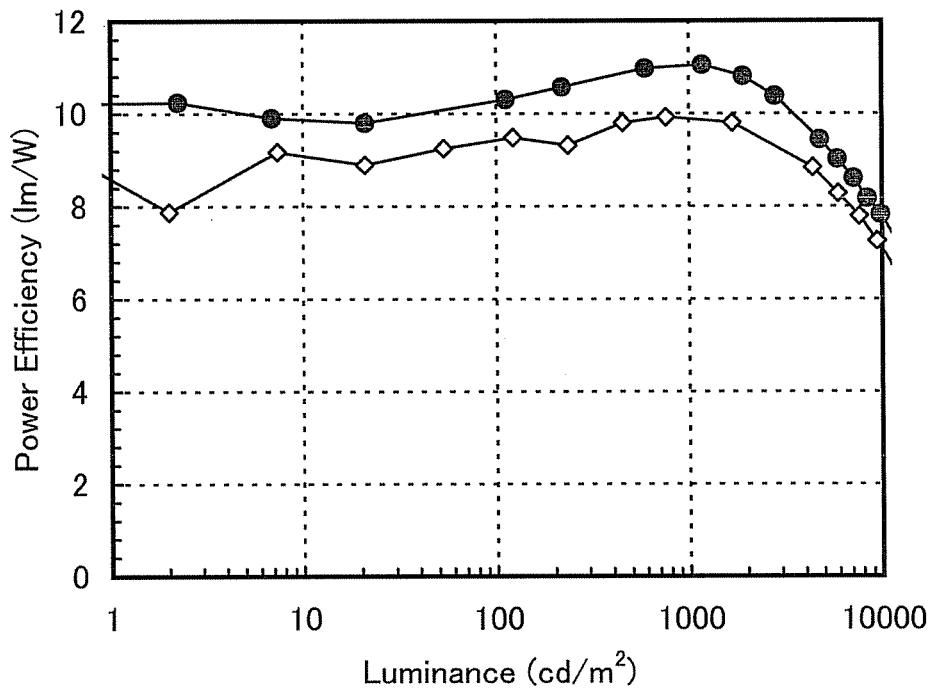
FIG. 12 shows luminance versus power efficiency characteristics of the light-emitting element 1 and the comparative light-emitting element 1.
Figure 13:
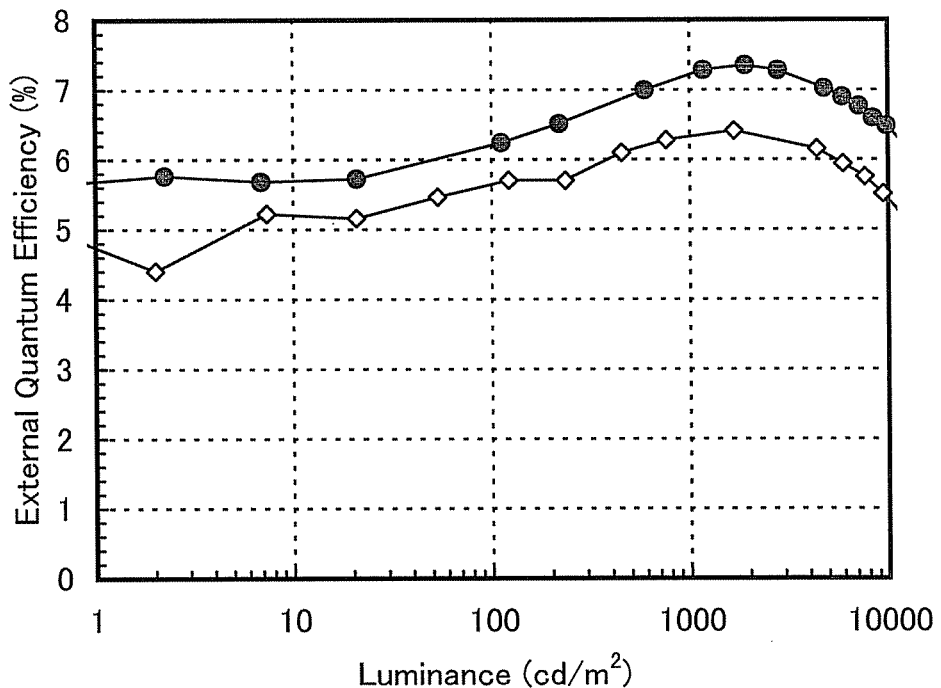
FIG. 13 shows luminance versus external quantum efficiency characteristics of the light-emitting element 1 and the comparative light-emitting element 1.

FIG. 10 shows luminance versus current efficiency characteristics of the light-emitting elements, FIG. 11 shows voltage versus luminance characteristics thereof, FIG. 12 shows luminance versus power efficiency characteristics thereof, and FIG. 13 shows luminance versus external quantum efficiency characteristics thereof. In FIG. 10, the vertical axis represents current efficiency (cd/A), and the horizontal axis represents luminance (cd/m$^2$). In FIG. 11, the vertical axis represents luminance (cd/m$^2$), and the horizontal axis represents voltage (V). In FIG. 12, the vertical axis represents power efficiency (lm/W), and the horizontal axis represents luminance (cd/m$^2$). In FIG. 13, the vertical axis represents external quantum efficiency (%), and the horizontal axis represents luminance (cd/m$^2$). Note that in FIG. 10, FIG. 11, FIG. 12, and FIG. 13, black circles represent characteristics of the light-emitting element 1, and white squares represent characteristics of the comparative light-emitting element 1.

FIG. 10 indicates that the light-emitting element 1 in which the composite material of the fluorene derivative FLPAnth and molybdenum oxide was used in the hole-injection layer has excellent luminance versus current efficiency characteristics as compared to the comparative light-emitting element 1 in which the composite material of PCzPA and molybdenum oxide was used in the same layer. Note that the light-emitting element 1 has large absolute values of luminance versus current efficiency characteristics, especially high efficiency at practical luminances (approximately 1000 cd/m$^2$ to 5000 cd/m$^2$). FIG. 12 and FIG. 13 show that the light-emitting element 1 has excellent luminance versus power efficiency characteristics and excellent luminance versus external quantum efficiency characteristics, also indicating that the light-emitting element 1 has high emission efficiency.

Figure 14:
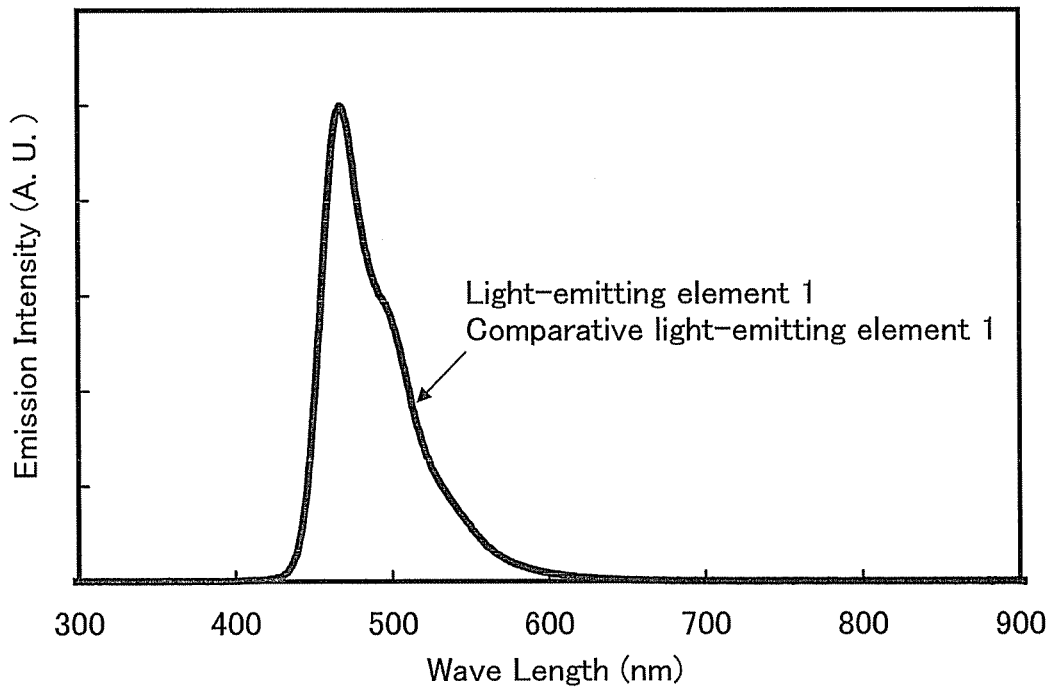
FIG. 14 shows emission spectra of the light-emitting element 1 and the comparative light-emitting element 1.

FIG. 14 shows emission spectra of the fabricated light-emitting element 1 and comparative light-emitting element 1 when a current of 1 mA was made to flow therein. In FIG. 14, the vertical axis represents emission intensity and the horizontal axis represents emission wave length (nm). The emission intensity is shown as a value relative to the greatest emission intensity assumed to be 1. As can be seen in FIG. 14, the emission spectra of the light-emitting element 1 and of the comparative light-emitting element 1 overlap with each other, and blue light originating from 1,6FLPAPrn, which is the emission center substance, was emitted from each element.

Table 1 shows main characteristics of the light-emitting element 1 and the comparative light-emitting element 1 around 1000 cd/m$^2$.

TABLE 1

| | Voltage (V) | Current (mA) | Current Efficiency (cd/A) | Power Efficiency (lm/W) | External Quantum Efficiency (%) |
|---|---|---|---|---|---|
| Comparative Light-emitting Element 1 | 3.6 | 0.65 | 7.1 | 6.2 | 4.7 |
| Light-emitting Element 1 | 3.1 | 0.43 | 11.0 | 11.0 | 7.3 |

Figure 15:
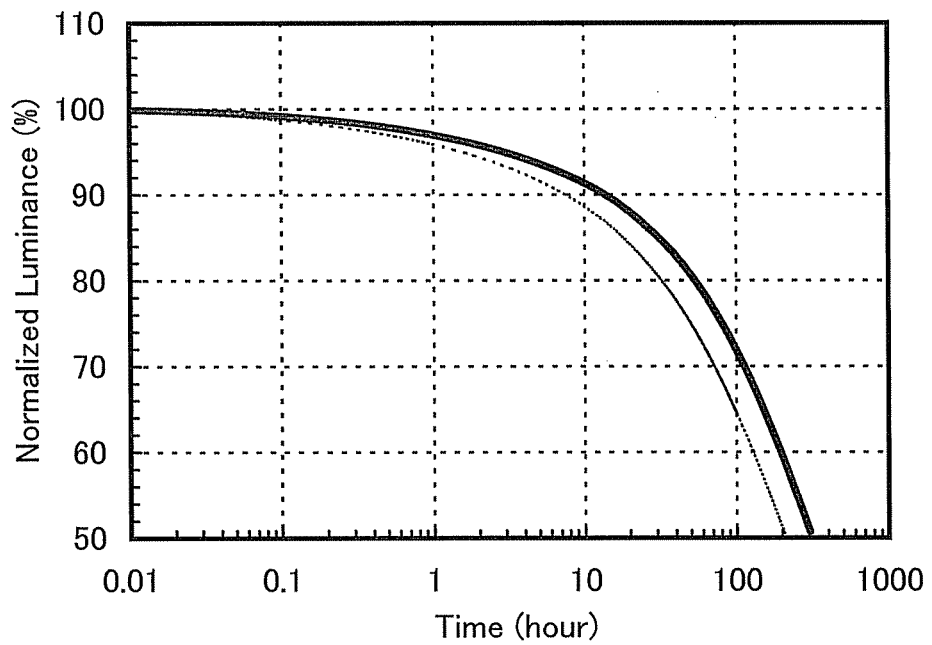
FIG. 15 shows time versus normalized luminance characteristics of the light-emitting element 1 and the comparative light-emitting element 1.

Next, the initial luminance was set at 5000 cd/m², the elements were driven under a condition where the current density was constant, and changes in luminance with respect to the driving time were examined. FIG. 15 shows time versus normalized luminance characteristics. From FIG. 15, it is found that both the light-emitting element 1 (solid line) and the comparative light-emitting element 1 (dotted line) have excellent characteristics despite the driving test at 5000 cd/m², a very high luminance, and thus have high reliability. Note that the light-emitting element 1 has a luminance half-life of approximately 300 hours, whereas the comparative light-emitting element 1 has a luminance half-life of approximately 200 hours; therefore, it is found that the life of the light-emitting element 1 is approximately 1.5 times as long as that of the comparative light-emitting element 1.

In the above manner, by merely replacing the organic compound included in the composite material in the hole-injection layer, the element has higher emission efficiency and approximately 1.5 times life. Therefore, it is found that the composite material which includes the hydrocarbon compound having the fluorene skeleton and the inorganic compound described in Embodiment 1 is suitable as a material included in a light-emitting element.

Example 3

Example 3 shows a method of synthesizing 9-phenyl-10-{4-(9-phenyl-9H-fluoren-9-yl)biphenyl-4'-yl}-anthracene (abbreviation: FLPPA) which can be used suitably as a fluorene derivative in the composite material described in Embodiment 1. Note that FLPPA can also be used suitably for a transport layer, a host material, or an emission center material in a light-emitting element. In particular, in the case where FLPPA is used as a host material for dispersing an emission center material that emits blue fluorescence in a light-emitting layer, a light-emitting element which emits light with higher color purity and sharp spectrum can be provided. Thus, the present invention can contribute to providing a display with high color reproducibility. The structural formula of FLPPA is shown below.

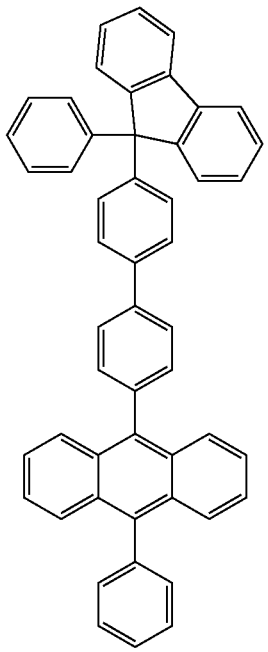

(227)

Step 1: Synthesis Method of 4-(9-Phenyl-9H-fluoren-9-yl)-phenyl Boronic Acid First, 4.0 g (10 mmol) of 9-phenyl-9-(4-bromophenyl)-phenyl-9H-fluorene was put in a 500 mL three-neck flask, the atmosphere in the flask was replaced with nitrogen, 100 mL of dehydrated tetrahydrofuran (abbreviation: THF) was then added to the flask, and the temperature was lowered to −78° C. Into this mixture solution, 7.6 mL (12 mmol) of a 1.59 mol/L n-butyllithium hexane solution was dropped, and the mixture was stirred for 2 hours. To this mixture, 1.4 mL (15 mmol) of trimethyl borate was added, and the mixture was stirred at −78° C. for 2 hours and at room temperature for 18 hours. After the reaction, this reaction solution was stirred while 1M diluted hydrochloric acid was added thereto until the solution became acid. This solution was subjected to ethyl acetate extraction, and an organic layer obtained was washed with a saturated saline. After the washing, magnesium sulfate was added to the organic layer to adsorb moisture. This suspension was filtered, the obtained filtrate was concentrated, and hexane was added thereto. The mixture was irradiated with ultrasonic waves and then recrystallized to obtain 3.5 g of the objective white powder in 97% yield. The reaction scheme of the synthesis method is shown in the following (A-1).

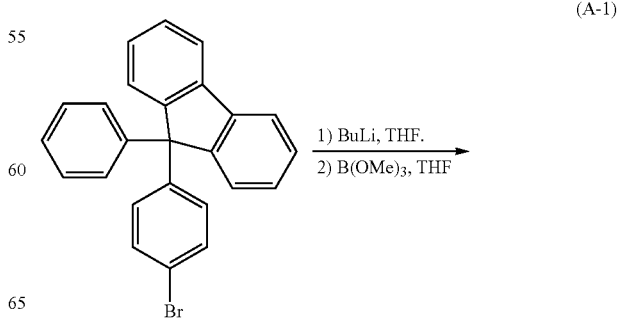

(A-1)

-continued

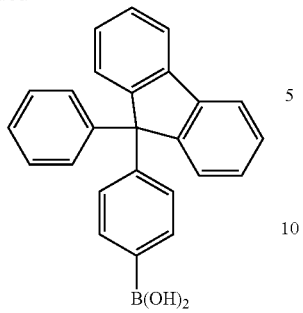

Step 2: Synthesis Method of 9-Phenyl-10-{4-(9-phenyl-9H-fluoren-9-yl)-biphenyl-4'-yl}-anthracene (abbreviation: FLPPA)

There was put a mixture of 2.1 g (5.0 mmol) of 9-(4-bromophenyl)-10-phenylanthracene, 3.6 g (10 mmol) of 4-(9-phenyl-9H-fluoren-9-yl)-phenyl boronic acid, 2.0 mg (10 μmol) of palladium(II) acetate, 6.0 mg (20 μmol) of tris(2-methylphenyl)phosphine, 15 mL of ethylene glycol dimethyl ether, and 5 mL of a 2 mol/L aqueous solution of potassium carbonate in a 50 mL three-neck flask. This mixture was degassed while being stirred under reduced pressure, and then was heated and stirred at 85° C. for 10 hours under a nitrogen atmosphere to cause a reaction.

After the reaction, this reaction mixture was filtered, and the residue was washed with water and toluene in this order. The obtained residue was recrystallized from toluene, so that 2.7 g of pale yellow powder was obtained in 84% yield. The reaction scheme of the synthesis method is shown in the following (A-2).

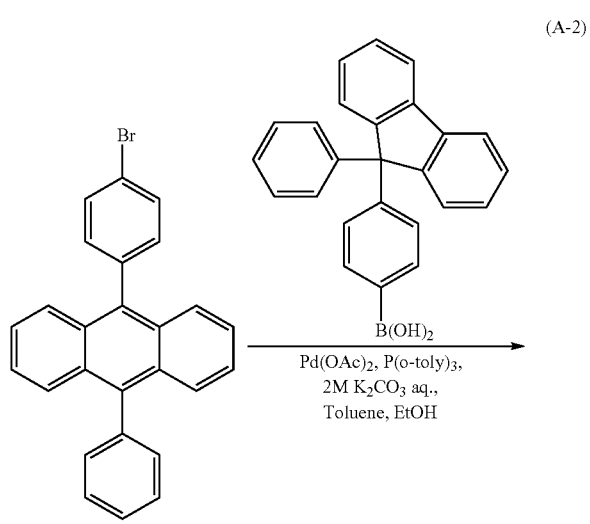

(A-2)

-continued

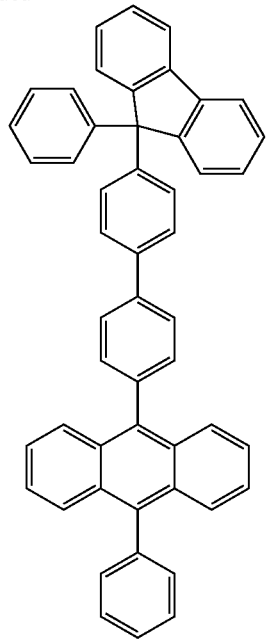

The Rf value of the obtained pale yellow powder by silica gel thin layer chromatography (TLC) (with a developing solvent containing ethyl acetate and hexane in a 1:5 ratio) was 0.63, and that of 9-(4-bromophenyl)-10-phenylanthracene was 0.78.

A compound that was obtained through Step 2 was subjected to a nuclear magnetic resonance (NMR) measurement. The measurement data are shown below.

$^1$H NMR (CDCl$_3$, 300 MHz): δ (ppm)=7.25-7.42 (m, 15H), 7.47-7.64 (m, 11H), 7.68-7.83 (m, 8H).

Figure 16A:
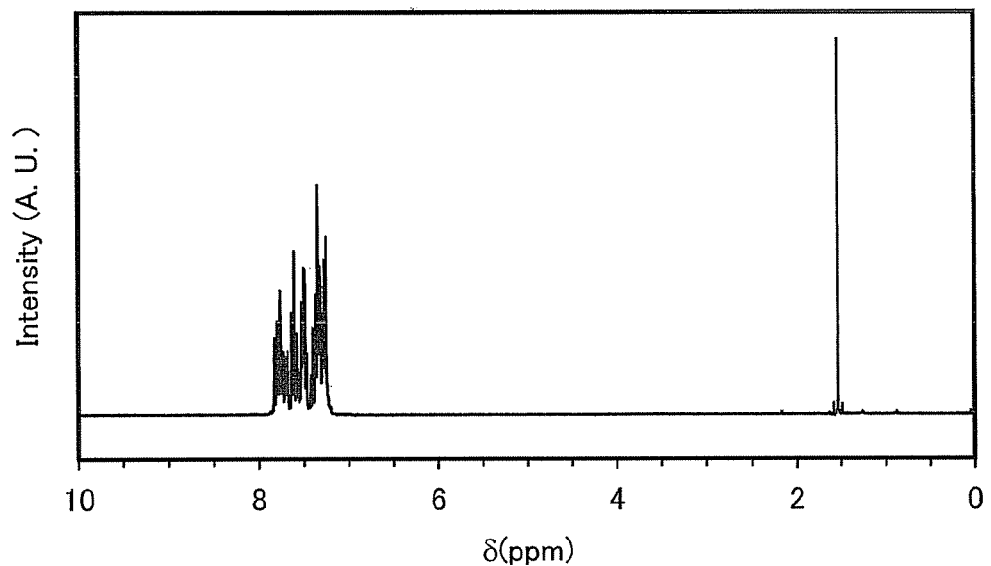
FIGS. 16A and 16B are $^1$H NMR charts of FLPPA.
Figure 16B:
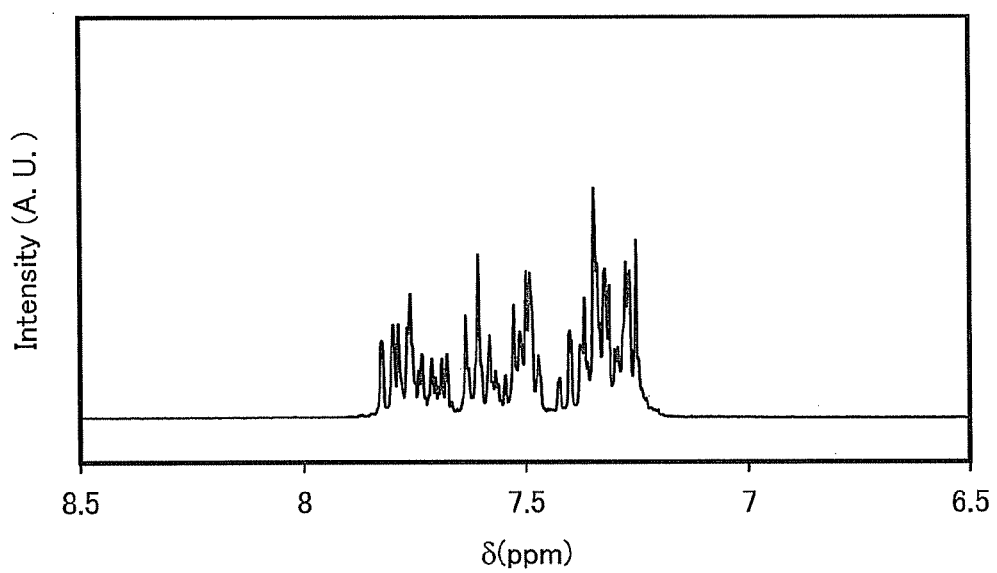

The $^1$H NMR chart is shown in FIGS. 16A and 16B. Note that FIG. 16B is an enlarged chart of FIG. 16A. The measurement results confirmed that FLPPA (abbreviation) that was the objective substance was obtained.

The molecular weight of the above compound was measured by a GC-MS detector (ITQ1100 ion trap GC-MS system, manufactured by Thermo Fisher Scientific K.K.). According to the measurement, it was confirmed that a main peak with a molecular weight of 646.6 (mode was EI+) was detected and FLPPA (abbreviation) that was the objective substance was obtained.

Figure 17:
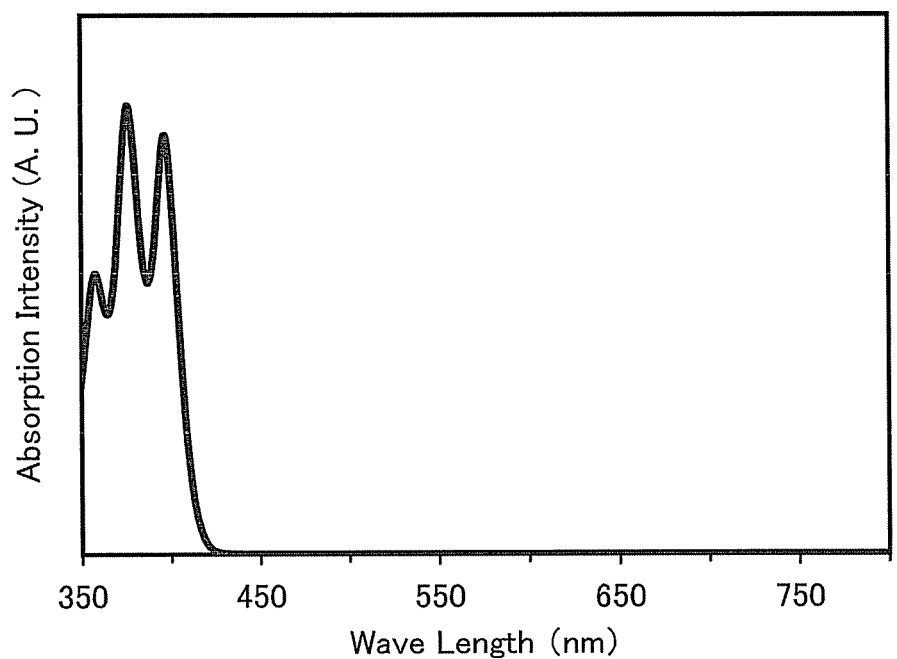
FIG. 17 shows an absorption spectrum of FLPPA in a solution state (solvent: toluene)
Figure 18:
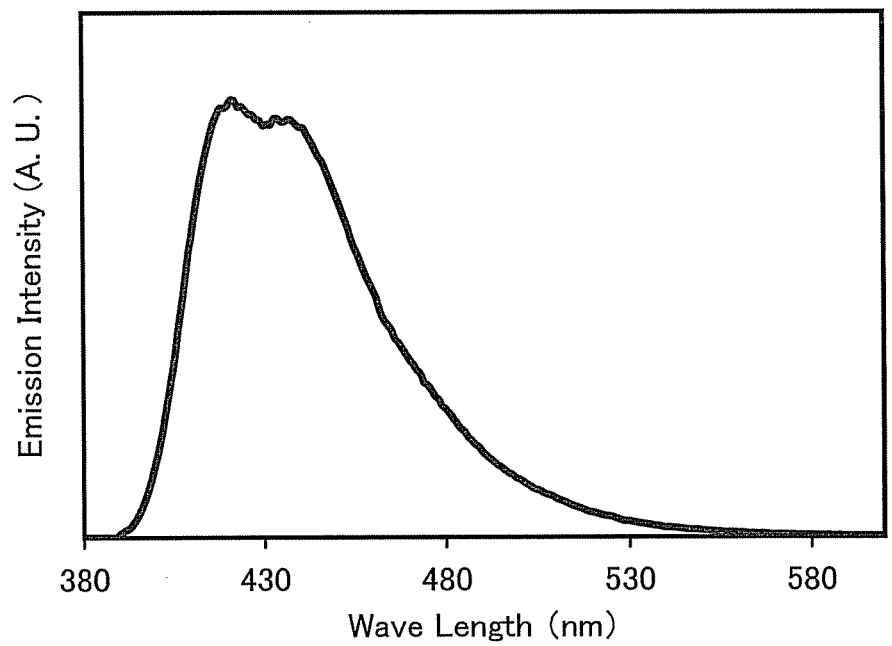
FIG. 18 shows an emission spectrum of FLPPA in a solution state (solvent: toluene)
Figure 19:
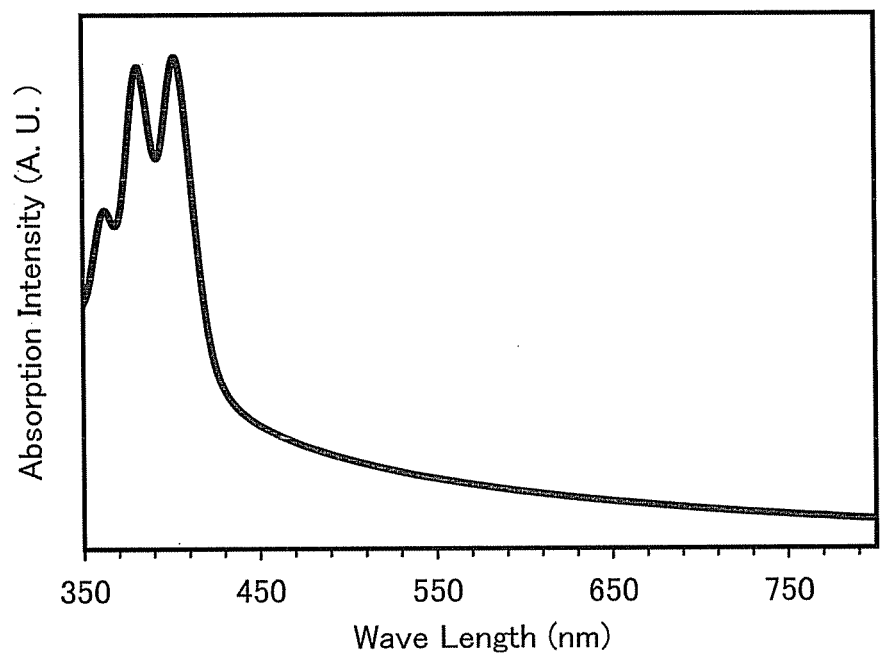
FIG. 19 shows an absorption spectrum of FLPPA in a thin film state.
Figure 20:
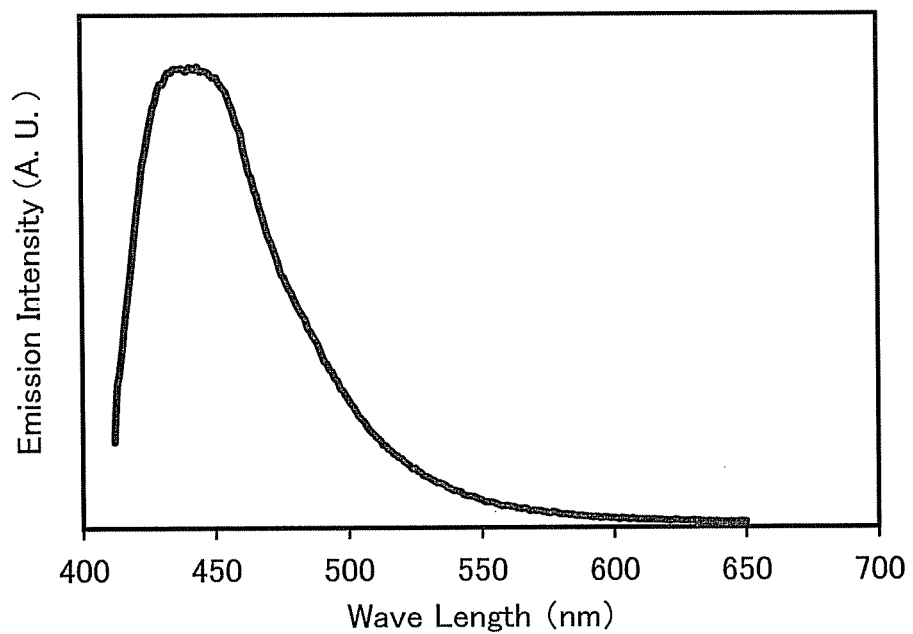
FIG. 20 shows an emission spectrum of FLPPA in a thin film state.

Next, FIG. 17 shows an absorption spectrum of FLPPA in a toluene solution of FLPPA, and FIG. 18 shows an emission spectrum thereof. FIG. 19 shows an absorption spectrum of a thin film of FLPPA, and FIG. 20 shows an emission spectrum thereof. An ultraviolet-visible spectrophotometer (V-550, manufactured by JASCO Corporation) was used for measurements of the spectra. The spectra of the toluene solution were measured with a toluene solution of FLPPA put in a quartz cell. The spectra of the thin film were measured with a sample prepared by evaporation of FLPPA on a quartz substrate. Note that in the case of the absorption spectrum of the toluene solution, the absorption spectrum obtained by subtraction of the absorption spectra of quartz and toluene from the measured spectra is shown in the drawing, and in the case of the absorption spectrum of the thin film, the absorption spectrum obtained by subtraction of that of the quartz substrate from the measured spectra is shown in the drawing.

FIG. 17 shows that the maximum absorption wave length of FLPPA in the toluene solution of FLPPA was around 397 nm, and FIG. 18 shows that the greatest emission wave lengths thereof were around 421 nm and 435 nm (at an excitation wave length of 376 nm). FIG. 19 shows that the maximum absorption wave length of the thin film of FLPPA was around 402 nm, and FIG. 20 shows that the maximum emission wave length thereof was around 445 nm (at an excitation wave length of 402 nm). From the above, it is found that the film formed by evaporating only FLPPA has a high light-transmitting property with a little absorption of light in most of the visible light region.

Further, the ionization potential of FLPPA in a thin film state was measured by a photoelectron spectrometer (AC-2, manufactured by Riken Keiki, Co., Ltd.) in the air. The obtained value of the ionization potential was converted to a negative value, so that the HOMO level of FLPPA was −5.83 eV. From the data of the absorption spectra of the thin film in FIG. 19, the absorption edge of FLPPA, which was obtained from Tauc plot with an assumption of direct transition, was 2.94 eV. Therefore, the optical energy gap of FLPPA in the solid state was estimated at 2.94 eV; from the values of the HOMO level obtained above and this energy gap, the LUMO level of FLPPA was estimated at −2.89 eV. It was thus found that FLPPA had a wide energy gap of 2.94 eV in the solid state.

The oxidation characteristics and reduction characteristics of FLPPA were measured. These were examined by cyclic voltammetry (CV) measurements. Note that an electrochemical analyzer (ALS model 600A or 600C, manufactured by BAS Inc.) was used for the measurements.

For a solution for the CV measurements, dehydrated N,N-dimethylformamide (DMF, product of Sigma-Aldrich Inc., 99.8%, catalog No. 22705-6) was used as a solvent, and tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration thereof was 100 mmol/L. Further, the object to be measured was also dissolved in the solvent such that the concentration thereof was 2 mmol/L. A platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurements were conducted at room temperature (20 to 25° C.). The scan speed at the CV measurements was set at 0.1 V/s.

Figure 21:
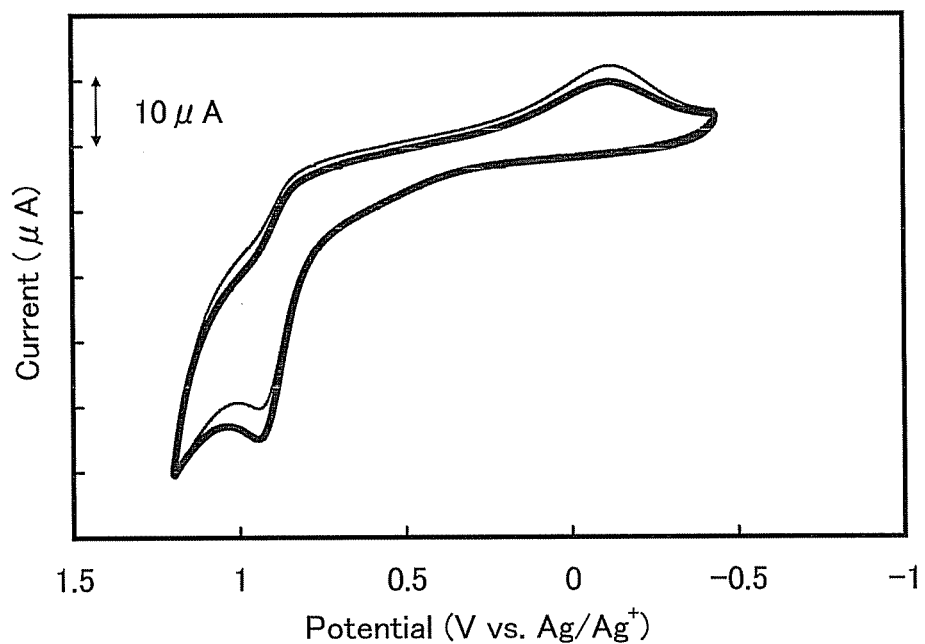
FIG. 21 shows CV charts (oxidation characteristics) of FLPPA.
Figure 22:
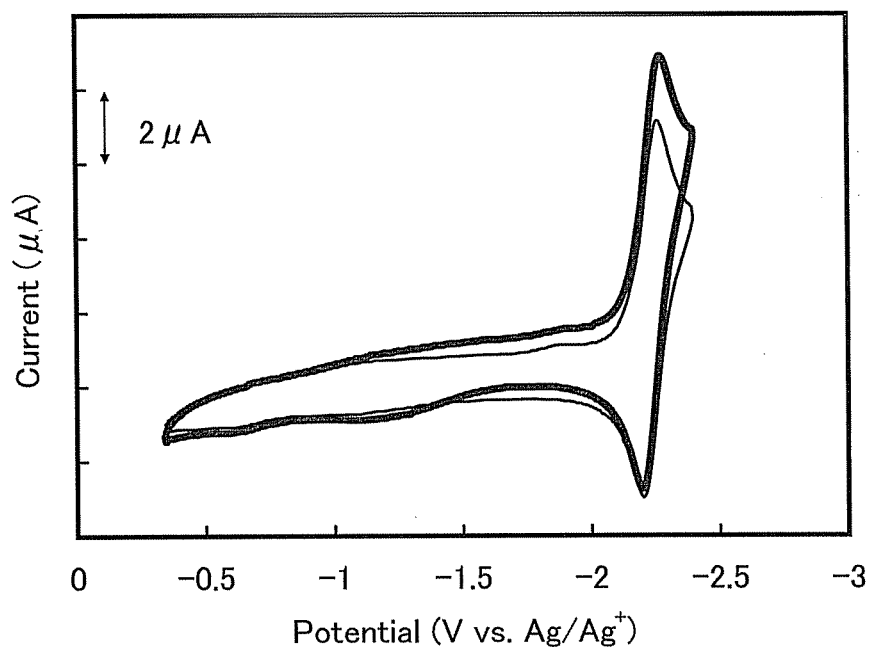
FIG. 22 shows CV charts (reduction characteristics) of FLPPA.

In the measurements of the oxidation characteristics, scanning in which the potential of the working electrode with respect to the reference electrode was changed from −0.43 V to 1.20 V and then changed from 1.20 V to −0.44 V was one cycle, and 100-cycle measurements were performed. In the measurements of the reduction characteristics, scanning in which the potential of the working electrode with respect to the reference electrode was changed from −0.35 V to −2.40 V and then changed from −2.40 V to −0.34 V was one cycle, and 100-cycle measurements were performed. Measurement results are shown in FIG. 21 and FIG. 22. Note that FIG. 21 shows a CV chart of the oxidation characteristics, and FIG. 22 shows a CV chart of the reduction characteristics. The bold line represents characteristics of the first cycle and the thin line represents characteristics of the 100th-cycle in FIG. 21 and FIG. 22.

The measurement results revealed that FLPPA showed a property effective against repetition of redox reactions between an oxidized state and a neutral state and repetition of redox reactions between a reduced state and a neutral state, without large variations in the oxidation and reduction peaks of the oxidation and reduction characteristics even after the 100-cycle measurements.

Further, the HOMO and LUMO levels of FLPPA were calculated also from the CV measurement results.

First, the potential energy of the reference electrode (Ag/Ag$^+$ electrode) with respect to the vacuum level, which was used, is −4.85 eV.

From FIG. 21 showing the oxidation characteristics, the oxidation peak potential $E_{pa}$ of FLPPA was 0.95 V, and the reduction peak potential $E_{pc}$ thereof was 0.80 V. Therefore, a half-wave potential (an intermediate potential between $E_{pa}$ and $E_{pc}$) can be calculated at 0.88 V. This means that FLPPA is oxidized by an electric energy of 0.88 [V versus Ag/Ag$^+$], and this energy corresponds to the HOMO level. Here, as described above, the potential energy of the reference electrode used in Example 3 with respect to the vacuum level is −4.85 [eV], and thus, it was found that the HOMO level of FLPPA was −5.73 [eV].

Similarly, from FIG. 22 showing the reduction characteristics, the oxidation peak potential $E_{pa}$ of FLPPA was −2.20 V, and the reduction peak potential $E_{pc}$ thereof was −2.27 V. Therefore, a half-wave potential (an intermediate potential between $E_{pa}$ and $E_{pc}$) can be calculated at −2.24 V. This mans that FLPPA is reduced by an electric energy of −2.24 [V versus Ag/Ag$^+$], and this energy corresponds to the LUMO level. Here, as described above, the potential energy of the reference electrode used in Example 3 with respect to the vacuum level was −4.85 [eV], and thus, it was found that the LUMO level of FLPPA was −2.62 [eV]. Note that the values were rounded to three significant digits.

Note that the potential energy of the reference electrode (Ag/Ag$^+$ electrode) with respect to the vacuum level corresponds to the Fermi level of the Ag/Ag$^+$ electrode, and should be calculated from a value obtained by measuring a substance whose potential energy with respect to the vacuum level is known, with the use of the reference electrode (Ag/Ag$^+$ electrode).

The following specifically shows how the potential energy (eV) of the reference electrode (Ag/Ag$^+$ electrode), which was used in this example, with respect to the vacuum level was determined by calculation. It is known that the oxidation-reduction potential of ferrocene in methanol is +0.610 [V versus SHE] with respect to a standard hydrogen electrode (Reference: Christian R. Goldsmith et al., J. Am. Chem. Soc., Vol. 124, No. 1, pp. 83-96, 2002). On the other hand, when the oxidation-reduction potential of ferrocene in methanol was calculated by using the reference electrode used in this example, it was +0.20 [V versus. Ag/Ag$^+$]. Thus, it was found that the potential energy of the reference electrode was lower than that of the standard hydrogen electrode by 0.41 [eV].

Here, it is known that the potential energy of the standard hydrogen electrode with respect to the vacuum level is −4.44 eV (Reference: Toshihiro Ohnishi and Tamami Koyama, High Molecular EL Material, Kyoritsu Shuppan, pp. 64-67). Therefore, the potential energy of the reference electrode used in this example with respect to the vacuum level can be calculated at −4.44−0.41=−4.85 [eV].

Example 4

Example 4 shows a light-emitting element (light-emitting element 2) in which a fluorene derivative, 9-phenyl-10-{4-(9-phenyl-9H-fluoren-9-yl)-biphenyl-4'-yl}-anthracene (abbreviation: FLPPA), was used as a host material in a light-emitting layer. As a comparative example, a light-emitting element (comparative light-emitting element 2) in which CzPA was used instead of FLPPA was also fabricated, and Example 4 also shows the comparative light-emitting element 2. Note that CzPA is a light-emitting element material with which a light-emitting element with high emission efficiency can be fabricated.

The molecular structures of organic compounds used in this example are represented by the following structural formulas. In the element structure used, an electron-injection layer was provided between the electron-transport layer 114 and the second electrode 104 in the structure in FIG. 1A.

(vi)

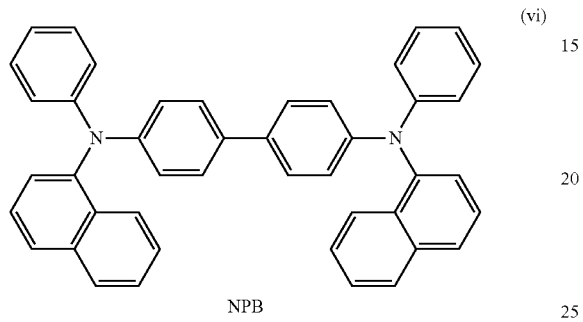

NPB (viii)

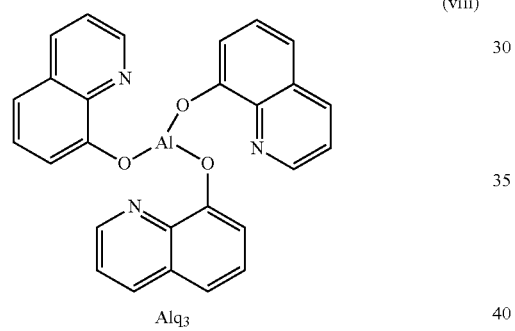

Alq₃

(ii)

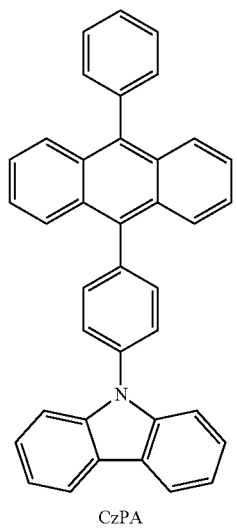

CzPA

-continued (227)

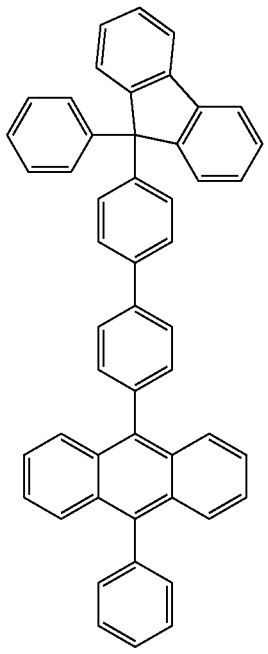

FLPPA (vii)

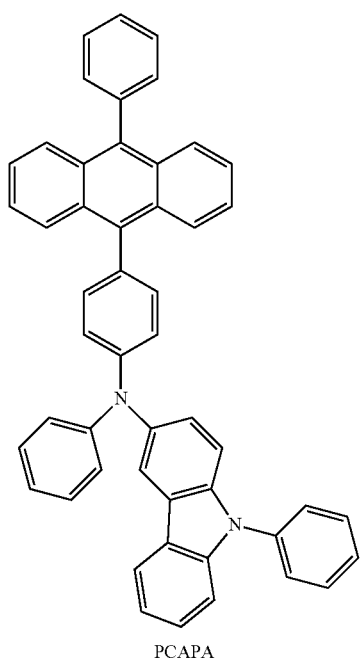

PCAPA

[Fabrication of Light-Emitting Element 2 and Comparative Light-Emitting Element 2]

First, the glass substrate 101 was prepared, over which indium tin oxide containing silicon (ITSO) with a thickness of 110 nm was formed as the first electrode 102. A surface of the ITSO film was covered with a polyimide film such that an area of 2 mm×2 mm of the surface was exposed, which corresponded to the electrode area. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus in which the pressure was reduced to approximately $10^{-4}$ Pa, vacuum baking at 170° C. for 30 minutes was performed in a heating chamber of the vacuum evaporation apparatus, and then the substrate was cooled down for approximately 30 minutes.

Then, the substrate 101 was fixed on a holder provided in the vacuum evaporation apparatus such that the surface of the substrate 101 provided with ITSO faced downward.

The pressure in the vacuum evaporation apparatus was reduced to $10^{-4}$ Pa, and then 4,4'-bis[N-(1-naphthyl)-N-phenylamino]biphenyl (abbreviation: NPB) represented by the above structural formula (vi) and molybdenum(VI) oxide were co-evaporated by adjusting evaporation rates such that the weight ratios of NPB to molybdenum oxide were 4:1, so that the hole-injection layer 111 was formed. The thickness was 50 nm. Note that a co-evaporation method is an evaporation method in which a plurality of different substances are concurrently vaporized from respective different evaporation sources.

Next, NPB was evaporated to a thickness of 10 nm, so that the hole-transport layer 112 was formed.

Further, over the hole-transport layer 112, FLPPA represented by the above structural formula and N,9-diphenyl-N-[4-(10-phenyl-9-anthryl)phenyl]-9H-carbazol-3-amine (abbreviation: PCAPA) represented by the above structural formula (vii) were evaporated to a thickness of 30 nm by adjusting evaporation rates such that the weight ratios of FLPPA to PCAPA were 1:0.05, so that the light-emitting layer 113 was formed.

Next, over the light-emitting layer 113, tris(8-quinolinolato)aluminum(III) (abbreviation: $Alq_3$) represented by the above structural formula (viii) was evaporated to a thickness of 10 nm, so that the electron-transport layer 114 was formed. Further, over the electron-transport layer 114, $Alq_3$ and lithium were co-evaporated by adjusting evaporation rates such that the weight ratios of $Alq_3$ to lithium were 1:0.01, so that the electron-injection layer was framed. The thickness was 20 nm. Finally, aluminum was deposited to a thickness of 200 nm as the second electrode 104 serving as a cathode, whereby the light-emitting element 2 was completed. Note that in the above evaporation process, evaporation was all performed by a resistance heating method.

The comparative light-emitting element 2 was fabricated by using CzPA represented by the above structural formula (ii) instead of FLPPA which was used as the host material in the light-emitting layer 113 in the method of fabricating the light-emitting element 2.

[Operation Characteristics of Light-Emitting Element 2 and Comparative Light-Emitting Element 2]

The thus obtained light-emitting element 2 and comparative light-emitting element 2 were put into a glove box under a nitrogen atmosphere, and the light-emitting elements were sealed so as not to be exposed to the air. Then, the operation characteristics of the light-emitting elements were measured. Note that the measurements were carried out at room temperature (in an atmosphere kept at 25° C.).

Figure 23:
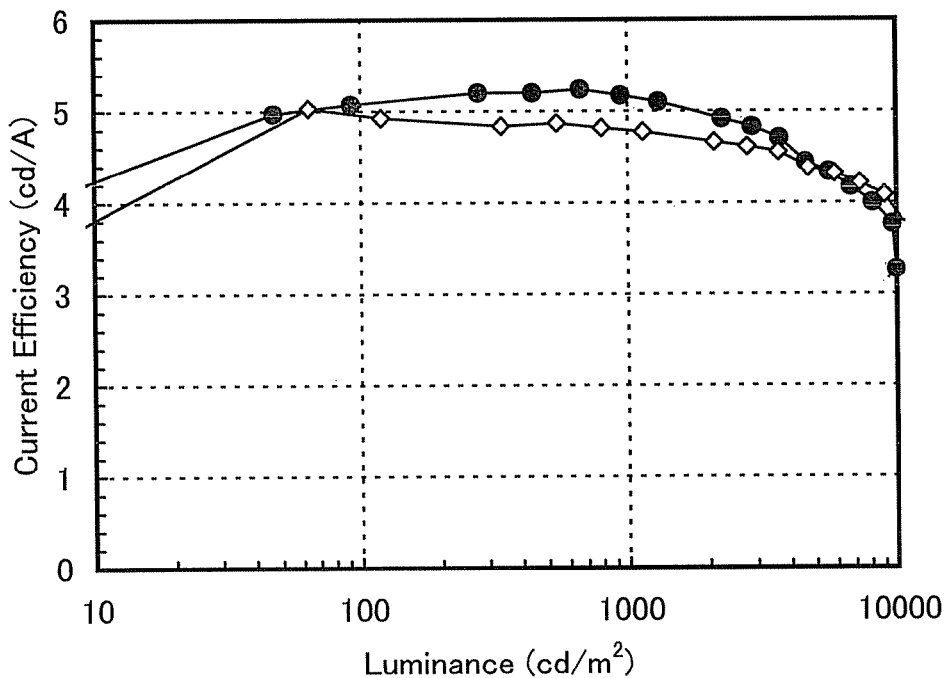
FIG. 23 shows luminance versus current efficiency characteristics of a light-emitting element 2 and a comparative light-emitting element 2.
Figure 24:
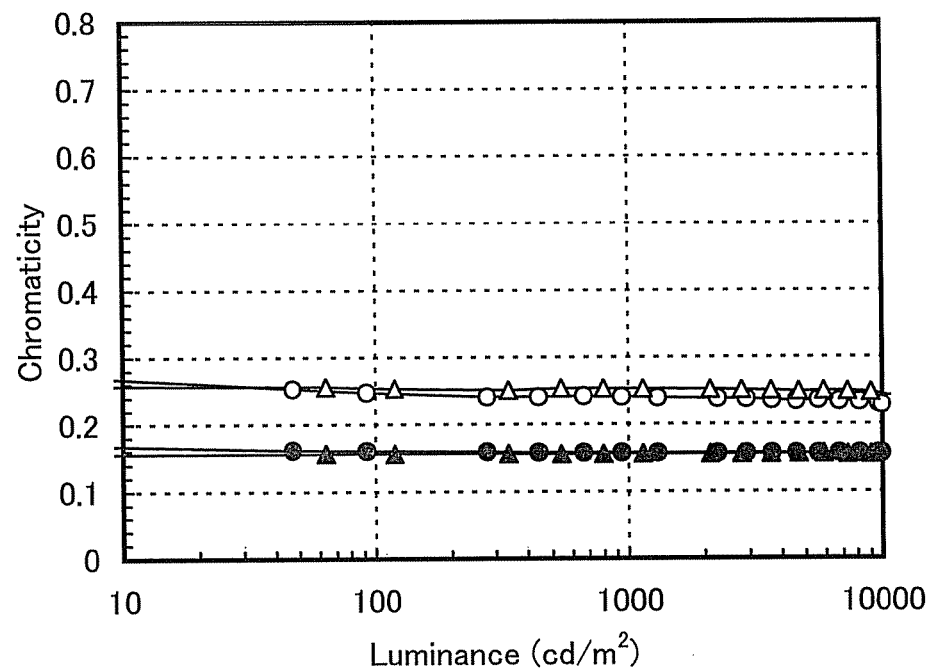
FIG. 24 shows luminance versus chromaticity characteristics of the light-emitting element 2 and the comparative light-emitting element 2.

FIG. 23 shows luminance versus current efficiency characteristics of the light-emitting elements, and FIG. 24 shows luminance versus chromaticity characteristics thereof. In FIG. 23, the vertical axis represents current efficiency (cd/A), and the horizontal axis represents luminance (cd/m$^2$), and black circles represent characteristics of the light-emitting element 2 and white squares represent characteristics of the comparative light-emitting element 2. In FIG. 24, the vertical axis represents chromaticity (no unit), and the horizontal axis represents luminance (cd/m$^2$), and black/white circles represent the x-component/y-component in chromaticity of the light-emitting element 2 and black/white triangles represent the x-component/y-component in chromaticity of the comparative light-emitting element 2.

FIG. 23 indicates that the light-emitting element in which FLPPA is used as the host material in the light-emitting layer of the light-emitting element that emits blue fluorescence has as excellent luminance versus emission efficiency characteristics as the light-emitting element in which CzPA is used as the host material, and thus has high emission efficiency. Characteristics at luminances from 100 cd/m$^2$ to 3000 cd/m$^2$ are especially excellent. This is because FLPPA can, owing to the wide energy gap thereof, effectively excite a light-emitting substance, even a blue fluorescent substance. FIG. 24 also indicates that the light-emitting element in which FLPPA is used as the host material in the light-emitting layer of the light-emitting element that emits blue fluorescence has an excellent carrier balance with a little change in color at respective luminances.

Table 2 shows main characteristics of the light-emitting element 2 and the comparative light-emitting element 2 around 1000 cd/m$^2$.

TABLE 2

| | Voltage (V) | Current (mA) | Chromaticity x | Chromaticity y | Current Efficiency (cd/A) | External Quantum Efficiency (%) |
|---|---|---|---|---|---|---|
| Light-emitting Element 2 | 5.4 | 0.73 | 0.16 | 0.24 | 5.2 | 3.1 |
| Comparative Light-emitting Element 2 | 4.8 | 0.96 | 0.16 | 0.25 | 4.8 | 2.8 |

Figure 25:
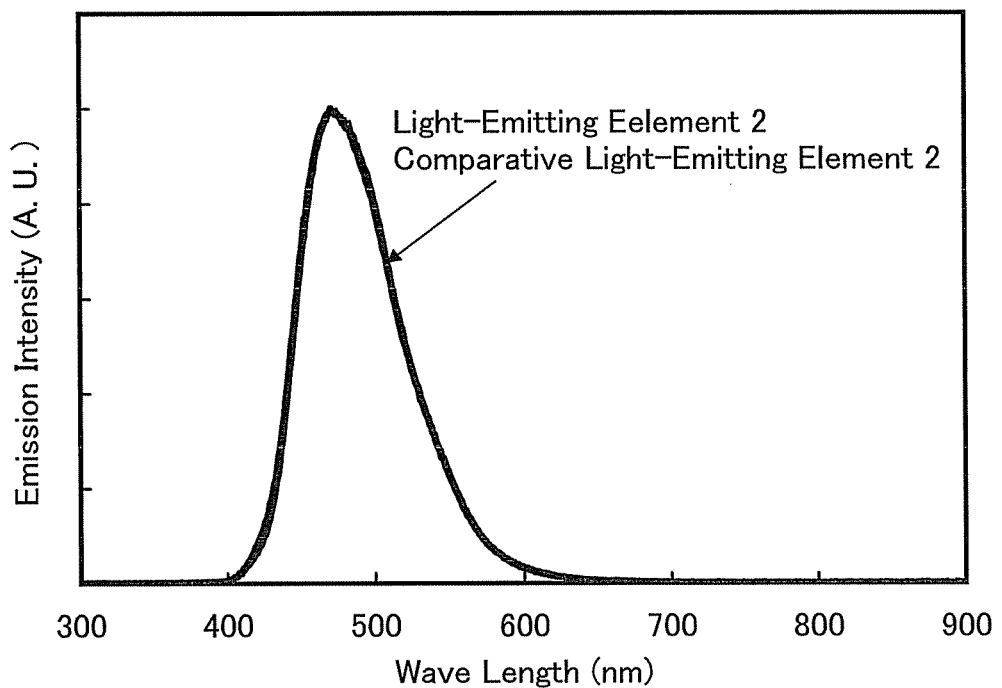
FIG. 25 shows emission spectra of the light-emitting element 2 and the comparative light-emitting element 2.

FIG. 25 shows emission spectra of the fabricated light-emitting element 2 and comparative light-emitting element 2 when a current of 1 mA was made to flow therein. In FIG. 25, the vertical axis represents emission intensity and the horizontal axis represents emission wave length (nm). The emission intensity is shown as a value relative to the greatest emission intensity assumed to be 1. As can be seen in FIG. 25, the emission spectra of the light-emitting element 2 and of the comparative light-emitting element 2 substantially overlap with each other, and blue fluorescence originating from PCAPA, which is the emission center substance, was emitted.

Example 5

Example 5 shows a light-emitting element (light-emitting element 3) in which a fluorene derivative, 9-phenyl-10-{4-(9-phenyl-9H-fluoren-9-yl)-biphenyl-4'-yl}-anthracene (abbreviation: FLPPA), was used as a host material in a light-emitting layer. As a comparative example, a light-emitting element (comparative light-emitting element 3) in which CzPA was used instead of FLPPA was also fabricated, and Example 5 also shows the comparative light-emitting element 3. Note that CzPA is a light-emitting element material with which a light-emitting element with high emission efficiency can be fabricated.

The molecular structures of organic compounds used in this example are represented by the following structural formulas. In the element structure used, an electron-injection layer was provided between the electron-transport layer 114 and the second electrode 104 in the structure in FIG. 1A.

(vi)

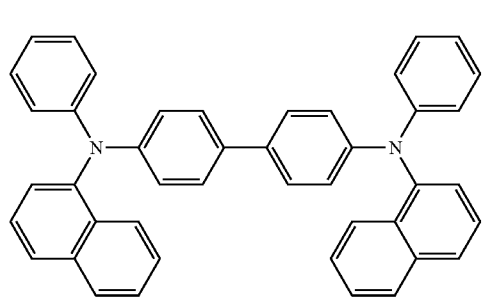

NPB (vii)

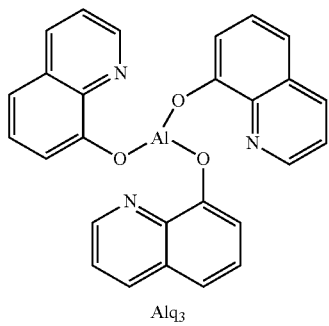

Alq₃

(ii)

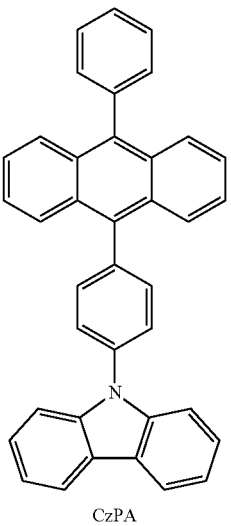

CzPA (227)

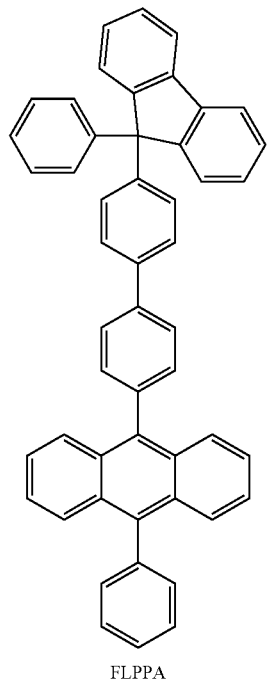

FLPPA (ix)

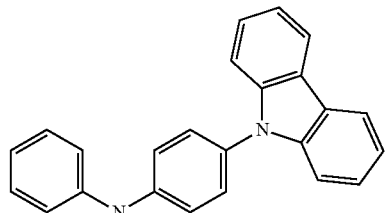

YGA2S

[Fabrication of Light-Emitting Element 3 and Comparative Light-Emitting Element 3]

First, the glass substrate 101 was prepared, over which indium tin oxide containing silicon (ITSO) with a thickness of 110 nm was formed as the first electrode 102. A surface of the ITSO film was covered with a polyimide film such that an area of 2 mm×2 mm of the surface was exposed, which corresponded to the electrode area. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus in which the pressure was reduced to approximately $10^{-4}$ Pa, vacuum baking at 170° C. for 30 minutes was performed in a heating chamber of the vacuum evaporation apparatus, and then the substrate was cooled down for approximately 30 minutes.

Then, the substrate 101 was fixed on a holder provided in the vacuum evaporation apparatus such that the surface of the substrate 101 provided with ITSO faced downward.

The pressure in the vacuum evaporation apparatus was reduced to $10^{-4}$ Pa, and then 4,4'-bis[N-(1-naphthyl)-N-phenylamino]biphenyl (abbreviation: NPB) represented by the above structural formula (vi) and molybdenum(VI) oxide were co-evaporated by adjusting evaporation rates such that the weight ratios of NPB to molybdenum oxide were 4:1, so that the hole-injection layer 111 was formed. The thickness was 50 nm. Note that a co-evaporation method is an evaporation method in which a plurality of different substances are concurrently vaporized from respective different evaporation sources.

Next, NPB was evaporated to a thickness of 10 nm, so that the hole-transport layer 112 was formed.

Further, over the hole-transport layer 112, FLPPA represented by the above structural formula and N,N'-bis[4-(9H-carbazol-9-yl)phenyl]-N,N'-diphenylstilbene-4,4'-diamine (abbreviation: YGA2S) represented by the above structural formula (ix) were evaporated to a thickness of 30 nm by adjusting evaporation rates such that the weight ratios of FLPPA to YGA2S were 1:0.05, so that the light-emitting layer 113 was formed.

Next, over the light-emitting layer 113, tris(8-quinolinolato)aluminum(III) (abbreviation: Alq$_3$) represented by the above structural formula (viii) was evaporated to a thickness of 10 nm, so that the electron-transport layer 114 was formed. Further, over the electron-transport layer 114, Alq$_3$ and lithium were co-evaporated by adjusting evaporation rates such that the weight ratios of Alq$_3$ to lithium were 1:0.01, so that the electron-injection layer was formed. The thickness was 20 nm. Finally, aluminum was deposited to a thickness of 200 nm as the second electrode 104 serving as a cathode, whereby the light-emitting element 3 was completed. Note that in the above evaporation process, evaporation was all performed by a resistance heating method.

The comparative light-emitting element 3 was fabricated by using CzPA instead of FLPPA which was used as the host material in the light-emitting layer 113 in the method of fabricating the light-emitting element 3.

[Operation Characteristics of Light-Emitting Element 3 and Comparative Light-Emitting Element 3]

The thus obtained light-emitting element 3 and comparative light-emitting element 3 were put into a glove box under a nitrogen atmosphere, and the light-emitting elements were sealed so as not to be exposed to the air. Then, the operation characteristics of the light-emitting elements were measured. Note that the measurements were carried out at room temperature (in an atmosphere kept at 25° C.).

Figure 26:
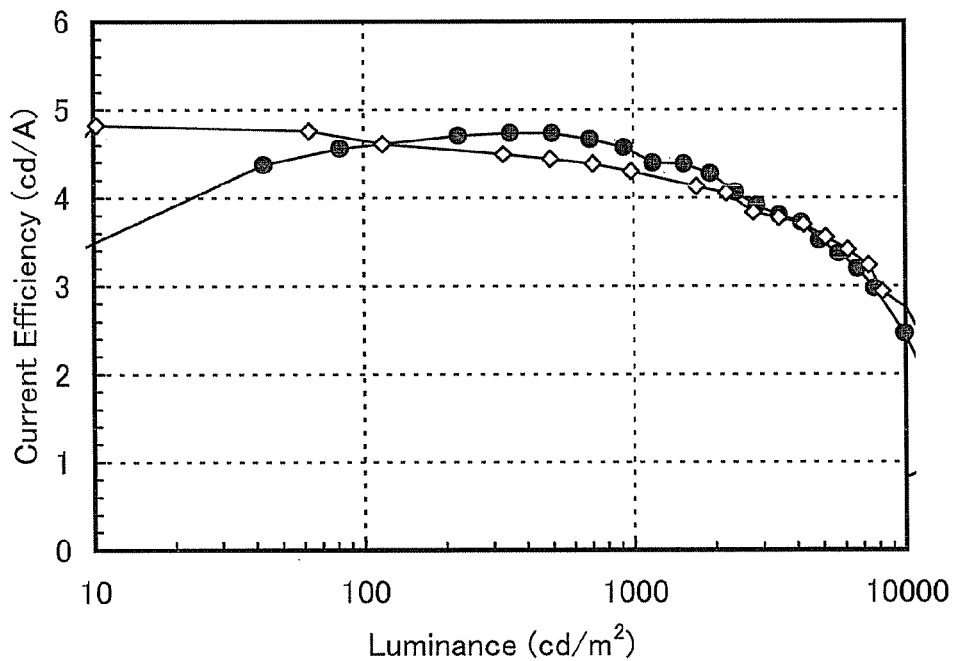
FIG. 26 shows luminance versus current efficiency characteristics of a light-emitting element 3 and a comparative light-emitting element 3.
Figure 27:
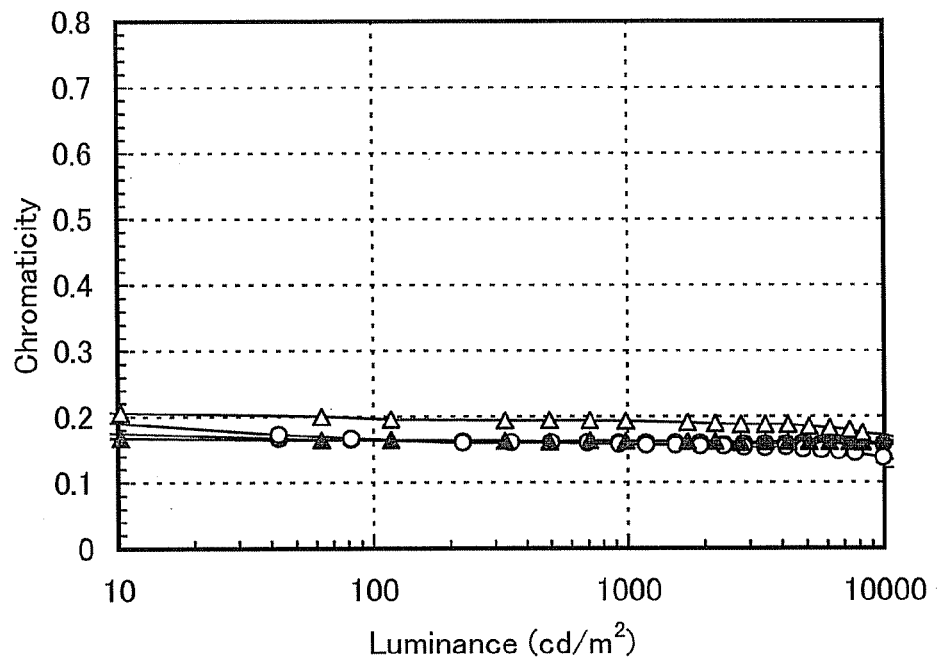
FIG. 27 shows luminance versus chromaticity characteristics of the light-emitting element 3 and the comparative light-emitting element 3.

FIG. 26 shows luminance versus current efficiency characteristics of the light-emitting elements, and FIG. 27 shows luminance versus chromaticity characteristics thereof. In FIG. 26, the vertical axis represents current efficiency (cd/A), and the horizontal axis represents luminance (cd/m$^2$), and black circles represent characteristics of the light-emitting element 3 and white squares represent characteristics of the comparative light-emitting element 3. In FIG. 27, the vertical axis represents chromaticity (no unit), and the horizontal axis represents luminance (cd/m$^2$), and black/white circles represent the x-component/y-component in chromaticity of the light-emitting element 3 and black/white triangles represent the x-component/y-component in chromaticity of the comparative light-emitting element 3.

FIG. 26 indicates that the light-emitting element in which FLPPA is used as the host material in the light-emitting layer of the light-emitting element that emits blue fluorescence has as excellent luminance versus emission efficiency characteristics as the light-emitting element in which CzPA is used as the host material, and thus has high emission efficiency. Characteristics at luminances from 200 cd/m$^2$ to 2000 cd/m$^2$ are especially excellent. This is because FLPPA can, owing to the wide energy gap thereof, effectively excite a light-emitting substance, even a blue fluorescent substance. FIG. 27 also indicates that the light-emitting element in which FLPPA is used as the host material in the light-emitting layer of the light-emitting element that emits blue fluorescence has an excellent carrier balance with a little change in color at respective luminances.

Table 3 shows main characteristics of the light-emitting element 3 and the comparative light-emitting element 3 around 1000 cd/m$^2$.

TABLE 3

| | Voltage (V) | Current (mA) | Chromaticity x | Chromaticity y | Current Efficiency (cd/A) | External Quantum Efficiency (%) |
|---|---|---|---|---|---|---|
| Light-emitting Element 3 | 5.4 | 0.81 | 0.16 | 0.16 | 4.6 | 3.5 |
| Comparative Light-emitting Element 3 | 4.8 | 0.91 | 0.16 | 0.19 | 4.3 | 2.9 |

Figure 28:
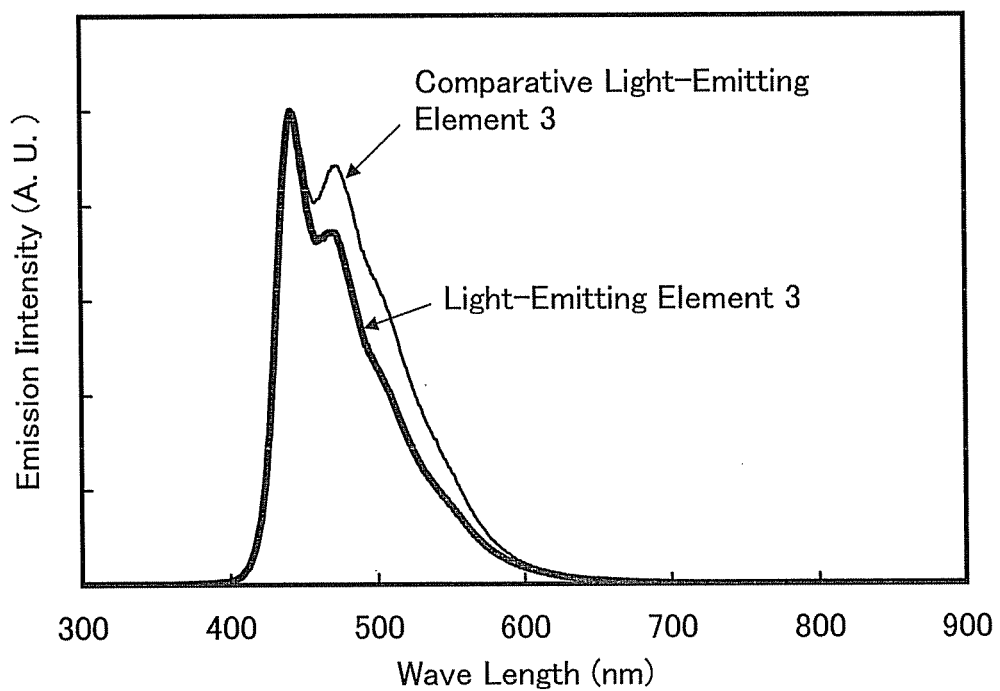
FIG. 28 shows emission spectra of the light-emitting element 3 and the comparative light-emitting element 3.

FIG. 28 shows emission spectra of the light-emitting element 3 and comparative light-emitting element 3 when a current of 1 mA was made to flow therein. In FIG. 28, the vertical axis represents emission intensity and the horizontal axis represents emission wave length (nm). The emission intensity is shown as a value relative to the greatest emission intensity assumed to be 1. As can be seen in FIG. 28, each of the light-emitting element 3 and the comparative light-emitting element 3 emits blue fluorescence originating from YGA2S, which is the emission center substance. In particular, it is found that the light-emitting element 3 emits blue light with higher color purity and sharper spectrum.

Example 6

Example 6 shows a light-emitting element (light-emitting element 4) in which a hole-injection layer is formed with a co-evaporation film of the composite material described in Embodiment 1, which contains 9,9-bis[4-(1-pyrenyl)phenyl]-9H-fluorenE (abbreviation: BPPF) (structural formula (118)) and molybdenum oxide.

The molecular structures of organic compounds used in this example are represented by the following structural formulas. In the element structure used, an electron-injection layer was provided between the electron-transport layer 114 and the second electrode 104 in the structure in FIG. 1A.

(118)

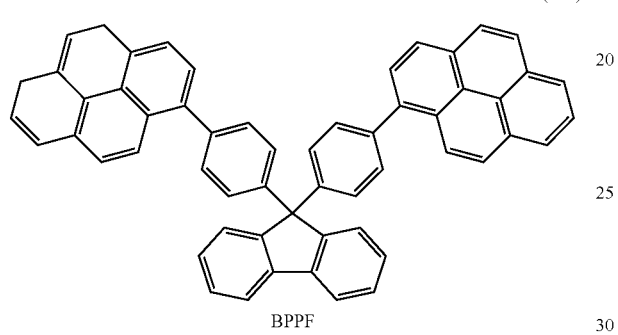

BPPF (ii)

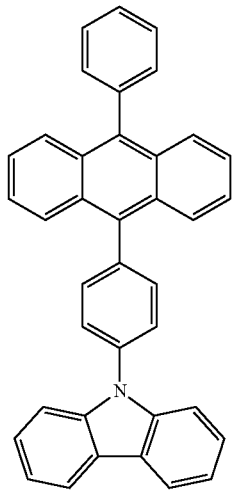

CzPA (v)

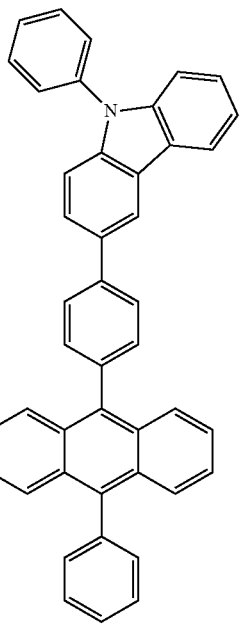

PCzPA (iv)

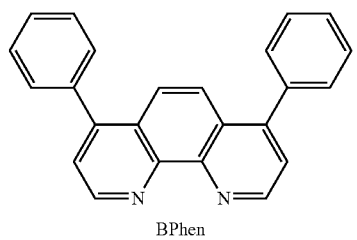

BPhen (x)

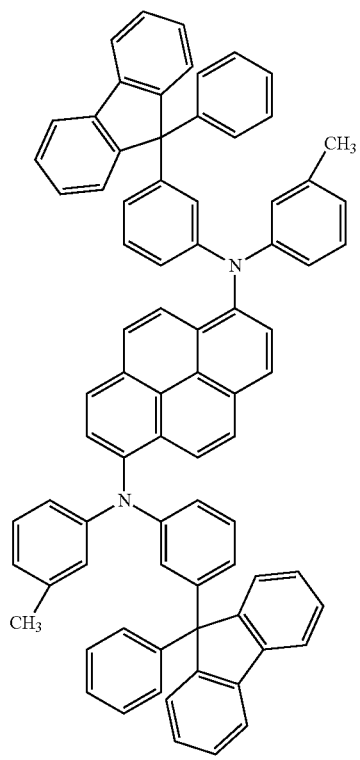

1,6mMemFLPAPrn

[Fabrication of Light-Emitting Element 4]

First, the glass substrate 101 was prepared, over which indium tin oxide containing silicon (ITSO) with a thickness of 110 nm was formed as the first electrode 102. A surface of the ITSO film was covered with a polyimide film such that an area of 2 mm×2 mm of the surface was exposed, which corresponded to the electrode area. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus in which the pressure was reduced to approximately $10^{-4}$ Pa, vacuum baking at 170° C. for 30 minutes was performed in a heating chamber of the vacuum evaporation apparatus, and then the substrate was cooled down for approximately 30 minutes.

Then, the substrate 101 was fixed on a holder provided in the vacuum evaporation apparatus such that the surface of the substrate 101 provided with ITSO faced downward.

The pressure in the vacuum evaporation apparatus was reduced to $10^{-4}$ Pa, and then BPPF represented by the structural formula (118) and molybdenum(VI) oxide were co-evaporated by adjusting evaporation rates such that the weight ratios of BPPF to molybdenum oxide were 2:1, so that the hole-injection layer 111 was formed. The thickness was 50 nm. Note that a co-evaporation method is an evaporation method in which a plurality of different substances are concurrently vaporized from respective different evaporation sources.

Next, 9-[4-(9-phenylcarbazol-3-yl)]phenyl-10-phenylanthracene (abbreviation: PCzPA) represented by the above structural formula (v) was deposited to a thickness of 10 nm, so that the hole-transport layer 112 was formed.

Further, over the hole-transport layer 112, 9-[4-(10-phenyl-9-anthryl)phenyl]-9H-carbazole (abbreviation: CzPA) represented by the above structural formula (ii) and N,N'-bis(3-methylphenyl)-N,N'-bis[3-(9-phenyl-9H-fluoren-9-yl)phenyl]-pyrene-1,6-diamine (abbreviation: 1,6mMemFLPA-Prn) represented by the above structural formula (x) were evaporated to a thickness of 30 nm by adjusting evaporation rates such that the weight ratios of CzPA to 1,6mMemFLPA-Prn were 1:0.04, so that the light-emitting layer 113 was formed.

Next, CzPA was evaporated to a thickness of 10 nm, and then bathophenanthroline (abbreviation: BPhen) represented by the above structural formula (iv) was evaporated to a thickness of 20 nm, so that the electron-transport layer 114 was formed. Further, lithium fluoride was evaporated to a thickness of 1 nm over the electron-transport layer 114, so that the electron-injection layer was formed. Finally, aluminum was deposited to a thickness of 200 nm as the second electrode 104 serving as a cathode, whereby the light-emitting element 4 was completed. Note that in the above evaporation process, evaporation was all performed by a resistance heating method.

[Operation Characteristics of Light-Emitting Element 4]

The thus obtained light-emitting element 4 was put into a glove box under a nitrogen atmosphere, and the light-emitting element was sealed so as not to be exposed to the air. Then, the operation characteristics of the light-emitting element were measured. Note that the measurements were carried out at room temperature (in an atmosphere kept at 25° C.).

Figure 30:
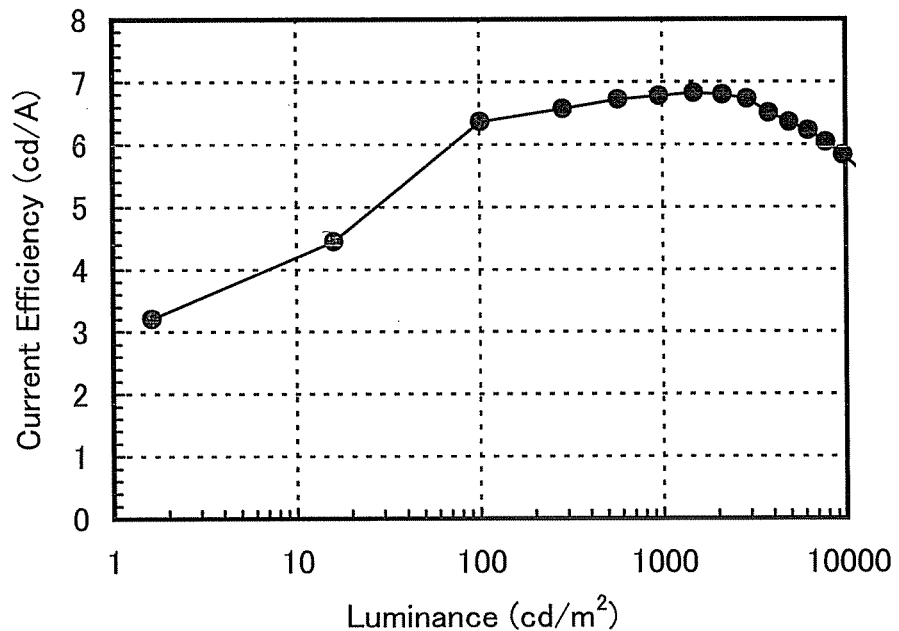
FIG. 30 shows luminance versus current efficiency characteristics of a light-emitting element 4.
Figure 31:
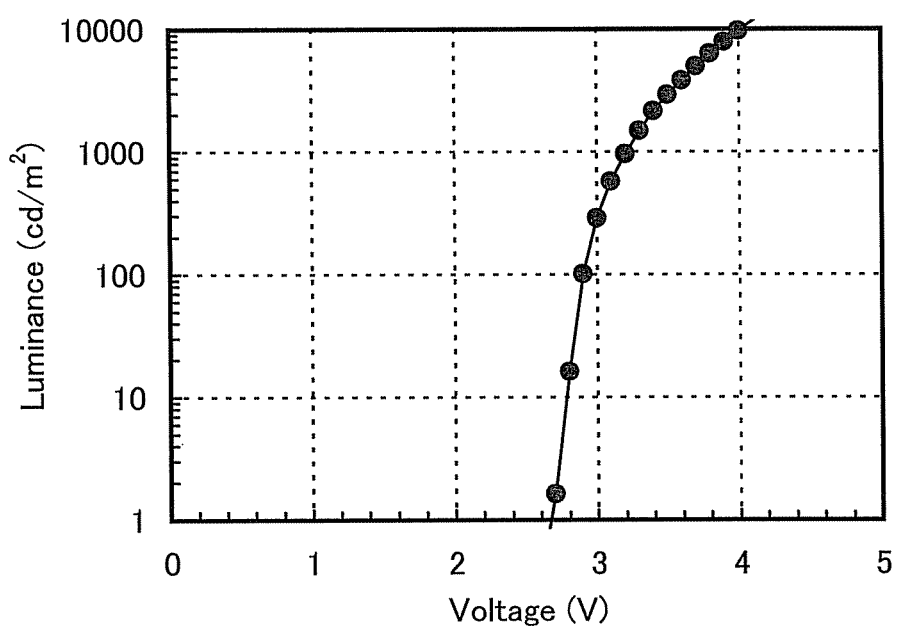
FIG. 31 shows voltage versus luminance characteristics of the light-emitting element 4.
Figure 32:
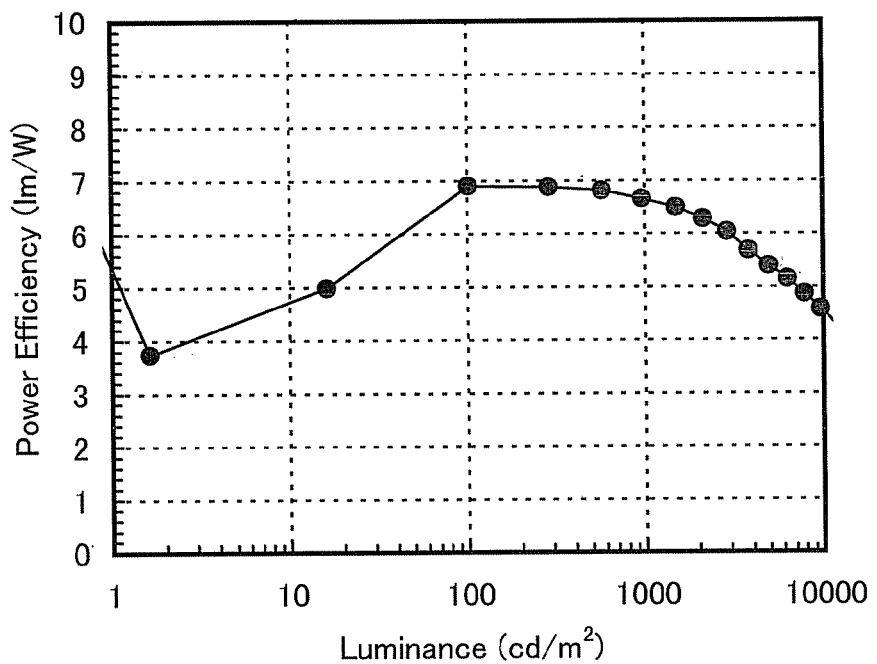
FIG. 32 shows luminance versus power efficiency characteristics of the light-emitting element 4.
Figure 33:
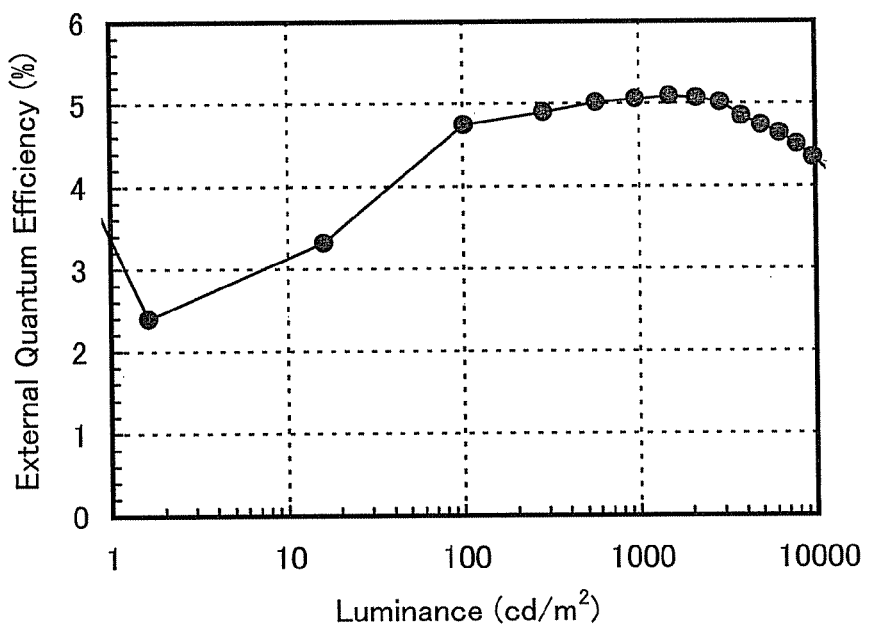
FIG. 33 shows luminance versus external quantum efficiency characteristics of the light-emitting element 4.

FIG. 30 shows luminance versus current efficiency characteristics of the light-emitting element, FIG. 31 shows voltage versus luminance characteristics thereof, FIG. 32 shows luminance versus power efficiency characteristics thereof, and FIG. 33 shows luminance versus external quantum efficiency characteristics thereof. In FIG. 30, the vertical axis represents current efficiency (cd/A), and the horizontal axis represents luminance (cd/m$^2$). In FIG. 31, the vertical axis represents luminance (cd/m$^2$), and the horizontal axis represents voltage (V). In FIG. 32, the vertical axis represents power efficiency (lm/W), and the horizontal axis represents luminance (cd/m$^2$). In FIG. 33, the vertical axis represents external quantum efficiency (%), and the horizontal axis represents luminance (cd/m$^2$).

FIG. 30 indicates that the light-emitting element 4 in which the composite material of the fluorene derivative BPPF and molybdenum oxide was used in the hole-injection layer has excellent luminance versus current efficiency characteristics. FIG. 32 and FIG. 33 show that the light-emitting element 4 has excellent luminance versus power efficiency characteristics and excellent luminance versus external quantum efficiency characteristics, indicating that the light-emitting element 4 has high emission efficiency.

Figure 34:
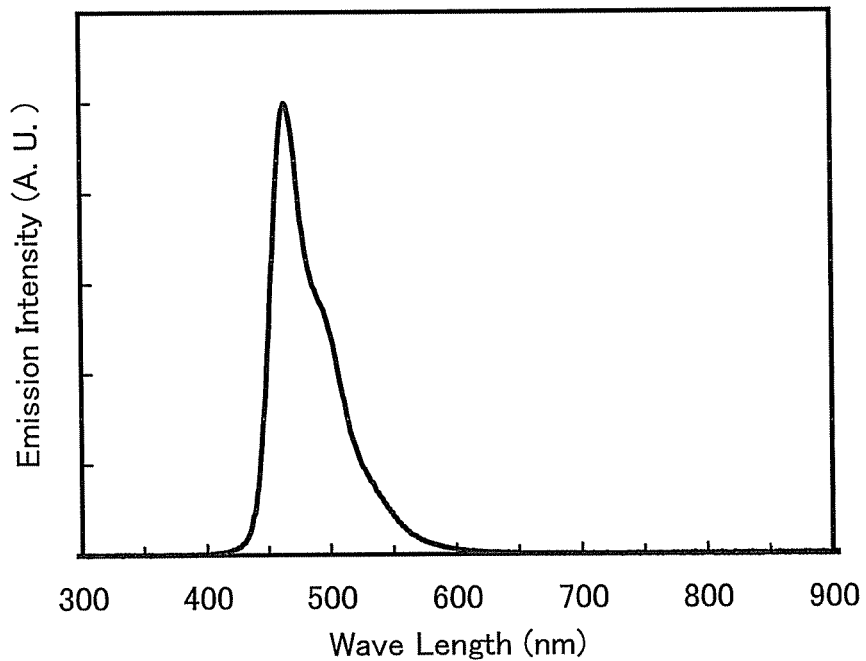
FIG. 34 shows an emission spectrum of the light-emitting element 4.

FIG. 34 shows an emission spectrum of the fabricated light-emitting element 4 when a current of 1 mA was made to flow therein. In FIG. 34, the vertical axis represents emission intensity and the horizontal axis represents emission wave length (nm). The emission intensity is shown as a value relative to the greatest emission intensity assumed to be 1. FIG. 34 shows that the light-emitting element 4 emits blue light originating from 1,6mMemFLPAPrn, which is the emission center substance.

Table 4 shows main characteristics of the light-emitting element 4 around 1000 cd/m$^2$.

TABLE 4

| | Voltage (V) | Current (mA) | Current Efficiency (cd/A) | Power Efficiency (lm/W) | External Quantum Efficiency (%) |
|---|---|---|---|---|---|
| Light-emitting Element 4 | 3.2 | 0.57 | 6.8 | 6.7 | 5.1 |

Figure 35:
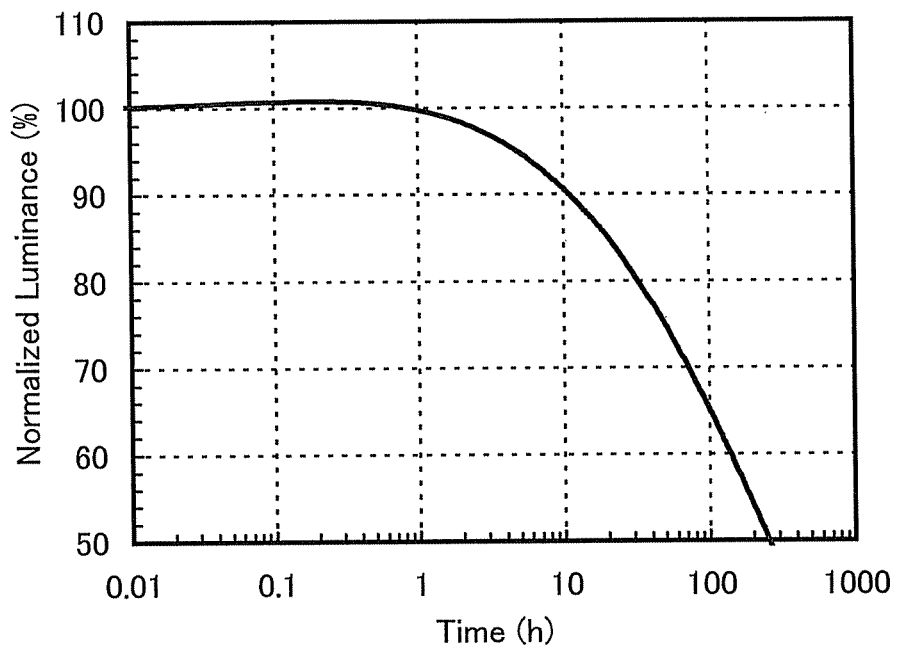
FIG. 35 shows time versus normalized luminance characteristics of the light-emitting element 4.

Next, the initial luminance was set at 5000 cd/m$^2$, the element was driven under a condition where the current density was constant, and changes in luminance with respect to the driving time were examined. FIG. 35 shows time versus normalized luminance characteristics. From FIG. 35, it is found that the light-emitting element 4 has excellent characteristics despite the driving test at 5000 cd/m$^2$, a very high luminance, and thus has high reliability.

In the above manner, it is found that the composite material which includes the hydrocarbon compound having the fluorene skeleton and the inorganic compound described in Embodiment 1 is suitable as a material included in a light-emitting element.

Example 7

Example 7 shows a light-emitting element (light-emitting element 5) in which a hole-injection layer is formed with a co-evaporation film of the composite material described in Embodiment 1, which contains 2,7-bis(1-pyrenyl)spiro[9H-fluoren-9,9'-[9H]fluorene] (abbreviation: Spiro-pye) (structural formula (517)) and molybdenum oxide.

The molecular structures of organic compounds used in this example are represented by the following structural formulas. In the element structure used, an electron-injection layer was provided between the electron-transport layer 114 and the second electrode 104 in the structure in FIG. 1A.

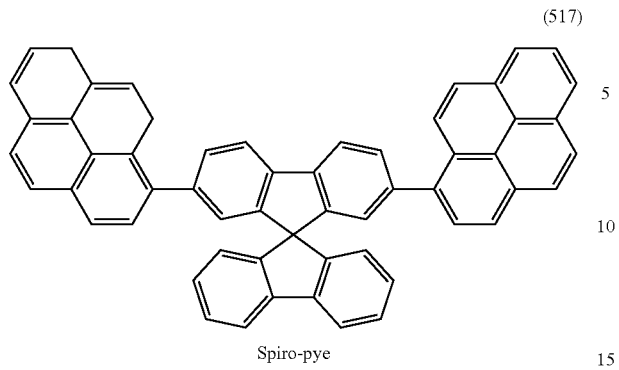

Spiro-pye

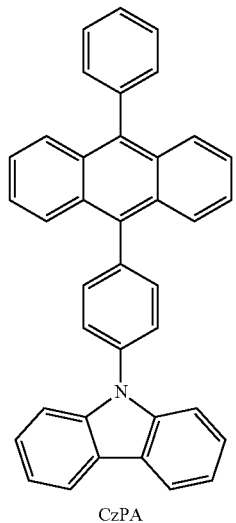

CzPA

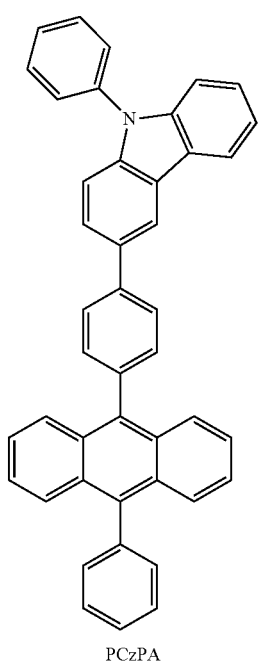

PCzPA

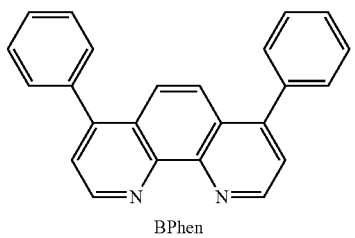

BPhen

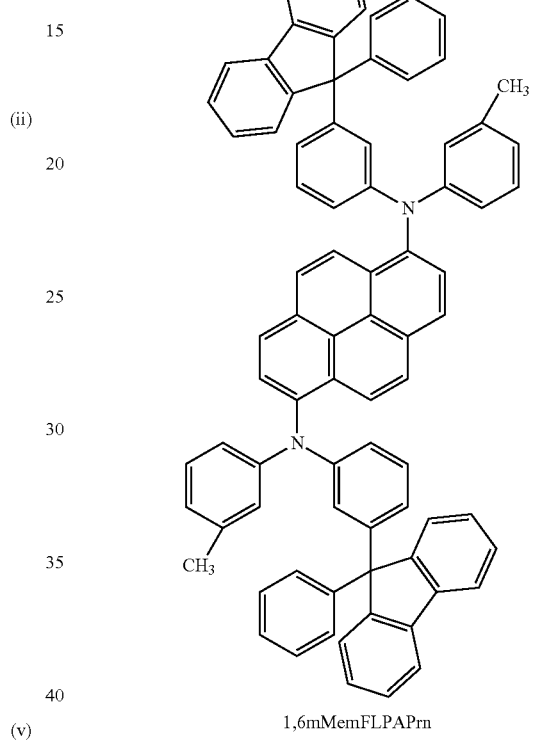

1,6mMemFLPAPrn

[Fabrication of Light-Emitting Element 5]

First, the glass substrate 101 was prepared, over which indium tin oxide containing silicon (ITSO) with a thickness of 110 nm was formed as the first electrode 102. A surface of the ITSO film was covered with a polyimide film such that an area of 2 mm×2 mm of the surface was exposed, which corresponded to the electrode area. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus in which the pressure was reduced to approximately $10^{-4}$ Pa, vacuum baking at 170° C. for 30 minutes was performed in a heating chamber of the vacuum evaporation apparatus, and then the substrate was cooled down for approximately 30 minutes.

Then, the substrate 101 was fixed on a holder provided in the vacuum evaporation apparatus such that the surface of the substrate 101 provided with ITSO faced downward.

The pressure in the vacuum evaporation apparatus was reduced to $10^{-4}$ Pa, and then 2,7-bis(1-pyrenyl)spiro[9H-fluoren-9,9'-[9H]fluorene] (abbreviation: Spiro-pye) and molybdenum(VI) oxide were co-evaporated by adjusting evaporation rates such that the weight ratios of Spiro-pye to molybdenum oxide were 2:1, so that the hole-injection layer 111 was formed. The thickness was 50 nm. Note that a co-evaporation method is an evaporation method in which a plurality of different substances are concurrently vaporized from respective different evaporation sources.

Next, 9-[4-(9-phenylcarbazol-3-yl)]phenyl-10-phenylanthracene (abbreviation: PCzPA) represented by the above structural formula (v) was deposited to a thickness of 10 nm, so that the hole-transport layer 112 was formed.

Further, over the hole-transport layer 112, 9-[4-(10-phenyl-9-anthryl)phenyl]-9H-carbazole (abbreviation: CzPA) represented by the above structural formula (ii) and N,N'-bis(3-methylphenyl)-N,N'-bis[3-(9-phenyl-9H-fluoren-9-yl)phenyl]-pyrene-1,6-diamine (abbreviation: 1,6mMemFLPA-Prn) represented by the above structural formula (x) were evaporated to a thickness of 30 nm by adjusting evaporation rates such that the weight ratios of CzPA to 1,6mMemFLPA-Prn were 1:0.04, so that the light-emitting layer 113 was formed.

Next, CzPA was evaporated to a thickness of 10 nm, and then bathophenanthroline (abbreviation: BPhen) represented by the above structural formula (iv) was evaporated to a thickness of 20 nm, so that the electron-transport layer 114 was formed. Further, lithium fluoride was evaporated to a thickness of 1 nm over the electron-transport layer 114, so that the electron-injection layer was formed. Finally, aluminum was deposited to a thickness of 200 nm as the second electrode 104 serving as a cathode, whereby the light-emitting element 5 was completed. Note that in the above evaporation process, evaporation was all performed by a resistance heating method.

[Operation Characteristics of Light-Emitting Element 5]

The thus obtained light-emitting element 5 was put into a glove box under a nitrogen atmosphere, and the light-emitting element was sealed so as not to be exposed to the air. Then, the operation characteristics of the light-emitting element were measured. Note that the measurements were carried out at room temperature (in an atmosphere kept at 25° C.).

Figure 36:
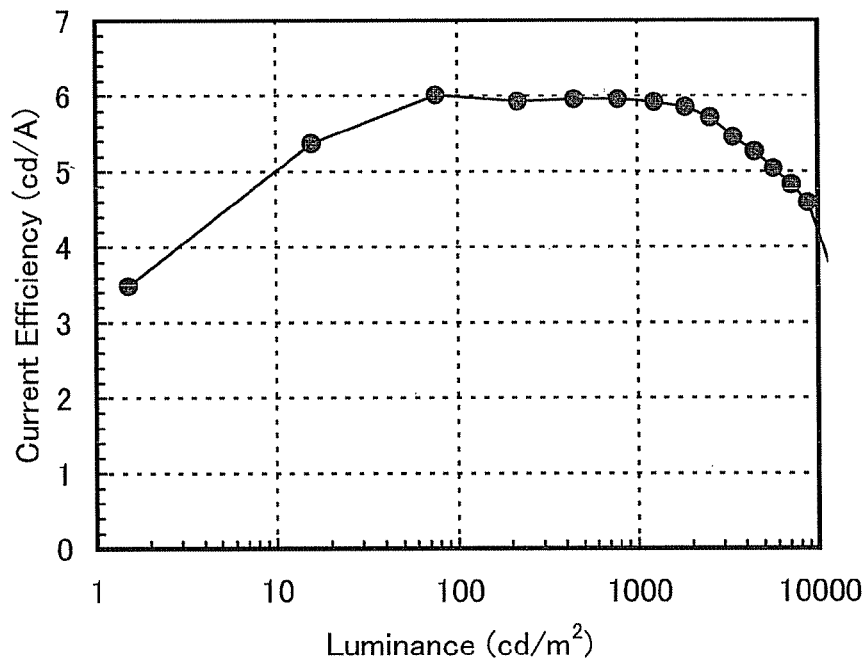
FIG. 36 shows luminance versus current efficiency characteristics of a light-emitting element 5.
Figure 37:
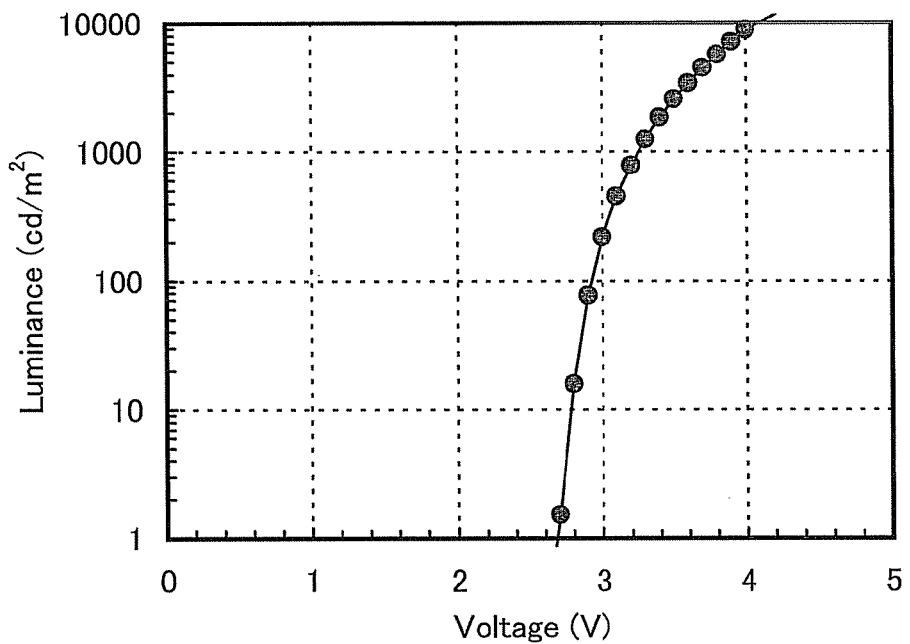
FIG. 37 shows voltage versus luminance characteristics of the light-emitting element 5.
Figure 38:
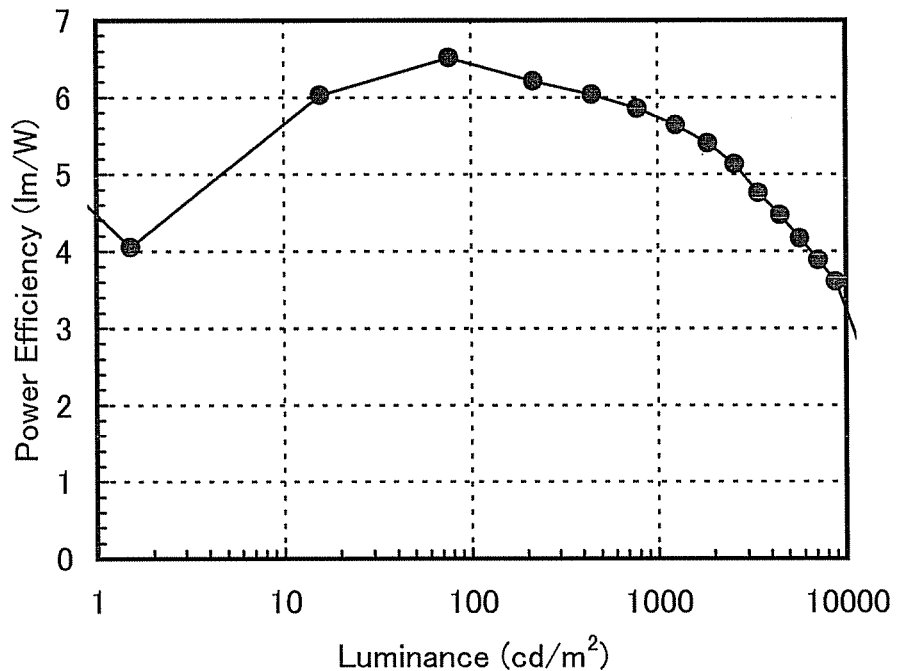
FIG. 38 shows luminance versus power efficiency characteristics of the light-emitting element 5.
Figure 39:
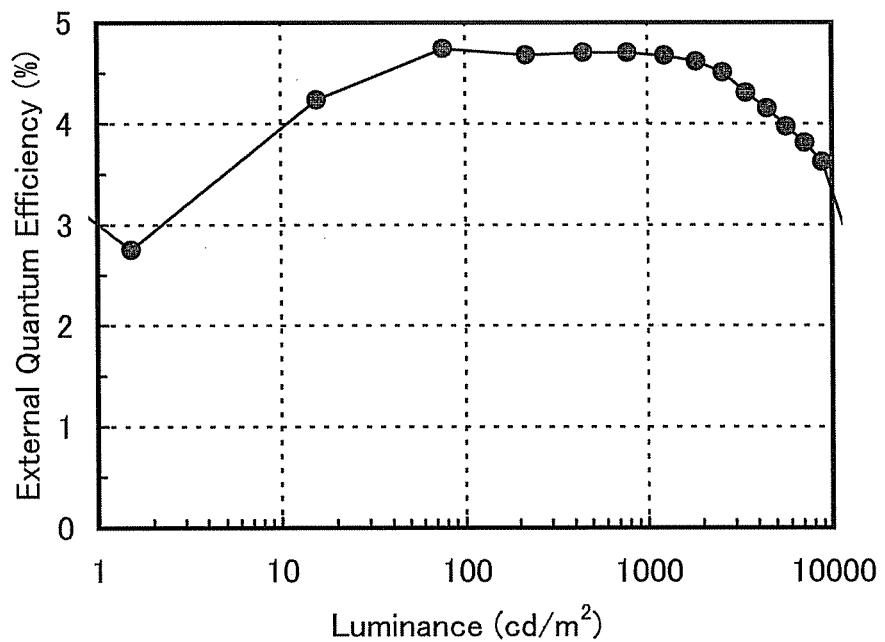
FIG. 39 shows luminance versus external quantum efficiency characteristics of the light-emitting element 5.

FIG. 36 shows luminance versus current efficiency characteristics of the light-emitting element, FIG. 37 shows voltage versus luminance characteristics thereof, FIG. 38 shows luminance versus power efficiency characteristics thereof, and FIG. 39 shows luminance versus external quantum efficiency characteristics thereof. In FIG. 36, the vertical axis represents current efficiency (cd/A), and the horizontal axis represents luminance (cd/m$^2$). In FIG. 37, the vertical axis represents luminance (cd/m$^2$), and the horizontal axis represents voltage (V). In FIG. 38, the vertical axis represents power efficiency (lm/W), and the horizontal axis represents luminance (cd/m$^2$). In FIG. 39, the vertical axis represents external quantum efficiency (%), and the horizontal axis represents luminance (cd/m$^2$).

FIG. 36 indicates that the light-emitting element 5 in which the composite material of the fluorene derivative Spiro-pye and molybdenum oxide was used in the hole-injection layer has excellent luminance versus current efficiency characteristics. FIG. 38 and FIG. 39 show that the light-emitting element 5 has excellent luminance versus power efficiency characteristics and excellent luminance versus external quantum efficiency characteristics, indicating that the light-emitting element 5 has high emission efficiency.

Figure 40:
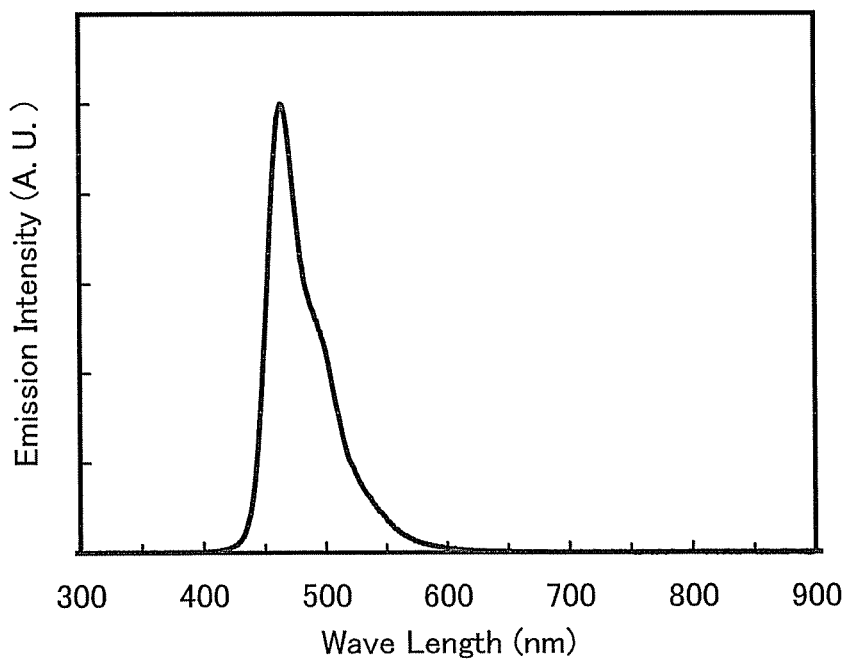
FIG. 40 shows an emission spectrum of the light-emitting element 5.

FIG. 40 shows an emission spectrum of the fabricated light-emitting element 5 when a current of 1 mA was made to flow therein. In FIG. 40, the vertical axis represents emission intensity and the horizontal axis represents emission wavelength (nm). The emission intensity is shown as a value relative to the greatest emission intensity assumed to be 1. FIG. 40 shows that the light-emitting element 5 emits blue light originating from 1,6mMemFLPAPrn, which is the emission center substance.

Table 5 shows main characteristics of the light-emitting element 5 around 1000 cd/m$^2$.

TABLE 5

| | Voltage (V) | Current (mA) | Current Efficiency (cd/A) | Power Efficiency (lm/W) | External Quantum Efficiency (%) |
|---|---|---|---|---|---|
| Light-emitting Element 5 | 3.2 | 0.53 | 6.0 | 5.9 | 4.7 |

Figure 41:
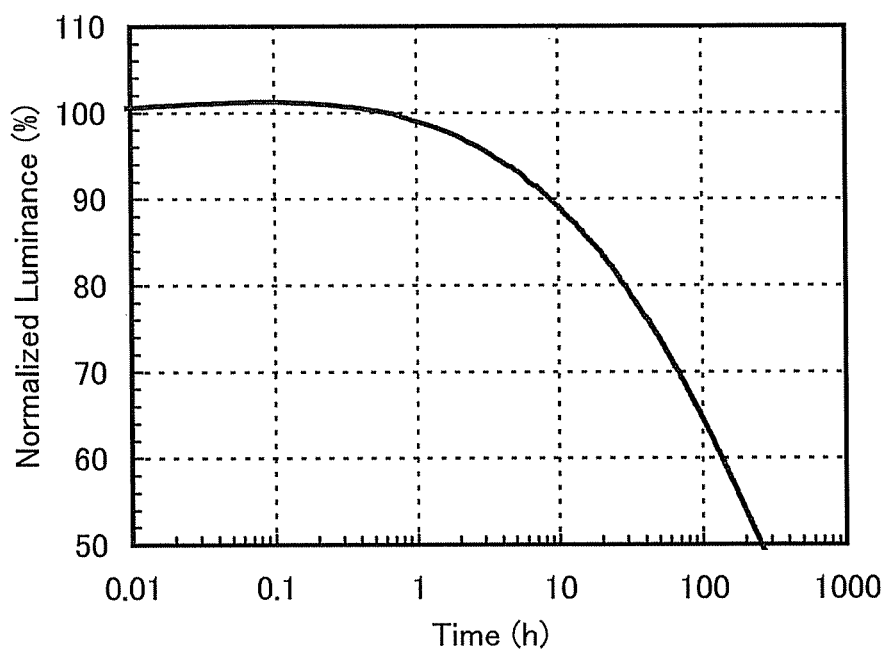
FIG. 41 shows time versus normalized luminance characteristics of the light-emitting element 5.

Next, the initial luminance was set at 5000 cd/m$^2$, the element was driven under a condition where the current density was constant, and changes in luminance with respect to the driving time were examined. FIG. 41 shows time versus normalized luminance characteristics. From FIG. 41, it is found that the light-emitting element 5 has excellent characteristics despite the driving test at 5000 cd/m$^2$, a very high luminance, and thus has high reliability.

In the above manner, it is found that the composite material which includes the hydrocarbon compound having the fluorene skeleton and the inorganic compound described in Embodiment 1 is suitable as a material included in a light-emitting element.

Example 8

Example 8 shows a light-emitting element (light-emitting element 6) in which a hole-injection layer is formed with a co-evaporation film of the composite material described in Embodiment 1, which contains 2,2"-bi(9,9'-spirobi[9H-fluorene]) (abbreviation: BSBF) (structural formula (518)) and molybdenum oxide.

The molecular structures of organic compounds used in this example are represented by the following structural formulas. In the element structure used, an electron-injection layer was provided between the electron-transport layer 114 and the second electrode 104 in the structure in FIG. 1A.

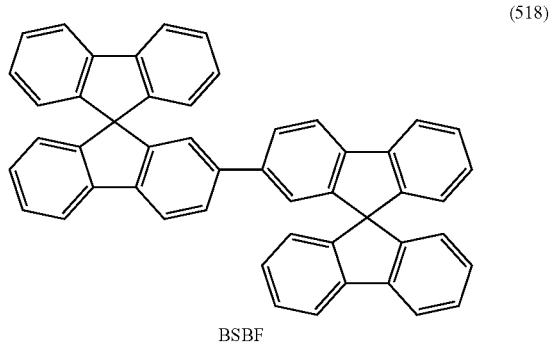

(518)

BSBF (ii)

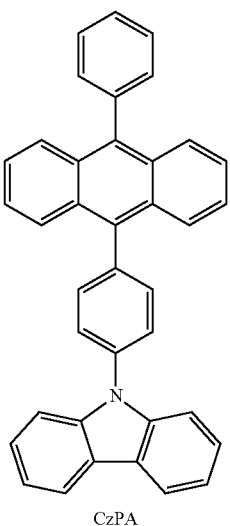

CzPA (v)

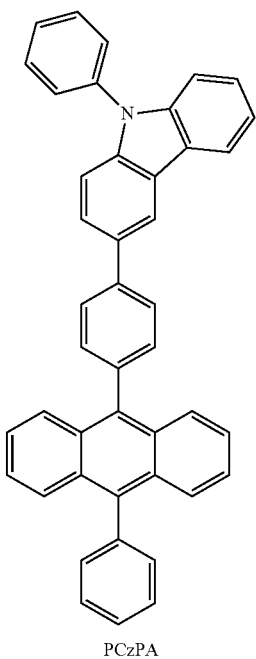

PCzPA (iv)

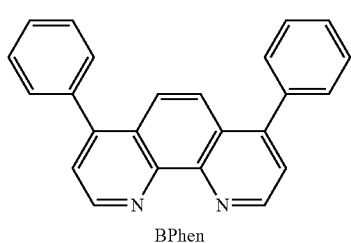

BPhen (x)

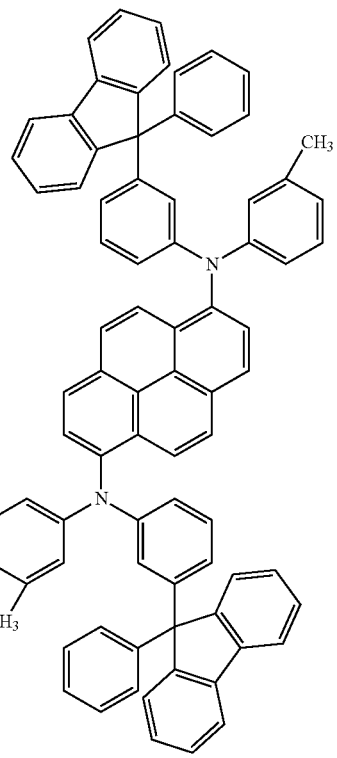

1,6mMemFLPAPrn

[Fabrication of Light-Emitting Element 6]

First, the glass substrate 101 was prepared, over which indium tin oxide containing silicon (ITSO) with a thickness of 110 nm was formed as the first electrode 102. A surface of the ITSO film was covered with a polyimide film such that an area of 2 mm×2 mm of the surface was exposed, which corresponded to the electrode area. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus in which the pressure was reduced to approximately $10^{-4}$ Pa, vacuum baking at 170° C. for 30 minutes was performed in a heating chamber of the vacuum evaporation apparatus, and then the substrate was cooled down for approximately 30 minutes.

Then, the substrate 101 was fixed on a holder provided in the vacuum evaporation apparatus such that the surface of the substrate 101 provided with ITSO faced downward.

The pressure in the vacuum evaporation apparatus was reduced to $10^{-4}$ Pa, and then 2,2″-bi(9,9′-spirobi[9H-fluorene]) (abbreviation: BSBF) represented by the above structural formula (518) and molybdenum(VI) oxide were co-evaporated by adjusting evaporation rates such that the weight ratios of BSBF to molybdenum oxide were 2:1, so that the hole-injection layer 111 was formed. The thickness was 50 nm. Note that a co-evaporation method is an evaporation method in which a plurality of different substances are concurrently vaporized from respective different evaporation sources.

Next, 9-[4-(9-phenylcarbazol-3-yl)]phenyl-10-phenylanthracene (abbreviation: PCzPA), represented by the above structural formula (v) was deposited to a thickness of 10 nm, so that the hole-transport layer 112 was formed.

Further, over the hole-transport layer 112, 9-[4-(10-phenyl-9-anthryl)phenyl]-9H-carbazole (abbreviation: CzPA) represented by the above structural formula (ii) and N,N'-bis(3-methylphenyl)-N,N'-bis[3-(9-phenyl-9H-fluoren-9-yl)phenyl]-pyrene-1,6-diamine (abbreviation: 1,6mMemFLPA-Prn) represented by the above structural formula (x) were evaporated to a thickness of 30 nm by adjusting evaporation rates such that the weight ratios of CzPA to 1,6mMemFLPA-Prn were 1:0.04, so that the light-emitting layer 113 was formed.

Next, CzPA was evaporated to a thickness of 10 nm, and then bathophenanthroline (abbreviation: BPhen) represented by the above structural formula (iv) was evaporated to a thickness of 20 nm, so that the electron-transport layer 114 was formed. Further, lithium fluoride was evaporated to a thickness of 1 nm over the electron-transport layer 114, so that the electron-injection layer was formed. Finally, aluminum was deposited to a thickness of 200 nm as the second electrode 104 serving as a cathode, whereby the light-emitting element 6 was completed. Note that in the above evaporation process, evaporation was all performed by a resistance heating method.

[Operation Characteristics of Light-Emitting Element 6]

The thus obtained light-emitting element 6 was put into a glove box under a nitrogen atmosphere, and the light-emitting element was sealed so as not to be exposed to the air. Then, the operation characteristics of the light-emitting element were measured. Note that the measurements were carried out at room temperature (in an atmosphere kept at 25° C.).

Figure 42:
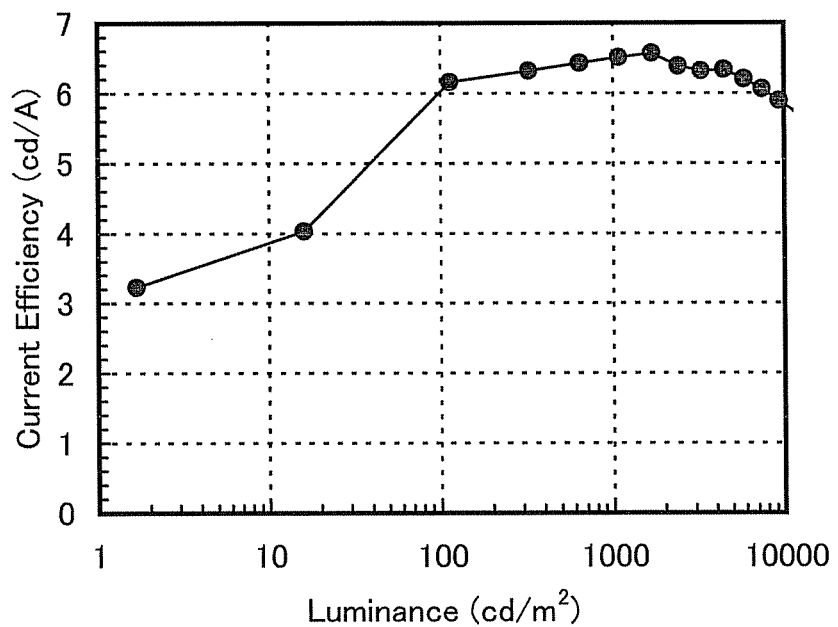
FIG. 42 shows luminance versus current efficiency characteristics of a light-emitting element 6.
Figure 43:
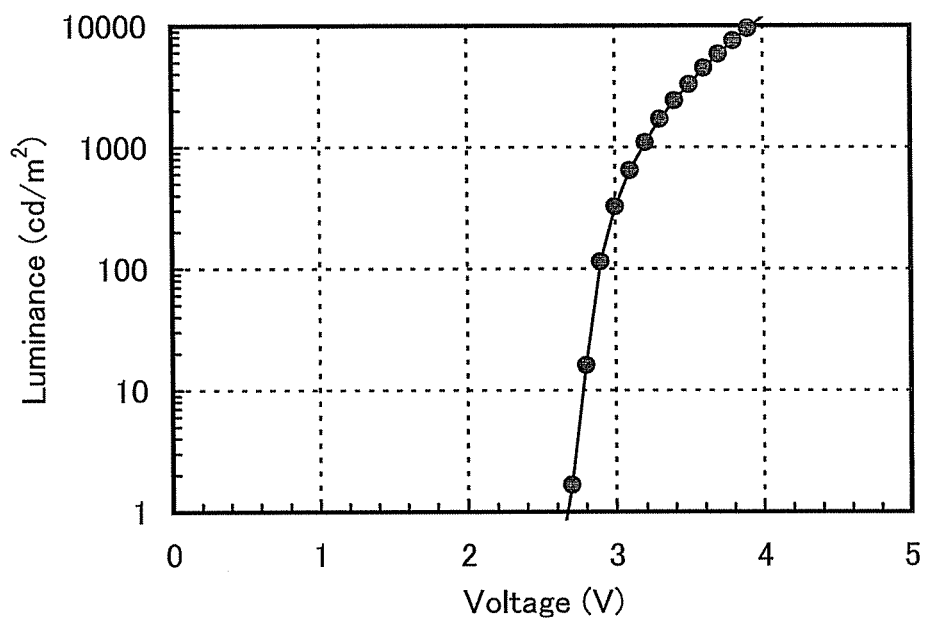
FIG. 43 shows voltage versus luminance characteristics of the light-emitting element 6.
Figure 44:
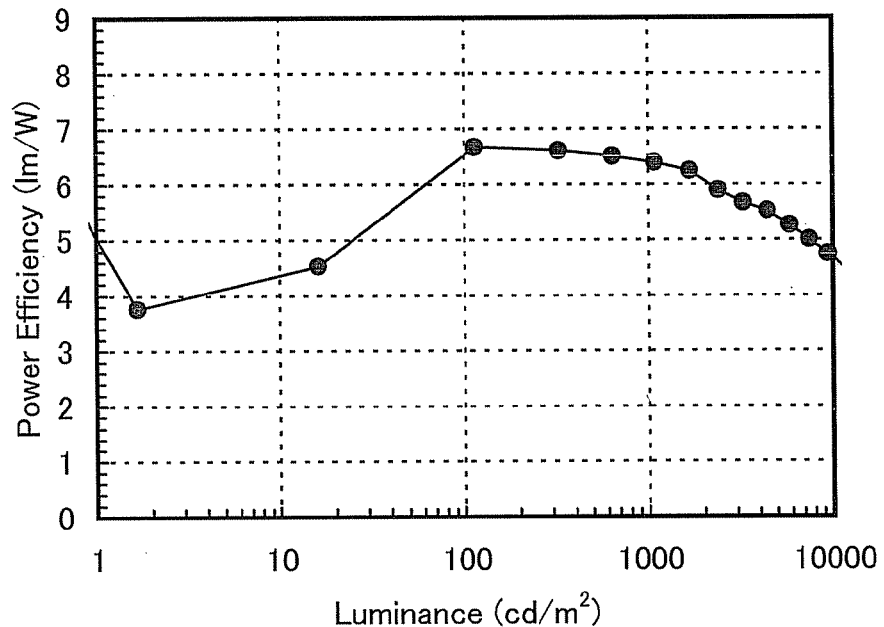
FIG. 44 shows luminance versus power efficiency characteristics of the light-emitting element 6.
Figure 45:
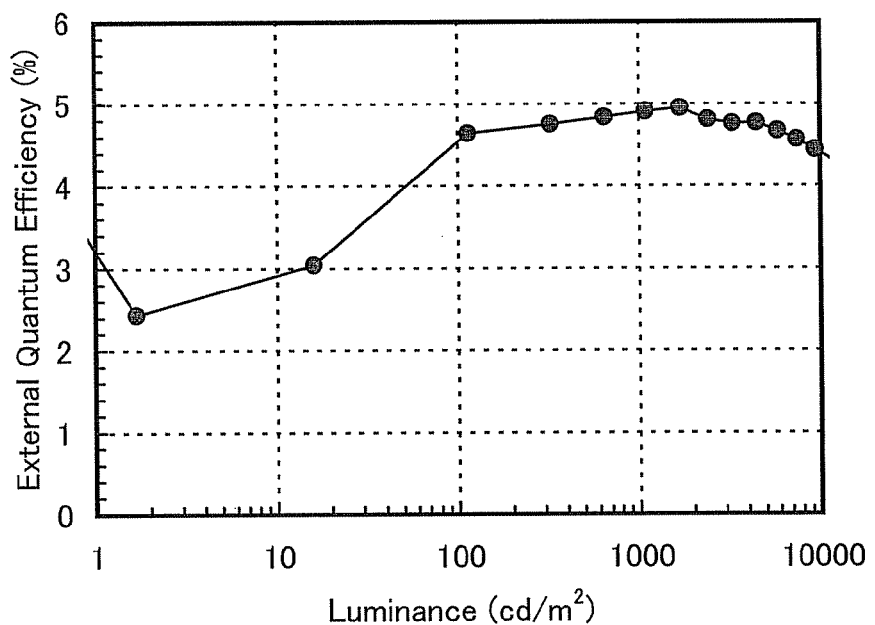
FIG. 45 shows luminance versus external quantum efficiency characteristics of the light-emitting element 6.

FIG. 42 shows luminance versus current efficiency characteristics of the light-emitting element, FIG. 43 shows voltage versus luminance characteristics thereof, FIG. 44 shows luminance versus power efficiency characteristics thereof, and FIG. 45 shows luminance versus external quantum efficiency characteristics thereof. In FIG. 42, the vertical axis represents current efficiency (cd/A), and the horizontal axis represents luminance (cd/m$^2$). In FIG. 43, the vertical axis represents luminance (cd/m$^2$), and the horizontal axis represents voltage (V). In FIG. 44, the vertical axis represents power efficiency (lm/W), and the horizontal axis represents luminance (cd/m$^2$). In FIG. 45, the vertical axis represents external quantum efficiency (%), and the horizontal axis represents luminance (cd/m$^2$).

FIG. 42 indicates that the light-emitting element 6 in which the composite material of the fluorene derivative BSBF and molybdenum oxide was used in the hole-injection layer has excellent luminance versus current efficiency characteristics. FIG. 44 and FIG. 45 show that the light-emitting element 6 has excellent luminance versus power efficiency characteristics and excellent luminance versus external quantum efficiency characteristics, indicating that the light-emitting element 6 has high emission efficiency.

Figure 46:
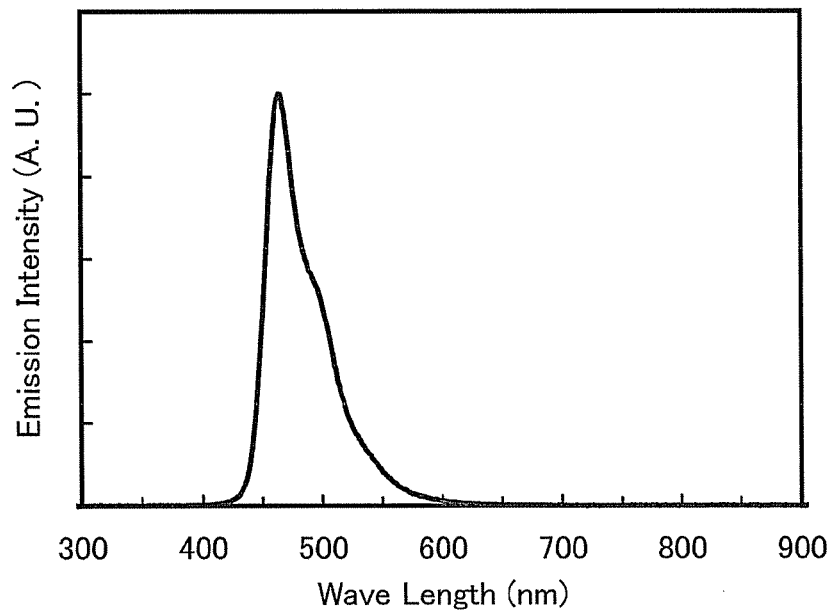
FIG. 46 shows an emission spectrum of the light-emitting element 6.

FIG. 46 shows an emission spectrum of the fabricated light-emitting element 6 when a current of 1 mA was made to flow therein. In FIG. 46, the vertical axis represents emission intensity and the horizontal axis represents emission wave length (nm). The emission intensity is shown as a value relative to the greatest emission intensity assumed to be 1. FIG. 46 shows that the light-emitting element 6 emits blue light originating from 1,6mMemFLPAPrn, which is the emission center substance.

Table 6 shows main characteristics of the light-emitting element 6 around 1000 cd/m$^2$.

TABLE 6

| | Voltage (V) | Current (mA) | Current Efficiency (cd/A) | Power Efficiency (lm/W) | External Quantum Efficiency (%) |
|---|---|---|---|---|---|
| Light-emitting Element 6 | 3.2 | 0.67 | 6.5 | 6.4 | 4.9 |

Figure 47:
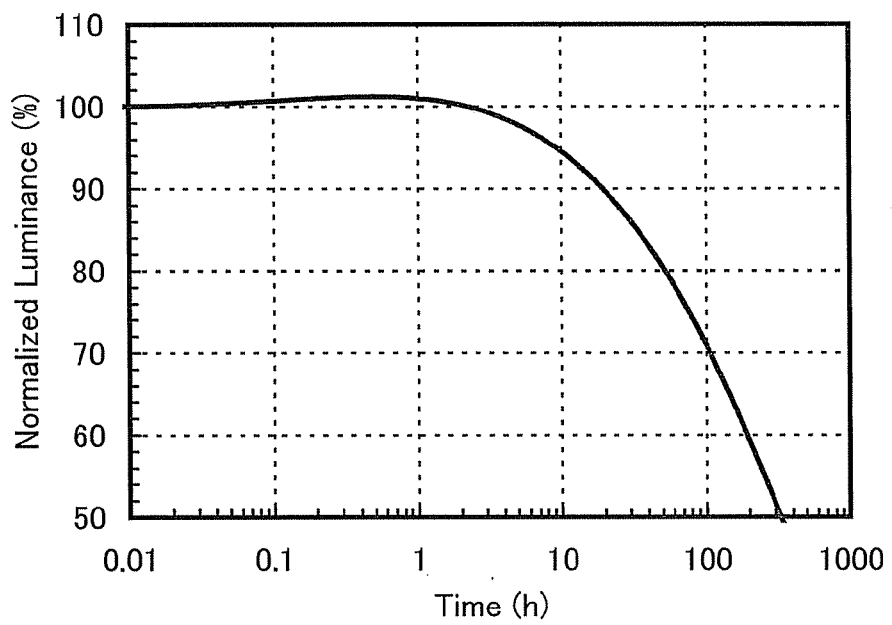
FIG. 47 shows time versus normalized luminance characteristics of the light-emitting element 6.

Next, the initial luminance was set at 5000 cd/m$^2$, the element was driven under a condition where the current density was constant, and changes in luminance with respect to the driving time were examined. FIG. 47 shows time versus normalized luminance characteristics. From FIG. 47, it is found that the light-emitting element 6 has excellent characteristics despite the driving test at 5000 cd/m$^2$, a very high luminance, and thus has high reliability.

In the above manner, it is found that the composite material which includes the hydrocarbon compound having the fluorene skeleton and the inorganic compound described in Embodiment 1 is suitable as a material included in a light-emitting element.

Example 9

Example 9 shows a light-emitting element (light-emitting element 7) in which a hole-injection layer is formed with a co-evaporation film of the composite material described in Embodiment 1, which contains 2,2''-bi(9,9'-spirobi[9H-fluorene]) (abbreviation: BSBF) (structural formula (518)) and molybdenum oxide, and in which a hole-transport layer is formed using BSBF.

The molecular structures of organic compounds used in this example are represented by the following structural formulas. In the element structure used, an electron-injection layer was provided between the electron-transport layer 114 and the second electrode 104 in the structure in FIG. 1A.

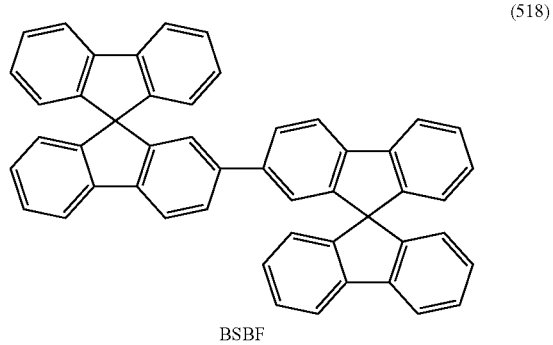

BSBF (518)

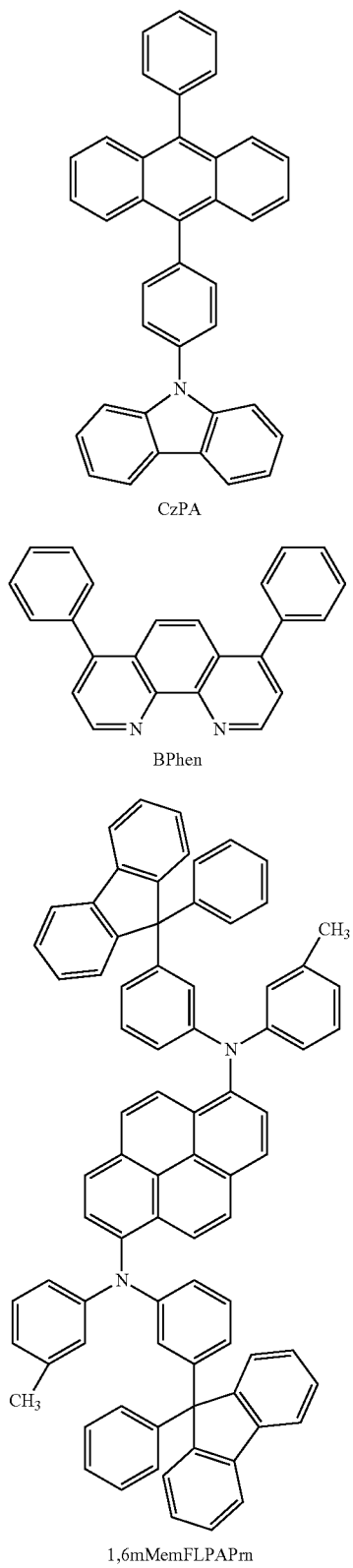

(ii) CzPA (iv) BPhen (x) 1,6mMemFLPAPrn

[Fabrication of Light-Emitting Element 7]

First, the glass substrate 101 was prepared, over which indium tin oxide containing silicon (ITSO) with a thickness of 110 nm was formed as the first electrode 102. A surface of the ITSO film was covered with a polyimide film such that an area of 2 mm×2 mm of the surface was exposed, which corresponded to the electrode area. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus in which the pressure was reduced to approximately $10^{-4}$ Pa, vacuum baking at 170° C. for 30 minutes was performed in a heating chamber of the vacuum evaporation apparatus, and then the substrate was cooled down for approximately 30 minutes.

Then, the substrate 101 was fixed on a holder provided in the vacuum evaporation apparatus such that the surface of the substrate 101 provided with ITSO faced downward.

The pressure in the vacuum evaporation apparatus was reduced to $10^{-4}$ Pa, and then 2,2"-bi(9,9'-spirobi[9H-fluorene]) (abbreviation: BSBF) represented by the above structural formula (518) and molybdenum(VI) oxide were co-evaporated by adjusting evaporation rates such that the weight ratios of BSBF to molybdenum oxide were 2:1, so that the hole-injection layer 111 was formed. The thickness was 50 nm. Note that a co-evaporation method is an evaporation method in which a plurality of different substances are concurrently vaporized from respective different evaporation sources.

Next, BSBF represented by the above structural formula (518) was deposited to a thickness of 10 nm, so that the hole-transport layer 112 was formed.

Further, over the hole-transport layer 112, 9-[4-(10-phenyl-9-anthryl)phenyl]-9H-carbazole (abbreviation: CzPA) represented by the above structural formula (ii) and N,N'-bis(3-methylphenyl)-N,N'-bis[3-(9-phenyl-9H-fluoren-9-yl)phenyl]-pyrene-1,6-diamine (abbreviation: 1,6mMemFLPA-Prn) represented by the above structural formula (x) were evaporated to a thickness of 30 nm by adjusting evaporation rates such that the weight ratios of CzPA to 1,6mMemFLPA-Prn were 1:0.04, so that the light-emitting layer 113 was formed.

Next, CzPA was evaporated to a thickness of 10 nm, and then bathophenanthroline (abbreviation: BPhen) represented by the above structural formula (iv) was evaporated to a thickness of 20 nm, so that the electron-transport layer 114 was formed. Further, lithium fluoride was evaporated to a thickness of 1 nm over the electron-transport layer 114, so that the electron-injection layer was formed. Finally, aluminum was deposited to a thickness of 200 nm as the second electrode 104 serving as a cathode, whereby the light-emitting element 7 was completed. Note that in the above evaporation process, evaporation was all performed by a resistance heating method.

[Operation Characteristics of Light-Emitting Element 7]

The thus obtained light-emitting element 7 was put into a glove box under a nitrogen atmosphere, and the light-emitting element was sealed so as not to be exposed to the air. Then, the operation characteristics of the light-emitting element were measured. Note that the measurements were carried out at room temperature (in an atmosphere kept at 25° C.).

Figure 48:
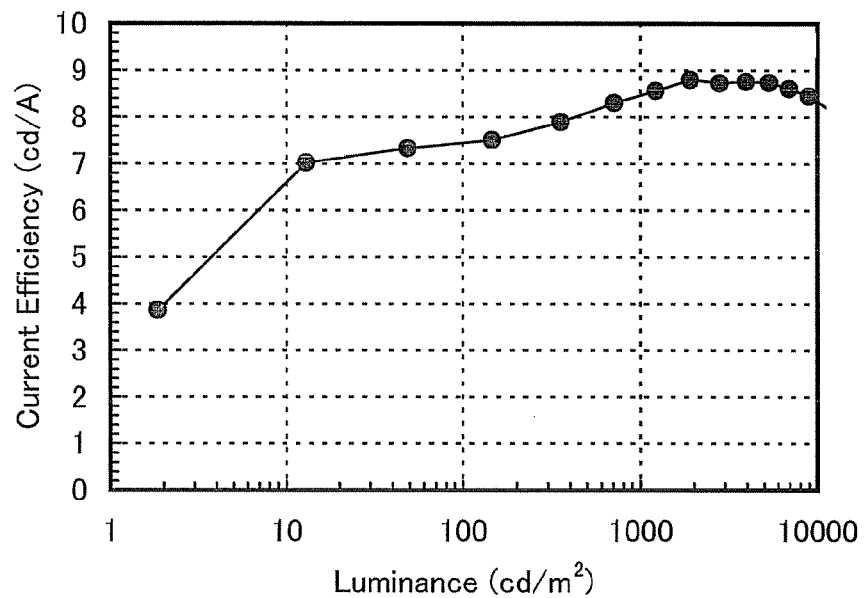
FIG. 48 shows luminance versus current efficiency characteristics of a light-emitting element 7.
Figure 49:
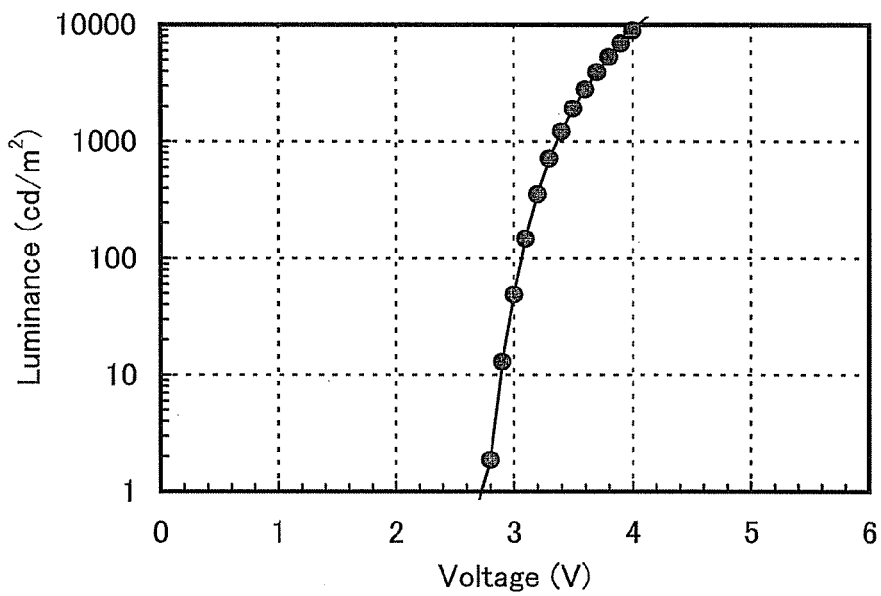
FIG. 49 shows voltage versus luminance characteristics of the light-emitting element 7.
Figure 50:
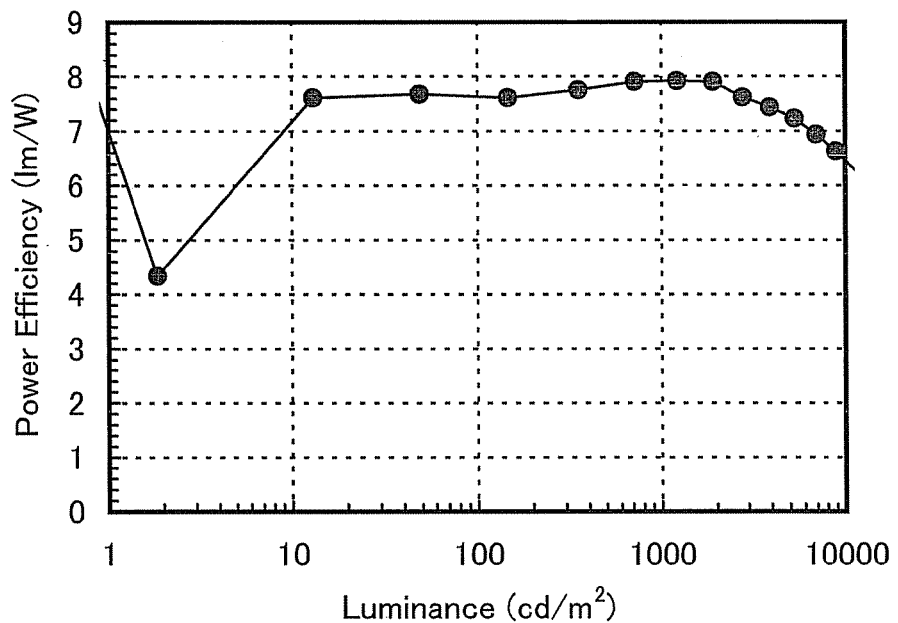
FIG. 50 shows luminance versus power efficiency characteristics of the light-emitting element 7.
Figure 51:
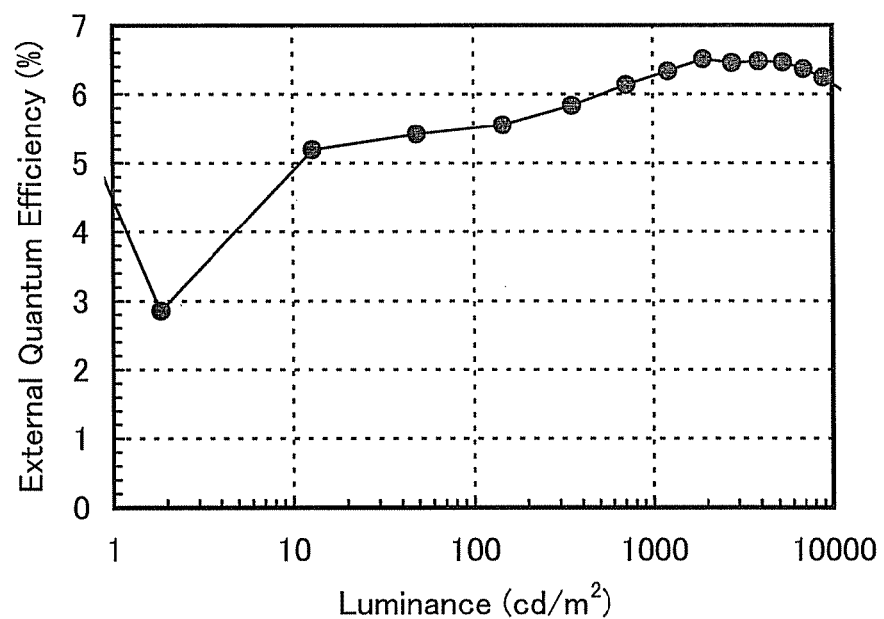
FIG. 51 shows luminance versus external quantum efficiency characteristics of the light-emitting element 7.

FIG. 48 shows luminance versus current efficiency characteristics of the light-emitting element, FIG. 49 shows voltage versus luminance characteristics thereof, FIG. 50 shows luminance versus power efficiency characteristics thereof, and FIG. 51 shows luminance versus external quantum efficiency characteristics thereof. In FIG. 48, the vertical axis represents current efficiency (cd/A), and the horizontal axis represents luminance (cd/m$^2$). In FIG. 49, the vertical axis represents luminance (cd/m$^2$), and the horizontal axis represents voltage (V). In FIG. 50, the vertical axis represents power efficiency (lm/W), and the horizontal axis represents luminance (cd/m²). In FIG. 51, the vertical axis represents external quantum efficiency (%), and the horizontal axis represents luminance (cd/m²).

FIG. 48 indicates that the light-emitting element 7 in which the composite material of the fluorene derivative BSBF and molybdenum oxide was used in the hole-injection layer and BSBF was used in the hole-transport layer has excellent luminance versus current efficiency characteristics. FIG. 50 and FIG. 51 show that the light-emitting element 7 has excellent luminance versus power efficiency characteristics and excellent luminance versus external quantum efficiency characteristics, indicating that the light-emitting element 7 has high emission efficiency.

Figure 52:
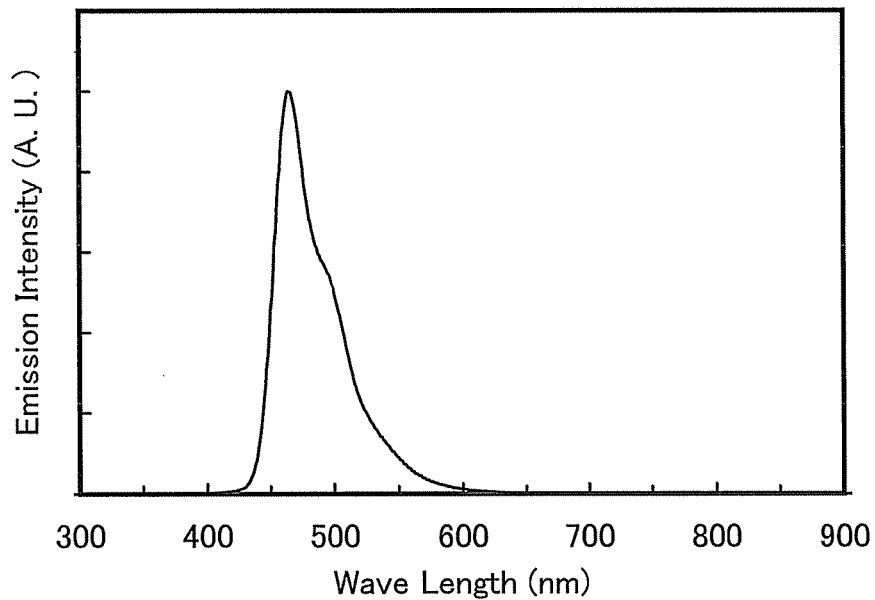
FIG. 52 shows an emission spectrum of the light-emitting element 7.

FIG. 52 shows an emission spectrum of the fabricated light-emitting element 7 when a current of 1 mA was made to flow therein. In FIG. 52, the vertical axis represents emission intensity and the horizontal axis represents emission wave length (nm). The emission intensity is shown as a value relative to the greatest emission intensity assumed to be 1. FIG. 52 shows that the light-emitting element 7 emits blue light originating from 1,6mMemFLPAPrn, which is the emission center substance.

Table 7 shows main characteristics of the light-emitting element 7 around 1000 cd/m².

TABLE 7

| | Voltage (V) | Current (mA) | Current Efficiency (cd/A) | Power Efficiency (lm/W) | External Quantum Efficiency (%) |
|---|---|---|---|---|---|
| Light-emitting Element 7 | 3.4 | 0.57 | 8.6 | 7.9 | 6.3 |

Figure 53:
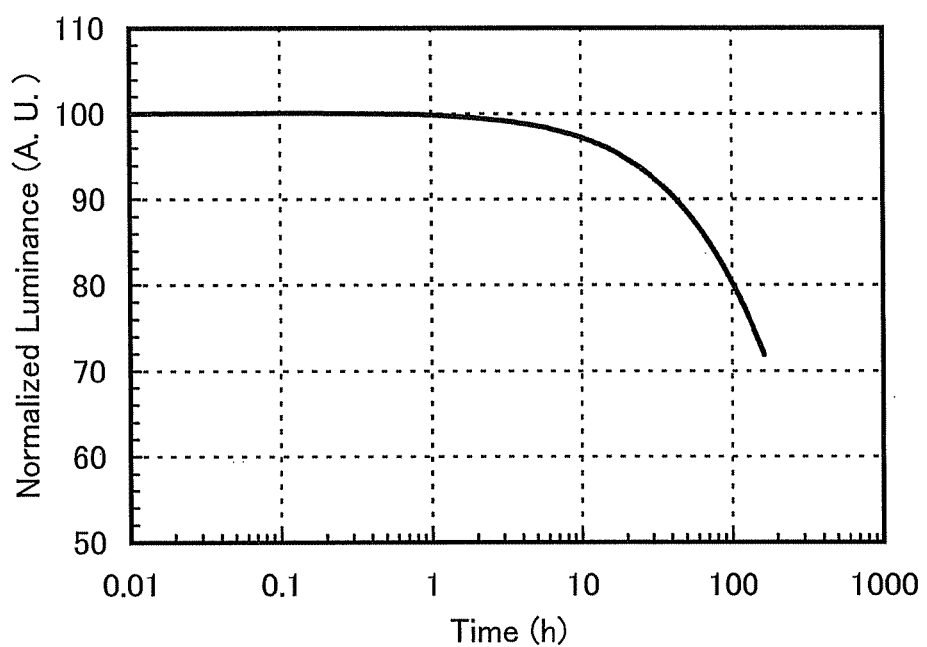
FIG. 53 shows time versus normalized luminance characteristics of the light-emitting element 7.

Next, the initial luminance was set at 5000 cd/m², the element was driven under a condition where the current density was constant, and changes in luminance with respect to the driving time were examined. FIG. 53 shows time versus normalized luminance characteristics. From FIG. 53, it is found that the light-emitting element 7 has excellent characteristics despite the driving test at 5000 cd/m², a very high luminance, and thus has high reliability.

In the above manner, it is found that the composite material which includes the hydrocarbon compound having the fluorene skeleton and the inorganic compound described in Embodiment 1 is suitable as a material included in a light-emitting element.

Example 10

Example 10 shows a light-emitting element (light-emitting element 8) in which a hole-injection layer is formed with a co-evaporation film of the composite material described in Embodiment 1, which contains triphenyl[4-(9-phenyl-9H-fluoren-9-yl)phenyl]silane (abbreviation: TpsiF) and molybdenum oxide.

The molecular structures of organic compounds used in this example are represented by the following structural formulas. In the element structure used, an electron-injection layer was provided between the electron-transport layer 114 and the second electrode 104 in the structure in FIG. 1A.

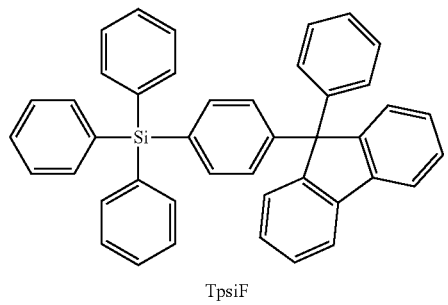

TpsiF

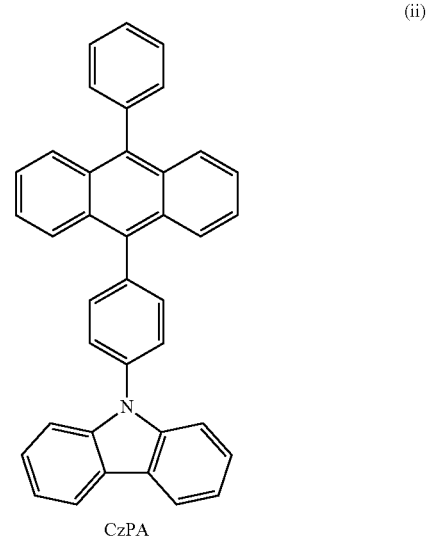

(ii)

CzPA

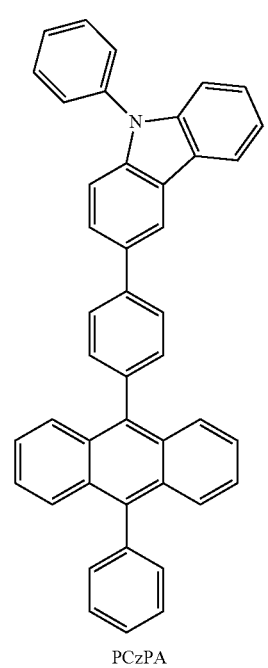

(v)

PCzPA

-continued

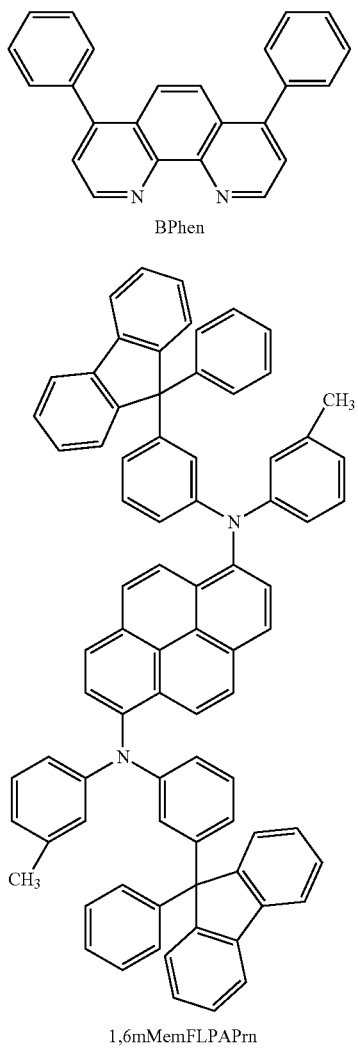

(iv) BPhen (x) 1,6mMemFLPAPrn

[Fabrication of Light-Emitting Element 8]

First, the glass substrate 101 was prepared, over which indium tin oxide containing silicon (ITSO) with a thickness of 110 nm was formed as the first electrode 102. A surface of the ITSO film was covered with a polyimide film such that an area of 2 mm×2 mm of the surface was exposed, which corresponded to the electrode area. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus in which the pressure was reduced to approximately $10^{-4}$ Pa, vacuum baking at 170° C. for 30 minutes was performed in a heating chamber of the vacuum evaporation apparatus, and then the substrate was cooled down for approximately 30 minutes.

Then, the substrate 101 was fixed on a holder provided in the vacuum evaporation apparatus such that the surface of the substrate 101 provided with ITSO faced downward.

The pressure in the vacuum evaporation apparatus was reduced to $10^{-4}$ Pa, and then triphenyl[4-(9-phenyl-9H-fluoren-9-yl)phenyl]silane (abbreviation: TpsiF) and molybdenum(VI) oxide were co-evaporated by adjusting evaporation rates such that the weight ratios of TpsiF to molybdenum oxide were 2:1, so that the hole-injection layer 111 was formed. The thickness was 50 nm. Note that a co-evaporation method is an evaporation method in which a plurality of different substances are concurrently vaporized from respective different evaporation sources.

Next, 9-[4-(9-phenylcarbazol-3-yl)]phenyl-10-phenylanthracene (abbreviation: PCzPA) represented by the above structural formula (v) was deposited to a thickness of 10 nm, so that the hole-transport layer 112 was formed.

Further, over the hole-transport layer 112, 9-[4-(10-phenyl-9-anthryl)phenyl]-9H-carbazole (abbreviation: CzPA) represented by the above structural formula (ii) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) represented by the above structural formula (x) were evaporated to a thickness of 30 nm by adjusting evaporation rates such that the weight ratios of CzPA to 1,6mMemFLPAPrn were 1:0.04, so that the light-emitting layer 113 was formed.

Next, CzPA was evaporated to a thickness of 10 nm, and then bathophenanthroline (abbreviation: BPhen) represented by the above structural formula (iv) was evaporated to a thickness of 20 nm, so that the electron-transport layer 114 was formed. Further, lithium fluoride was evaporated to a thickness of 1 nm over the electron-transport layer 114, so that the electron-injection layer was formed. Finally, aluminum was deposited to a thickness of 200 nm as the second electrode 104 serving as a cathode, whereby the light-emitting element 8 was completed. Note that in the above evaporation process, evaporation was all performed by a resistance heating method.

[Operation Characteristics of Light-Emitting Element 8]

The thus obtained light-emitting element 8 was put into a glove box under a nitrogen atmosphere, and the light-emitting element was sealed so as not to be exposed to the air. Then, the operation characteristics of the light-emitting element were measured. Note that the measurements were carried out at room temperature (in an atmosphere kept at 25° C.).

Figure 54:
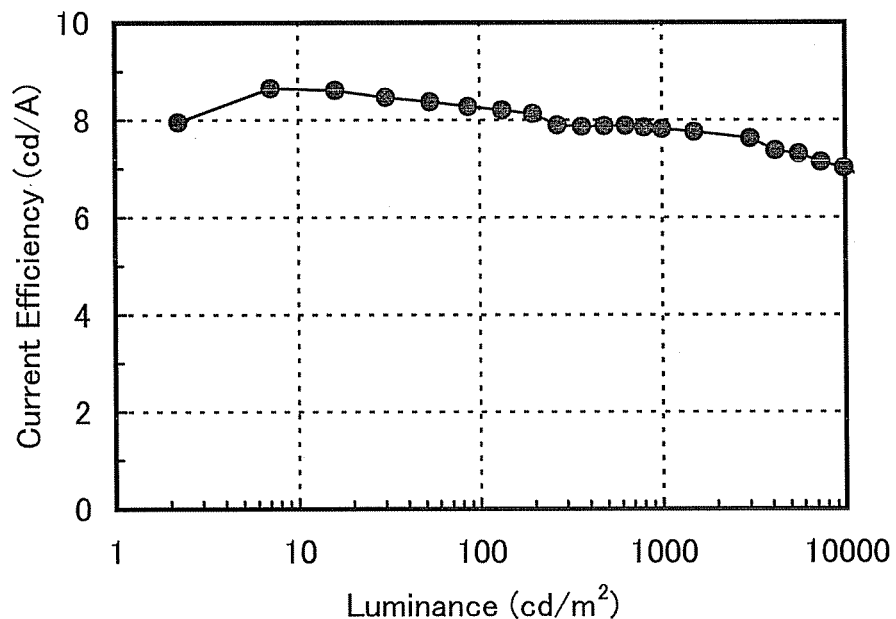
FIG. 54 shows luminance versus current efficiency characteristics of a light-emitting element 8.
Figure 55:
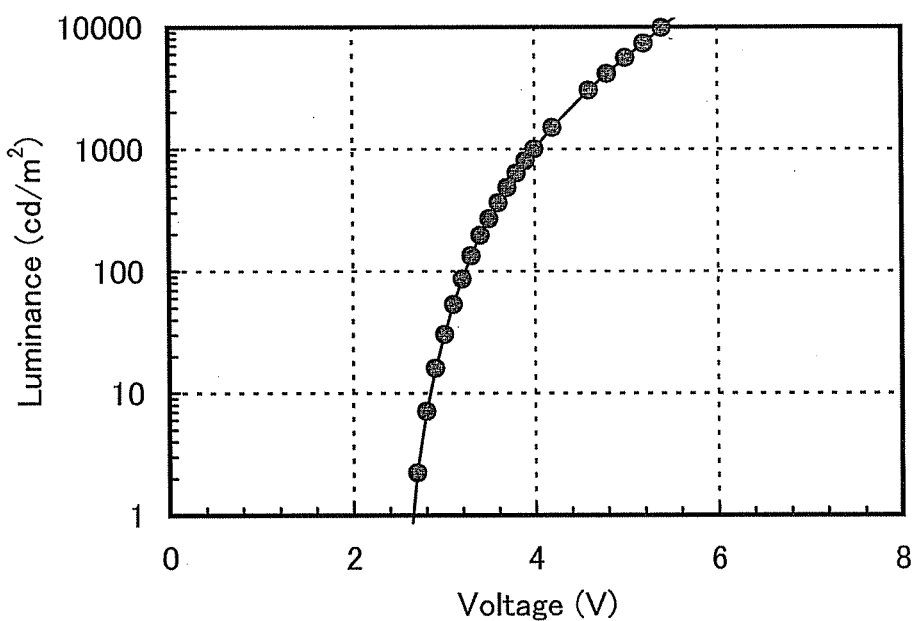
FIG. 55 shows voltage versus luminance characteristics of the light-emitting element 8.
Figure 56:
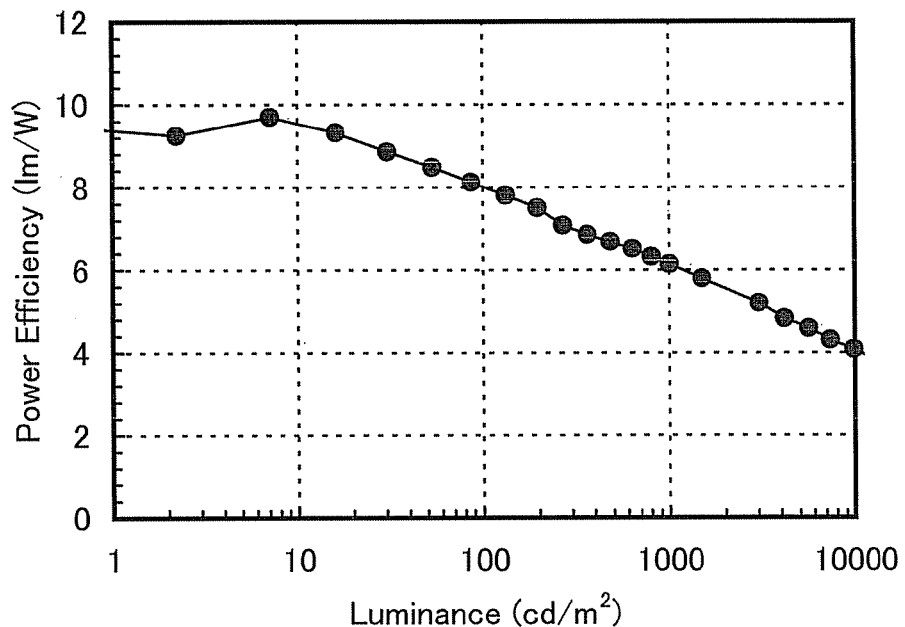
FIG. 56 shows luminance versus power efficiency characteristics of the light-emitting element 8.
Figure 57:
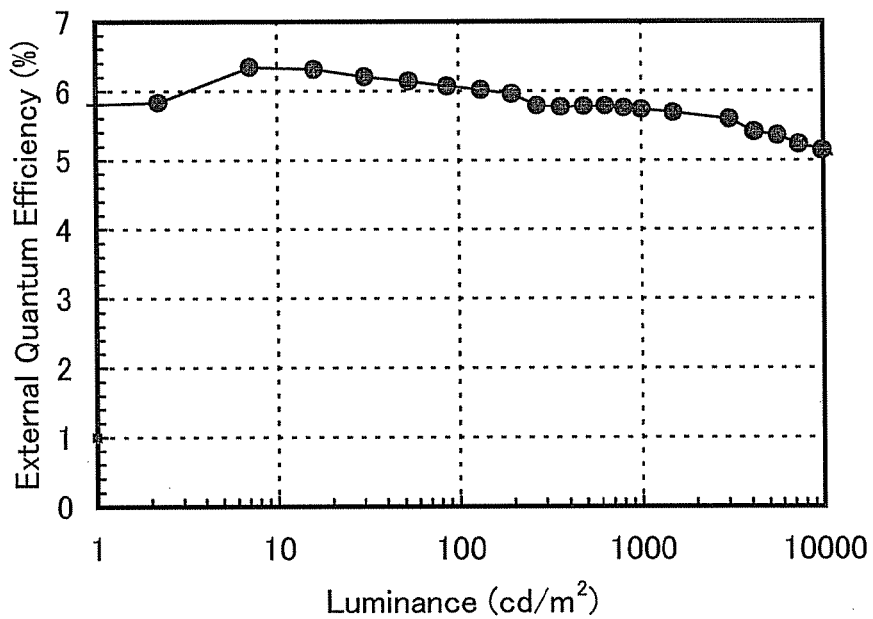
FIG. 57 shows luminance versus external quantum efficiency characteristics of the light-emitting element 8.

FIG. 54 shows luminance versus current efficiency characteristics of the light-emitting element, FIG. 55 shows voltage versus luminance characteristics thereof, FIG. 56 shows luminance versus power efficiency characteristics thereof, and FIG. 57 shows luminance versus external quantum efficiency characteristics thereof. In FIG. 54, the vertical axis represents current efficiency (cd/A), and the horizontal axis represents luminance (cd/m$^2$). In FIG. 55, the vertical axis represents luminance (cd/m$^2$), and the horizontal axis represents voltage (V). In FIG. 56, the vertical axis represents power efficiency (lm/W), and the horizontal axis represents luminance (cd/m$^2$). In FIG. 57, the vertical axis represents external quantum efficiency (%), and the horizontal axis represents luminance (cd/m$^2$).

FIG. 54 indicates that the light-emitting element 8 in which the composite material of the silicon compound having a fluorene skeleton TpsiF and molybdenum oxide was used in the hole-injection layer has excellent luminance versus current efficiency characteristics. FIG. 56 and FIG. 57 show that the light-emitting element 8 has excellent luminance versus power efficiency characteristics and excellent luminance versus external quantum efficiency characteristics, indicating that the light-emitting element 8 has high emission efficiency.

Figure 58:
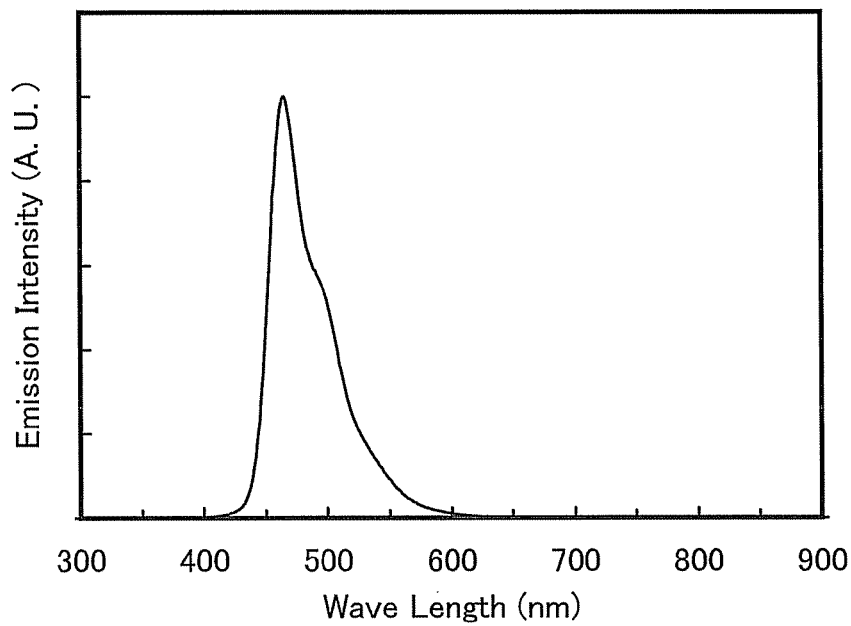
FIG. 58 shows an emission spectrum of the light-emitting element 8.

FIG. 58 shows an emission spectrum of the fabricated light-emitting element 8 when a current of 1 mA was made to flow therein. In FIG. 58, the vertical axis represents emission intensity and the horizontal axis represents emission wave length (nm). The emission intensity is shown as a value relative to the greatest emission intensity assumed to be 1. FIG. 58 shows that the light-emitting element 8 emits blue light originating from 1,6mMemFLPAPrn, which is the emission center substance.

Table 8 shows main characteristics of the light-emitting element 8 around 1000 cd/m².

TABLE 8

| | Voltage (V) | Current (mA) | Current Efficiency (cd/A) | Power Efficiency (lm/W) | External Quantum Efficiency (%) |
|---|---|---|---|---|---|
| Light-emitting Element 8 | 4.0 | 0.51 | 7.8 | 6.1 | 5.7 |

Figure 59:
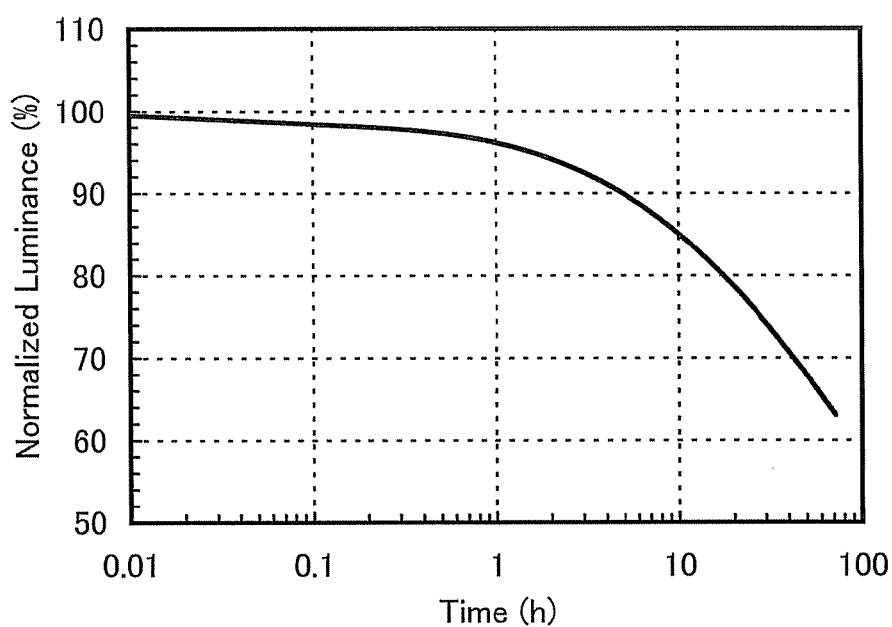
FIG. 59 shows time versus normalized luminance characteristics of the light-emitting element 8.

Next, the initial luminance was set at 5000 cd/m², the element was driven under a condition where the current density was constant, and changes in luminance with respect to the driving time were examined. FIG. 59 shows time versus normalized luminance characteristics. From FIG. 59, it is found that the light-emitting element 8 has excellent characteristics despite the driving test at 5000 cd/m², a very high luminance, and thus has high reliability.

In the above manner, it is found that the composite material which includes the silicon compound having the fluorene skeleton and the inorganic compound is suitable as a material included in a light-emitting element.

Reference Example 1

Reference Example 1 specifically shows a method of synthesizing N,N'-bis[4-(9-phenyl-9H-fluoren-9-yl)phenyl]-N,N'-diphenylpyrene-1,6-diamine (abbreviation: 1,6FLPAPrn) (structural formula (iii)) used in the above Examples. The structure of 1,6FLPAPrn is shown below.

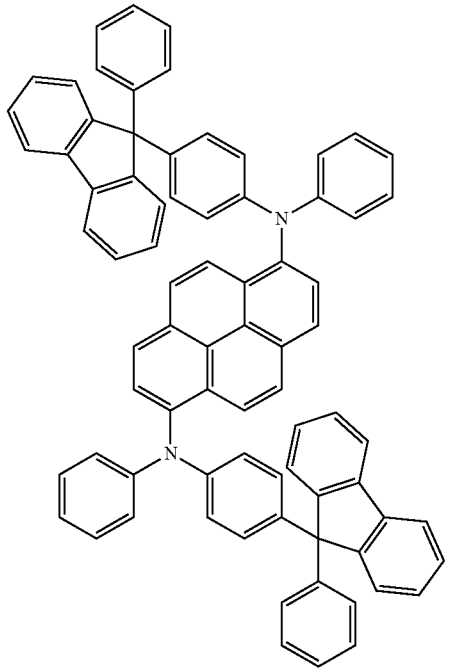

1,6FLPAPrn (iii)

Step 1: Synthesis Method of 9-(4-Bromophenyl)-9-phenylfluorene

In a 100 mL three-neck flask, 1.2 g (50 mmol) of magnesium was heated and stirred under reduced pressure for 30 minutes to be activated. After the flask was cooled to room temperature and was made to have a nitrogen atmosphere, several drops of dibromoethane were added, so that foam formation and heat generation were confirmed. After 12 g (50 mmol) of 2-bromobiphenyl dissolved in 10 mL of diethyl ether was slowly dropped into this mixture, the mixture was stirred and heated under reflux for 2.5 hours and made into a Grignard reagent.

In a 500 mL three-neck flask, 10 g (40 mmol) of 4-bromobenzophenone and 100 mL of diethyl ether were put. After the Grignard reagent which was synthesized in advance was slowly dropped into this mixture, the mixture was stirred and heated under reflux for 9 hours After the reaction, this mixture was filtered to obtain a residue. The obtained residue was dissolved in 150 mL of ethyl acetate, and 1N-hydrochloric acid was added to the mixture, and the mixture was stirred for 2 hours. The organic layer of this liquid was washed with water, and magnesium sulfate was added thereto so as to adsorb moisture. This suspension was filtered, and the obtained filtrate was concentrated to give a highly viscous substance.

In a 500 mL recovery flask, this highly viscous substance, 50 mL of glacial acetic acid, and 1.0 mL of hydrochloric acid were put. The mixture was heated and stirred under a nitrogen atmosphere at 130° C. for 1.5 hours to be reacted.

After the reaction, this reaction mixture solution was filtered to obtain a residue. The obtained residue was washed with water, a sodium hydroxide aqueous solution, water, and methanol in this order, and then was dried, whereby 11 g of the objective white powder was obtained in 69% yield. The synthesis scheme of Step 1 is shown in the following (E1-1).

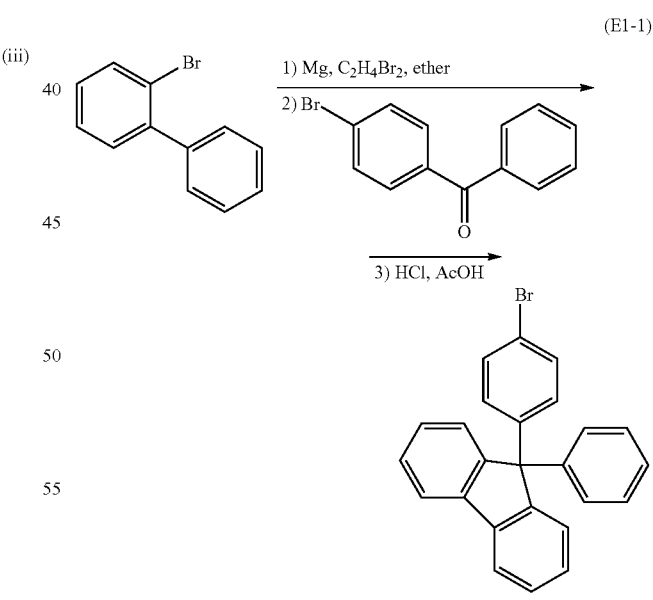

(E1-1)

Step 2: Synthesis Method of 4-(9-Phenyl-9H-fluoren-9-yl)diphenylamine (abbreviation: FLPA)

There were put 5.8 g (14.6 mmol) of 9-(4-bromophenyl)-9-phenylfluorene, 1.7 mL (18.6 mmol) of aniline, and 4.2 g (44.0 mmol) of sodium tert-butoxide in a 200 mL three-neck flask. The air in the flask was replaced with nitrogen. Then, 147.0 mL of toluene and 0.4 mL of a 10% hexane solution of tri(tert-butyl)phosphine were added to this mixture. The temperature of this mixture was set to 60° C., and 66.1 mg (0.1 mmol) of bis(dibenzylideneacetone)palladium(0) was added to the mixture, followed by stirring for 3.5 hours. After the stirring, suction filtration through Florisil (produced by Wako Pure Chemical Industries, Ltd., Catalog No. 540-00135), Celite (produced by Wako Pure Chemical Industries, Ltd., Catalog No. 531-16855), and alumina was carried out to obtain a filtrate. The obtained filtrate was concentrated. The obtained filtrate was concentrated to give a solid, which was then purified by silica gel column chromatography (with a developing solvent containing hexane and toluene in a 2:1 ratio). The obtained fraction was concentrated to give 6.0 g of the objective white solid in 99% yield. The synthesis scheme of Step 2 is shown in the following (E1-2).

a yellow solid. The obtained solid was washed with a mixed solvent of toluene and hexane, and then the mixture was suction-filtered to give a yellow solid. The obtained yellow solid was washed with a mixed solvent of chloroform and hexane, so that 0.8 g of a pale yellow powdered solid was obtained in 68% yield.

By a train sublimation method, 0.8 g of the obtained pale yellow solid was purified. Under a pressure of 2.7 Pa with a flow rate of argon gas at 5.0 mL/min, the sublimation purification was carried out at 360° C. After the purification, 0.4 g of the objective substance was obtained in 56% yield. The synthesis scheme of Step 3 is shown in the following (E2-A).

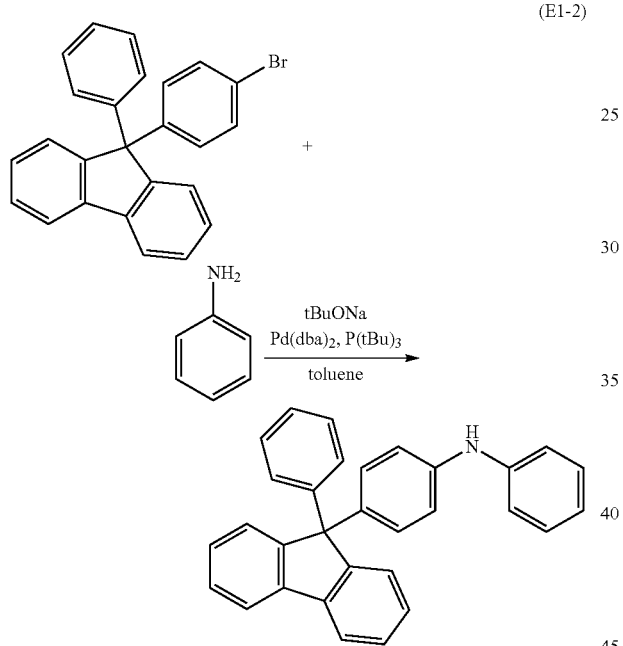

(E1-2)

Step 3: Synthesis Method of N,N'-Bis[4-(9-phenyl-9H-fluoren-9-yl)phenyl]-N,N'-diphenylpyrene-1,6-diamine (abbreviation: 1,6FLPAPrn)

There were put 0.4 g (1.2 mmol) of 1,6-dibromopyrene, 1.0 g (2.4 mmol) of 4-(9-phenyl-9H-fluoren-9-yl)diphenylamine (abbreviation: FLPA) obtained in Step 2 of Reference Example 1, and 0.3 g (3.6 mmol) of sodium tert-butoxide in a 50 mL three-neck flask. The air in the flask was replaced with nitrogen. Then, 11.5 mL of toluene and 0.20 mL of a 10% hexane solution of tri(tert-butyl)phosphine were added to this mixture. The temperature of this mixture was set to 70° C., and 31.1 mg (0.05 mmol) of bis(dibenzylideneacetone)palladium(0) was added to the mixture, followed by stirring for 4.0 hours. After the stirring, the mixture was suction-filtered through Florisil, Celite, and alumina to give a filtrate. The obtained filtrate was concentrated. The obtained filtrate was concentrated to give a solid, which was then purified by silica gel column chromatography (with a developing solvent of chloroform). The obtained fraction was concentrated to give

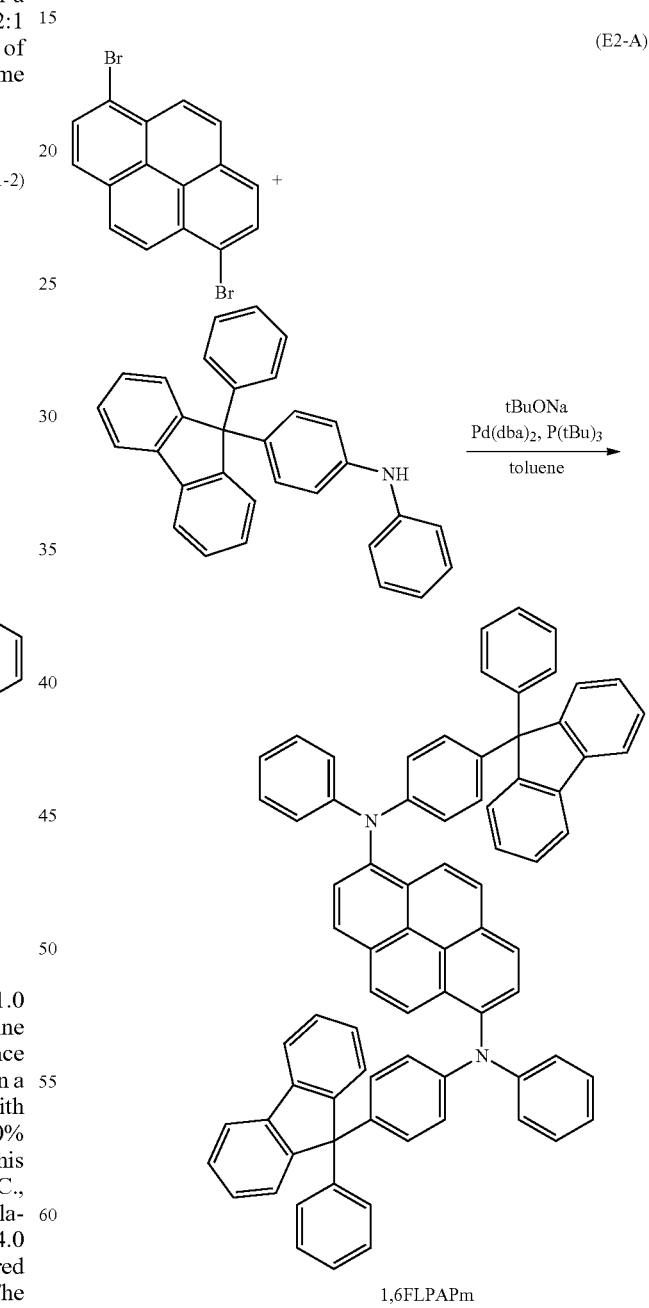

1,6FLPAPm

A nuclear magnetic resonance (NMR) method and a mass spectrometry identified the obtained compound as N,N'-bis

[4-(9-phenyl-9H-fluoren-9-yl)phenyl]-N,N'-diphenylpyrene-1,6-diamine (abbreviation: 1,6FLPAPrn). The $^1$H NMR data is shown below.

$^1$H NMR (CDCl$_3$, 300 MHz): δ=6.88-6.91 (m, 6H), 7.00-7.03 (m, 8H), 7.13-7.40 (m, 26H), 7.73-7.80 (m, 6H), 7.87 (d, J=9.0 Hz, 2H), 8.06-8.09 (m, 4H).

Reference Example 2

Reference Example 2 specifically shows a method of synthesizing 9-{4-(9-H-9-phenylcarbazol-3-yl)-phenylyl}-phenanthrene (abbreviation: PCPPn) (structural formula (i)) used in the above Examples. The structure of PCPPn is shown below.

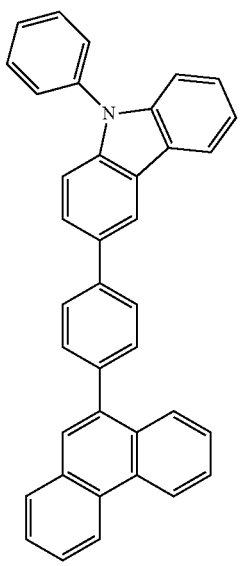

(102)

Step 1: Synthesis Method of
3-(4-Bromophenyl)-9-phenyl-9H-carbazole

There was put a mixture of 14 g (50 mmol) of 4-bromoiodobenzene, 14 g (50 mmol) of 9-phenyl-9H-carbazol-3-boronic acid, 110 mg (0.5 mmol) of palladium(II) acetate, 300 mg (1.0 mmol) of tri(o-tolyl)phosphine, 50 mL of toluene, 10 mL of ethanol, and 25 mL of a potassium carbonate aqueous solution (2 mol/L) in a 300 mL three-neck flask. The mixture was deaerated while being stirred under reduced pressure and was heated and stirred under a nitrogen atmosphere at 80° C. for 6 hours to be reacted.

After the reaction, 200 mL of toluene was added to the reaction mixture solution, and the resulting suspension was filtered through Florisil and Celite. The obtained filtrate was washed with water, and magnesium sulfate was added thereto to adsorb moisture. This suspension was filtered to obtain a filtrate. The obtained filtrate was concentrated, and purified by silica gel column chromatography. At this time, a mixed solvent of toluene and hexane (toluene:hexane=1:4) was used as a developing solvent for the chromatography. The obtained fraction was concentrated, and hexane was added thereto. The mixture was irradiated with ultrasonic wave and then recrystallized, so that 15 g of the objective white powder was obtained at 75% yield. The reaction scheme of Step 1 is shown in the following (F1-1).

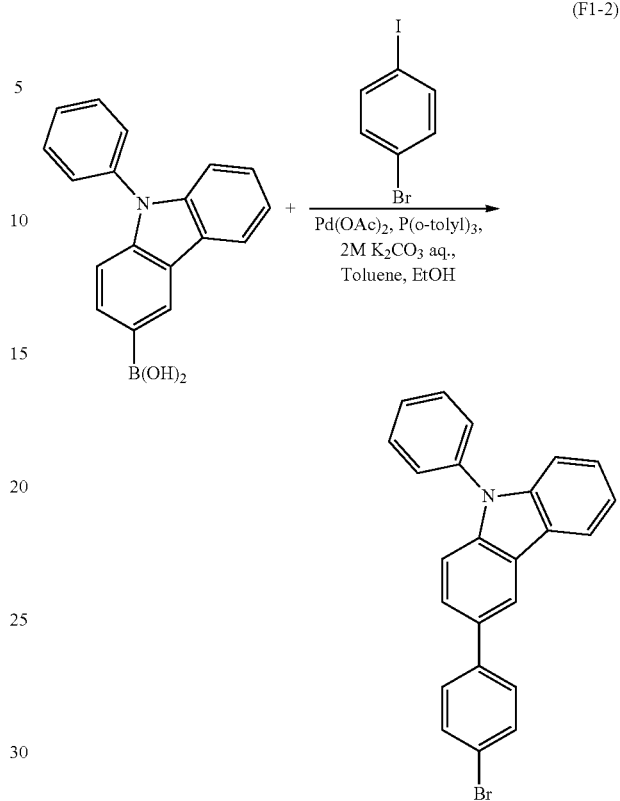

(F1-2)

The Rf value of the objective substance by silica gel thin layer chromatography (TLC) (with a developing solvent containing ethyl acetate and hexane in a 1:10 ratio) was 0.32, and that of 4-bromoiodobenzene was 0.74.

The compound obtained in Step 1 was subjected to a nuclear magnetic resonance (NMR) measurement. The measurement data is shown below. The measurement results confirmed that 3-(4-bromophenyl)-9-phenyl-9H-carbazole was obtained.

$^1$H NMR (CDCl$_3$, 300 MHz): δ (ppm)=7.24-7.32 (m, 1H), 7.40-7.64 (m, 13H), 8.17 (d, J=7.2 Hz, 1H), 8.29 (s, 1H).

Step 2: Synthesis Method of
4-(9-Phenyl-9-H-carbazol-3-yl)phenylboronic acid

Next, 8.0 g (20 mmol) of 3-(4-bromophenyl)-9-phenyl-9H-carbazole obtained in the reaction scheme (F1-2) was put into a 300 mL three-neck flask, the atmosphere in the flask was replaced with nitrogen, 100 mL of dehydrated tetrahydrofuran (abbreviation: THF) was then added to the flask, and the temperature was lowered to −78° C. Into this mixture solution, 15 mL (24 mmol) of a 1.65 mol/L n-butyllithium hexane solution was dropped, and the mixture solution with the n-butyllithium hexane solution added was stirred for 2 hours. To this mixture, 3.4 mL (30 mmol) of trimethyl borate was added, and the mixture with the trimethyl borate added was stirred at −78° C. for 2 hours and at room temperature for 18 hours. After the reaction, 1M diluted hydrochloric acid was added to this reaction solution until the solution became acid, and the solution with the diluted hydrochloric acid added was stirred for 7 hours. This solution was subjected to extraction with ethyl acetate, and the obtained organic layer was washed with a saturated saline. After the washing, magnesium sulfate was added to the organic layer to adsorb moisture. This suspension was filtered, and the obtained filtrate was concentrated, and hexane was added thereto. The mixture was irradiated with ultrasonic waves and then recrystallized to give 6.4 g of white powder in 88% yield. The reaction scheme of Step 2 is shown in the following (F2-1).

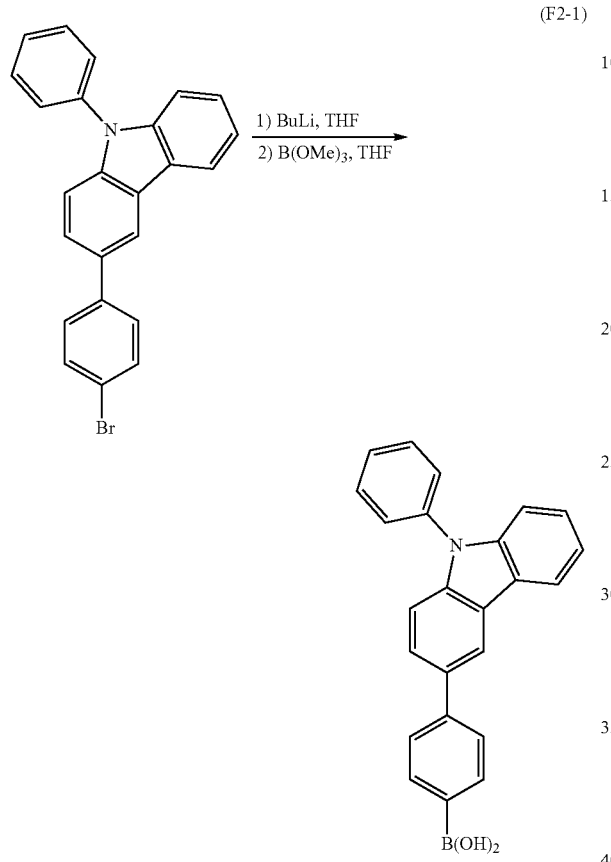

The Rf value of the objective substance obtained by silica gel thin layer chromatography (TLC) (with a developing solvent containing ethyl acetate and hexane in a 1:10 ratio) was 0 (origin), and that of the 3-(4-bromophenyl)-9-phenyl-9H-carbazole was 0.53. In addition, the Rf value of the objective substance obtained by silica gel thin layer chromatography (TLC) using ethyl acetate as the developing solvent was 0.72, and that of the 3-(4-bromophenyl)-9-phenyl-9H-carbazole was 0.93.

Step 3: Synthesis Method of 3-[4-(9-Phenanthryl)-phenyl]-9-phenyl-9H-carbazole (abbreviation: PCPPn)

There was put a mixture of 1.5 g (5.0 mmol) of 9-phenyl-9H-carbazol-3-yl-phenyl-4-boronic acid, 3.2 g (11 mmol) of 9-bromophenanthrene, 11 mg (0.1 mmol) of palladium(II) acetate, 30 mg (0.1 mmol) of tri(o-tolyl)phosphine, 30 mL of toluene, 3 mL of ethanol, and 5 mL of a potassium carbonate aqueous solution (2 mol/L) in a 200 mL three-neck flask. The mixture was deaerated while being stirred under reduced pressure, and then heated and stirred in a nitrogen atmosphere at 90° C. for 6 hours to be reacted.

After the reaction, 200 mL of toluene was added to the reaction mixture solution, and an organic layer of the mixture solution was filtered through Florisil, alumina, and Celite. The obtained filtrate was washed with water, and magnesium sulfate was added thereto to adsorb moisture. This suspension was filtered to obtain a filtrate. The obtained filtrate was concentrated and purified by silica gel column chromatography. At this time, a mixed solvent of toluene and hexane (toluene:hexane=1:4) was used as a developing solvent for the chromatography. The obtained fraction was concentrated, and acetone and methanol were added thereto. The mixture was irradiated with ultrasonic waves and then recrystallized to give 2.2 g of white powder in 75% yield. The reaction scheme of Step 3 is shown in the following (F2-2).

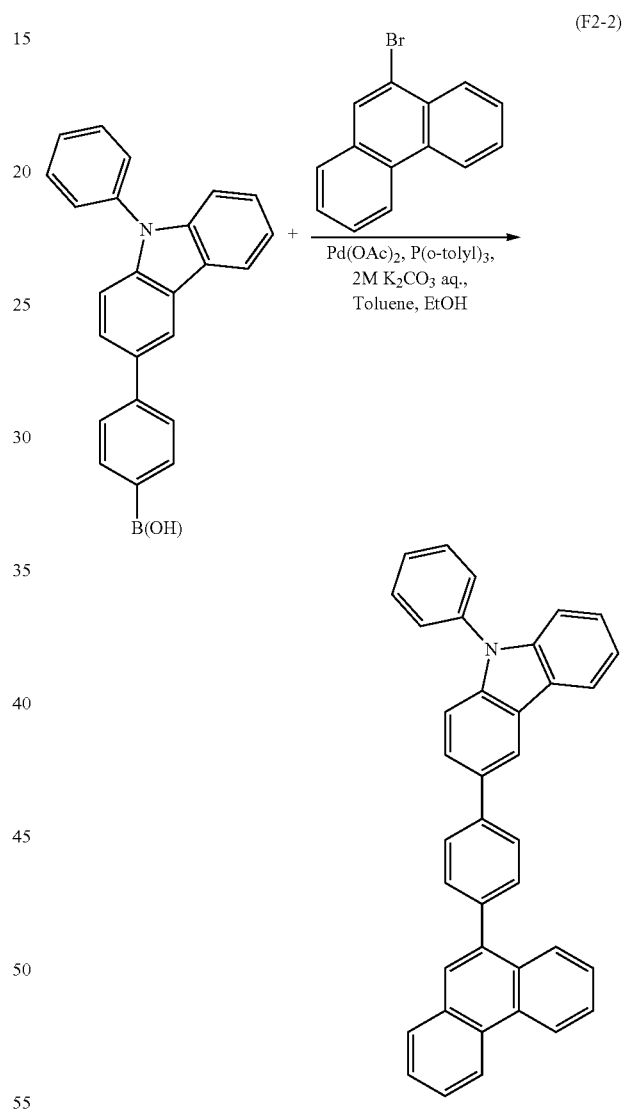

The Rf value of the objective substance by silica gel thin layer chromatography (TLC) (with a developing solvent containing ethyl acetate and hexane in a 1:10 ratio) was 0.33, and that of 9-bromophenanthrene was 0.70.

The obtained compound was subjected to a nuclear magnetic resonance (NMR) measurement. The measurement data is shown below. The measurement results confirmed that PCPPn (abbreviation) that was the objective substance was obtained.

$^1$H NMR (CDCl$_3$, 300 MHz): δ (ppm)=7.30-7.35 (m, 11H), 7.43-7.78 (m, 16H), 7.86-7.93 (m, 3H), 8.01 (dd, J=0.9

Hz, 7.8 Hz, 1H), 8.23 (d, J=7.8 Hz, 1H), 8.47 (d, J=1.5 Hz, 1H), 8.74 (d, J=8.1 Hz, 1H), 8.80 (d, J=7.8 Hz, 1H).

Reference Example 3

Reference Example 3 shows a method of synthesizing N,N'-bis(3-methylphenyl)-N,N'-bis[3-(9-phenyl-9H-fluoren-9-yl)phenyl]-pyrene-1,6-diamine (abbreviation: 1,6mMemFLPAPrn) used in the above Examples. The structural formula of 1,6mMemFLPAPrn is shown below.

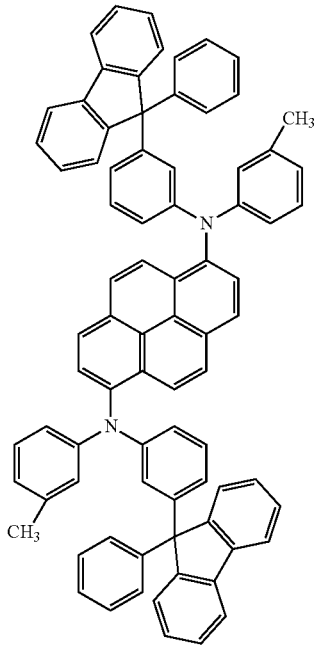 [SMILES: Cc1cccc(N(c2cccc(C3(c4ccccc4)c4ccccc4-c4ccccc43)c2)c2ccc3ccc4c(N(c5cccc(C)c5)c5cccc(C6(c7ccccc7)c7ccccc7-c7ccccc76)c5)ccc5ccc2c3c54)c1]

Step 1: Synthesis Method of 3-Methylphenyl-3-(9-phenyl-9H-fluoren-9-yl)phenylamine (abbreviation: mMemFLPA)

There were put 3.2 g (8.1 mmol) of 9-(3-bromophenyl)-9-phenylfluorene and 2.3 g (24.1 mmol) of sodium tert-butoxide in a 200 mL three-neck flask. The air in the flask was replaced with nitrogen. Then, 40.0 mL of toluene, 0.9 mL (8.3 mmol) of m-toluidine, and 0.2 mL of a 10% hexane solution of tri(tert-butyl)phosphine were added to this mixture. The temperature of this mixture was set to 60° C., and 44.5 mg (0.1 mmol) of bis(dibenzylideneacetone)palladium(0) was added to the mixture. The temperature of the mixture was raised to 80° C., followed by stirring for 2.0 hours. After the stirring, the mixture was suction-filtered through Florisil (produced by Wako Pure Chemical Industries, Ltd., Catalog No. 540-00135), Celite (produced by Wako Pure Chemical Industries, Ltd., Catalog No. 531-16855), and alumina to give a filtrate. The filtrate was concentrated to give a solid, which was then purified by silica gel column chromatography (with a developing solvent containing hexane and toluene in a 1:1 ratio). Recrystallization was performed from a mixed solvent of toluene and hexane. Accordingly, 2.8 g of the objective white solid was obtained in 82% yield. The synthesis scheme of Step 1 is shown below.

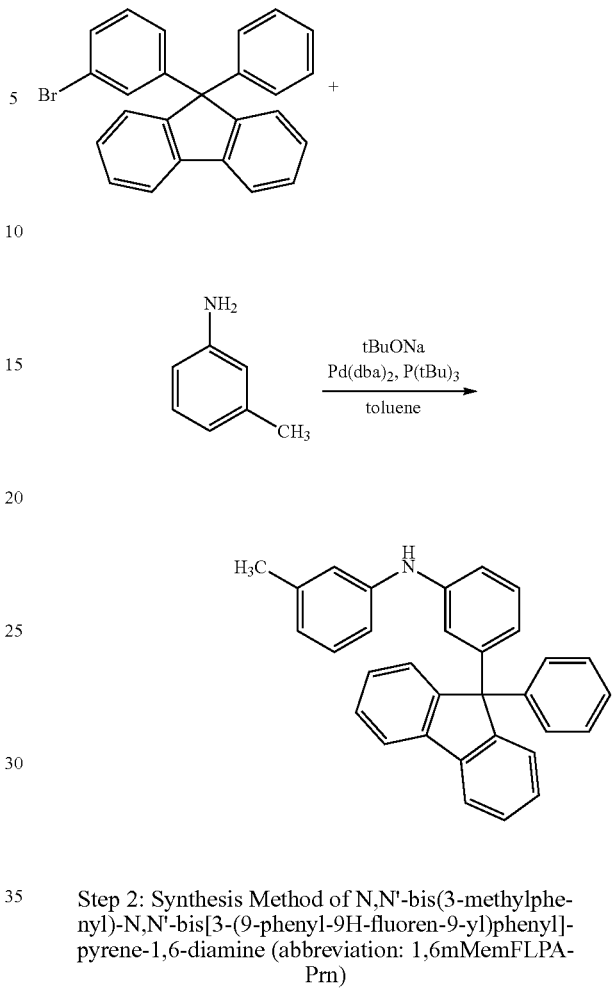

Step 2: Synthesis Method of N,N'-bis(3-methylphenyl)-N,N'-bis[3-(9-phenyl-9H-fluoren-9-yl)phenyl]-pyrene-1,6-diamine (abbreviation: 1,6mMemFLPAPrn)

There were put 0.6 g (1.7 mmol) of 1,6-dibromopyrene, 1.4 g (3.4 mmol) of 3-methylphenyl-3-(9-phenyl-9H-fluoren-9-yl)phenylamine, and 0.5 g (5.1 mmol) of sodium tert-butoxide in a 100 mL three-neck flask. The air in the flask was replaced with nitrogen. To this mixture were added 21.0 mL of toluene and 0.2 mL of a 10% hexane solution of tri(tert-butyl)phosphine. The temperature of this mixture was set to 60° C., and 34.9 mg (0.1 mmol) of bis(dibenzylideneacetone)palladium(0) was added to the mixture. The temperature of this mixture was set to 80° C., followed by stirring for 3.0 hours. After the stirring, 400 mL of toluene was added to the mixture, and the mixture was heated. While the mixture was kept hot, it was suction-filtered through Florisil (produced by Wako Pure Chemical Industries, Ltd., Catalog No. 540-00135), Celite (produced by Wako Pure Chemical Industries, Ltd., Catalog No. 531-16855), and alumina to give a filtrate. The filtrate was concentrated to give a solid, which was then purified by silica gel column chromatography (with a developing solvent containing hexane and toluene in a 3:2 ratio) to give a yellow solid. Recrystallization of the obtained yellow solid from a mixed solvent of toluene and hexane gave 1.2 g of the objective yellow solid in 67% yield.

By a train sublimation method, 1.0 g of the obtained yellow solid was purified. In the purification, the yellow solid was heated at 317° C. under a pressure of 2.2 Pa with a flow rate of argon gas of 5.0 mL/min. After the purification, 1.0 g of the objective yellow solid was obtained in 93% yield. The synthesis scheme of Step 2 is shown below.

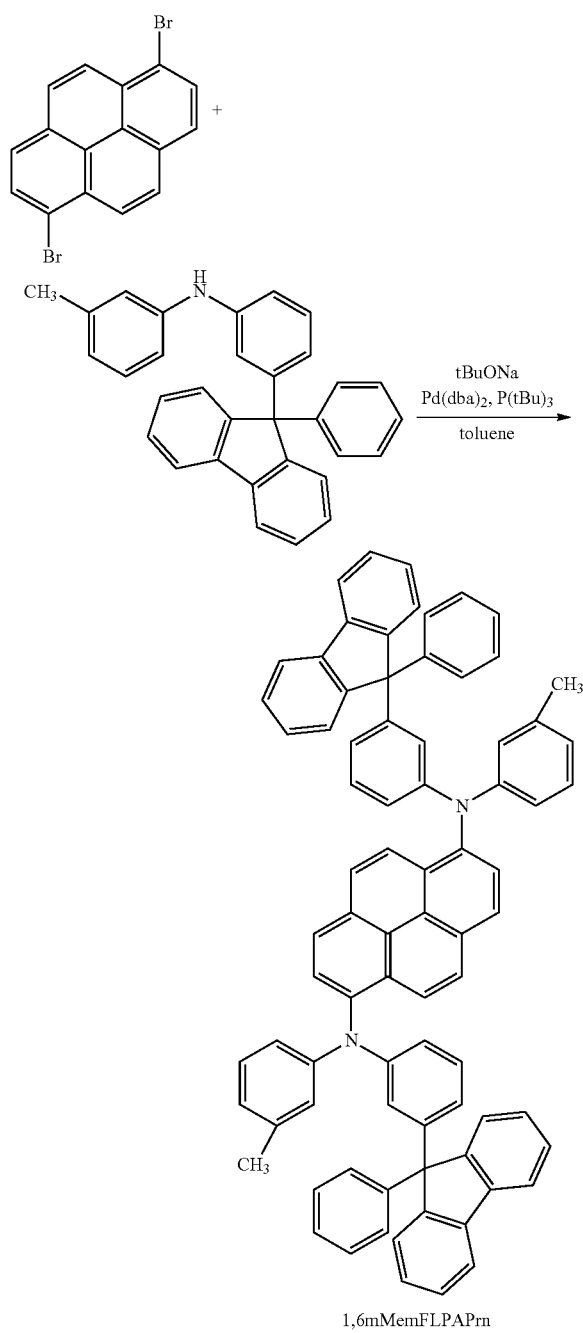

1,6mMemFLPAPrn

A nuclear magnetic resonance (NMR) method identified this compound as N,N'-bis(3-methylphenyl)-N,N'-bis[3-(9-phenyl-9H-fluoren-9-yl)phenyl]-pyrene-1,6-diamine (abbreviation: 1,6mMemFLPAPrn), which was the objective substance.

$^1$H NMR data of the obtained compound is shown below.

$^1$H NMR (CDCl$_3$, 300 MHz): δ=2.21 (s, 6H), 6.67 (d, J=7.2 Hz, 2H), 6.74 (d, J=7.2 Hz, 2H), 7.17-7.23 (m, 34H), 7.62 (d, J=7.8 Hz, 4H), 7.74 (d, J=7.8 Hz, 2H), 7.86 (d, J=9.0 Hz, 2H), 8.04 (d, J=8.7 Hz, 4H).

This application is based on Japanese Patent Application serial no. 2011-017164 filed with Japan Patent Office on Jan. 28, 2010, the entire contents of which are hereby incorporated by reference.

What is claimed is:

1. A composite material comprising:
   a hydrocarbon compound having a molecular weight of greater than or equal to 400 and less than or equal to 2000, the hydrocarbon compound including
   a fluorene unit, and
   an aryl group bonded to the fluorene unit; and
   an inorganic compound which exhibits an electron-accepting property with respect to the hydrocarbon compound.

2. The composite material according to claim 1, wherein the aryl group is bonded to a 9-position of the fluorene unit via one phenylene group or two phenylene groups.

3. A composite material according to claim 1, wherein the aryl group includes any of a bicyclic condensed ring, a tricyclic condensed ring, or a tetracyclic condensed ring.

4. The composite material according to claim 1, wherein the aryl group is bonded to a 2-position or a 7-position of the fluorene unit.

5. The composite material according to claim 1, wherein the aryl group is one selected from the group consisting of substituted and unsubstituted phenyl groups, substituted and unsubstituted naphthyl groups, substituted and unsubstituted anthryl groups, substituted and unsubstituted phenanthryl groups, substituted and unsubstituted triphenylenyl groups, substituted and unsubstituted pyrenyl groups, substituted and unsubstituted chrysenyl groups, and substituted and unsubstituted tetracenyl groups.

6. The composite material according to claims 1, wherein the molecular weight of the hydrocarbon compound is less than or equal to 1500.

7. The composite material according to claims 1, wherein the inorganic compound is a transition metal oxide.

8. The composite material according to claims 1, wherein the inorganic compound is one selected from the group consisting of titanium oxide, vanadium oxide, tantalum oxide, molybdenum oxide, tungsten oxide, rhenium oxide, ruthenium oxide, a chromium oxide, zirconium oxide, hafnium oxide, and silver oxide.

9. The composite material according to claims 1, wherein the inorganic compound is molybdenum oxide.

10. The composite material according to claim 1, wherein the aryl group is bonded to the fluorene unit via one phenylene group or two phenylene groups.

11. The composite material according to claims 1, wherein the hydrocarbon compound is represented by the following general formula (G1),

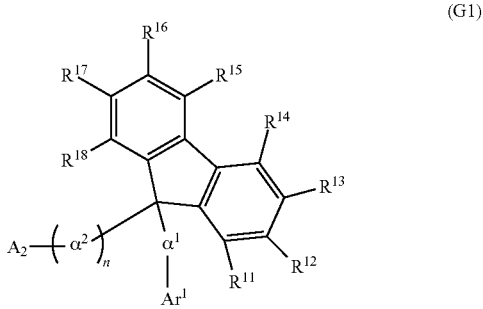

(G1)

wherein:
α$^1$ and α$^2$ separately represent a substituted or unsubstituted phenylene group or a substituted or unsubstituted biphenyldiyl group;
n is 0 or 1;

Ar¹ represents a substituted or unsubstituted aryl group;
Ar² represents a substituted or unsubstituted aryl group; and
$R^{11}$ to $R^{18}$ separately represent any of hydrogen, an alkyl group having 1 to 6 carbon atoms, a substituted or unsubstituted phenyl group, a substituted or unsubstituted biphenyl group, a substituted or unsubstituted naphthyl group, and a substituted or unsubstituted phenanthryl group.

12. The composite material according to claim 11, wherein Ar¹ is any of a substituted or unsubstituted bicyclic condensed aryl group, a substituted or unsubstituted tricyclic condensed aryl group, and a substituted or unsubstituted tetracyclic condensed aryl group, and
wherein Ar² is any of a substituted or unsubstituted aryl group having 6 to 18 carbon atoms.

13. The composite material according to claim 1,
wherein the hydrocarbon compound is represented by the following general formula (G2),

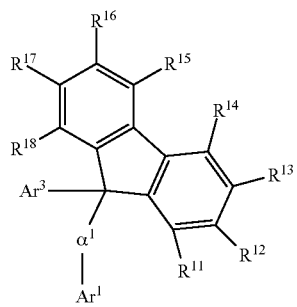

(G2)

wherein:
α¹ represents a substituted or unsubstituted phenylene group or a substituted or unsubstituted biphenyldiyl group,
Ar¹ represents any of a substituted or unsubstituted bicyclic condensed aryl group, a substituted or unsubstituted tricyclic condensed aryl group, and a substituted or unsubstituted tetracyclic condensed aryl group,
Ar³ represents a substituted or unsubstituted phenyl group or a substituted or unsubstituted biphenyl group, and
$R^{11}$ to $R^{18}$ separately represent any of hydrogen, an alkyl group having 1 to 6 carbon atoms, a substituted or unsubstituted phenyl group, a substituted or unsubstituted biphenyl group, a substituted or unsubstituted naphthyl group, and a substituted or unsubstituted phenanthryl group.

14. The composite material according to claim 1,
wherein the hydrocarbon compound is represented by the following general formula (G3),

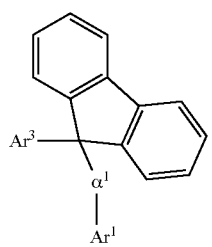

(G3)

wherein:
α¹ represents a substituted or unsubstituted phenylene group or a substituted or unsubstituted biphenyldiyl group;
Ar¹ represents any of a substituted or unsubstituted bicyclic condensed aryl group, a substituted or unsubstituted tricyclic condensed aryl group, and a substituted or unsubstituted tetracyclic condensed aryl group; and
Ar³ represents a substituted or unsubstituted phenyl group or a substituted or unsubstituted biphenyl group.

15. The composite material according to claim 11, wherein $R^{11}$ to $R^{18}$ separately represent any one of hydrogen, an alkyl group having 1 to 6 carbon atoms, and groups represented by the following structural formulas (R-1) to (R-6).

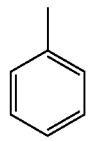

(R-1)

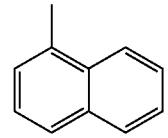

(R-2)

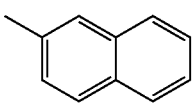

(R-3)

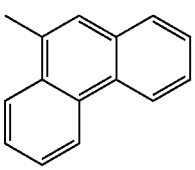

(R-4)

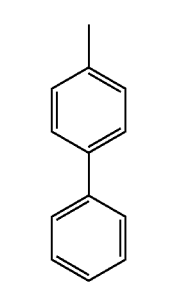

(R-5)

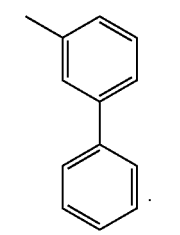

(R-6)

16. The composite material according to claim 11, wherein Ar¹ is any one of a substituted or unsubstituted naphthyl group, a substituted or unsubstituted anthryl group, a substituted or unsubstituted phenanthryl group, a substituted or unsubstituted triphenylenyl group, a substituted or unsubstituted pyrenyl group, a substituted or unsubstituted chrysenyl group, and a substituted or unsubstituted tetracenyl group.

17. The composite material according to claim 11, wherein $Ar^1$ is selected so that a substance where $Ar^1$—H does not have a peak in a range of greater than or equal to 450 nm and less than or equal to 800 nm in an absorption spectrum thereof.

18. The composite material according to claim 11, wherein $Ar^1$ has a substituent selected from the group consisting of a phenyl group, a naphthyl group, a phenanthryl group, and groups represented by the following general formula ($Ar^1$-1),

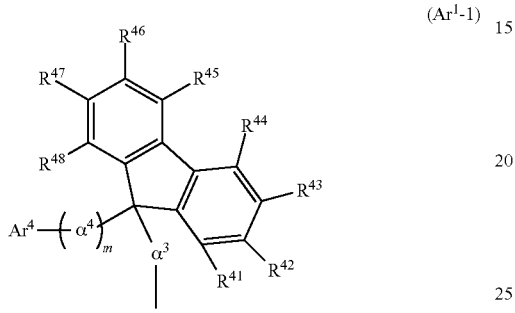
($Ar^1$-1)

wherein:

$\alpha^3$ and $\alpha^4$ separately represent a substituted or unsubstituted phenylene group or a substituted or unsubstituted biphenyldiyl group;

m is 0 or 1;

$Ar^4$ represents any of a substituted or unsubstituted aryl group having 6 to 18 carbon atoms; and $R^{41}$ to $R^{48}$ separately represent any of hydrogen, an alkyl group having 1 to 6 carbon atoms, a phenyl group, a biphenyl group, a naphthyl group, and a phenanthryl group.

19. The composite material according to claim 11, wherein $\alpha^1$ and $\alpha^2$ separately represents any of the following structural formulas ($\alpha$-1) to ($\alpha$-6).

($\alpha$-1)

($\alpha$-2)

($\alpha$-3)

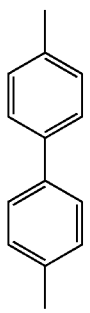
($\alpha$-4)

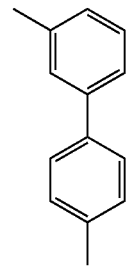
($\alpha$-5)

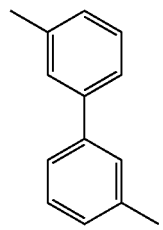
($\alpha$-6)

20. The composite material according to claim 1, wherein the hydrocarbon compound is represented, by the following general formula (G4),

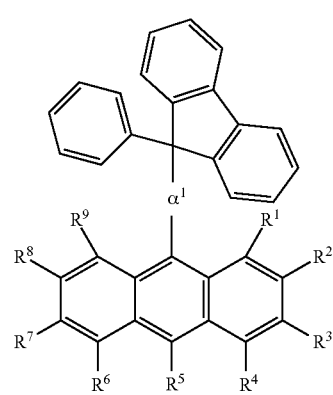
(G4)

wherein:

$\alpha^1$ represents a substituted or unsubstituted phenylene group or a substituted or unsubstituted biphenyldiyl group; and $R^1$ to $R^9$ separately represent any of hydrogen, an alkyl group having 1 to 6 carbon atoms, a phenyl group, a biphenyl group, a naphthyl group, a phenanthryl group, and a group represented by the following general formula ($Ar^1$-2), (Ar¹-2)

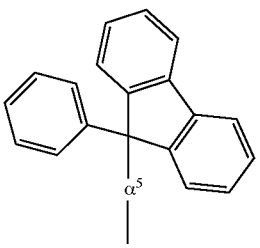

wherein $\alpha^5$ represents a substituted or unsubstituted phenylene group or a substituted or unsubstituted biphenyldiyl group.

21. The composite material according to claim 1, wherein the hydrocarbon compound is represented by the following general formula (G5), (G5)

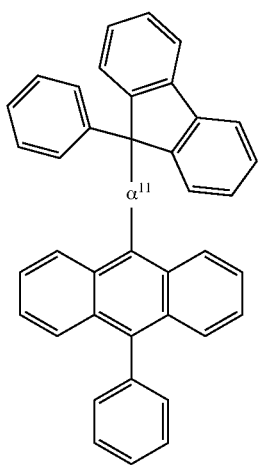

wherein $\alpha^{11}$ represents a phenylene group or a biphenyldiyl group.

22. The composite material according to claims 1, wherein the hydrocarbon compound is represented by the following general formula (G6);

(G6)

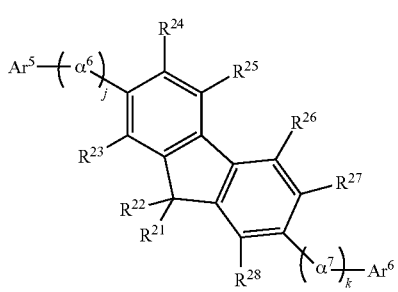

wherein:
Ar⁵ represents a substituted or unsubstituted aryl group having 6 to 18 carbon atoms;
Ar⁶ represents hydrogen or a substituted or unsubstituted aryl group having 6 to 18 carbon atoms, $\alpha^6$ and $\alpha^7$ separately represent a substituted or unsubstituted phenylene group or a substituted or unsubstituted biphenyldiyl group, j and k are separately 0 or 1, $R^{21}$ to $R^{28}$ separately represent any of hydrogen, an alkyl group having 1 to 6 carbon atoms, a substituted or unsubstituted phenyl group, a substituted or unsubstituted biphenyl group, a substituted or unsubstituted naphthyl group, and a substituted or unsubstituted phenanthryl group.

23. The composite material according to claims 22,
wherein Ar⁵ is one selected from the group consisting of substituted and unsubstituted phenyl groups, substituted and unsubstituted naphthyl groups, substituted and unsubstituted anthryl groups, substituted and unsubstituted phenanthryl groups, substituted and unsubstituted triphenylenyl groups, substituted and unsubstituted pyrenyl groups, substituted and unsubstituted chrysenyl groups, and substituted and unsubstituted tetracenyl groups, and wherein Ar⁶ is one selected from the group consisting of hydrogen, substituted and unsubstituted phenyl groups, substituted and unsubstituted naphthyl groups, substituted and unsubstituted anthryl groups, substituted and unsubstituted phenanthryl groups, substituted and unsubstituted triphenylenyl groups, substituted or unsubstituted pyrenyl groups, substituted or unsubstituted chrysenyl groups, and substituted or unsubstituted tetracenyl groups.

24. The composite material according to claims 1,
wherein the hydrocarbon compound is represented by the following general formula (G7), (G7)

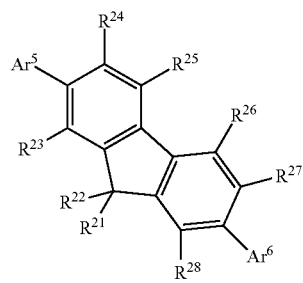

wherein:
Ar⁵ represents a substituted or unsubstituted aryl group having 6 to 18 carbon atoms;
Ar⁶ represents hydrogen or a substituted or unsubstituted aryl group having 6 to 18 carbon atoms; and
$R^{21}$ to $R^{28}$ separately represent any of hydrogen, an alkyl group having 1 to 6 carbon atoms, a substituted or unsubstituted phenyl group, a substituted or unsubstituted biphenyl group, a substituted or unsubstituted naphthyl group, and a substituted or unsubstituted phenanthryl group.

25. The composite material according to claims 1,
wherein the hydrocarbon compound is represented by the following general formula (G6'),

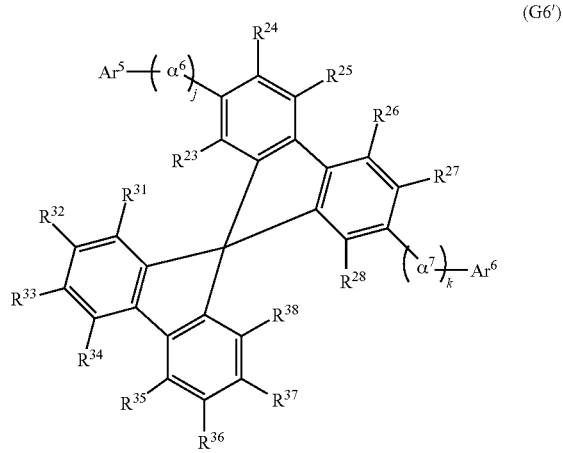

wherein:
Ar⁵ represents a substituted or unsubstituted aryl group having 6 to 18 carbon atoms;
Ar⁶ represents hydrogen or a substituted or unsubstituted aryl group having 6 to 18 carbon atoms;
α⁶ and α⁷ separately represent a substituted or unsubstituted phenylene group or a substituted or unsubstituted biphenyldiyl group;
j and k is separately 0 or 1; and
R²³ to R²⁸ and R³¹ to R³⁸ separately represent any of hydrogen, an alkyl group having 1 to 6 carbon atoms, a substituted or unsubstituted phenyl group, a substituted or unsubstituted biphenyl group, a substituted or unsubstituted naphthyl group, and a substituted or unsubstituted phenanthryl group.

26. The composite material according to claims 1,
wherein the hydrocarbon compound is represented by the following general formula (G7'),

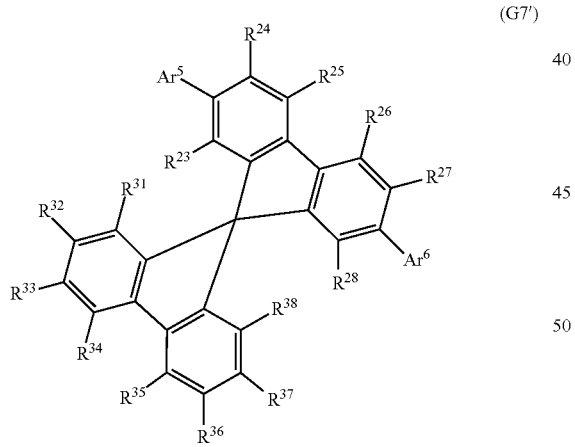

wherein:
Ar⁵ represents a substituted or unsubstituted aryl group having 6 to 18 carbon atoms;
Ar⁶ represents hydrogen or a substituted or unsubstituted aryl group having 6 to 18 carbon atoms; and
R²³ to R²⁸ and R³¹ to R³⁸ separately represent any of hydrogen, an alkyl group having 1 to 6 carbon atoms, a substituted or unsubstituted phenyl group, a substituted or unsubstituted biphenyl group, a substituted or unsubstituted naphthyl group, and a substituted or unsubstituted phenanthryl group.

27. A light-emitting element comprising:
a first electrode;
a second electrode; and
a layer including an organic compound between the first electrode and the second electrode,
wherein the layer including the organic compound includes
a layer including an emission center substance, and
a layer including the composite material according to a claim 1.

28. The light-emitting element according to claim 27, wherein the layer including the composite material is in contact with the first electrode functioning as an anode.

29. A light-emitting element comprising:
a layer including an organic compound between a pair of electrodes,
wherein the layer including the organic compound includes
a layer including the composite material according to claim 1,
a first light-emitting unit, and
a second light-emitting unit,
wherein each of the first light-emitting unit and the second light-emitting unit includes a layer including an emission center substance, and
wherein the layer including the composite material is interposed between the first light-emitting unit and the second light-emitting unit.

30. A light-emitting device comprising:
the light-emitting element according to claim 29.

31. An electronic device comprising:
the light-emitting device according to claim 30, in a display portion.

32. A lighting device comprising:
the light-emitting device according to claim 30, in a light-emitting portion.

33. A fluorene derivative represented by the following structural formula:

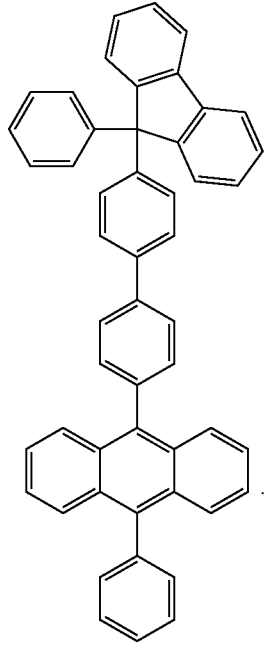 [SMILES: c1ccc(-c2c3ccccc3c(-c3ccc(-c4ccc(C5(c6ccccc6)c6ccccc6-c6ccccc65)cc4)cc3)c3ccccc23)cc1]

* * * * *

UNITED STATES PATENT AND TRADEMARK OFFICE
CERTIFICATE OF CORRECTION

PATENT NO. : 8,421,346 B2
APPLICATION NO. : 13/358975
DATED : April 16, 2013
INVENTOR(S) : Harue Osaka et al.

It is certified that error appears in the above-identified patent and that said Letters Patent is hereby corrected as shown below:

In the Specification:

Column 2, line 13; Change "Vol. 64, No. 10;" to --Vol. 64, No. 10,--.
Column 4, line 21; Change "the fluorene, skeleton;" to --the fluorene skeleton;--.
Column 19, line 44; Change "be perforated at" to --be performed at--.
Column 20, line 3; Change "atoms fowling a ring" to --atoms forming a ring--.
Column 76, line 15; Change "the organic, compound and" to --the organic compound and--.
Column 77, line 35; Change "be fainted" to --be formed--.
Column 78, line 3; Change "a layer foamed" to --a layer formed--.
Column 78, line 38; Change "N,N'-diphenyl[1, 1'-biphenyl]-4,4'-diamine"
         to --N,N'-diphenyl-[1, 1'-biphenyl]-4,4'-diamine--.
Column 79, line 52; Change "[1,2-a]" to --[1,2-α]--.
Column 81, line 64; Change "$10^{-6}$ cm$^2$ V•s" to --$10^{-6}$ cm$^2$/V•s--.
Column 84, line 45; Change "$10^{-6}$ cm$^2$ V•s" to --$10^{-6}$ cm$^2$/V•s--.
Column 93, line 18; Change "electrode. 401." to --electrode 401.--.
Column 95, line 3; Change "as a material:" to --as a material.--.
Column 107, line 51; Change "was framed." to --was formed.--.

Signed and Sealed this
Tenth Day of December, 2013

Margaret A. Focarino
*Commissioner for Patents of the United States Patent and Trademark Office*